US012571002B2

(12) United States Patent
Abeliovich et al.

(10) Patent No.: US 12,571,002 B2
(45) Date of Patent: \*Mar. 10, 2026

(54) GENE THERAPIES FOR LYSOSOMAL DISORDERS

(71) Applicant: Prevail Therapeutics, Inc., New York, NY (US)

(72) Inventors: Asa Abeliovich, New York, NY (US); Laura Heckman, Yardley, PA (US); Herve Rhinn, New York, NY (US)

(73) Assignee: PREVAIL THERAPEUTICS, INC, Indianapolis, IN (US)

( \* ) Notice: Subject to any disclaimer, the term of this patent is extended or adjusted under 35 U.S.C. 154(b) by 1281 days.

This patent is subject to a terminal disclaimer.

(21) Appl. No.: 17/369,168

(22) Filed: Jul. 7, 2021

(65) Prior Publication Data

US 2021/0332385 A1      Oct. 28, 2021

Related U.S. Application Data

(63) Continuation of application No. 17/024,117, filed on Sep. 17, 2020, now Pat. No. 11,060,113, which is a continuation of application No. 16/689,865, filed on Nov. 20, 2019, now Pat. No. 10,837,028, which is a continuation of application No. PCT/US2018/054225, filed on Oct. 3, 2018.

(60) Provisional application No. 62/567,296, filed on Oct. 3, 2017.

(51) Int. Cl.
| | |
|---|---|
| *C12N 15/86* | (2006.01) |
| *A61K 48/00* | (2006.01) |
| *C07K 14/435* | (2006.01) |
| *C07K 14/705* | (2006.01) |
| *C12N 7/00* | (2006.01) |
| *C12N 9/24* | (2006.01) |
| *C12N 15/113* | (2010.01) |
| *C12N 15/52* | (2006.01) |
| *C12N 15/861* | (2006.01) |
| *C12N 15/864* | (2006.01) |
| *A61K 9/00* | (2006.01) |

(52) U.S. Cl.
CPC ........ *C12N 15/861* (2013.01); *A61K 48/0058* (2013.01); *C07K 14/435* (2013.01); *C07K 14/70596* (2013.01); *C12N 7/00* (2013.01); *C12N 9/2402* (2013.01); *C12N 15/113* (2013.01); *C12N 15/86* (2013.01); *C12Y 302/01045* (2013.01); *A61K 9/0019* (2013.01); *A61K 48/00* (2013.01); *C12N 2310/14* (2013.01); *C12N 2310/141* (2013.01); *C12N 2710/14043* (2013.01); *C12N 2750/14143* (2013.01)

(58) Field of Classification Search
None
See application file for complete search history.

(56) References Cited

U.S. PATENT DOCUMENTS

| | | | |
|---|---|---|---|
| 5,879,680 A | 3/1999 | Ginns et al. | |
| 6,696,272 B1 | 2/2004 | Mahuran et al. | |
| 7,172,893 B2 | 2/2007 | Rabinowitz | |
| 7,452,716 B2 | 11/2008 | Yew | |
| 8,454,954 B2 | 6/2013 | Schlossmacher et al. | |
| 8,962,273 B2 | 2/2015 | Reczek | |
| 9,034,836 B2 | 5/2015 | Dodge et al. | |
| 9,347,107 B2 | 5/2016 | Lai et al. | |
| 10,213,494 B2 | 2/2019 | Schlossmacher et al. | |
| 10,837,028 B2 * | 11/2020 | Abeliovich .......... | C07K 14/435 |
| 11,060,113 B2 * | 7/2021 | Abeliovich ............ | C12N 15/86 |
| 11,802,294 B2 | 10/2023 | Abeliovich et al. | |
| 11,807,849 B2 | 11/2023 | Abeliovich et al. | |
| 11,903,985 B2 | 2/2024 | Abeliovich et al. | |
| 2003/0133924 A1 | 7/2003 | Canfield | |
| 2006/0292117 A1 | 12/2006 | Loiler et al. | |
| 2008/0003204 A1 | 1/2008 | Flotte et al. | |
| 2015/0284472 A1 | 10/2015 | Sardi et al. | |
| 2016/0237414 A1 | 8/2016 | Grabowski et al. | |
| 2016/0243260 A1 | 8/2016 | Blits | |
| 2017/0035860 A1 | 2/2017 | Flynn | |
| 2018/0071373 A1 | 3/2018 | Melvor et al. | |
| 2018/0147300 A1 | 5/2018 | Park et al. | |

(Continued)

FOREIGN PATENT DOCUMENTS

| | | |
|---|---|---|
| EP | 3091087 A1 | 11/2016 |
| EP | 3701030 A1 | 9/2020 |

(Continued)

OTHER PUBLICATIONS

Garcia-Gomez, M., et al., "Modelling Gaucher Disease Through Interference RNA Technology," Human Gene Therapy, Sep. 1, 2015, PO37, 26(9):A22-A23.

(Continued)

*Primary Examiner* — Maria Marvich

(74) *Attorney, Agent, or Firm* — Brian C. Cholewa

(57) ABSTRACT

The disclosure relates, in some aspects, to compositions and methods for treatment of diseases associated with aberrant lysosomal function, for example Parkinson's disease and Gaucher disease. In some embodiments, the disclosure provides expression constructs comprising a transgene encoding beta-Glucocerebrosidase (GBA) or a portion thereof, Lysosomal Membrane Protein 2 (LIMP2), Prosaposin, or any combination of the foregoing. In some embodiments, the disclosure provides methods of Parkinson's disease by administering such expression constructs to a subject in need thereof.

23 Claims, 26 Drawing Sheets

Specification includes a Sequence Listing.

(56)　　　　　　References Cited

U.S. PATENT DOCUMENTS

| | | | |
|---|---|---|---|
| 2019/0038773 A1 | 2/2019 | Esteves et al. |
| 2019/0055578 A1 | 2/2019 | Sah et al. |
| 2019/0282662 A1 | 9/2019 | Kay et al. |
| 2019/0328906 A1 | 10/2019 | Chen Plotkin et al. |
| 2020/0071726 A1 | 3/2020 | Abeliovich et al. |
| 2020/0231954 A1 | 7/2020 | Abeliovich et al. |
| 2020/0231970 A1 | 7/2020 | Abeliovich et al. |
| 2020/0338148 A1 | 10/2020 | Abeliovich et al. |
| 2021/0010032 A1 | 1/2021 | Abeliovich et al. |
| 2022/0211871 A1 | 7/2022 | Abeliovich et al. |
| 2023/0310654 A1 | 10/2023 | Abeliovich et al. |
| 2024/0123003 A1 | 4/2024 | Abeliovich et al. |

FOREIGN PATENT DOCUMENTS

| | | | |
|---|---|---|---|
| KR | 20140130495 A | 11/2014 |
| WO | WO-0183692 A2 | 11/2001 |
| WO | WO 02/24932 A2 | 3/2002 |
| WO | WO 2004/098648 A1 | 11/2004 |
| WO | WO-2010098861 A1 | 9/2010 |
| WO | WO-2011133890 A1 | 10/2011 |
| WO | WO-2013121405 A1 | 8/2013 |
| WO | WO-2014011237 A1 | 1/2014 |
| WO | WO 2014186579 A1 | 11/2014 |
| WO | WO 2016/081927 A2 | 3/2016 |
| WO | WO 2017/077451 A1 | 5/2017 |
| WO | WO 2017136202 A1 | 8/2017 |
| WO | WO 2019/070891 A1 | 4/2019 |
| WO | WO 2019/070893 A1 | 4/2019 |
| WO | WO-2020210615 A1 | 10/2020 |

OTHER PUBLICATIONS

Ciesielska, et al., "Cerebral Infusion of AAV9 Vector-encoding Non-self Proteins Can Elicit Cell-mediated Immune Responses." Mol Ther. Jan. 2013, 21(1):158-166.

Fischell and Fishman, "A Multifaceted Approach to Optimizing AAV Delivery to the Brain for the Treatment of Neurodegenerative Diseases," Frontiers in Neuroscience, Sep. 24, 2021, 15(747726):1-20.

François, A., et al., "The Cellular TATA Binding Protein is Required for Rep-Dependent Replication of a Minimal Adeno-Associated Virus Type 2 p5 Element," Journal of Virology, Sep. 2005, 79(17):11082-11094.

GenBank Accession No. AF043303.1, "Adeno-associated virus 2, complete genome," May 20, 2010, 5 pages.

GenBank Accession No. NM_000157.3, "(GBA1):c.1448T>C and Gaucher disease type III", Mar. 5, 2022, 2 pages.

Giasson, B. et al. "Neuronal α-Synucleinopathy with Severe Movement Disorder in Mice Expressing A53T Human α-Synuclein," Neuron, May 16, 2002, 34:521-533.

Lonser et al., "Convection-enhanced delivery to the central nervous system" J Neurosurg. Mar. 2015, 122(3):697-706. Epub Nov. 14, 2014.

Marchi et al., "Delivery of therapeutic AAV9 vector via cisterna magna to treat neurological disorders", Trends Mol Med. Jan. 2022, 28(1):79-80. Epub Oct. 28, 2021.

Mazzulli, J. et al. "Cytosolic Catechols Inhibit α-Synuclein Aggregation and Facilitate the Formation of Intracellular Soluble Oligomeric Intermediates," The Journal of Neuroscience, Sep. 27, 2006, 26(39):10068-10078.

Mazzulli, J. et al. "Gaucher Disease Glucocerebrosidase and α-Synuclein Form a Bidirectional Pathogenic Loop in Synucleinopathies," Cell, Jul. 8, 2011, 146:37-52.

Orme et al. "The Genetics of Dementia with Lewy Bodies: Current Understanding and Future Directions," Curr Neurol Neurosci Rep. Aug. 10, 2018, 18(10):67, 13 pages.

Samaranch, et al., "AAV9-mediated Expression of a Non-self Protein in Nonhuman Primate Central Nervous System Triggers Widespread Neuroinflammation Driven by Antigen-presenting Cell Transduction." Mol Ther. Feb. 2014, 22(2):329-337.

Zhang et al., "Disease-modifying therapeutics directions for Lewy-Body dementias," Frontiers in Neuroscience, Aug. 2015, 9:1-9.

WANG., et al., "GBA mutations and Parkinson's disease," Acta Physiologica Sinica, 70(3):294-300, Jun. 25, 2018. Abstract.

Alcalay, R. N. et al., "SCARB2 variants and glucocerebrosidase activity in Parkinson's disease," NPJ Parkinsons Dis., 2:16004 (2016). doi: 10.1038/npjparkd.2016.4. Epub Mar. 10, 2016; 4 pages.

Fumoto et al, "Targeted Gene Delivery: Importance of Administration Routes," Chapter 1, Intech, 2013, 3-31.

GenBank Accession No. AAP36904.1 "*Homo sapiens* glucosidase, beta; acid (includes glucosylceramidase), partial [synthetic construct]" Jul. 25, 2016 [online].

GenBank Accession No. BT008212.1 "Synthetic construct Homo sapiens glucosidase, beta; acid (includes glucosylceramidase) mRNA, partial cds" Jul. 25, 2016 [online].

GenBank Accession No. NP_000148.2 "lysosomal acid glucosylceramidase isoform 1 precursor [*Homo sapiens*]" Jan. 8, 2020 [online].

GenBank Accession No. NP_005497.1 "lysosome membrane protein 2 isoform 1 precursor [*Homo sapiens*]" Jan. 1, 2020 [online].

GenBank Accession No. NP_002769.1 "prosaposin isoform a preproprotein [*Homo sapiens*]" Sep. 27, 2019 [online].

GenBank Accession No. NP_001191184.1 "lysosome membrane protein 2 isoform 2 precursor [*Homo sapiens*]" Jan. 4, 2020 [online].

GenBank Accession No. AAH01503.1 "Prosaposin [*Homo sapiens*]" Aug. 4, 2008 [online].

GenBank Accession No. AAH07612.1 "Prosaposin [*Homo sapiens*]" Aug. 4, 2008 [online].

GenBank Accession No. AAH04275.1 "Prosaposin [*Homo sapiens*]" Aug. 4, 2008 [online].

GenBank Accession No. AAA60303.1 "Prosaposin [*Homo sapiens*]" Jan. 9, 1995 [online].

GenBank Accession No. NP_001005742.1 "lysosomal acid glucosylceramidase isoform 1 precursor [*Homo sapiens*]" Nov. 11, 2019 [online].

GenBank Accession No. NP_001165282.1 "lysosomal acid glucosylceramidase isoform 2 [*Homo sapiens*]" Nov. 11, 2019 [online].

GenBank Accession No. NP_001165283.1 "lysosomal acid glucosylceramidase isoform 3 [*Homo sapiens*]" Nov. 11, 2019 [online].

GenBank Accession No. NP_065995.1 "non-lysosomal glucosylceramidase isoform 1 [*Homo sapiens*]" Aug. 22, 2019 [online].

GenBank Accession No. NP_000144.2 "galactocerebrosidase isoform a precursor [*Homo sapiens*]" Sep. 26, 2019 [online].

GenBank Accession No. NP_001899.1 "cathepsin B isoform 1 preproprotein [*Homo sapiens*]" Jan. 27, 2020 [online].

GenBank Accession No. NP_000534.3 "sphingomyelin phosphodiesterase isoform 1 precursor [*Homo sapiens*]" Jan. 13, 2020 [online].

GenBank Accession No. NP_003920.1 "ras-related protein Rab-7L1 isoform 1 [*Homo sapiens*]" Dec. 31, 2019 [online].

GenBank Accession No. NP_060676.2 "vacuolar protein sorting-associated protein 35 [*Homo sapiens*]" Oct. 11, 2019 [online].

GenBank Accession No. NP_689669.2 "interleukin-34 isoform 1 precursor [*Homo sapiens*]" Dec. 25, 2019 [online].

GenBank Accession No. NP_061838.1 "triggering receptor expressed on myeloid cells 2 precursor isoform 1 precursor [*Homo sapiens*]" Feb. 2, 2020 [online].

GenBank Accession No. NP_060844.2 "transmembrane protein 106B [*Homo sapiens*]" Jul. 28, 2019 [online].

GenBank Accession No. NP_002078.1 "progranulin precursor [*Homo sapiens*]" Jan. 21, 2020 [online].

GenBank Accession No. NP_001317589.1 "non-lysosomal glucosylceramidase isoform 2 [*Homo sapiens*]" Aug. 7, 2019 [online].

GenBank Accession No. EAW81359.1 "galactosylceramidase, isoform CRA_a [*Homo sapiens*]" Mar. 23, 2015 [online].

GenBank Accession No. EAW81360.1 "galactosylceramidase, isoform CRA_b [*Homo sapiens*]" Mar. 23, 2015 [online].

(56)                     References Cited

OTHER PUBLICATIONS

GenBank Accession No. EAW81362.1 "galactosylceramidase, isoform CRA_c [*Homo sapiens*]" Mar. 23, 2015 [online].
GenBank Accession No. EAW68726.1 "sphingomyelin phosphodiesterase 1, acid lysosomal (acid sphingomyelinase), isoform CRA_a [*Homo sapiens*]" Mar. 23, 2015 [online].
GenBank Accession No. EAW68727.1 "sphingomyelin phosphodiesterase 1, acid lysosomal (acid sphingomyelinase), isoform CRA_b [*Homo sapiens*]" Mar. 23, 2015 [online].
GenBank Accession No. EAW68728.1 "sphingomyelin phosphodiesterase 1, acid lysosomal (acid sphingomyelinase), isoform CRA_c [*Homo sapiens*]" Mar. 23, 2015 [online].
GenBank Accession No. EAW68729.1 "sphingomyelin phosphodiesterase 1, acid lysosomal (acid sphingomyelinase), isoform CRA_d [*Homo sapiens*]" Mar. 23, 2015 [online].
GenBank Accession No. AAC37547.1 "cathepsin B [*Homo sapiens*]" Apr. 7, 1994 [online].
GenBank Accession No. AAH95408.1 "Cathepsin B [*Homo sapiens*]" Jul. 17, 2006 [online].
GenBank Accession No. AAH10240.1 "Cathepsin B [*Homo sapiens*]" Jul. 15, 2006 [online].
GenBank Accession No. AAH02585.1 "RAB7, member RAS oncogene family-like 1 [*Homo sapiens*]" Jul. 15, 2006 [online].
GenBank Accession No. AAH25415.1 "GTP cyclohydrolase 1 [*Homo sapiens*]" Aug. 7, 2008 [online].
GenBank Accession No. AAH29804.1 "Interleukin 34 [*Homo sapiens*]" Jun. 9, 2008 [online].
GenBank Accession No. AAF69824.1 "triggering receptor expressed on myeloid cells 2 [*Homo sapiens*]" May 23, 2000 [online].
GenBank Accession No. NP_002087.1 "general transcription factor IIF, polypeptide 1, 74kDa [*Homo sapiens*]" Jun. 3, 2007 [online].
GenBank Accession No. NP_000152.1 "GTP cyclohydrolase 1 isoform 1 [*Homo sapiens*]" Dec. 30, 2019 [online].

Hurdy, "Therapeutic AAV Gene Transfer to the Nervous System: A Clinical Reality," Neuron, Mar. 6, 2019, 101, 839-862.
Lazio et al., "Cell-based therapies for disorders of the CNS," Expert Opin. Ther. Patents, 2005, 15(10), 1361-1376.
Ling et al., "The Adeno-Associated Virus Genome Packaging Puzzle," J Mol Genet Med, 2015, pp. 1-10.
Manno et al., "Successful transduction of liver in hemophilia by AAV-Factor IX and limitations imposed by the host immune response," Nature Medicine, 2006, 342-349 and 592.
Molnar et al., "Gene therapy in neurology: review of ongoing clinical trials," Clin. Invest., 2012, 2(6), 639-652.
Naso, et al., "Adeno-Associated Virus (AAV) as a Vector for Gene Therapy," BioDrugs, 2017, 31, 317-334.
Niederkoffer et al., Characterization of relevant mouse models for new biomarkers, Poster No. 141, 2019, QPS.
Salmon et al., "Safety profile of recombinant adeno-associated viral vectors: focus on alipogene tiparvovec (Glybera)," Expert Rev. V Clin. Pharmacol., 2014, 7(1), 53-65.
Shanks et al. "Are animal models predictive for humans?" Philosophy, Ethics, and Humanities in Medicine, 2009, 1-20.
Sinclair, et al., "Synonymous codon usage bias and the expression of human glucocerebrosidase in the methylotrophic yeast, *Pichia pastrois*," Protein Expression and Purification, 2002, 26, 96-105.
Supplemental European Search Report issued in EP Application No. 18865080.8, dated Jan. 10, 2022, 1-19.
Supplementary Partial European Search Report issued in EP application No. 18865080.8, dated Aug. 16, 2021, 1-18.
Wang, et al., "Adeno-Associated Virus Type 2 DNA Replication in Vivo: Mutation Analyses of the D Sequence in Viral Inverted Terminal Repeats," Journal of Virology, Apr. 1997, 71(4), 3077-3082.
Wong et al., "Lysosomal Trafficking Defects Link Parkinson's Disease with Gaucher's Disease," Movement Disorders, 2013, pp. 1610-1618.

* cited by examiner

PrevailVector_FP1_JetLong_GBA1_bGH_JetLong_SCARB2_SV40L_4464nt
11,420 bp

Beam Walk - Speed

Beam Walk - Slips Per Speed

PSAP_qRT-PCR

PSAP_ELISA

SEQUENCE LISTING

```
<160> NUMBER OF SEQ ID NOS: 31

<210> SEQ ID NO 1
<211> LENGTH: 10697
<212> TYPE: DNA
<213> ORGANISM: Artificial Sequence
<220> FEATURE:
<223> OTHER INFORMATION: Synthetic polynucleotide

<400> SEQUENCE: 1
ttggccactc cctctctgcg cgctcgctcg ctcactgagg ccgggcgacc aaaggtcgcc      60
cgacgcccgg gctttgcccg ggcggcctca gtgagcgagc gagcgcgcag agagggagtg     120
gccaactcca tcactagggg ttcctgctag ctctgggtat ttaagcccga gtgagcacgc     180
agggtctcca ttttgaagcg ggaggttacg cgttcgtcga ctactagtgg gtaccagagc     240
tccctaggtt ctagaaccgg tgacgtctcc catggtgaag cttggatctg aattcggtac     300
cctagttatt aatagtaatc aattacgggg tcattagttc atagcccata tatggagttc     360
cgcgttacat aacttacggt aaatggcccg cctggctgac cgcccaacga cccccgccca     420
ttgacgtcaa taatgacgta tgttcccata gtaacgccaa tagggacttt ccattgacgt     480
caatgggtgg actatttacg gtaaactgcc cacttggcag tacatcaagt gtatcatatg     540
ccaagtacgc cccctattga cgtcaatgac ggtaaatggc ccgcctggca ttatgcccag     600
tacatgacct tatgggactt tcctacttgg cagtacatct acgtattagt catcgctatt     660
accatggtcg aggtgagccc cacgttctgc ttcactctcc ccatctcccc ccctccccca     720
cccccaattt tgtatttatt tattttttaa ttattttgtg cagcgatggg ggcggggggg     780
gggggggggc gcgcgccagg cggggcgggg cggggcgagg ggcggggcgg ggcgaggcgg     840
agaggtgcgg cggcagccaa tcagagcggc gcgctccgaa agtttccttt tatggcgagg     900
cggcggcggc ggcggcccta taaaaagcga agcgcgcggc gggcgggagt cgctgcgacg     960
ctgccttcgc cccgtgcccc gctccgcgc cgcctcgcgc cgcccgcccc ggctctgact    1020
gaccgcgtta ctcccacagg tgagcgggcg ggacggccct tctcctccgg gctgtaatta    1080
gcgcttggtt taatgacggc ttgtttctg tggctgcgtg aaagccttga ggggctccgg    1140
gagctagagc ctctgctaac catgttcatg ccttcttctt tttcctacag ctcctgggca    1200
acgtgctggt tattgtgctg tctcatcatt ttggcaaaga attcctcgaa gatccgaagg    1260
gaaagtcttc cacgactgtg ggatccgttc gaagatatca ccggttgagc caccatggaa    1320
ttcagcagcc ccagcagaga ggaatgcccc aagcctctga gccgggtgtc aatcatggcc    1380
ggatctctga caggactgct gctgcttcag gccgtgtctt gggcttctgg cgctagacct    1440
tgcatcccca agagcttcgg ctacagcagc gtcgtgtgcg tgtgcaatgc cacctactgc    1500
gacagcttcg accctcctac ctttcctgct ctgggcacct tcagcagata cgagagcacc    1560
agatccggca gacggatgga actgagcatg ggaccatcc aggccaatca cacaggcact    1620
ggcctgctgc tgacactgca gcctgagcag aaattccaga aagtgaaagg cttcggcgga    1680
gccatgacag atgccgccgc tctgaatatc ctggctctgt ctccaccagc tcagaacctg    1740
ctgctcaaga gctacttcag cgaggaaggc atcggctaca acatcatcag agtgcccatg    1800
gccagctgcg acttcagcat caggacctac acctacgccg acacacccga cgatttccag    1860
```

-continued

```
ctgcacaact tcagcctgcc tgaagaggac accaagctga agatccctct gatccacaga    1920
gccctgcagc tggcacaaag acccgtgtca ctgctggcct ctccatggac atctcccacc    1980
tggctgaaaa caaatggcgc cgtgaatggc aagggcagcc tgaaaggcca acctggcgac    2040
atctaccacc agacctgggc cagatacttc gtgaagttcc tggacgccta tgccgagcac    2100
aagctgcagt tttgggccgt gacagccgag aacgaacctt ctgctggact gctgagcggc    2160
tacccctttc agtgcctggg ctttacaccc gagcaccagc gggactttat cgcccgtgat    2220
ctgggaccca cactggccaa tagcacccac cataatgtgc ggctgctgat gctggacgac    2280
cagagactgc ttctgcccca ctgggctaaa gtggtgctga cagatcctga ggccgccaaa    2340
tacgtgcacg gaatcgccgt gcactggtat ctggactttc tggcccctgc caaggccaca    2400
ctgggagaga cacacagact gttccccaac accatgctgt tcgccagcga agcctgtgtg    2460
ggcagcaagt tttgggaaca gagcgtgcgg ctcggcagct gggatagagg catgcagtac    2520
agccacagca tcatcaccaa cctgctgtac cacgtcgtcg gctggaccga ctggaatctg    2580
gccctgaatc ctgaaggcgg ccctaactgg gtccgaaact cgtggacag ccccatcatc     2640 gtggacatca ccaaggacac cttctacaag cagcccatgt tctaccacct gggacacttc    2700
agcaagttca tccccgaggg ctctcagcgc gttggactgg tggcttccca gaagaacgat    2760
ctggacgccg tggctctgat gcaccctgat ggatctgctg tggtggtggt cctgaaccgc    2820
agcagcaaag atgtgcccct gaccatcaag gatcccgccg tgggattcct ggaaacaatc    2880
agccctggct actccatcca cacctacctg tggcgtagac agtgacaatt gttaattaag    2940
tttaaaccct cgaggccgca agcttatcga taatcaacct ctggattaca aaatttgtga    3000
aagattgact ggtattctta actatgttgc tccttttacg ctatgtggat acgctgcttt    3060
aatgcctttg tatcatgcta ttgcttcccg tatggctttc attttctcct ccttgtataa    3120
atcctggttg ctgtctcttt atgaggagtt gtggcccgtt gtcaggcaac gtggcgtggt    3180
gtgcactgtg tttgctgacg caaccccca ctggttgggg cattgccacca cctgtcagct     3240 cctttccggg actttcgctt tccccctccc tattgccacg gcggaactca tcgccgcctg    3300
ccttgcccgc tgctgacag gggctcggct gttgggcact gacaattccg tggtgttgtc     3360
ggggaaatca tcgtcctttc cttggctgct cgcctgtgtt gccacctgga ttctgcgcgg    3420
gacgtccttc tgctacgtcc cttcggccct caatccagcg gaccttcctt cccgcggcct    3480
gctgccggct ctgcggcctc ttccgcgtct tcgccttcgc cctcagacga gtcggatctc    3540
cctttgggcc gcctccccgc atcgatacc g tcgactagag ctcgctgatc agcctcgact    3600
gtgccttcta gttgccagcc atctgttgtt tgcccctccc ccgtgccttc cttgaccctg    3660
gaaggtgcca ctcccactgt cctttcctaa taaaatgagg aaattgcatc gcattgtctg    3720
agtaggtgtc attctattct ggggggtggg gtggggcagg acagcaaggg ggaggattgg    3780
gaagacaata gcaggcatgc tggggagaga tccacgataa caaacagctt ttttggggtg    3840
aacatattga ctgaattccc tgcaggttgg ccactcctc tctgcgcgct cgctcgctca     3900
ctgaggccgc ccgggcaaag cccgggcgtc gggcgacctt tggtcgcccg gcctcagtga    3960
gcgagcgagc gcgcagagag ggagtggcca actccatcac tagggttcc tgcggccgct     4020 cgtacggtct cgaggaattc ctgcaggata acttgccaac ctcattctaa aatgtatata    4080
gaagcccaaa agacaataac aaaaatattc ttgtagaaca aaatgggaaa gaatgttcca    4140
ctaaatatca agatttagag caaagcatga gatgtgtggg gatagacagt gaggctgata    4200
aaatagagta gagctcagaa acagacccat tgatatatgt aagtgaccta tgaaaaaaat    4260
```

-continued

```
atggcatttt acaatgggaa aatgatggtc tttttctttt ttagaaaaac agggaaatat    4320
atttatatgt aaaaaataaa agggaaccca tatgtcatac catacacaca aaaaaattcc    4380
agtgaattat aagtctaaat ggagaaggca aaactttaaa tcttttagaa aataatatag    4440
aagcatgcag accagcctgg ccaacatgat gaaaccctct ctactaataa taaaatcagt    4500
agaactactc aggactactt tgagtgggaa gtccttttct atgaagactt ctttggccaa    4560
aattaggctc taaatgcaag gagatagtgc atcatgcctg gctgcactta ctgataaatg    4620
atgttatcac catctttaac caaatgcaca ggaacaagtt atggtactga tgtgctggat    4680
tgagaaggag ctctacttcc ttgacaggac acatttgtat caacttaaaa aagcagattt    4740
ttgccagcag aactattcat tcagaggtag gaaacttaga atagatgatg tcactgatta    4800
gcatggcttc cccatctcca cagctgcttc ccacccaggt tgcccacagt tgagtttgtc    4860
cagtgctcag ggctgcccac tctcagtaag aagccccaca ccagcccctc tccaaatatg    4920
ttggctgttc cttccattaa agtgacccca ctttagagca gcaagtggat ttctgtttct    4980
tacagttcag gaaggaggag tcagctgtga gaacctggag cctgagatgc ttctaagtcc    5040
cactgctact ggggtcaggg aagccagact ccagcatcag cagtcaggag cactaagccc    5100
ttgccaacat cctgtttctc agagaaactg cttccattat aatggttgtc cttttttaag    5160
ctatcaagcc aaacaaccag tgtctaccat tattctcatc acctgaagcc aagggttcta    5220
gcaaaagtca agctgtcttg taatggttga tgtgcctcca gcttctgtct tcagtcactc    5280
cactcttagc ctgctctgaa tcaactctga ccacagttcc ctggagcccc tgccacctgc    5340 tgccctgcc accttctcca tctgcagtgc tgtgcagcct tctgcactct tgcagagcta    5400
ataggtggag acttgaagga agaggaggaa agtttctcat aatagccttg ctgcaagctc    5460
aaatgggagg tgggcactgt gcccaggagc cttggagcaa aggctgtgcc caacctctga    5520
ctgcatccag gtttggtctt gacagagata agaagccctg gcttttggag ccaaaatcta    5580
ggtcagactt aggcaggatt ctcaaagttt atcagcagaa catgaggcag aagacccttt    5640
ctgctccagc ttcttcaggc tcaaccttca tcagaataga tagaaagaga ggctgtgagg    5700
gttcttaaaa cagaagcaaa tctgactcag agaataaaca acctcctagt aaactacagc    5760
ttagacagag catctggtgg tgagtgtgct cagtgtccta ctcaactgtc tggtatcagc    5820
cctcatgagg acttctcttc tttccctcat agacctccat ctctgttttc cttagcctgc    5880
agaaatctgg atggctattc acagaatgcc tgtgctttca gagttgcatt ttttctctgg    5940
tattctggtt caagcatttg aaggtaggaa aggttctcca agtgcaagaa agccagccct    6000
gagcctcaac tgcctggcta gtgtggtcag taggatgcaa aggctgttga atgccacaag    6060
gccaaacttt aacctgtgta ccacaagcct agcagcagag gcagctctgc tcactggaac    6120
tctctgtctt cttttctcctg agcctttct tttcctgagt tttctagctc tcctcaacct    6180
tacctctgcc ctacccagga caaacccaag agccactgtt tctgtgatgt cctctccagc    6240
cctaattagg catcatgact tcagcctgac cttccatgct cagaagcagt gctaatccac    6300
ttcagatgag ctgctctatg caacacaggc agagcctaca aacctttgca ccagagccct    6360
ccacatatca gtgtttgttc atactcactt caacagcaaa tgtgactgct gagattaaga    6420
ttttacacaa gatggtctgt aatttcacag ttagtttat cccattaggt atgaaagaat    6480
tagcataatt ccccttaaac atgaatgaat cttagatttt ttaataaata gttttggaag    6540
taaagacaga gacatcagga gcacaaggaa tagcctgaga ggacaaacag aacaagaaag    6600
```

```
agtctggaaa tacacaggat gttcttggcc tcctcaaagc aagtgcaagc agatagtacc       6660
agcagcccca ggctatcaga gcccagtgaa gagaagtacc atgaaagcca cagctctaac       6720
caccctgttc cagagtgaca gacagtcccc aagacaagcc agcctgagcc agagagagaa       6780
ctgcaagaga aagtttctaa tttaggttct gttagattca gacaagtgca ggtcatcctc       6840
tctccacagc tactcacctc tccagcctaa caaagcctgc agtccacact ccaaccctgg       6900
tgtctcacct cctagcctct cccaacatcc tgctctctga ccatcttctg catctctcat       6960
ctcaccatct cccactgtct acagcctact cttgcaacta ccatctcatt ttctgacatc       7020
ctgtctacat cttctgccat actctgccat ctaccatacc acctcttacc atctaccaca       7080
ccatctttta tctccatccc tctcagaagc ctccaagctg aatcctgctt tatgtgttca       7140
tctcagcccc tgcatggaaa gctgacccca gaggcagaac tattcccaga gagcttggcc       7200
aagaaaaaca aaactaccag cctggccagg ctcaggagta gtaagctgca gtgtctgttg       7260
tgttctagct tcaacagctg caggagttcc actctcaaat gctccacatt tctcacatcc       7320
tcctgattct ggtcactacc catcttcaaa gaacagaata tctcacatca gcatactgtg       7380
aaggactagt catgggtgca gctgctcaga gctgcaaagt cattctggat ggtggagagc       7440
ttacaaacat ttcatgatgc tcccccgct ctgatggctg gagcccaatc cctacacaga       7500
ctcctgctgt atgtgttttc ctttcactct gagccacagc cagagggcag gcattcagtc       7560
tcctcttcag gctggggctg gggcactgag aactcaccca acaccttgct ctcactcctt       7620
ctgcaaaaca agaaagagct ttgtgctgca gtagccatga agaatgaaag gaaggctta       7680 actaaaaat gtcagagatt attttcaacc ccttactgtg gatcaccagc aaggaggaaa       7740
cacaacacag agacattttt tcccctcaaa ttatcaaaag aatcactgca tttgttaaag       7800
agagcaactg aatcaggaag cagagttttg aacatatcag aagttaggaa tctgcatcag       7860
agacaaatgc agtcatggtt gtttgctgca taccagccct aatcattaga gcctcatgg       7920 acttcaaaca tcattccctc tgacaagatg ctctagccta actccatgag ataaaataaa       7980
tctgcctttc agagccaaag aagagtccac cagcttcttc tcagtgtgaa caagagctcc       8040
agtcaggtta gtcagtccag tgcagtagag gagaccagtc tgcatcctct aattttcaaa       8100
ggcaagaaga tttgtttacc ctggacacca ggcacaagtg aggtcacaga gctcttagat       8160
atgcagtcct catgagtgag gagactaaag cgcatgccat caagacttca gtgtagagaa       8220
aacctccaaa aaagcctcct cactacttct ggaatagctc agaggccgag gcggcctcgg       8280
cctctgcata aataaaaaa attagtcagc catgggcgg agaatgggcg gaactgggcg       8340
gagttagggg cgggatgggc ggagttaggg gcgggactat ggttgctgac taattgagat       8400
gcatgctttg catacttctg cctgctgggg agcctgggga cttttccac ctggttgctg       8460 actaattgag atgcatgctt tgcatacttc tgcctgctgg ggagcctggg gactttccac       8520
accctaactg acacacattc cacagctgca ttaatgaatc ggccaacgcg cggggagagg       8580
cggtttgcgt attgggcgct cttccgcttc ctcgctcact gactcgctgc gctcggtcgt       8640
tcggctgcgg cgagcggtat cagctcactc aaaggcggta atacggttat ccacagaatc       8700
aggggataac gcaggaaaga acatgtgagc aaaaggccag caaaaggcca ggaaccgtaa       8760
aaaggccgcg ttgctggcgt ttttccatag gctccgcccc cctgacgagc atcacaaaaa       8820
tcgacgctca agtcagaggt ggcgaaaccc gacaggacta taaagatacc aggcgtttcc       8880
ccctggaagc tccctcgtgc gctctcctgt tccgaccctg ccgcttaccg gatacctgtc       8940
cgcctttctc ccttcgggaa gcgtggcgct ttctcatagc tcacgctgta ggtatctcag       9000
```

```
ttcggtgtag gtcgttcgct ccaagctggg ctgtgtgcac gaaccccccg ttcagcccga    9060
ccgctgcgcc ttatccggta actatcgtct tgagtccaac ccggtaagac acgacttatc    9120
gccactggca gcagccactg gtaacaggat tagcagagcg aggtatgtag gcggtgctac    9180
agagttcttg aagtggtggc ctaactacgg ctacactaga agaacagtat ttggtatctg    9240
cgctctgctg aagccagtta ccttcggaaa aagagttggt agctcttgat ccggcaaaca    9300
aaccaccgct ggtagcggtg gttttttttgt ttgcaagcag cagattacgc gcagaaaaaa    9360
aggatctcaa gaagatcctt tgatcttttc tacggggtct gacgctcagt ggaacgaaaa    9420
ctcacgttaa gggattttgg tcatgagatt atcaaaaagg atcttcacct agatcctttt    9480
aaattaaaaa tgaagtttta aatcaatcta agtatatat gagtaaactt ggtctgacag    9540
ttaccaatgc ttaatcagtg aggcacctat ctcagcgatc tgtctatttc gttcatccat    9600
agttgcctga ctcctgcaaa ccacgttgtg tctcaaaatc tctgatgtta cattgcacaa    9660
gataaaaata tatcatcatg aacaataaaa ctgtctgctt acataaacag taatacaagg    9720
ggtgttatga gccatattca acgggaaacg tcttgctcga ggccgcgatt aaattccaac    9780
atggatgctg atttatatgg gtataaatgg ctcgcgata atgtcgggca atcaggtgcg    9840
acaatctatc gattgtatgg gaagcccgat gcgccagagt tgtttctgaa acatggcaaa    9900
ggtagcgttg ccaatgatgt tacagatgag atggtcagac taaactggct gacggaattt    9960
atgcctcttc cgaccatcaa gcattttatc cgtactcctg atgatgcatg gttactcacc   10020
actgcgatcc ccgggaaaac agcattccag gtattagaag aatatcctga ttcaggtgaa   10080
aatattgttg atgcgctggc agtgttcctg cgccggttgc attcgattcc tgtttgtaat   10140
tgtcctttta acagcgatcg cgtatttcgt ctcgctcagg cgcaatcacg aatgaataac   10200
ggtttggttg atgcgagtga ttttgatgac gagcgtaatg gctggcctgt tgaacaagtc   10260
tggaaagaaa tgcataagct tttgccattc tcaccggatt cagtcgtcac tcatggtgat   10320
ttctcacttg ataaccttat ttttgacgag gggaaattaa taggttgtat tgatgttgga   10380
cgagtcggaa tcgcagaccg ataccaggat cttgccatcc tatggaactg cctcggtgag   10440
ttttctcctt cattacagaa acggcttttt caaaaatatg gtattgataa tcctgatatg   10500
aataaattgc agtttcattt gatgctcgat gagtttttct aagggcggcc tgccaccata   10560
cccacgccga aacaagcgct catgagcccg aagtggcgag cccgatcttc ccatcggtg   10620 atgtcggcga tataggcgcc agcaaccgca cctgtggcgc cggtgatgag ggcgcgccaa   10680
gtcgacgtcc ggcagtc                                                   10697
```

```
<210> SEQ ID NO 2
<211> LENGTH: 11355
<212> TYPE: DNA
<213> ORGANISM: Artificial Sequence
<220> FEATURE:
<223> OTHER INFORMATION: Synthetic polynucleotide

<400> SEQUENCE: 2
ttggccactc cctctctgcg cgctcgctcg ctcactgagg ccgggcgacc aaaggtcgcc     60
cgacgcccgg gctttgcccg ggcggcctca gtgagcgagc gagcgcgcag agagggagtg    120
gccaactcca tcactagggg ttcctgctag ctctgggtat ttaagcccga gtgagcacgc    180
agggtctcca ttttgaagcg ggaggttacg cgttcgtcga ctactagtgg gtaccagagc    240
tccctaggtt ctagaaccgg tgacgtctcc catggtgaag cttggatctg agggcggagt    300
```

-continued

```
tagggcggag ccaatcagcg tgcgccgttc cgaaagttgc cttttatggc tgggcggaga      360
atgggcggtg aacgccgatg attatataag gacgcgccgg gtgtggcaca gctagttccg      420
tcgcagccgg gatttgggtc gcggttcttg tttgtggatc cctgtgatcg tcacttggta      480
agtcactgac tgtctatgcc tgggaaaggg tgggcaggag atggggcagt gcaggaaaag      540
tggcactatg aaccctgcag ccctaggaat gcatctagac aattgtacta accttcttct      600
ctttcctctc ctgacagtcc ggaaagccac catgggccgc tgctgcttct acaccgccgg      660
caccctgagc ctgctgctgc tggtgaccag cgtgaccctg ctggtggccc gcgtgttcca      720
gaaggccgtg gaccagagca tcgagaagaa gatcgtgctg cgcaacggca ccgaggcctt      780
cgacagctgg gagaagcccc ccctgcccgt gtacacccag ttctacttct tcaacgtgac      840
caaccccgag gagatcctgc gcggcgagac ccccgcgtg gaggaggtgg cccctacac       900 ctaccgcgag ctgcgcaaca aggccaacat ccagttcggc gacaacggca ccaccatcag      960
cgccgtgagc aacaaggcct acgtgttcga gcgcgaccag agcgtgggcg accccaagat     1020
cgacctgatc cgcaccctga acatccccgt gctgaccgtg atcgagtgga gccaggtgca     1080
cttcctgcgc gagatcatcg aggccatgct gaaggcctac cagcagaagc tgttcgtgac     1140
ccacaccgtg gacgagctgc tgtggggcta caaggacgag atcctgagcc tgatccacgt     1200
gttccgcccc gacatcagcc cctacttcgg cctgttctac gagaagaacg caccaacga     1260 cggcgactac gtgttcctga ccggcgagga cagctacctg aacttcacca agatcgtgga     1320
gtggaacggc aagaccagcc tggactggtg gatcaccgac aagtgcaaca tgatcaacgg     1380
caccgacggc gacagcttcc accccctgat caccaaggac gaggtgctgt acgtgttccc     1440
cagcgacttc tgccgcagcg tgtacatcac cttcagcgac tacgagagcg tgcagggcct     1500
gcccgccttc cgctacaagg tgcccgccga gatcctggcc aacaccagcg acaacgccgg     1560
cttctgcatc cccgagggca actgcctggg cagcggcgtg ctgaacgtga gcatctgcaa     1620
gaacggcgcc cccatcatca tgagcttccc ccacttctac caggccgacg agcgcttcgt     1680
gagcgccatc gagggcatgc accccaacca ggaggaccac gagaccttcg tggacatcaa     1740
ccccctgacc ggcatcatcc tgaaggccgc caagcgcttc cagatcaaca tctacgtgaa     1800
gaagctggac gacttcgtgg agaccggcga catccgcacc atggtgttcc ccgtgatgta     1860
cctgaacgag agcgtgcaca tcgacaagga gaccgccagc cgcctgaaga gcatgatcaa     1920
caccaccctg atcatcacca acatcccta catcatcatg gccctgggcg tgttcttcgg     1980
cctggtgttc acctggctgg cctgcaaggg ccagggcagc atggacgagg gcaccgccga     2040
cgagcgcgcc ccctgatcc gcacctgatt gtggccgaac cgccgaactc agaggccggc     2100
cccagaaaac ccgagcgagt aggggcggc gcgcaggagg gaggagaact gggggcgcgg     2160
gaggctggtg ggtgtggggg gtggagatgt agaagatgtg acgccgcggc ccggcgggtg     2220
ccagattagc ggacgcggtg cccgcggttg caacgggatc ccgggcgctg cagcttggga     2280
ggcggctctc cccaggcggc gtccgcgag acacccatcc gtgaacccca ggtcccgggc     2340
cgccggctcg ccgcgcacca gggggccggc gacagaagag cggccgagcg gctcgaggct     2400
gggggaccgc gggcgcggcc gcgcgctgcc gggcgggagg ctggggggcc ggggccgggg     2460
ccgtgccccg gagcgggtcg gaggccgggg ccggggccgg gggacggcgg ctccccgcgc     2520
ggctccagcg gctcgggat cccggccggg ccccgcaggg accatgatgg aattcagcag     2580
ccccagcaga gaggaatgcc ccaagcctct gagccgggtg tcaatcatgg ccggatctct     2640
gacaggactg ctgctgcttc aggccgtgtc ttgggcttct ggcgctagac cttgcatccc     2700
```

-continued

```
caagagcttc ggctacagca gcgtcgtgtg cgtgtgcaat gccacctact gcgacagctt    2760
cgaccctcct acctttcctg ctctgggcac cttcagcaga tacgagagca ccagatccgg    2820
cagacggatg gaactgagca tgggacccat ccaggccaat cacacaggca ctggcctgct    2880
gctgacactg cagcctgagc agaaattcca gaaagtgaaa ggcttcggcg gagccatgac    2940
agatgccgcc gctctgaata tcctggctct gtctccacca gctcagaacc tgctgctcaa    3000
gagctacttc agcgaggaag gcatcggcta caacatcatc agagtgccca tggccagctg    3060
cgacttcagc atcaggacct acacctacgc cgacacaccc gacgatttcc agctgcacaa    3120
cttcagcctg cctgaagagg acaccaagct gaagatccct ctgatccaca gagccctgca    3180
gctggcacaa agacccgtgt cactgctggc ctctccatgg acatctccca cctggctgaa    3240
aacaaatggc gccgtgaatg gcaagggcag cctgaaaggc caacctggcg acatctacca    3300
ccagacctgg gccagatact tcgtgaagtt cctggacgcc tatgccgagc acaagctgca    3360
gttttgggcc gtgacagccg agaacgaacc ttctgctgga ctgctgagcg gctacccctt    3420
tcagtgcctg ggctttacac ccgagcacca gcgggacttt atcgcccgtg atctgggacc    3480
cacactggcc aatagcaccc accataatgt gcggctgctg atgctggacg accagagact    3540
gcttctgccc cactgggcta aagtggtgct gacagatcct gaggccgcca aatacgtgca    3600
cggaatcgcc gtgcactggt atctggactt tctggcccct gccaaggcca cactgggaga    3660
gacacacaga ctgttcccca acaccatgct gttcgccagc gaagcctgtg tgggcagcaa    3720
gttttgggaa cagagcgtgc ggctcggcag ctgggataga ggcatgcagt acagccacag    3780
catcatcacc aacctgctgt accacgtcgt cggctggacc gactggaatc tggccctgaa    3840
tcctgaaggc ggccctaact gggtccgaaa cttcgtggac agccccatca tcgtggacat    3900
caccaaggac accttctaca agcagcccat gttctaccac ctgggacact tcagcaagtt    3960
catccccgag ggctctcagc gcgttggact ggtggcttcc cagaagaacg atctggacgc    4020
cgtggctctg atgcaccctg atggatctgc tgtggtggtg gtcctgaacc gcagcagcaa    4080
agatgtgccc ctgaccatca aggatcccgc cgtgggattc ctggaaacaa tcagccctgg    4140
ctactccatc cacacctacc tgtggcgtag acagtgacaa ttgttaatta agtttaaacc    4200
ctcgaggccg caagccgcat cgataccgtc gactagagct cgctgatcag cctcgactgt    4260
gccttctagt tgccagccat ctgttgtttg cccctccccc gtgccttcct tgaccctgga    4320
aggtgccact cccactgtcc tttcctaata aaatgaggaa attgcatcgc attgtctgag    4380
taggtgtcat tctattctgg ggggtggggt ggggcaggac agcaaggggg aggattggga    4440
agacaatagc aggcatgctg gggagagatc cacgataaca aacagctttt ttggggtgaa    4500
catattgact gaattccctg caggttggcc actccctctc tgcgcgctcg ctcgctcact    4560
gaggccgccc gggcaaagcc cgggcgtcgg gcgacctttg gtcgcccggc ctcagtgagc    4620
gagcgagcgc gcagagaggg agtggccaac tccatcacta ggggttcctg cggccgctcg    4680
tacggtctcg aggaattcct gcaggataac ttgccaacct cattctaaaa tgtatataga    4740
agcccaaaag acaataacaa aaatattctt gtagaacaaa atgggaaaga atgttccact    4800
aaatatcaag atttagagca aagcatgaga tgtgtgggga tagacagtga ggctgataaa    4860
atagagtaga gctcagaaac agacccattg atatatgtaa gtgacctatg aaaaaaatat    4920
ggcattttac aatgggaaaa tgatggtctt tttctttttt agaaaaacag ggaaatatat    4980
ttatatgtaa aaaataaaag ggaacccata tgtcatacca tacacacaaa aaaattccag    5040
```

-continued

```
tgaattataa gtctaaatgg agaaggcaaa actttaaatc ttttagaaaa taatatagaa      5100
gcatgcagac cagcctggcc aacatgatga aaccctctct actaataata aaatcagtag      5160
aactactcag gactactttg agtgggaagt ccttttctat gaagacttct ttggccaaaa      5220
ttaggctcta aatgcaagga gatagtgcat catgcctggc tgcacttact gataaatgat      5280
gttatcacca tctttaacca aatgcacagg aacaagttat ggtactgatg tgctggattg      5340
agaaggagct ctacttcctt gacaggacac atttgtatca acttaaaaaa gcagattttt      5400
gccagcagaa ctattcattc agaggtagga aacttagaat agatgatgtc actgattagc      5460
atggcttccc catctccaca gctgcttccc acccaggttg cccacagttg agtttgtcca      5520
gtgctcaggg ctgcccactc tcagtaagaa gccccacacc agccctctc caaatatgtt       5580 ggctgttcct tccattaaag tgaccccact ttagagcagc aagtggattt ctgtttctta      5640
cagttcagga aggaggagtc agctgtgaga acctggagcc tgagatgctt ctaagtccca      5700
ctgctactgg ggtcagggaa gccagactcc agcatcagca gtcaggagca ctaagccctt      5760
gccaacatcc tgtttctcag agaaactgct tccattataa tggttgtcct ttttttaagct     5820 atcaagccaa acaaccagtg tctaccatta ttctcatcac ctgaagccaa gggttctagc      5880
aaaagtcaag ctgtcttgta atggttgatg tgcctccagc ttctgtcttc agtcactcca      5940
ctcttagcct gctctgaatc aactctgacc acagttccct ggagcccctg ccacctgctg      6000
cccctgccac cttctccatc tgcagtgctg tgcagccttc tgcactcttg cagagctaat      6060
aggtggagac ttgaaggaag aggaggaaag tttctcataa tagccttgct gcaagctcaa      6120
atgggaggtg ggcactgtgc ccaggagcct tggagcaaag gctgtgccca acctctgact      6180
gcatccaggt ttggtcttga cagagataag aagccctggc ttttggagcc aaaatctagg      6240
tcagacttag gcaggattct caaagtttat cagcagaaca tgaggcagaa gacccttct      6300 gctccagctt cttcaggctc aaccttcatc agaatagata gaaagagagg ctgtgagggt      6360
tcttaaaaca gaagcaaatc tgactcagag aataaacaac ctcctagtaa actacagctt      6420
agacagagca tctggtggtg agtgtgctca gtgtcctact caactgtctg gtatcagccc      6480
tcatgaggac ttctcttctt tccctcatag acctccatct ctgttttcct tagcctgcag      6540
aaatctggat ggctattcac agaatgcctg tgctttcaga gttgcatttt ttctctggta      6600
ttctggttca agcatttgaa ggtaggaaag gttctccaag tgcaagaaag ccagccctga      6660
gcctcaactg cctggctagt gtggtcagta ggatgcaaag gctgttgaat gccacaaggc      6720
caaactttaa cctgtgtacc acaagcctag cagcagaggc agctctgctc actggaactc      6780
tctgtcttct ttctcctgag ccttttcttt tcctgagttt tctagctctc ctcaacctta      6840
cctctgccct acccaggaca aacccaagag ccactgtttc tgtgatgtcc tctccagccc      6900
taattaggca tcatgacttc agcctgacct tccatgctca gaagcagtgc taatccactt      6960
cagatgagct gctctatgca acacaggcag agcctacaaa cctttgcacc agagccctcc      7020
acatatcagt gtttgttcat actcacttca acagcaaatg tgactgctga gattaagatt      7080
ttacacaaga tggtctgtaa tttcacagtt agttttatcc cattaggtat gaaagaatta     7140
gcataattcc ccttaaacat gaatgaatct tagattttttt aataaatagt tttggaagta    7200
aagacagaga catcaggagc acaaggaata gcctgagagg acaaacagaa caagaaagag      7260
tctggaaata cacaggatgt tcttggcctc ctcaaagcaa gtgcaagcag atagtaccag      7320
cagccccagg ctatcagagc ccagtgaaga gaagtaccat gaaagccaca gctctaacca      7380
ccctgttcca gagtgacaga cagtccccaa gacaagccag cctgagccag agagagaact      7440
```

```
gcaagagaaa gtttctaatt taggttctgt tagattcaga caagtgcagg tcatcctctc    7500
tccacagcta ctcacctctc cagcctaaca aagcctgcag tccacactcc aaccctggtg    7560
tctcacctcc tagcctctcc caacatcctg ctctctgacc atcttctgca tctctcatct    7620
caccatctcc cactgtctac agcctactct tgcaactacc atctcatttt ctgacatcct    7680
gtctacatct tctgccatac tctgccatct accataccac ctcttaccat ctaccacacc    7740
atcttttatc tccatccctc tcagaagcct ccaagctgaa tcctgcttta tgtgttcatc    7800
tcagcccctg catggaaagc tgaccccaga ggcagaacta ttcccagaga gcttggccaa    7860
gaaaaacaaa actaccagcc tggccaggct caggagtagt aagctgcagt gtctgttgtg    7920
ttctagcttc aacagctgca ggagttccac tctcaaatgc tccacatttc tcacatcctc    7980
ctgattctgg tcactaccca tcttcaaaga acagaatatc tcacatcagc atactgtgaa    8040
ggactagtca tgggtgcagc tgctcagagc tgcaaagtca ttctggatgg tggagagctt    8100
acaaacattt catgatgctc cccccgctct gatggctgga gcccaatccc tacacagact    8160
cctgctgtat gtgtttccct ttcactctga gccacagcca gagggcaggc attcagtctc    8220
ctcttcaggc tggggctggg gcactgagaa ctcacccaac accttgctct cactccttct    8280
gcaaaacaag aaagagcttt gtgctgcagt agccatgaag aatgaaagga aggctttaac    8340
taaaaaatgt cagagattat tttcaacccc ttactgtgga tcaccagcaa ggaggaaaca    8400
caacacagag acatttttc ccctcaaatt atcaaaagaa tcactgcatt tgttaaagag    8460
agcaactgaa tcaggaagca gagttttgaa catatcagaa gttaggaatc tgcatcagag    8520
acaaatgcag tcatggttgt ttgctgcata ccagccctaa tcattagaag cctcatggac    8580
ttcaaacatc attccctctg acaagatgct ctagcctaac tccatgagat aaaataaatc    8640
tgcctttcag agccaaagaa gagtccacca gcttcttctc agtgtgaaca agagctccag    8700
tcaggttagt cagtccagtg cagtagagga gaccagtctg catcctctaa ttttcaaagg    8760
caagaagatt tgtttaccct ggacaccagg cacaagtgag gtcacagagc tcttagatat    8820
gcagtcctca tgagtgagga gactaaagcg catgccatca agacttcagt gtagagaaaa    8880
cctccaaaaa agcctcctca ctacttctgg aatagctcag aggccgaggc ggcctcggcc    8940
tctgcataaa taaaaaaaat tagtcagcca tggggcggag aatgggcgga actgggcgga    9000
gttaggggcg ggatgggcgg agttaggggc gggactatgg ttgctgacta attgagatgc    9060
atgctttgca tacttctgcc tgctggggag cctggggact ttccacacct ggttgctgac    9120
taattgagat gcatgctttg catacttctg cctgctgggg agcctgggga ctttccacac    9180
cctaactgac acacattcca cagctgcatt aatgaatcgg ccaacgcgcg gggagaggcg    9240
gtttgcgtat tgggcgctct ccgcttcct cgctcactga ctcgctgcgc tcggtcgttc    9300
ggctgcggcg agcggtatca gctcactcaa aggcggtaat acggttatcc acagaatcag    9360
gggataacgc aggaaagaac atgtgagcaa aaggccagca aaaggccagg aaccgtaaaa    9420
aggccgcgtt gctggcgttt ttccataggc tccgcccccc tgacgagcat cacaaaaatc    9480
gacgctcaag tcagaggtgg cgaaacccga caggactata aagataccag gcgtttcccc    9540
ctggaagctc cctcgtgcgc tctcctgttc cgaccctgcc gcttaccgga tacctgtccg    9600
cctttctccc ttcgggaagc gtggcgcttt ctcatagctc acgctgtagg tatctcagtt    9660
cggtgtaggt cgttcgctcc aagctgggct gtgtgcacga accccccgtt cagcccgacc    9720
gctgcgcctt atccggtaac tatcgtcttg agtccaaccc ggtaagacac gacttatcgc    9780
```

-continued

```
cactggcagc agccactggt aacaggatta gcagagcgag gtatgtaggc ggtgctacag    9840
agttcttgaa gtggtggcct aactacggct acactagaag aacagtattt ggtatctgcg    9900
ctctgctgaa gccagttacc ttcggaaaaa gagttggtag ctcttgatcc ggcaaacaaa    9960
ccaccgctgg tagcggtggt tttttgttt gcaagcagca gattacgcgc agaaaaaaag    10020
gatctcaaga agatcctttg atcttttcta cggggtctga cgctcagtgg aacgaaaact    10080
cacgttaagg gattttggtc atgagattat caaaaaggat cttcacctag atccttttaa    10140
attaaaaatg aagttttaaa tcaatctaaa gtatatatga gtaaacttgg tctgacagtt    10200
accaatgctt aatcagtgag gcacctatct cagcgatctg tctatttcgt tcatccatag    10260
ttgcctgact cctgcaaacc acgttgtgtc tcaaaatctc tgatgttaca ttgcacaaga    10320
taaaaatata tcatcatgaa caataaaact gtctgcttac ataaacagta atacaagggg    10380
tgttatgagc catattcaac gggaaacgtc ttgctcgagg ccgcgattaa attccaacat    10440
ggatgctgat ttatatgggt ataaatgggc tcgcgataat gtcgggcaat caggtgcgac    10500
aatctatcga ttgtatggga agcccgatgc gccagagttg tttctgaaac atggcaaagg    10560
tagcgttgcc aatgatgtta cagatgagat ggtcagacta aactggctga cggaatttat    10620
gcctcttccg accatcaagc attttatccg tactcctgat gatgcatggt tactcaccac    10680
tgcgatcccc gggaaaacag cattccaggt attagaagaa tatcctgatt caggtgaaaa    10740
tattgttgat gcgctggcag tgttcctgcg ccggttgcat tcgattcctg tttgtaattg    10800
tccttttaac agcgatcgcg tatttcgtct cgctcaggcg caatcacgaa tgaataacgg    10860
tttggttgat gcgagtgatt ttgatgacga gcgtaatggc tggcctgttg aacaagtctg    10920
gaaagaaatg cataagcttt tgccattctc accggattca gtcgtcactc atggtgattt    10980
ctcacttgat aaccttattt ttgacgaggg gaaattaata ggttgtattg atgttggacg    11040
agtcggaatc gcagaccgat accaggatct tgccatccta tggaactgcc tcggtgagtt    11100
ttctccttca ttacagaaac ggcttttttca aaaatatggt attgataatc ctgatatgaa    11160
taaattgcag tttcatttga tgctcgatga gtttttctaa gggcggcctg ccaccatacc    11220
cacgccgaaa caagcgctca tgagcccgaa gtggcgagcc cgatcttccc catcggtgat    11280
gtcggcgata taggcgccag caaccgcacc tgtggcgccg gtgatgaggg cgcgccaagt    11340
cgacgtccgg cagtc                                                      11355
```

<210> SEQ ID NO 3
<211> LENGTH: 11420
<212> TYPE: DNA
<213> ORGANISM: Artificial Sequence
<220> FEATURE:
<223> OTHER INFORMATION: Synthetic polynucleotide

<400> SEQUENCE: 3

```
ttggccactc cctctctgcg cgctcgctcg ctcactgagg ccgggcgacc aaaggtcgcc      60
cgacgcccgg gctttgcccg ggcggcctca gtgagcgagc gagcgcgcag agagggagtg     120
gccaactcca tcactagggg ttcctgctag ctctgggtat ttaagcccga gtgagcacgc     180
agggtctcca tttttgaagcg ggaggttacg cgttcgtcga ctactagtgg gtaccagagc    240
tccctaggtt ctagaaccgg tgacgtctcc catggtgaag cttggatctg agggcggagt     300
tagggcggag ccaatcagcg tgcgccgttc cgaaagttgc cttttatggc tgggcggaga     360
atgggcggtg aacgccgatg attatataag gacgcgccgg gtgtggcaca gctagttccg     420
tcgcagccgg gatttgggtc gcggttcttg tttgtggatc cctgtgatcg tcacttggta     480
```

-continued

```
agtcactgac tgtctatgcc tgggaaaggg tgggcaggag atggggcagt gcaggaaaag      540
tggcactatg aaccctgcag ccctaggaat gcatctagac aattgtacta accttcttct      600
ctttcctctc ctgacagtcc ggaaagccac catggaattc agcagcccca gcagagagga      660
atgccccaag cctctgagcc gggtgtcaat catggccgga tctctgacag gactgctgct      720
gcttcaggcc gtgtcttggg cttctggcgc tagaccttgc atccccaaga gcttcggcta      780
cagcagcgtc gtgtgcgtgt gcaatgccac ctactgcgac agcttcgacc ctcctacctt      840
tcctgctctg ggcaccttca gcagatacga gagcaccaga tccggcagac ggatggaact      900
gagcatggga cccatccagg ccaatcacac aggcactggc ctgctgctga cactgcagcc      960
tgagcagaaa ttccagaaag tgaaaggctt cggcggagcc atgacagatg ccgccgctct     1020
gaatatcctg gctctgtctc caccagctca gaacctgctg ctcaagagct acttcagcga     1080
ggaaggcatc ggctacaaca tcatcagagt gcccatggcc agctgcgact tcagcatcag     1140
gacctacacc tacgccgaca cacccgacga tttccagctg cacaacttca gcctgcctga     1200
agaggacacc aagctgaaga tccctctgat ccacagagcc ctgcagctgg cacaaagacc     1260
cgtgtcactg ctggcctctc catggacatc tcccacctgg ctgaaaacaa atggcgccgt     1320
gaatggcaag ggcagcctga aaggccaacc tggcgacatc taccaccaga cctgggccag     1380
atacttcgtg aagttcctgg acgcctatgc cgagcacaag ctgcagtttt gggccgtgac     1440
agccgagaac gaaccttctg ctggactgct gagcggctac ccctttcagt gcctgggctt     1500
tacacccgag caccagcggg actttatcgc ccgtgatctg ggacccacac tggccaatag     1560
cacccaccat aatgtgcggc tgctgatgct ggacgaccag agactgcttc tgcccccactg     1620 ggctaaagtg gtgctgacag atcctgaggc cgccaaatac gtgcacggaa tcgccgtgca     1680
ctggtatctg gactttctgg cccctgccaa ggccacactg ggagagacac acagactgtt     1740
ccccaacacc atgctgttcg ccagcgaagc ctgtgtgggc agcaagtttt gggaacagag     1800
cgtgcggctc ggcagctggg atagaggcat gcagtacagc cacagcatca tcaccaacct     1860
gctgtaccac gtcgtcggct ggaccgactg gaatctggcc ctgaatcctg aaggcggccc     1920
taactgggtc cgaaacttcg tggacagccc catcatcgtg gacatcacca aggacacctt     1980
ctacaagcag cccatgttct accacctggg acacttcagc aagttcatcc ccgagggctc     2040
tcagcgcgtt ggactggtgg cttcccagaa gaacgatctg gacgccgtgg ctctgatgca     2100
ccctgatgga tctgctgtgg tggtggtcct gaaccgcagc agcaaagatg tgcccctgac     2160
catcaaggat cccgccgtgg gattcctgga acaatcagc cctggctact ccatccacac     2220
ctacctgtgg cgtagacagt gacaattgtt aattaagttt catcgatacc gtcgactaga     2280
gctcgctgat cagcctcgac tgtgccttct agttgccagc catctgttgt ttgcccctcc     2340
cccgtgcctt ccttgaccct ggaaggtgcc actcccactg tcctttccta ataaaatgag     2400
gaaattgcat cgcattgtct gagtaggtgt cattctattc tggggggtgg ggtgggcag     2460 gacagcaagg gggaggattg ggaagacaat agcaggcatg ctggggagag atccacgata     2520
acaaacagct ttttggggg ggcggagtta gggcggagcc aatcagcgtg cgccgttccg     2580
aaagttgcct tttatggctg ggcggagaat gggcggtgaa cgccgatgat tatataagga     2640
cgcgccgggt gtggcacagc tagttccgtc gcagccggga tttgggtcgc ggttcttgtt     2700
tgtggatccc tgtgatcgtc acttggtaag tcactgactg tctatgcctg ggaaagggtg     2760
ggcaggagat ggggcagtgc aggaaaagtg cactatgaa ccctgcagcc ctaggaatgc     2820
```

-continued

| | | | | |
|---|---|---|---|---|
| atctagacaa | ttgtactaac | cttcttctct | ttcctctcct | gacagtccgg aaagccacca | 2880 |
| tgggccgctg | ctgcttctac | accgccggca | ccctgagcct | gctgctgctg gtgaccagcg | 2940 |
| tgaccctgct | ggtggcccgc | gtgttccaga | aggccgtgga | ccagagcatc gagaagaaga | 3000 |
| tcgtgctgcg | caacggcacc | gaggccttcg | acagctggga | gaagcccccc ctgcccgtgt | 3060 |
| acacccagtt | ctacttcttc | aacgtgacca | accccgagga | gatcctgcgc ggcgagaccc | 3120 |
| cccgcgtgga | ggaggtgggc | ccctacacct | accgcgagct | gcgcaacaag gccaacatcc | 3180 |
| agttcggcga | caacggcacc | accatcagcg | ccgtgagcaa | caaggcctac gtgttcgagc | 3240 |
| gcgaccagag | cgtgggcgac | cccaagatcg | acctgatccg | caccctgaac atccccgtgc | 3300 |
| tgaccgtgat | cgagtggagc | caggtgcact | tcctgcgcga | gatcatcgag gccatgctga | 3360 |
| aggcctacca | gcagaagctg | ttcgtgaccc | acaccgtgga | cgagctgctg tggggctaca | 3420 |
| aggacgagat | cctgagcctg | atccacgtgt | ccgccccga | catcagcccc tacttcggcc | 3480 |
| tgttctacga | gaagaacggc | accaacgacg | gcgactacgt | gttcctgacc ggcgaggaca | 3540 |
| gctacctgaa | cttcaccaag | atcgtggagt | ggaacggcaa | gaccagcctg gactggtgga | 3600 |
| tcaccgacaa | gtgcaacatg | atcaacggca | ccgacggcga | cagcttccac cccctgatca | 3660 |
| ccaaggacga | ggtgctgtac | gtgttcccca | gcgacttctg | ccgcagcgtg tacatcacct | 3720 |
| tcagcgacta | cgagagcgtg | cagggcctgc | ccgccttccg | ctacaaggtg cccgccgaga | 3780 |
| tcctggccaa | caccagcgac | aacgccggct | tctgcatccc | cgagggcaac tgcctgggca | 3840 |
| gcggcgtgct | gaacgtgagc | atctgcaaga | acggcgcccc | catcatcatg agcttccccc | 3900 |
| acttctacca | ggccgacgag | cgcttcgtga | gcgccatcga | gggcatgcac cccaaccagg | 3960 |
| aggaccacga | gaccttcgtg | gacatcaacc | ccctgaccgg | catcatcctg aaggccgcca | 4020 |
| agcgcttcca | gatcaacatc | tacgtgaaga | agctggacgc | cttcgtggag accggcgaca | 4080 |
| tccgcaccat | ggtgttcccc | gtgatgtacc | tgaacgagag | cgtgcacatc gacaaggaga | 4140 |
| ccgccagccg | cctgaagagc | atgatcaaca | ccaccctgat | catcaccaac atcccctaca | 4200 |
| tcatcatggc | cctgggcgtg | ttcttcggcc | tggtgttcac | ctggctggcc tgcaagggcc | 4260 |
| agggcagcat | ggacgagggc | accgccgacg | agcgcgcccc | cctgatccgc acctgaccca | 4320 |
| ggggactcaa | tcagcctcga | agacatgata | agatacattg | atgagtttgg acaaaccaca | 4380 |
| acaagaatgc | agtgaaaaaa | atgctttatt | tgtgaaattt | gtgatgctat tgctttattt | 4440 |
| gtaaccatta | taagctgcaa | taaacaagtt | aacaacaaca | attgcattca ttttatgttt | 4500 |
| caggttcagg | gggagatgtg | ggaggttttt | taaagcaagt | aaaacctcta caaatgtggt | 4560 |
| atgaacatat | tgactgaatt | ccctgcaggt | tggccactcc | ctctctgcgc gctcgctcgc | 4620 |
| tcactgaggc | cgcccgggca | aagcccgggc | gtcgggcgac | ctttggtcgc ccggcctcag | 4680 |
| tgagcgagcg | agcgcgcaga | gagggagtgg | ccaactccat | cactaggggt tcctgcggcc | 4740 |
| gctcgtacgg | tctcgaggaa | ttcctgcagg | ataacttgcc | aacctcattc taaaatgtat | 4800 |
| atagaagccc | aaaagacaat | aacaaaaata | ttcttgtaga | acaaaatggg aaagaatgtt | 4860 |
| ccactaaata | tcaagattta | gagcaaagca | tgagatgtgt | ggggatagac agtgaggctg | 4920 |
| ataaaataga | gtagagctca | gaaacagacc | cattgatata | tgtaagtgac ctatgaaaaa | 4980 |
| aatatggcat | tttacaatgg | gaaatgatg | gtctttttct | tttttagaaa aacagggaaa | 5040 |
| tatatttata | tgtaaaaaat | aaaagggaac | ccatatgtca | taccatacac acaaaaaaat | 5100 |
| tccagtgaat | tataagtcta | aatggagaag | gcaaaacttt | aaatctttta gaaaataata | 5160 |
| tagaagcatg | cagaccagcc | tggccaacat | gatgaaaccc | tctctactaa taataaaatc | 5220 |

```
agtagaacta ctcaggacta cttttgagtgg gaagtccttt tctatgaaga cttctttggc    5280
caaaattagg ctctaaatgc aaggagatag tgcatcatgc ctggctgcac ttactgataa    5340
atgatgttat caccatcttt aaccaaatgc acaggaacaa gttatggtac tgatgtgctg    5400
gattgagaag gagctctact tccttgacag gacacatttg tatcaactta aaaaagcaga    5460
tttttgccag cagaactatt cattcagagg taggaaactt agaatagatg atgtcactga    5520
ttagcatggc ttccccatct ccacagctgc ttcccaccca ggttgcccac agttgagttt    5580
gtccagtgct cagggctgcc cactctcagt aagaagcccc acaccagccc ctctccaaat    5640
atgttggctg ttccttccat taaagtgacc ccactttaga gcagcaagtg gatttctgtt    5700
tcttacagtt caggaaggag gagtcagctg tgagaacctg gagcctgaga tgcttctaag    5760
tcccactgct actggggtca gggaagccag actccagcat cagcagtcag gagcactaag    5820
cccttgccaa catcctgttt ctcagagaaa ctgcttccat tataatggtt gtcctttttt    5880
aagctatcaa gccaaacaac cagtgtctac cattattctc atcacctgaa gccaagggtt    5940
ctagcaaaag tcaagctgtc ttgtaatggt tgatgtgcct ccagcttctg tcttcagtca    6000
ctccactctt agcctgctct gaatcaactc tgaccacagt tccctggagc ccctgccacc    6060
tgctgcccct gccaccttct ccatctgcag tgctgtgcag ccttctgcac tcttgcagag    6120
ctaataggtg gagacttgaa ggaagaggag gaaagtttct cataatagcc ttgctgcaag    6180
ctcaaatggg aggtgggcac tgtgcccagg agccttggag caaaggctgt gcccaacctc    6240
tgactgcatc caggtttggt cttgacagag ataagaagcc ctggcttttg gagccaaaat    6300
ctaggtcaga cttaggcagg attctcaaag tttatcagca gaacatgagg cagaagaccc    6360
tttctgctcc agcttcttca ggctcaacct tcatcagaat agatagaaag agaggctgtg    6420
agggttctta aaacagaagc aaatctgact cagagaataa acaacctcct agtaaactac    6480
agcttagaca gagcatctgg tggtgagtgt gctcagtgtc ctactcaact gtctggtatc    6540
agccctcatg aggacttctc ttctttccct catagacctc catctctgtt ttccttagcc    6600
tgcagaaatc tggatggcta ttcacagaat gcctgtgctt tcagagttgc attttttctc    6660
tggtattctg gttcaagcat ttgaaggtag gaaaggttct ccaagtgcaa gaaagccagc    6720
cctgagcctc aactgcctgg ctagtgtggt cagtaggatg caaaggctgt tgaatgccac    6780
aaggccaaac tttaacctgt gtaccacaag cctagcagca gaggcagctc tgctcactgg    6840
aactctctgt cttctttctc ctgagccttt tcttttcctg agttttctag ctctcctcaa    6900
ccttacctct gccctaccca ggacaaaccc aagagccact gtttctgtga tgtcctctcc    6960
agccctaatt aggcatcatg acttcagcct gaccttccat gctcagaagc agtgctaatc    7020
cacttcagat gagctgctct atgcaacaca ggcagagcct acaaaccttt gcaccagagc    7080
cctccacata tcagtgtttg ttcatactca cttcaacagc aaatgtgact gctgagatta    7140
agattttaca caagatggtc tgtaatttca cagttagttt tatcccatta ggtatgaaag    7200
aattagcata attcccctta aacatgaatg aatcttagat tttttaataa atagtttttgg   7260 aagtaaagac agagacatca ggagcacaag gaatagcctg agaggacaaa cagaacaaga    7320
aagagtctgg aaatacacag gatgttcttg gcctcctcaa agcaagtgca agcagatagt    7380
accagcagcc ccaggctatc agagcccagt gaagagaagt accatgaaag ccacagctct    7440
aaccaccctg ttccagagtg acagacagtc cccaagacaa gccagcctga gccagagaga    7500
gaactgcaag agaaagtttc taatttaggt tctgttagat tcagacaagt gcaggtcatc    7560
```

```
ctctctccac agctactcac ctctccagcc taacaaagcc tgcagtccac actccaaccc    7620
tggtgtctca cctcctagcc tctcccaaca tcctgctctc tgaccatctt ctgcatctct    7680
catctcacca tctcccactg tctacagcct actcttgcaa ctaccatctc attttctgac    7740
atcctgtcta catcttctgc catactctgc catctaccat accacctctt accatctacc    7800
acaccatctt ttatctccat ccctctcaga agcctccaag ctgaatcctg ctttatgtgt    7860
tcatctcagc ccctgcatgg aaagctgacc ccagaggcag aactattccc agagagcttg    7920
gccaagaaaa acaaaactac cagcctggcc aggctcagga gtagtaagct gcagtgtctg    7980
ttgtgttcta gcttcaacag ctgcaggagt tccactctca aatgctccac atttctcaca    8040
tcctcctgat tctggtcact acccatcttc aaagaacaga atatctcaca tcagcatact    8100
gtgaaggact agtcatgggt gcagctgctc agagctgcaa agtcattctg gatggtggag    8160
agcttacaaa catttcatga tgctccccc gctctgatgg ctggagccca atccctacac    8220
agactcctgc tgtatgtgtt ttcctttcac tctgagccac agccagaggg caggcattca    8280
gtctcctctt caggctgggg ctgggcact gagaactcac ccaacacctt gctctcactc    8340
cttctgcaaa acaagaaaga gctttgtgct gcagtagcca tgaagaatga aaggaaggct    8400
ttaactaaaa aatgtcagag attattttca accccttact gtggatcacc agcaaggagg    8460
aaacacaaca cagagacatt ttttcccctc aaattatcaa aagaatcact gcatttgtta    8520
aagagagcaa ctgaatcagg aagcagagtt ttgaacatat cagaagttag gaatctgcat    8580
cagagacaaa tgcagtcatg gttgtttgct gcataccagc cctaatcatt agaagcctca    8640
tggacttcaa acatcattcc ctctgacaag atgctctagc ctaactccat gagataaaat    8700
aaatctgcct ttcagagcca aagaagagtc caccagcttc ttctcagtgt gaacaagagc    8760
tccagtcagg ttagtcagtc cagtgcagta gaggagacca gtctgcatcc tctaattttc    8820
aaaggcaaga agatttgttt accctggaca ccaggcacaa gtgaggtcac agagctctta    8880
gatatgcagt cctcatgagt gaggagacta aagcgcatgc catcaagact tcagtgtaga    8940
gaaaacctcc aaaaaagcct cctcactact tctggaatag ctcagaggcc gaggcggcct    9000
cggcctctgc ataaataaaa aaaattagtc agccatgggg cggagaatgg gcggaactgg    9060
gcggagttag gggcgggatg ggcggagtta ggggcgggac tatggttgct gactaattga    9120
gatgcatgct ttgcatactt ctgcctgctg gggagcctgg ggactttcca cacctggttg    9180
ctgactaatt gagatgcatg ctttgcatac ttctgcctgc tggggagcct ggggactttc    9240 cacacctaa ctgacacaca ttccacagct gcattaatga atcggccaac gcgcggggag    9300
aggcggtttg cgtattgggc gctcttccgc ttcctcgctc actgactcgc tgcgctcggt    9360
cgttcggctg cggcgagcgg tatcagctca ctcaaaggcg gtaatacggt tatccacaga    9420 atcagggat aacgcaggaa agaacatgtg agcaaaaggc cagcaaaagg ccaggaaccg    9480
taaaaaggcc gcgttgctgg cgtttttcca taggctccgc cccctgacg agcatcacaa    9540 aaatcgacgc tcaagtcaga ggtggcgaaa cccgacagga ctataaagat accaggcgtt    9600 tcccctgga agctccctcg tgcgctctcc tgttccgacc ctgccgctta ccggatacct    9660 gtccgcttt ctcccttcgg gaagcgtggc gctttctcat agctcacgct gtaggtatct    9720
cagttcggtg taggtcgttc gctccaagct gggctgtgtg cacgaacccc ccgttcagcc    9780
cgaccgctgc gccttatccg gtaactatcg tcttgagtcc aacccggtaa gacacgactt    9840
atcgccactg gcagcagcca ctggtaacag gattagcaga gcgaggtatg taggcggtgc    9900
tacagagttc ttgaagtggt ggcctaacta cggctacact agaagaacag tatttggtat    9960
```

-continued

```
ctgcgctctg ctgaagccag ttaccttcgg aaaaagagtt ggtagctctt gatccggcaa    10020
acaaaccacc gctggtagcg gtggtttttt tgtttgcaag cagcagatta cgcgcagaaa    10080
aaaaggatct caagaagatc ctttgatctt ttctacgggg tctgacgctc agtggaacga    10140
aaactcacgt taagggattt tggtcatgag attatcaaaa aggatcttca cctagatcct    10200
tttaaattaa aaatgaagtt ttaaatcaat ctaaagtata tatgagtaaa cttggtctga    10260
cagttaccaa tgcttaatca gtgaggcacc tatctcagcg atctgtctat ttcgttcatc    10320
catagttgcc tgactcctgc aaaccacgtt gtgtctcaaa atctctgatg ttacattgca    10380
caagataaaa atatatcatc atgaacaata aaactgtctg cttacataaa cagtaataca    10440
aggggtgtta tgagccatat tcaacgggaa acgtcttgct cgaggccgcg attaaattcc    10500
aacatggatg ctgatttata tgggtataaa tgggctcgcg ataatgtcgg gcaatcaggt    10560
gcgacaatct atcgattgta tgggaagccc gatgcgccag agttgtttct gaaacatggc    10620
aaaggtagcg ttgccaatga tgttacagat gagatggtca gactaaactg gctgacggaa    10680
tttatgcctc ttccgaccat caagcatttt atccgtactc ctgatgatgc atggttactc    10740
accactgcga tccccgggaa aacagcattc caggtattag aagaatatcc tgattcaggt    10800
gaaaatattg ttgatgcgct ggcagtgttc ctgcgccggt tgcattcgat tcctgtttgt    10860
aattgtcctt ttaacagcga tcgcgtattt cgtctcgctc aggcgcaatc acgaatgaat    10920
aacggtttgg ttgatgcgag tgattttgat gacgagcgta atggctggcc tgttgaacaa    10980
gtctggaaag aaatgcataa gcttttgcca ttctcaccgg attcagtcgt cactcatggt    11040
gatttctcac ttgataacct tattttttgac gaggggaaat aataggttg tattgatgtt    11100 ggacgagtcg gaatcgcaga ccgataccag gatcttgcca tcctatggaa ctgcctcggt    11160
gagttttctc cttcattaca gaaacggctt tttcaaaaat atggtattga taatcctgat    11220
atgaataaat tgcagtttca tttgatgctc gatgagtttt tctaagggcg gcctgccacc    11280
atacccacgc cgaaacaagc gctcatgagc ccgaagtggc gagcccgatc ttccccatcg    11340
gtgatgtcgg cgatataggc gccagcaacc gcacctgtgg cgccggtgat gagggcgcgc    11400
caagtcgacg tccggcagtc                                                11420
```

```
<210> SEQ ID NO 4
<211> LENGTH: 11171
<212> TYPE: DNA
<213> ORGANISM: Artificial Sequence
<220> FEATURE:
<223> OTHER INFORMATION: Synthetic polynucleotide

<400> SEQUENCE: 4
ttggccactc cctctctgcg cgctcgctcg ctcactgagg ccgggcgacc aaaggtcgcc       60
cgacgcccgg gctttgcccg ggcggcctca gtgagcgagc gagcgcgcag agagggagtg      120
gccaactcca tcactagggg ttcctgctag ctctgggtat ttaagcccga gtgagcacgc      180
agggtctcca tttttgaagcg ggaggttacg cgttcgtcga ctactagtgg gtaccagagc      240
tccctaggtt ctagaaccgg tgacgtctcc catggtgaag cttggatctg agggcggagt      300
tagggcggag ccaatcagcg tgcgccgttc cgaaagttgc cttttatggc tgggcggaga      360
atgggcggtg aacgccgatg attatataag gacgcgccgg gtgtggcaca gctagttccg      420
tcgcagccgg gatttgggtc gcggttcttg tttgtggatc cctgtgatcg tcacttggta      480
agtcactgac tgtctatgcc tgggaaaggg tgggcaggag atggggcagt gcaggaaaag      540
```

-continued

```
tggcactatg aaccctcctg gtggcgaggg gaggggggtg gtcctcgaac gccttgcaga      600
actggcctgg atacagagtg gaccggctgg ccccatctgg aagacttcga gatacactgt      660
tgtcttactg cgctcaacag tgtatctcga agtcttccaa atggtgccag ccatcgcagc      720
ggggtgcagg aaatgggggc agccccctt tttggctatc cttccacgtg ttcttttttg       780
tatcttttgt gtttcctaga aaacatctca gtcaccaccg cagccctagg aatgcatcta      840
gacaattgta ctaaccttct tctctttcct ctcctgacag tccggaaagc caccatgggc      900
cgctgctgct tctacaccgc cggcaccctg agcctgctgc tgctggtgac cagcgtgacc      960
ctgctggtgg cccgcgtgtt ccagaaggcc gtggaccaga gcatcgagaa gaagatcgtg     1020
ctgcgcaacg gcaccgaggc cttcgacagc tgggagaagc ccccctgcc cgtgtacacc      1080 cagttctact tcttcaacgt gaccaacccc gaggagatcc tgcgcggcga ccccccgc       1140 gtggaggagg tgggccccta cacctaccgc gagctgcgca acaaggccaa catccagttc     1200
ggcgacaacg gcaccaccat cagcgccgtg agcaacaagg cctacgtgtt cgagcgcgac     1260
cagagcgtgg gcgaccccaa gatcgacctg atccgcaccc tgaacatccc cgtgctgacc     1320
gtgatcgagt ggagccaggt gcacttcctg cgcgagatca tcgaggccat gctgaaggcc     1380
taccagcaga agctgttcgt gacccacacc gtggacgagc tgctgtgggg ctacaaggac     1440
gagatcctga gcctgatcca cgtgttccgc cccgacatca gcccctactt cggcctgttc     1500
tacgagaaga acggcaccaa cgacggcgac tacgtgttcc tgaccggcga ggacagctac     1560
ctgaacttca ccaagatcgt ggagtggaac ggcaagacca gcctggactg gtggatcacc     1620
gacaagtgca acatgatcaa cggcaccgac ggcgacagct ccacccccct gatcaccaag     1680
gacgaggtgc tgtacgtgtt ccccagcgac ttctgccgca gcgtgtacat caccttcagc     1740
gactacgaga gcgtgcaggg cctgcccgcc ttccgctaca aggtgcccgc cgagatcctg     1800
gccaacacca gcgacaacgc cggcttctgc atccccgagg gcaactgcct gggcagcggc     1860
gtgctgaacg tgagcatctg caagaacggc gcccccatca tcatgagctt cccccacttc     1920
taccaggccg acgagcgctt cgtgagcgcc atcgagggca tgcaccccaa ccaggaggac     1980
cacgagacct tcgtggacat caaccccctg accggcatca tcctgaaggc cgccaagcgc     2040
ttccagatca acatctacgt gaagaagctg gacgacttcg tggagaccgg cgacatccgc     2100
accatggtgt tccccgtgat gtacctgaac gagagcgtgc acatcgacaa ggagaccgcc     2160
agccgcctga gagcatgat caacaccacc ctgatcatca ccaacatccc ctacatcatc     2220
atggccctgg gcgtgttctt cggcctggtt ttcacctggc tggcctgcaa gggccagggc     2280
agcatggacg agggcaccgc cgacgagcgc gcccccctga tccgcaccga gggcagagga     2340
agtcttctga catgcggaga cgtggaagag aatcccggcc ctatggaatt cagcagcccc     2400
agcagagagg aatgccccaa gcctctgagc cgggtgtcaa tcatggccgg atctctgaca     2460
ggactgctgc tgcttcaggc cgtgtcttgg gcttctggcg ctagaccttg catccccaag     2520
agcttcggct acagcagcgt cgtgtgcgtg tgcaatgcca cctactgcga cagcttcgac     2580
cctcctacct ttcctgctct gggcaccttc agcagatacg agagcaccag atccggcaga     2640
cggatggaac tgagcatggg aacccatcag gccaatcaca caggcactgg cctgctgctg     2700
acactgcagc ctgagcagaa attccagaaa gtgaaaggct cggcggagc catgacagat      2760 gccgccgctc tgaatatcct ggctctgtct ccaccagctc agaacctgct gctcaagagc     2820
tacttcagcg aggaaggcat cggctacaac atcatcagag tgcccatggc cagctgcgac     2880
ttcagcatca ggacctacac ctacgccgac acacccgacg atttccagct gcacaacttc     2940
```

```
agcctgcctg aagaggacac caagctgaag atccctctga tccacagagc cctgcagctg    3000
gcacaaagac ccgtgtcact gctggcctct ccatggacat ctcccacctg gctgaaaaca    3060
aatggcgccg tgaatggcaa gggcagcctg aaaggccaac ctggcgacat ctaccaccag    3120
acctgggcca gatacttcgt gaagttcctg gacgcctatg ccgagcacaa gctgcagttt    3180
tgggccgtga cagccgagaa cgaaccttct gctggactgc tgagcggcta ccccttttcag   3240 tgcctgggct ttacacccga gcaccagcgg gactttatcg cccgtgatct gggacccaca    3300
ctggccaata gcacccacca taatgtgcgg ctgctgatgc tggacgacca gagactgctt    3360
ctgccccact gggctaaagt ggtgctgaca gatcctgagg ccgccaaata cgtgcacgga    3420
atcgccgtgc actggtatct ggactttctg gcccctgcca aggccacact gggagagaca    3480
cacagactgt tccccaacac catgctgttc gccagcgaag cctgtgtggg cagcaagttt    3540
tgggaacaga gcgtgcggct cggcagctgg gatagaggca tgcagtacag ccacagcatc    3600
atcaccaacc tgctgtacca cgtcgtcggc tggaccgact ggaatctggc cctgaatcct    3660
gaaggcggcc ctaactgggt ccgaaacttc gtggacagcc ccatcatcgt ggacatcacc    3720
aaggacacct tctacaagca gcccatgttc taccacctgg acacttcag caagttcatc     3780 cccgagggct ctcagcgcgt tggactggtg gcttcccaga agaacgatct ggacgccgtg    3840
gctctgatgc accctgatgg atctgctgtg gtggtggtcc tgaaccgcag cagcaaagat    3900
gtgcccctga ccatcaagga tcccgccgtg ggattcctgg aaacaatcag ccctggctac    3960
tccatccaca cctacctgtg gcgtagacag tgacaattgt taattaagtt taaaccctcg    4020
aggccgcaag ccgcatcgat accgtcgact agagctcgct gatcagcctc gactgtgcct    4080
tctagttgcc agccatctgt tgtttgcccc tccccgtgc cttccttgac cctggaaggt     4140
gccactccca ctgtcctttc ctaataaaat gaggaaattg catcgcattg tctgagtagg    4200
tgtcattcta ttctggggggg tggggtgggg caggacagca agggggagga ttgggaagac    4260
aatagcaggc atgctgggga gagatccacg ataacaaaca gctttttttgg ggtgaacata    4320 ttgactgaat ccctgcagg ttggccactc cctctctgcg cgctcgctcg ctcactgagg      4380
ccgcccgggc aaagcccggg cgtcgggcga cctttggtcg cccggcctca gtgagcgagc     4440
gagcgcgcag agagggagtg gccaactcca tcactagggg ttcctgcggc cgctcgtacg    4500
gtctcgagga attcctgcag gataacttgc caacctcatt ctaaaatgta tatagaagcc    4560
caaaagacaa taacaaaaat attcttgtag aacaaaatgg gaaagaatgt tccactaaat    4620
atcaagattt agagcaaagc atgagatgtg tggggataga cagtgaggct gataaaatag    4680
agtagagctc agaaacagac ccattgatat atgtaagtga cctatgaaaa aaatatggca    4740
ttttacaatg ggaaaatgat ggtctttttc ttttttagaa aaacagggaa atatattat     4800 atgtaaaaaa taaaagggaa cccatatgtc ataccataca cacaaaaaaa ttccagtgaa    4860
ttataagtct aaatggagaa ggcaaaactt taaatctttt agaaaataat atagaagcat    4920
gcagaccagc ctggccaaca tgatgaaacc ctctctacta ataataaaat cagtagaact    4980
actcaggact actttgagtg ggaagtcctt ttctatgaag acttctttgg ccaaaattag    5040
gctctaaatg caaggagata gtgcatcatg cctggctgca cttactgata aatgatgtta    5100
tcaccatctt taaccaaatg cacaggaaca agttatggta ctgatgtgct ggattgagaa    5160
ggagctctac ttccttgaca ggacacattt gtatcaactt aaaaaagcag atttttgcca   5220
gcagaactat tcattcagag gtaggaaact tagaatagat gatgtcactg attagcatgg    5280
```

-continued

```
cttccccatc tccacagctg cttcccaccc aggttgccca cagttgagtt tgtccagtgc      5340
tcagggctgc ccactctcag taagaagccc cacaccagcc cctctccaaa tatgttggct      5400
gttccttcca ttaaagtgac cccactttag agcagcaagt ggatttctgt ttcttacagt      5460
tcaggaagga ggagtcagct gtgagaacct ggagcctgag atgcttctaa gtcccactgc      5520
tactggggtc agggaagcca gactccagca tcagcagtca ggagcactaa gcccttgcca      5580
acatcctgtt tctcagagaa actgcttcca ttataatggt tgtccttttt taagctatca      5640
agccaaacaa ccagtgtcta ccattattct catcacctga agccaagggt tctagcaaaa      5700
gtcaagctgt cttgtaatgg ttgatgtgcc tccagcttct gtcttcagtc actccactct      5760
tagcctgctc tgaatcaact ctgaccacag ttccctggag cccctgccac ctgctgcccc      5820
tgccaccttc tccatctgca gtgctgtgca gccttctgca ctcttgcaga gctaataggt      5880
ggagacttga aggaagagga ggaaagtttc tcataatagc cttgctgcaa gctcaaatgg      5940
gaggtgggca ctgtgcccag gagccttgga gcaaaggctg tgcccaacct ctgactgcat      6000
ccaggtttgg tcttgacaga gataagaagc cctggctttt ggagccaaaa tctaggtcag      6060
acttaggcag gattctcaaa gtttatcagc agaacatgag gcagaagacc ctttctgctc      6120
cagcttcttc aggctcaacc ttcatcagaa tagatagaaa gagaggctgt gagggttctt      6180
aaaacagaag caaatctgac tcagagaata aacaacctcc tagtaaacta cagcttagac      6240
agagcatctg gtggtgagtg tgctcagtgt cctactcaac tgtctggtat cagccctcat      6300
gaggacttct cttctttccc tcatagacct ccatctctgt tttccttagc ctgcagaaat      6360
ctggatggct attcacagaa tgcctgtgct ttcagagttg catttttttct ctggtattct      6420 ggttcaagca tttgaaggta ggaaaggttc tccaagtgca agaaagccag ccctgagcct      6480
caactgcctg gctagtgtgg tcagtaggat gcaaaggctg ttgaatgcca caaggccaaa      6540
ctttaacctg tgtaccacaa gcctagcagc agaggcagct ctgctcactg gaactctctg      6600
tcttctttct cctgagcctt ttcttttcct gagttttcta gctctcctca accttaccttc      6660 tgccctaccc aggacaaacc caagagccac tgtttctgtg atgtcctctc cagccctaat      6720
taggcatcat gacttcagcc tgaccttcca tgctcagaag cagtgctaat ccacttcaga      6780
tgagctgctc tatgcaacac aggcagagcc tacaaacctt tgcaccagag ccctccacat      6840
atcagtgttt gttcatactc acttcaacag caaatgtgac tgctgagatt aagattttac      6900
acaagatggt ctgtaatttc acagttagtt ttatcccatt aggtatgaaa gaattagcat      6960
aattcccctt aaacatgaat gaatcttaga tttttttaata aatagttttg gaagtaaaga      7020
cagagacatc aggagcacaa ggaatagcct gagaggacaa acagaacaag aaagagtctg      7080
gaaatacaca ggatgttctt ggcctcctca aagcaagtgc aagcagatag taccagcagc      7140
cccaggctat cagagcccag tgaagagaag taccatgaaa gccacagctc taaccaccct      7200
gttccagagt gacagacagt ccccaagaca agccagcctg agccagagag agaactgcaa      7260
gagaaagttt ctaatttagg ttctgttaga ttcagacaag tgcaggtcat cctctctcca      7320
cagctactca cctctccagc ctaacaaagc ctgcagtcca cactccaacc ctggtgtctc      7380
acctcctagc ctctcccaac atcctgctct ctgaccatct tctgcatctc tcatctcacc      7440
atctcccact gtctacagcc tactcttgca actaccatct cattttctga catcctgtct      7500
acatcttctg ccatactctg ccatctacca taccacctct taccatctac cacaccatct      7560
tttatctcca tccctctcag aagcctccaa gctgaatcct gctttatgtg ttcatctcag      7620
cccctgcatg gaaagctgac cccagaggca gaactattcc cagagagctt ggccaagaaa      7680
```

-continued

```
aacaaaacta ccagcctggc caggctcagg agtagtaagc tgcagtgtct gttgtgttct    7740
agcttcaaca gctgcaggag ttccactctc aaatgctcca catttctcac atcctcctga    7800
ttctggtcac tacccatctt caaagaacag aatatctcac atcagcatac tgtgaaggac    7860
tagtcatggg tgcagctgct cagagctgca aagtcattct ggatggtgga gagcttacaa    7920
acatttcatg atgctccccc cgctctgatg gctggagccc aatccctaca cagactcctg    7980
ctgtatgtgt tttcctttca ctctgagcca cagccagagg gcaggcattc agtctcctct    8040
tcaggctggg gctggggcac tgagaactca cccaacacct tgctctcact ccttctgcaa    8100
aacaagaaag agctttgtgc tgcagtagcc atgaagaatg aaaggaaggc tttaactaaa    8160
aaatgtcaga gattattttc aaccccttac tgtggatcac cagcaaggag gaaacacaac    8220
acagagacat tttttcccct caaattatca aaagaatcac tgcatttgtt aaagagagca    8280
actgaatcag gaagcagagt tttgaacata tcagaagtta ggaatctgca tcagagacaa    8340
atgcagtcat ggttgtttgc tgcataccag ccctaatcat tagaagcctc atggacttca    8400
aacatcattc cctctgacaa gatgctctag cctaactcca tgagataaaa taaatctgcc    8460
tttcagagcc aaagaagagt ccaccagctt cttctcagtg tgaacaagag ctccagtcag    8520
gttagtcagt ccagtgcagt agaggagacc agtctgcatc ctctaatttt caaaggcaag    8580
aagatttgtt taccctggac accaggcaca agtgaggtca cagagctctt agatatgcag    8640
tcctcatgag tgaggagact aaagcgcatg ccatcaagac ttcagtgtag agaaaacctc    8700
caaaaaagcc tcctcactac ttctggaata gctcagaggc cgaggcggcc tcggcctctg    8760
cataaataaa aaaaattagt cagccatggg gcggagaatg ggcggaactg ggcggagtta    8820
ggggcgggat gggcggagtt aggggcggga ctatggttgc tgactaattg agatgcatgc    8880
tttgcatact tctgcctgct ggggagcctg gggactttcc acacctggtt gctgactaat    8940
tgagatgcat gctttgcata cttctgcctg ctggggagcc tggggacttt ccacacccta    9000
actgacacac attccacagc tgcattaatg aatcggccaa cgcgcgggga gaggcggttt    9060
gcgtattggg cgctcttccg cttcctcgct cactgactcg ctgcgctcgg tcgttcggct    9120
gcggcgagcg gtatcagctc actcaaaggc ggtaatacgg ttatccacag aatcagggga    9180
taacgcagga aagaacatgt gagcaaaagg ccagcaaaag gccaggaacc gtaaaaaggc    9240
cgcgttgctg gcgtttttcc ataggctccg cccccctgac gagcatcaca aaaatcgacg    9300
ctcaagtcag aggtggcgaa acccgacagg actataaaga taccaggcgt ttccccctgg    9360
aagctccctc gtgcgctctc ctgttccgac cctgccgctt accggatacc tgtccgcctt    9420
tctcccttcg ggaagcgtgg cgctttctca tagctcacgc tgtaggtatc tcagttcggt    9480
gtaggtcgtt cgctccaagc tgggctgtgt gcacgaaccc cccgttcagc ccgaccgctg    9540
cgccttatcc ggtaactatc gtcttgagtc caacccggta agacacgact tatcgccact    9600
ggcagcagcc actggtaaca ggattagcag agcgaggtat gtaggcggtg ctacagagtt    9660
cttgaagtgg tggcctaact acggctacac tagaagaaca gtatttggta tctgcgctct    9720
gctgaagcca gttaccttcg gaaaaagagt tggtagctct tgatccggca aacaaaccac    9780
cgctggtagc ggtggttttt ttgtttgcaa gcagcagatt acgcgcagaa aaaaggatc    9840 tcaagaagat cctttgatct tttctacggg gtctgacgct cagtggaacg aaaactcacg    9900
ttaagggatt ttggtcatga gattatcaaa aaggatcttc acctagatcc ttttaaatta    9960
aaaatgaagt tttaaatcaa tctaaagtat atatgagtaa acttggtctg acagttacca    10020
```

-continued

```
atgcttaatc agtgaggcac ctatctcagc gatctgtcta tttcgttcat ccatagttgc    10080
ctgactcctg caaaccacgt tgtgtctcaa aatctctgat gttacattgc acaagataaa    10140
aatatatcat catgaacaat aaaactgtct gcttacataa acagtaatac aagggggtgtt   10200 atgagccata ttcaacggga aacgtcttgc tcgaggccgc gattaaattc caacatggat    10260
gctgatttat atgggtataa atgggctcgc gataatgtcg ggcaatcagg tgcgacaatc    10320
tatcgattgt atgggaagcc cgatgcgcca gagttgtttc tgaaacatgg caaaggtagc    10380
gttgccaatg atgttacaga tgagatggtc agactaaact ggctgacgga atttatgcct    10440
cttccgacca tcaagcattt tatccgtact cctgatgatg catggttact caccactgcg    10500
atccccggga aaacagcatt ccaggtatta gaagaatatc ctgattcagg tgaaaatatt    10560 gttgatcgc tggcagtgtt cctgcgccgg ttgcattcga ttcctgtttg taattgtcct     10620
tttaacagcg atcgcgtatt tcgtctcgct caggcgcaat cacgaatgaa taacggtttg    10680
gttgatgcga gtgattttga tgacgagcgt aatggctggc ctgttgaaca agtctggaaa    10740
gaaatgcata agcttttgcc attctcaccg gattcagtcg tcactcatgg tgatttctca    10800
cttgataacc ttattttga cgaggggaaa ttaataggtt gtattgatgt tggacgagtc     10860
ggaatcgcag accgatacca ggatcttgcc atcctatgga actgcctcgg tgagttttct    10920
ccttcattac agaaacggct ttttcaaaaa tatggtattg ataatcctga tatgaataaa    10980
ttgcagtttc atttgatgct cgatgagttt ttctaagggc ggcctgccac catcccacg     11040 ccgaaacaag cgctcatgag cccgaagtgg cgagcccgat cttccccatc ggtgatgtcg    11100
gcgatatagg cgccagcaac cgcacctgtg gcgccggtga tgagggcgcg ccaagtcgac    11160
gtccggcagt c                                                         11171

<210> SEQ ID NO 5
<211> LENGTH: 11309
<212> TYPE: DNA
<213> ORGANISM: Artificial Sequence
<220> FEATURE:
<223> OTHER INFORMATION: Synthetic polynucleotide

<400> SEQUENCE: 5
ttggccactc cctctctgcg cgctcgctcg ctcactgagg ccgggcgacc aaaggtcgcc      60
cgacgcccgg gctttgcccg ggcggcctca gtgagcgagc gagcgcgcag agagggagtg      120
gccaactcca tcactagggg ttcctgctag ctctgggtat ttaagcccga gtgagcacgc      180
agggtctcca ttttgaagcg ggaggttacg cgttcgtcga ctactagtgg gtaccagagc      240
tccctaggtt ctagaaccgg tgacgtctcc catggtgaag cttggatctg agggcggagt      300
tagggcggag ccaatcagcg tgcgccgttc cgaaagttgc ctttttatggc tgggcggaga     360 atgggcggtg aacgccgatg attatataag gacgcgccgg gtgtggcaca gctagttccg      420
tcgcagccgg gatttgggtc gcggttcttg tttgtggatc cctgtgatcg tcacttggta      480
agtcactgac tgtctatgcc tgggaaaggg tgggcaggag atggggcagt gcaggaaaag      540
tggcactatg aaccctcctg gtggcgaggg gaggggggtg gtcctcgaac gccttgcaga      600
actggcctgg atacagagtg gaccggctgg ccccatctgg aagacttcga gatacactgt      660
tgtcttactg cgctcaacag tgtatctcga agtcttccaa atggtgccag ccatcgcagc      720 gggggtgcagg aaatggggc agccccccctt tttggctatc cttccacgtg ttctttttttg     780 tatcttttgt gtttcctaga aaacatctca gtcaccaccg cagccctagg aatgcatcta      840
gacaattgta ctaaccttct tctctttcct ctcctgacag tccggaaagc caccatgtac      900
```

-continued

```
gccctgttcc tgctggccag cctgctgggc gccgccctgg ccggccccgt gctgggcctg      960
aaggagtgca cccgcggcag cgccgtgtgg tgccagaacg tgaagaccgc cagcgactgc     1020
ggcgccgtga agcactgcct gcagaccgtg tggaacaagc ccaccgtgaa gagcctgccc     1080
tgcgacatct gcaaggacgt ggtgaccgcc gccggcgaca tgctgaagga caacgccacc     1140
gaggaggaga tcctggtgta cctggagaag acctgcgact ggctgcccaa gcccaacatg     1200
agcgccagct gcaaggagat cgtggacagc tacctgcccg tgatcctgga catcatcaag     1260
ggcgagatga gccgccccgg cgaggtgtgc agcgccctga acctgtgcga gagcctgcag     1320
aagcacctgg ccgagctgaa ccaccagaag cagctggaga gcaacaagat ccccgagctg     1380
gacatgaccg aggtggtggc cccccttcatg gccaacatcc ccctgctgct gtaccccag      1440 gacgccccc gcagcaagcc ccagcccaag gacaacggcg acgtgtgcca ggactgcatc      1500
cagatggtga ccgacatcca gaccgccgtg cgcaccaaca gcaccttcgt gcaggccctg     1560
gtggagcacg tgaaggagga gtgcgaccgc ctgggccccg gcatggccga catctgcaag     1620
aactacatca gccagtacag cgagatcgcc atccagatga tgatgcacat gcagcccaag     1680
gagatctgcg ccctggtggg cttctgcgac gaggtgaagg agatgcccat gcagaccctg     1740
gtgcccgcca aggtggccag caagaacgtg atccccgccc tggagctggt ggagcccatc     1800
aagaagcacg aggtgcccgc caagagcgac gtgtactgcg aggtgtgcga gttcctggtg     1860
aaggaggtga ccaagctgat cgacaacaac aagaccgaga aggagatcct ggacgccttc     1920
gacaagatgt gcagcaagct gcccaagagc ctgagcgagg agtgccagga ggtggtggac     1980
acctacggca gcagcatcct gagcatcctg ctggaggagg tgagccccga gctggtgtgc     2040
agcatgctgc acctgtgcag cggcaccccgc ctgcccgccc tgaccgtgca cgtgacccag     2100
cccaaggacg gcggcttctg cgaggtgtgc aagaagctgg tgggctacct ggaccgcaac     2160
ctggagaaga cagcaccaa gcaggagatc ctggccgccc tggagaaggg ctgcagcttc     2220
ctgcccgacc cctaccagaa gcagtgcgac cagttcgtgg ccgagtacga gcccgtgctg     2280
atcgagatcc tggtggaggt gatggacccc agcttcgtgt gcctgaagat cggcgcctgc     2340
cccagcgccc acaagcccct gctgggcacc gagaagtgca tctgggggccc cagctactgg     2400 tgccagaaca ccgagaccgc cgcccagtgc aacgccgtgg agcactgcaa gcgccacgtg     2460
tggaacgagg gcagaggaag tcttctgaca tgcggagacg tggaagagaa tcccggccct     2520
atggaattca gcagccccag cagagaggaa tgccccaagc ctctgagccg ggtgtcaatc     2580
atggccggat ctctgacagg actgctgctg cttcaggccg tgtcttgggc ttctggcgct     2640
agaccttgca tccccaagag cttcggctac agcagcgtcg tgtgcgtgtg caatgccacc     2700
tactgcgaca gcttcgaccc tcctacctttt cctgctctgg gcaccttcag cagatacgag     2760
agcaccagat ccggcagacg gatggaactg agcatgggac ccatccaggc caatcacaca     2820
ggcactggcc tgctgctgac actgcagcct gagcagaaat ccagaaagt gaaaggcttc     2880 ggcggagcca tgacagatgc cgccgctctg aatatcctgg ctctgtctcc accagctcag     2940
aacctgctgc tcaagagcta cttcagcgag gaaggcatcg ctacaacat catcagagtg     3000 cccatggcca gctgcgactt cagcatcagg acctacacct acgccgacac acccgacgat     3060
ttccagctgc acaacttcag cctgcctgaa gaggacacca agctgaagat ccctctgatc     3120
cacagagccc tgcagctggc acaaagaccc gtgtcactgc tggcctctcc atggacatct     3180
cccacctggc tgaaaacaaa tggcgccgtg aatggcaagg gcagcctgaa aggccaacct     3240
```

-continued

```
ggcgacatct accaccagac ctgggccaga tacttcgtga agttcctgga cgcctatgcc      3300
gagcacaagc tgcagttttg ggccgtgaca gccgagaacg aaccttctgc tggactgctg      3360
agcggctacc cctttcagtg cctgggcttt acacccgagc accagcggga ctttatcgcc      3420
cgtgatctgg acccacact ggccaatagc acccaccata atgtgcggct gctgatgctg       3480
gacgaccaga gactgcttct gccccactgg gctaaagtgg tgctgacaga tcctgaggcc      3540
gccaaatacg tgcacggaat cgccgtgcac tggtatctgg actttctggc ccctgccaag      3600
gccacactgg gagagacaca cagactgttc cccaacacca tgctgttcgc cagcgaagcc      3660
tgtgtgggca gcaagttttg ggaacagagc gtgcggctcg gcagctggga tagaggcatg      3720
cagtacagcc acagcatcat caccaacctg ctgtaccacg tcgtcggctg gaccgactgg      3780
aatctggccc tgaatcctga aggcggccct aactgggtcc gaaacttcgt ggacagcccc      3840
atcatcgtgg acatcaccaa ggacaccttc tacaagcagc ccatgttcta ccacctggga      3900
cacttcagca agttcatccc cgagggctct cagcgcgttg gactggtggc ttcccagaag      3960
aacgatctgg acgccgtggc tctgatgcac cctgatggat ctgctgtggt ggtggtcctg      4020
aaccgcagca gcaaagatgt gcccctgacc atcaaggatc ccgccgtggg attcctggaa      4080
acaatcagcc ctggctactc catccacacc tacctgtggc gtagacagtg acaattgtta      4140
attaagttta aaccctcgag gccgcaagcc gcatcgatac cgtcgactag agctcgctga      4200
tcagcctcga ctgtgccttc tagttgccag ccatctgttg tttgcccctc ccccgtgcct      4260
tccttgaccc tggaaggtgc cactcccact gtcctttcct aataaaatga ggaaattgca      4320
tcgcattgtc tgagtaggtg tcattctatt ctggggggtg gggtggggca ggacagcaag      4380
ggggaggatt gggaagacaa tagcaggcat gctggggaga gatccacgat aacaaacagc      4440 tttttgggg tgaacatatt gactgaattc cctgcaggtt ggccactccc tctctgcgcg      4500
ctcgctcgct cactgaggcc gcccgggcaa agcccgggcg tcgggcgacc tttggtcgcc      4560
cggcctcagt gagcgagcga gcgcgcagag agggagtggc caactccatc actaggggtt      4620
cctgcggccg ctcgtacggt ctcgaggaat tcctgcagga taacttgcca acctcattct      4680
aaaatgtata tagaagccca aaagacaata acaaaaatat tcttgtagaa caaaatggga      4740
aagaatgttc cactaaatat caagatttag agcaaagcat gagatgtgtg gggatagaca      4800
gtgaggctga taaaatagag tagagctcag aaacagaccc attgatatat gtaagtgacc      4860
tatgaaaaaa atatggcatt ttacaatggg aaaatgatgg tcttttttctt ttttagaaaa      4920 acagggaaat atatttatat gtaaaaaata aaagggaacc catatgtcat accatacaca      4980
caaaaaaatt ccagtgaatt ataagtctaa atggagaagg caaaacttta aatcttttag      5040
aaaataatat agaagcatgc agaccagcct ggccaacatg atgaaaccct ctctactaat      5100
aataaaatca gtagaactac tcaggactac tttgagtggg aagtcctttt ctatgaagac      5160
ttctttggcc aaaattaggc tctaaatgca aggagatagt gcatcatgcc tggctgcact      5220
tactgataaa tgatgttatc accatcttta accaaatgca caggaacaag ttatggtact      5280
gatgtgctgg attgagaagg agctctactt ccttgacagg acacatttgt atcaacttaa      5340
aaaagcagat ttttgccagc agaactattc attcagaggt aggaaactta gaatagatga      5400
tgtcactgat tagcatggct tccccatctc cacagctgct tcccacccag gttgcccaca      5460
gttgagtttg tccagtgctc agggctgccc actctcagta agaagcccca caccagcccc      5520
tctccaaata tgttggctgt tccttccatt aaagtgaccc cacttttagag cagcaagtgg      5580 atttctgttt cttacagttc aggaaggagg agtcagctgt gagaacctgg agcctgagat      5640
```

-continued

```
gcttctaagt cccactgcta ctggggtcag ggaagccaga ctccagcatc agcagtcagg    5700
agcactaagc ccttgccaac atcctgtttc tcagagaaac tgcttccatt ataatggttg    5760
tcctttttta agctatcaag ccaaacaacc agtgtctacc attattctca tcacctgaag    5820
ccaagggttc tagcaaaagt caagctgtct tgtaatggtt gatgtgcctc cagcttctgt    5880
cttcagtcac tccactctta gcctgctctg aatcaactct gaccacagtt ccctggagcc    5940
cctgccacct gctgcccctg ccaccttctc catctgcagt gctgtgcagc cttctgcact    6000
cttgcagagc taataggtgg agacttgaag gaagaggagg aaagtttctc ataatagcct    6060
tgctgcaagc tcaaatggga ggtgggcact gtgcccagga gccttggagc aaaggctgtg    6120
cccaacctct gactgcatcc aggtttggtc ttgacagaga taagaagccc tggcttttgg    6180
agccaaaatc taggtcagac ttaggcagga ttctcaaagt ttatcagcag aacatgaggc    6240
agaagaccct ttctgctcca gcttcttcag gctcaacctt catcagaata gatagaaaga    6300
gaggctgtga gggttcttaa aacagaagca aatctgactc agagaataaa caacctccta    6360
gtaaactaca gcttagacag agcatctggt ggtgagtgtg ctcagtgtcc tactcaactg    6420
tctggtatca gccctcatga ggacttctct tctttccctc atagacctcc atctctgttt    6480
tccttagcct gcagaaatct ggatggctat tcacagaatg cctgtgcttt cagagttgca    6540
ttttttctct ggtattctgg ttcaagcatt tgaaggtagg aaaggttctc caagtgcaag    6600
aaagccagcc ctgagcctca actgcctggc tagtgtggtc agtaggatgc aaaggctgtt    6660
gaatgccaca aggccaaact ttaacctgtg taccacaagc ctagcagcag aggcagctct    6720
gctcactgga actctctgtc ttctttctcc tgagcctttt cttttcctga gttttctagc    6780
tctcctcaac cttacctctg ccctacccag gacaaaccca agagccactg tttctgtgat    6840
gtcctctcca gccctaatta ggcatcatga cttcagcctg accttccatg ctcagaagca    6900
gtgctaatcc acttcagatg agctgctcta tgcaacacag gcagagccta caaacctttg    6960
caccagagcc ctccacatat cagtgtttgt tcatactcac ttcaacagca aatgtgactg    7020
ctgagattaa gattttacac aagatggtct gtaatttcac agttagtttt atcccattag    7080
gtatgaaaga attagcataa ttccccttaa acatgaatga atcttagatt ttttaataaa    7140
tagtttggga agtaaagaca gagacatcag gagcacaagg aatagcctga gaggacaaac    7200
agaacaagaa agagtctgga aatacacagg atgttcttgg cctcctcaaa gcaagtgcaa    7260
gcagatagta ccagcagccc caggctatca gagcccagtg aagagaagta ccatgaaagc    7320
cacagctcta accaccctgt tccagagtga cagacagtcc ccaagacaag ccagcctgag    7380
ccagagagag aactgcaaga gaaagtttct aatttaggtt ctgttagatt cagacaagtg    7440
caggtcatcc tctctccaca gctactcacc tctccagcct aacaaagcct gcagtccaca    7500
ctccaaccct ggtgtctcac ctcctagcct ctcccaacat cctgctctct gaccatcttc    7560
tgcatctctc atctcaccat ctcccactgt ctacagccta ctcttgcaac taccatctca    7620
ttttctgaca tcctgtctac atcttctgcc atactctgcc atctaccata ccacctctta    7680
ccatctacca caccatcttt tatctccatc cctctcagaa gcctccaagc tgaatcctgc    7740
tttatgtgtt catctcagcc cctgcatgga aagctgaccc cagaggcaga actattccca    7800
gagagcttgg ccaagaaaaa caaaactacc agcctggcca ggctcaggag tagtaagctg    7860
cagtgtctgt tgtgttctag cttcaacagc tgcaggagtt ccactctcaa atgctccaca    7920
tttctcacat cctcctgatt ctggtcacta cccatcttca aagaacagaa tatctcacat    7980
```

-continued

```
cagcatactg tgaaggacta gtcatgggtg cagctgctca gagctgcaaa gtcattctgg     8040
atggtggaga gcttacaaac atttcatgat gctcccccg ctctgatggc tggagcccaa      8100
tccctacaca gactcctgct gtatgtgttt tcctttcact ctgagccaca gccagagggc     8160
aggcattcag tctcctcttc aggctggggc tggggcactg agaactcacc caacaccttg     8220
ctctcactcc ttctgcaaaa caagaaagag ctttgtgctg cagtagccat gaagaatgaa     8280
aggaaggctt taactaaaaa atgtcagaga ttattttcaa ccccttactg tggatcacca     8340
gcaaggagga aacacaacac agagacattt tttcccctca aattatcaaa agaatcactg     8400
catttgttaa agagagcaac tgaatcagga agcagagttt tgaacatatc agaagttagg     8460
aatctgcatc agagacaaat gcagtcatgg ttgtttgctg cataccagcc ctaatcatta     8520
gaagcctcat ggacttcaaa catcattccc tctgacaaga tgctctagcc taactccatg     8580
agataaaata aatctgcctt tcagagccaa agaagagtcc accagcttct tctcagtgtg     8640
aacaagagct ccagtcaggt tagtcagtcc agtgcagtag aggagaccag tctgcatcct     8700
ctaattttca aaggcaagaa gatttgttta ccctggacac caggcacaag tgaggtcaca     8760
gagctcttag atatgcagtc ctcatgagtg aggagactaa agcgcatgcc atcaagactt     8820
cagtgtagag aaaacctcca aaaaagcctc ctcactactt ctggaatagc tcagaggccg     8880
aggcggcctc ggcctctgca taaataaaaa aaattagtca gccatggggc ggagaatggg     8940
cggaactggg cggagttagg ggcgggatgg gcggagttag gggcgggact atggttgctg     9000
actaattgag atgcatgctt tgcatacttc tgcctgctgg ggagcctggg gactttccac     9060
acctggttgc tgactaattg agatgcatgc tttgcatact tctgcctgct ggggagcctg     9120
gggactttcc acaccctaac tgacacacat tccacagctg cattaatgaa tcggccaacg     9180
cgcggggaga ggcggtttgc gtattgggcg ctcttccgct tcctcgctca ctgactcgct     9240
gcgctcggtc gttcggctgc ggcgagcggt atcagctcac tcaaaggcgg taatacggtt     9300
atccacagaa tcaggggata acgcaggaaa gaacatgtga gcaaaaggcc agcaaaaggc     9360
caggaaccgt aaaaaggccg cgttgctggc gttttttccat aggctccgcc cccctgacga    9420
gcatcacaaa aatcgacgct caagtcagag gtggcgaaac ccgacaggac tataaagata     9480
ccaggcgttt cccctggaa gctccctcgt gcgctctcct gttccgaccc tgccgcttac      9540
cggatacctg tccgcctttc tcccttcggg aagcgtggcg ctttctcata gctcacgctg     9600
taggtatctc agttcggtgt aggtcgttcg ctccaagctg ggctgtgtgc acgaaccccc     9660
cgttcagccc gaccgctgcg ccttatccgg taactatcgt cttgagtcca acccggtaag     9720
acacgactta tcgccactgg cagcagccac tggtaacagg attagcagag cgaggtatgt     9780
aggcggtgct acagagttct tgaagtggtg gcctaactac ggctacacta agaacagt      9840 atttggtatc tgcgctctgc tgaagccagt taccttcgga aaaagagttg gtagctcttg     9900
atccggcaaa caaaccaccg ctggtagcgg tggttttttt gtttgcaagc agcagattac     9960
gcgcagaaaa aaaggatctc aagaagatcc tttgatcttt tctacggggt ctgacgctca     10020
gtggaacgaa aactcacgtt aagggatttt ggtcatgaga ttatcaaaaa ggatcttcac     10080
ctagatcctt ttaaattaaa aatgaagttt taaatcaatc taaagtatat atgagtaaac     10140
ttggtctgac agttaccaat gcttaatcag tgaggcacct atctcagcga tctgtctatt     10200
tcgttcatcc atagttgcct gactccgca aaccacgttg tgtctcaaaa tctctgatgt      10260
tacattgcac aagataaaaa tatatcatca tgaacaataa aactgtctgc ttacataaac     10320
agtaatacaa ggggtgttat gagccatatt caacgggaaa cgtcttgctc gaggccgcga     10380
```

-continued

```
ttaaattcca acatggatgc tgatttatat gggtataaat gggctcgcga taatgtcggg   10440
caatcaggtg cgacaatcta tcgattgtat gggaagcccg atgcgccaga gttgtttctg   10500
aaacatggca aaggtagcgt tgccaatgat gttacagatg agatggtcag actaaactgg   10560
ctgacggaat ttatgcctct tccgaccatc aagcatttta tccgtactcc tgatgatgca   10620
tggttactca ccactgcgat ccccgggaaa acagcattcc aggtattaga agaatatcct   10680
gattcaggtg aaaatattgt tgatgcgctg gcagtgttcc tgcgccggtt gcattcgatt   10740
cctgtttgta attgtccttt aacagcgat cgcgtatttc gtctcgctca ggcgcaatca   10800
cgaatgaata acggtttggt tgatgcgagt gattttgatg acgagcgtaa tggctggcct   10860
gttgaacaag tctggaaaga aatgcataag cttttgccat tctcaccgga ttcagtcgtc   10920
actcatggtg atttctcact tgataacctt attttgacg aggggaaatt aataggttgt   10980
attgatgttg gacgagtcgg aatcgcagac cgataccagg atcttgccat cctatggaac   11040
tgcctcggtg agttttctcc ttcattacag aaacggcttt ttcaaaaata tggtattgat   11100
aatcctgata tgaataaatt gcagtttcat ttgatgctcg atgagttttt ctaagggcgg   11160
cctgccacca tacccacgcc gaaacaagcg ctcatgagcc cgaagtggcg agcccgatct   11220
tccccatcgg tgatgtcggc gatataggcg ccagcaaccg cacctgtggc gccggtgatg   11280
agggcgcgcc aagtcgacgt ccggcagtc                                     11309
```

<210> SEQ ID NO 6
<211> LENGTH: 11293
<212> TYPE: DNA
<213> ORGANISM: Artificial Sequence
<220> FEATURE:
<223> OTHER INFORMATION: Synthetic polynucleotide

<400> SEQUENCE: 6

```
ttggccactc cctctctgcg cgctcgctcg ctcactgagg ccgggcgacc aaaggtcgcc     60
cgacgcccgg gctttgcccg ggcggcctca gtgagcgagc gagcgcgcag agagggagtg    120
gccaactcca tcactagggg ttcctgctag ctctgggtat ttaagcccga gtgagcacgc    180
agggtctcca ttttgaagcg ggaggttacg cgttcgtcga ctactagtgg gtaccagagc    240
tccctaggtt ctagaaccgg tgacgtctcc catggtgaag cttggatctg agggcggagt    300
tagggcggag ccaatcagcg tgcgccgttc cgaaagttgc cttttatggc tgggcggaga    360
atgggcggtg aacgccgatg attatataag gacgcgccgg gtgtggcaca gctagttccg    420
tcgcagccgg gatttgggtc gcggttcttg tttgtggatc cctgtgatcg tcacttggta    480
agtcactgac tgtctatgcc tgggaaaggg tgggcaggag atggggcagt gcaggaaaag    540
tggcactatg aaccctgcag ccctaggaat gcatctagac aattgtacta accttcttct    600
ctttcctctc ctgacagtcc ggaaagccac catgtacgcc ctgttcctgc tggccagcct    660
gctgggcgcc gccctggccg gcccgtgct gggcctgaag gagtgcaccc gcggcagcgc    720
cgtgtggtgc cagaacgtga agaccgccag cgactgcggc gccgtgaagc actgcctgca    780
gaccgtgtgg aacaagccca ccgtgaagag cctgccctgc gacatctgca aggacgtggt    840
gaccgccgcc ggcgacatgc tgaaggacaa cgccaccgag gaggagatcc tggtgtacct    900
ggagaagacc tgcgactggc tgcccaagcc caacatgagc gccagctgca aggagatcgt    960
ggacagctac ctgcccgtga tcctggacat catcaagggc gagatgagcc gccccggcga   1020
ggtgtgcagc gccctgaacc tgtgcgagag cctgcagaag cacctggccg agctgaacca   1080
```

-continued

```
ccagaagcag ctggagagca acaagatccc cgagctggac atgaccgagg tggtggcccc   1140
cttcatggcc aacatccccc tgctgctgta cccccaggac ggcccccgca gcaagcccca   1200
gcccaaggac aacggcgacg tgtgccagga ctgcatccag atggtgaccg acatccagac   1260
cgccgtgcgc accaacagca ccttcgtgca ggccctggtg gagcacgtga aggaggagtg   1320
cgaccgcctg ggcccccggca tggccgacat ctgcaagaac tacatcagcc agtacagcga   1380
gatcgccatc cagatgatga tgcacatgca gcccaaggat atctgcgccc tggtgggctt   1440
ctgcgacgag gtgaaggaga tgcccatgca gaccctggtg cccgccaagg tggccagcaa   1500
gaacgtgatc cccgccctgg agctggtgga gcccatcaag aagcacgagg tgcccgccaa   1560
gagcgacgtg tactgcgagg tgtgcgagtt cctggtgaag gaggtgacca agctgatcga   1620
caacaacaag accgagaagg agatcctgga cgccttcgac aagatgtgca gcaagctgcc   1680
caagagcctg agcgaggagt gccaggaggt ggtggacacc tacggcagca gcatcctgag   1740
catcctgctg gaggaggtga gccccgagct ggtgtgcagc atgctgcacc tgtgcagcgg   1800
cacccgcctg cccgccctga ccgtgcacgt gacccagccc aaggacggcg gcttctgcga   1860
ggtgtgcaag aagctggtgg gctacctgga ccgcaacctg gagaagaaca gcaccaagca   1920
ggagatcctg gccgccctgg agaagggctg cagcttcctg cccgacccct accagaagca   1980
gtgcgaccag ttcgtggccg agtacgagcc cgtgctgatc gagatcctgg tggaggtgat   2040
ggaccccagc ttcgtgtgcc tgaagatcgg cgcctgcccc agcgcccaca gcccctgct   2100 gggcaccgag aagtgcatct ggggccccag ctactggtgc agaacaccg agaccgccgc   2160 ccagtgcaac gccgtggagc actgcaagcg ccacgtgtgg aactgattgt ggccgaaccg   2220
ccgaactcag aggccggccc cagaaaaccc gagcgagtag ggggcggcgc gcaggaggga   2280
ggagaactgg gggcgcggga ggctggtggg tgtggggggt ggagatgtag aagatgtgac   2340
gccgcggccc ggcgggtgcc agattagcgg acgcggtgcc cgcggttgca acgggatccc   2400
gggcgctgca gcttgggagg cggctctccc caggcggcgt ccgcggagac acccatccgt   2460
gaaccccagg tcccgggccg ccggctcgcc gcgcaccagg ggccggcgga cagaagagcg   2520
gccgagcggc tcgaggctgg gggaccgcg gcgcggccgc gcgctgccgg gcgggaggct   2580
ggggggccgg ggccggggcc gtgccccgga gcgggtcgga ggccggggcc ggggccgggg   2640
gacggcggct cccgcgcgg ctccagcggc tcggggatcc cggccgggcc ccgcagggac   2700
catgatggaa ttcagcagcc ccagcagaga ggaatgcccc aagcctctga gccgggtgtc   2760
aatcatggcc ggatctctga caggactgct gctgcttcag gccgtgtctt gggcttctgg   2820
cgctagacct tgcatcccca agagcttcgg ctacagcagc gtcgtgtgcg tgtgcaatgc   2880
cacctactgc gacagcttcg accctcctac ctttcctgct ctgggcacct tcagcagata   2940
cgagagcacc agatccggca gacggatgga actgagcatg ggacccatcc aggccaatca   3000
cacaggcact ggcctgctgc tgacactgca gcctgagcag aaattccaga agtgaaagg   3060 cttcggcgga gccatgacag atgccgccgc tctgaatatc ctggctctgt ctccaccagc   3120
tcagaacctg ctgctcaaga gctacttcag cgaggaaggc atcggctaca acatcatcag   3180
agtgcccatg gccagctgcg acttcagcat caggacctac acctacgccg acacacccga   3240
cgatttccag ctgcacaact tcagcctgcc tgaagaggac accaagctga agatccctct   3300
gatccacaga gccctgcagc tggcacaaag acccgtgtca ctgctggcct ctccatggac   3360
atctcccacc tggctgaaaa caaatggcgc cgtgaatggc aagggcagcc tgaaaggcca   3420
acctggcgac atctaccacc agacctgggc cagatacttc gtgaagttcc tggacgccta   3480
```

-continued

```
tgccgagcac aagctgcagt tttgggccgt gacagccgag aacgaacctt ctgctggact    3540
gctgagcggc tacccctttc agtgcctggg ctttacaccc gagcaccagc gggactttat    3600
cgcccgtgat ctgggaccca cactggccaa tagcacccac cataatgtgc ggctgctgat    3660
gctggacgac cagagactgc ttctgcccca ctgggctaaa gtggtgctga cagatcctga    3720
ggccgccaaa tacgtgcacg gaatcgccgt gcactggtat ctggactttc tggccctgc     3780 caaggccaca ctgggagaga cacacagact gttccccaac accatgctgt cgccagcga    3840 agcctgtgtg ggcagcaagt tttgggaaca gagcgtgcgg ctcggcagct gggatagagg    3900
catgcagtac agccacagca tcatcaccaa cctgctgtac cacgtcgtcg ctggaccga    3960 ctggaatctg gccctgaatc ctgaaggcgg ccctaactgg gtccgaaact cgtggacag    4020 ccccatcatc gtggacatca ccaaggacac cttctacaag cagcccatgt tctaccacct    4080
gggacacttc agcaagttca tccccgaggg ctctcagcgc gttggactgg tggcttccca    4140
gaagaacgat ctgacgccg tggctctgat gcaccctgat ggatctgctg tggtggtggt    4200
cctgaaccgc agcagcaaag atgtgcccct gaccatcaag gatcccgccg tgggattcct    4260
ggaaacaatc agccctggct actccatcca cacctacctg tggcgtagac agtgacaatt    4320
gttaattaag tttaaaccct cgaggccgca agcaataaaa tatctttatt ttcattacat    4380
ctgtgtgttg gtttttttgtg tggagatcca cgataacaaa cagctttttt ggggtgaaca    4440
tattgactga attccctgca ggttggccac tccctctctg cgcgctcgct cgctcactga    4500
ggccgcccgg gcaaagcccg ggcgtcgggc gacctttggt cgcccggcct cagtgagcga    4560
gcgagcgcgc agagagggag tggccaactc catcactagg ggttcctgcg gccgctcgta    4620
cggtctcgag gaattcctgc aggataactt gccaacctca ttctaaaatg tatatagaag    4680
cccaaaagac aataacaaaa atattcttgt agaacaaaat gggaaagaat gttccactaa    4740
atatcaagat ttagagcaaa gcatgagatg tgtggggata gacagtgagg ctgataaaat    4800
agagtagagc tcagaaacag acccattgat atatgtaagt gacctatgaa aaaaatatgg    4860
cattttacaa tgggaaaatg atggtctttt tctttttttag aaaaacaggg aaatatattt    4920
atatgtaaaa aataaaaggg aacccatatg tcataccata cacacaaaaa aattccagtg    4980
aattataagt ctaaatggag aaggcaaaac tttaaatctt ttagaaaata atatagaagc    5040
atgcagacca gcctggccaa catgatgaaa ccctctctac taataataaa atcagtagaa    5100
ctactcagga ctactttgag tgggaagtcc ttttctatga agacttcttt ggccaaaatt    5160
aggctctaaa tgcaaggaga tagtgcatca tgcctggctg cacttactga taaatgatgt    5220
tatcaccatc tttaaccaaa tgcacaggaa caagttatgg tactgatgtg ctggattgag    5280
aaggagctct acttccttga caggacacat ttgtatcaac ttaaaaaagc agatttttgc    5340
cagcagaact attcattcag aggtaggaaa cttagaatag atgatgtcac tgattagcat    5400
ggcttcccca tctccacagc tgcttccac ccaggttgcc cacagttgag tttgtccagt    5460
gctcagggct gcccactctc agtaagaagc cccacaccag ccctctcca aatatgttgg    5520 ctgttccttc cattaaagtg accccacttt agagcagcaa gtggatttct gtttcttaca    5580
gttcaggaag gaggagtcag ctgtgagaac ctggagcctg agatgcttct aagtcccact    5640
gctactgggg tcagggaagc cagactccag catcagcagt caggagcact aagcccttgc    5700
caacatcctg tttctcagag aaactgcttc cattataatg gttgtccttt tttaagctat    5760
caagccaaac aaccagtgtc taccattatt ctcatcacct gaagccaagg gttctagcaa    5820
```

-continued

```
aagtcaagct gtcttgtaat ggttgatgtg cctccagctt ctgtcttcag tcactccact    5880
cttagcctgc tctgaatcaa ctctgaccac agttccctgg agcccctgcc acctgctgcc    5940
cctgccacct tctccatctg cagtgctgtg cagccttctg cactcttgca gagctaatag    6000
gtggagactt gaaggaagag gaggaaagtt tctcataata gccttgctgc aagctcaaat    6060
gggaggtggg cactgtgccc aggagccttg gagcaaaggc tgtgcccaac ctctgactgc    6120
atccaggttt ggtcttgaca gagataagaa gccctggctt ttggagccaa aatctaggtc    6180
agacttaggc aggattctca aagtttatca gcagaacatg aggcagaaga ccctttctgc    6240
tccagcttct tcaggctcaa ccttcatcag aatagataga aagagaggct gtgagggttc    6300
ttaaaacaga agcaaatctg actcagagaa taaacaacct cctagtaaac tacagcttag    6360
acagagcatc tggtggtgag tgtgctcagt gtcctactca actgtctggt atcagccctc    6420
atgaggactt ctcttctttc cctcatagac ctccatctct gttttcctta gcctgcagaa    6480
atctggatgg ctattcacag aatgcctgtg ctttcagagt tgcatttttt ctctggtatt    6540
ctggttcaag catttgaagg taggaaaggt tctccaagtg caagaaagcc agccctgagc    6600
ctcaactgcc tggctagtgt ggtcagtagg atgcaaaggc tgttgaatgc cacaaggcca    6660
aactttaacc tgtgtaccac aagcctagca gcagaggcag ctctgctcac tggaactctc    6720
tgtcttcttt ctcctgagcc ttttcttttc ctgagttttc tagctctcct caaccttacc    6780
tctgccctac ccaggacaaa cccaagagcc actgtttctg tgatgtcctc tccagcccta    6840
attaggcatc atgacttcag cctgaccttc catgctcaga agcagtgcta atccacttca    6900
gatgagctgc tctatgcaac acaggcagag cctacaaacc tttgcaccag agccctccac    6960
atatcagtgt ttgttcatac tcacttcaac agcaaatgtg actgctgaga ttaagatttt    7020
acacaagatg gtctgtaatt tcacagttag ttttatccca ttaggtatga aagaattagc    7080
ataattcccc ttaaacatga atgaatctta gattttttaa taaatagttt tggaagtaaa    7140
gacagagaca tcaggagcac aaggaatagc ctgagaggac aaacagaaca agaaagagtc    7200
tggaaataca caggatgttc ttggcctcct caaagcaagt gcaagcagat agtaccagca    7260
gccccaggct atcagagccc agtgaagaga agtaccatga aagccacagc tctaaccacc    7320
ctgttccaga gtgacagaca gtccccaaga caagccagcc tgagccagag agagaactgc    7380
aagagaaagt ttctaattta ggttctgtta gattcagaca agtgcaggtc atcctctctc    7440
cacagctact cacctctcca gcctaacaaa gcctgcagtc cacactccaa ccctggtgtc    7500
tcacctccta gcctctccca acatcctgct ctctgaccat cttctgcatc tctcatctca    7560
ccatctccca ctgtctacag cctactcttg caactaccat ctcattttct gacatcctgt    7620
ctacatcttc tgccatactc tgccatctac cataccacct cttaccatct accacaccat    7680
cttttatctc catccctctc agaagcctcc aagctgaatc ctgctttatg tgttcatctc    7740 agccctgca tggaaagctg accccagagg cagaactatt cccagagagc ttggccaaga    7800 aaacaaaac taccagcctg gccaggctca ggagtagtaa gctgcagtgt ctgttgtgtt    7860
ctagcttcaa cagctgcagg agttccactc tcaaatgctc cacatttctc acatcctcct    7920
gattctggtc actacccatc ttcaaagaac agaatatctc acatcagcat actgtgaagg    7980
actagtcatg ggtgcagctg ctcagagctg caaagtcatt ctggatggtg gagagcttac    8040
aaacatttca tgatgctccc cccgctctga tggctggagc ccaatcccta cacagactcc    8100
tgctgtatgt gttttccttt cactctgagc cacagccaga gggcaggcat tcagtctcct    8160
cttcaggctg gggctggggc actgagaact cacccaacac cttgctctca ctccttctgc    8220
```

-continued

```
aaaacaagaa agagctttgt gctgcagtag ccatgaagaa tgaaaggaag gctttaacta   8280
aaaaatgtca gagattattt tcaaccccct actgtggatc accagcaagg aggaaacaca   8340
acacagagac atttttttccc ctcaaattat caaaagaatc actgcatttg ttaaagagag   8400
caactgaatc aggaagcaga gttttgaaca tatcagaagt taggaatctg catcagagac   8460
aaatgcagtc atggttgttt gctgcatacc agccctaatc attagaagcc tcatggactt   8520
caaacatcat tccctctgac aagatgctct agcctaactc catgagataa aataaatctg   8580
cctttcagag ccaaagaaga gtccaccagc ttcttctcag tgtgaacaag agctccagtc   8640
aggttagtca gtccagtgca gtagaggaga ccagtctgca tcctctaatt ttcaaaggca   8700
agaagatttg tttaccctgg acaccaggca caagtgaggt cacagagctc ttagatatgc   8760
agtcctcatg agtgaggaga ctaaagcgca tgccatcaag acttcagtgt agagaaaacc   8820
tccaaaaaag cctcctcact acttctggaa tagctcagag gccgaggcgg cctcggcctc   8880
tgcataaata aaaaaaatta gtcagccatg gggcggagaa tgggcggaac tgggcggagt   8940
tagggcgggg atgggcggag ttaggggcgg gactatggtt gctgactaat tgagatgcat   9000
gctttgcata cttctgcctg ctggggagcc tggggacttt ccacacctgg ttgctgacta   9060
attgagatgc atgctttgca tacttctgcc tgctggggag cctggggact ttccacaccc   9120
taactgacac acattccaca gctgcattaa tgaatcggcc aacgcgcggg gagaggcggt   9180
ttgcgtattg ggcgctcttc cgcttcctcg ctcactgact cgctgcgctc ggtcgttcgg   9240
ctgcggcgag cggtatcagc tcactcaaag gcggtaatac ggttatccac agaatcaggg   9300
gataacgcag gaaagaacat gtgagcaaaa ggccagcaaa aggccaggaa ccgtaaaaag   9360
gccgcgttgc tggcgttttt ccataggctc cgcccccctg acgagcatca caaaaatcga   9420
cgctcaagtc agaggtggcg aaacccgaca ggactataaa gataccaggc gtttccccct   9480
ggaagctccc tcgtgcgctc tcctgttccg accctgccgc ttaccggata cctgtccgcc   9540
tttctccctt cgggaagcgt ggcgctttct catagctcac gctgtaggta tctcagttcg   9600
gtgtaggtcg ttcgctccaa gctgggctgt gtgcacgaac cccccgttca gcccgaccgc   9660
tgcgccttat ccggtaacta tcgtcttgag tccaacccgg taagacacga cttatcgcca   9720
ctggcagcag ccactggtaa caggattagc agagcgaggt atgtaggcgg tgctacagag   9780
ttcttgaagt ggtggcctaa ctacggctac actagaagaa cagtatttgg tatctgcgct   9840
ctgctgaagc cagttacctt cggaaaaaga gttggtagct cttgatccgg caaacaaacc   9900
accgctggta gcggtggttt ttttgtttgc aagcagcaga ttacgcgcag aaaaaaagga   9960
tctcaagaag atcctttgat cttttctacg gggtctgacg ctcagtggaa cgaaaactca   10020
cgttaaggga ttttggtcat gagattatca aaaaggatct tcacctagat ccttttaaat   10080
taaaaatgaa gttttaaatc aatctaaagt atatatgagt aaacttggtc tgacagttac   10140
caatgcttaa tcagtgaggc acctatctca gcgatctgtc tatttcgttc atccatagtt   10200
gcctgactcc tgcaaaccac gttgtgtctc aaaatctctg atgttacatt gcacaagata   10260
aaaatatatc atcatgaaca ataaaactgt ctgcttacat aaacagtaat acaaggggtg   10320
ttatgagcca tattcaacgg gaaacgtctt gctcgaggcc gcgattaaat tccaacatgg   10380
atgctgattt atatgggtat aaatgggctc gcgataatgt cgggcaatca ggtgcgacaa   10440
tctatcgatt gtatgggaag cccgatgcgc cagagttgtt tctgaaacat ggcaaaggta   10500
gcgttgccaa tgatgttaca gatgagatgg tcagactaaa ctggctgacg gaatttatgc   10560
```

-continued

```
ctcttccgac catcaagcat tttatccgta ctcctgatga tgcatggtta ctcaccactg    10620
cgatccccgg gaaaacagca ttccaggtat tagaagaata tcctgattca ggtgaaaata    10680
ttgttgatgc gctggcagtg ttcctgcgcc ggttgcattc gattcctgtt tgtaattgtc    10740
cttttaacag cgatcgcgta tttcgtctcg ctcaggcgca atcacgaatg aataacggtt    10800
tggttgatgc gagtgatttt gatgacgagc gtaatggctg gcctgttgaa caagtctgga    10860
aagaaatgca taagcttttg ccattctcac cggattcagt cgtcactcat ggtgatttct    10920
cacttgataa ccttattttt gacgagggga aattaatagg ttgtattgat gttggacgag    10980
tcggaatcgc agaccgatac caggatcttg ccatcctatg gaactgcctc ggtgagtttt    11040
ctccttcatt acagaaacgg cttttttcaaa aatatggtat tgataatcct gatatgaata    11100
aattgcagtt tcatttgatg ctcgatgagt ttttctaagg gcggcctgcc accatacccca    11160 cgccgaaaca agcgctcatg agcccgaagt ggcgagcccg atcttcccca tcggtgatgt    11220
cggcgatata ggcgccagca accgcacctg tggcgccggt gatgagggcg cgccaagtcg    11280
acgtccggca gtc                                                       11293
```

<210> SEQ ID NO 7
<211> LENGTH: 10700
<212> TYPE: DNA
<213> ORGANISM: Artificial Sequence
<220> FEATURE:
<223> OTHER INFORMATION: Synthetic polynucleotide

<400> SEQUENCE: 7

```
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg     120
gccaactcca tcactagggg ttcctgctag ctctgggtat ttaagcccga gtgagcacgc     180
agggtctcca tttttgaagcg ggaggttacg cgttcgtcga ctactagtgg gtaccagagc     240
tccctaggtt ctagaaccgg tgacgtctcc catggtgaag cttggatctg aattcggtac     300
ctagttatta atagtaatca attacggggt cattagttca tagcccatat atggagttcc     360
gcgttacata acttacggta aatggcccgc ctggctgacc gcccaacgac ccccgcccat     420
tgacgtcaat aatgacgtat gttcccatag taacgccaat agggactttc cattgacgtc     480
aatgggtgga gtatttacgg taaactgccc acttggcagt acatcaagtg tatcatatgc     540
caagtacgcc ccctattgac gtcaatgacg gtaaatggcc cgcctggcat tatgcccagt     600
acatgacctt atgggacttt cctacttggc agtacatcta cgtattagtc atcgctatta     660
ccatggtcga ggtgagcccc acgttctgct tcactctccc catctccccc ccctccccac     720
ccccaatttt gtatttattt attttttaat tattttgtgc agcgatgggg gcggggggggg     780 gggggggggcg cgcgccaggc ggggcggggc ggggcgaggg gcgggcgggg gcgaggcgga     840
gaggtgcggc ggcagccaat cagagcggcg cgctccgaaa gtttcctttt atggcgaggc     900
ggcggcggcg gcggccctat aaaaagcgaa gcgcgcggcg ggcgggagtc gctgcgacgc     960
tgccttcgcc ccgtgccccg ctccgccgcc gcctcgcgcc gcccgccccg gctctgactg    1020
accgcgttac tcccacaggt gagcgggcgg gacggccctt ctcctccggg ctgtaattag    1080
cgcttggttt aatgacggct tgtttctttt ctgtggctgc gtgaaagcct tgaggggctc    1140
cgggagctag agcctctgct aaccatgttc atgccttctt ctttttccta cagctcctgg    1200
gcaacgtgct ggttattgtg ctgtctcatc attttggcaa agaattcctc gaagatccga    1260
agggaaagtc ttccacgact gtgggatccg ttcgaagata tcaccggttg agccaccatg    1320
```

-continued

```
gaattcagca gccccagcag agaggaatgc cccaagcctc tgagccgggt gtcaatcatg     1380
gccggatctc tgacaggact gctgctgctt caggccgtgt cttgggcttc tggcgctaga     1440
ccttgcatcc ccaagagctt cggctacagc agcgtcgtgt gcgtgtgcaa tgccacctac     1500
tgcgacagct tcgaccctcc tacctttcct gctctgggca ccttcagcag atacgagagc     1560
accagatccg gcagacggat ggaactgagc atgggaccca tccaggccaa tcacacaggc     1620
actggcctgc tgctgacact gcagcctgag cagaaattcc agaaagtgaa aggcttcggc     1680
ggagccatga cagatgccgc cgctctgaat atcctggctc tgtctccacc agctcagaac     1740
ctgctgctca agagctactt cagcgaggaa ggcatcggct acaacatcat cagagtgccc     1800
atggccagct gcgacttcag catcaggacc tacacctacg ccgacacacc cgacgatttc     1860
cagctgcaca acttcagcct gcctgaagag gacaccaagc tgaagatccc tctgatccac     1920
agagccctgc agctggcaca aagacccgtg tcactgctgg cctctccatg gacatctccc     1980
acctggctga aaacaaatgg cgccgtgaat ggcaagggca gcctgaaagg ccaacctggc     2040
gacatctacc accagacctg gccagatac ttcgtgaagt tcctggacgc ctatgccgag     2100
cacaagctgc agttttgggc cgtgacagcc gagaacgaac cttctgctgg actgctgagc     2160
ggctacccct ttcagtgcct gggctttaca cccgagcacc agcgggactt tatcgcccgt     2220
gatctgggac ccacactggc caatagcacc caccataatg tgcggctgct gatgctggac     2280
gaccagagac tgcttctgcc ccactgggct aaagtggtgc tgacagatcc tgaggccgcc     2340
aaatacgtgc acggaatcgc cgtgcactgg tatctggact ttctggcccc tgccaaggcc     2400
acactgggag agacacacag actgttcccc aacaccatgc tgttcgccag cgaagcctgt     2460
gtgggcagca gtttttggga acagagcgtg cggctcggca gctgggatag aggcatgcag     2520
tacagccaca gcatcatcac caacctgctg taccacgtcg tcggctggac cgactggaat     2580
ctggccctga tcctgaagg cggccctaac tgggtccgaa acttcgtgga cagccccatc     2640
atcgtggaca tcaccaagga caccttctac aagcagccca tgttctacca cctgggacac     2700
ttcagcaagt tcatccccga gggctctcag cgcgttggac tggtggcttc ccagaagaac     2760
gatctggacg ccgtggctct gatgcaccct gatggatctg ctgtggtggt ggtcctgaac     2820
cgcagcagca agatgtgccc cctgaccatc aaggatcccg ccgtgggatt cctggaaaca     2880
atcagccctg ctactccat ccacacctac ctgtggcgta gacagtgaca attgttaatt     2940
aagtttaaac cctcgaggcc gcaagcttat cgataatcaa cctctggatt acaaaatttg     3000
tgaaagattg actggtattc ttaactatgt tgctcctttt acgctatgtg gatacgctgc     3060
tttaatgcct ttgtatcatg ctattgcttc ccgtatggct ttcattttct cctccttgta     3120
taaatcctgg ttgctgtctc tttatgagga gttgtggccc gttgtcaggc aacgtggcgt     3180
ggtgtgcact gtgtttgctg acgcaacccc cactggttgg ggcattgcca ccacctgtca     3240 gctccttt cc gggactttcg ctttccccct ccctattgcc acggcggaac tcatcgccgc     3300
ctgccttgcc cgctgctgga cagggctcg gctgttgggc actgacaatt ccgtggtgtt     3360 gtcgggggaaa tcatcgtcct ttccttggct gctcgcctgt gttgccacct ggattctgcg     3420
cgggacgtcc ttctgctacg tcccttcggc cctcaatcca gcggaccttc cttcccgcgg     3480
cctgctgccg gctctgcggc ctcttccgcg tcttcgcctt cgccctcaga cgagtcggat     3540
ctccctttgg gccgcctccc cgcatcgata ccgtcgacta gagctcgctg atcagcctcg     3600
actgtgcctt ctagttgcca gccatctgtt gtttgccct ccccgtgcc ttccttgacc     3660
```

-continued

```
ctggaaggtg ccactcccac tgtcctttcc taataaaatg aggaaattgc atcgcattgt      3720
ctgagtaggt gtcattctat tctggggggt ggggtggggc aggacagcaa gggggaggat      3780
tgggaagaca atagcaggca tgctggggag agatccacga taacaaacag ctttttttggg     3840 gtgaacatat tgactgaatt ccctgcaggt tggccactcc ctctctgcgc gctcgctcgc      3900
tcactgaggc cgcccgggca aagcccgggc gtcgggcgac ctttggtcgc ccggcctcag      3960
tgagcgagcg agcgcgcaga gagggagtgg ccaactccat cactagggt tcctgcggcc      4020 gctcgtacgg tctcgaggaa ttcctgcagg ataacttgcc aacctcattc taaaatgtat      4080
atagaagccc aaaagacaat aacaaaaata ttcttgtaga acaaaatggg aaagaatgtt      4140
ccactaaata tcaagattta gagcaaagca tgagatgtgt ggggatagac agtgaggctg      4200
ataaaataga gtagagctca gaaacagacc cattgatata tgtaagtgac ctatgaaaaa      4260
aatatggcat tttacaatgg gaaaatgatg gtcttttttct tttttagaaa aacagggaaa    4320
tatatttata tgtaaaaaat aaaagggaac ccatatgtca taccatacac acaaaaaaat      4380
tccagtgaat tataagtcta aatggagaag gcaaaacttt aaatctttta gaaaataata      4440
tagaagcatg cagaccagcc tggccaacat gatgaaaccc tctctactaa taataaaatc      4500
agtagaacta ctcaggacta ctttgagtgg gaagtccttt tctatgaaga cttctttggc      4560
caaaattagg ctctaaatgc aaggagatag tgcatcatgc ctggctgcac ttactgataa      4620
atgatgttat caccatcttt aaccaaatgc acaggaacaa gttatggtac tgatgtgctg      4680
gattgagaag gagctctact tccttgacag gacacatttg tatcaactta aaaaagcaga      4740
tttttgccag cagaactatt cattcagagg taggaaactt agaatagatg atgtcactga      4800
ttagcatggc ttccccatct ccacagctgc ttcccaccca ggttgcccac agttgagttt      4860
gtccagtgct cagggctgcc cactctcagt aagaagcccc acaccagccc ctctccaaat      4920
atgttggctg ttccttccat taaagtgacc ccactttaga gcagcaagtg gatttctgtt      4980
tcttacagtt caggaaggag gagtcagctg tgagaacctg gagcctgaga tgcttctaag      5040
tcccactgct actggggtca gggaagccag actccagcat cagcagtcag gagcactaag      5100
cccttgccaa catcctgttt ctcagagaaa ctgcttccat tataatggtt gtcctttttt      5160
aagctatcaa gccaaacaac cagtgtctac cattattctc atcacctgaa gccaagggtt      5220
ctagcaaaag tcaagctgtc ttgtaatggt tgatgtgcct ccagcttctg tcttcagtca      5280
ctccactctt agcctgctct gaatcaactc tgaccacagt tccctggagc ccctgccacc      5340
tgctgcccct gccaccttct ccatctgcag tgctgtgcag ccttctgcac tcttgcagag      5400
ctaataggtg gagacttgaa ggaagaggag gaaagtttct cataatagcc ttgctgcaag      5460
ctcaaatggg aggtgggcac tgtgcccagg agccttggag caaaggctgt gcccaacctc      5520
tgactgcatc caggtttggt cttgacagag ataagaagcc ctggctttg gagccaaaat       5580 ctaggtcaga cttaggcagg attctcaaag tttatcagca gaacatgagg cagaagaccc      5640
tttctgctcc agcttcttca ggctcaacct tcatcagaat agatagaaag agaggctgtg      5700
agggttctta aaacagaagc aaatctgact cagagaataa acaacctcct agtaaactac      5760
agcttagaca gagcatctgg tggtgagtgt gctcagtgtc ctactcaact gtctggtatc      5820
agccctcatg aggacttctc ttctttccct catagacctc catctctgtt ttccttagcc      5880
tgcagaaatc tggatggcta ttcacagaat gcctgtgctt tcagagttgc attttttctc      5940
tggtattctg gttcaagcat ttgaaggtag gaaaggttct ccaagtgcaa gaaagccagc      6000
cctgagcctc aactgcctgg ctagtgtggt cagtaggatg caaaggctgt tgaatgccac      6060
```

-continued

```
aaggccaaac tttaacctgt gtaccacaag cctagcagca gaggcagctc tgctcactgg      6120
aactctctgt cttctttctc ctgagccttt tcttttcctg agttttctag ctctcctcaa      6180
ccttacctct gccctaccca ggacaaaccc aagagccact gtttctgtga tgtcctctcc      6240
agccctaatt aggcatcatg acttcagcct gaccttccat gctcagaagc agtgctaatc      6300
cacttcagat gagctgctct atgcaacaca ggcagagcct acaaaccttt gcaccagagc      6360
cctccacata tcagtgtttg ttcatactca cttcaacagc aaatgtgact gctgagatta      6420
agattttaca caagatggtc tgtaatttca cagttagttt tatcccatta ggtatgaaag      6480
aattagcata attccccttaa aacatgaatg aatcttagat tttttaataa atagttttgg      6540
aagtaaagac agagacatca ggagcacaag gaatagcctg agaggacaaa cagaacaaga      6600
aagagtctgg aaatacacag gatgttcttg gcctcctcaa agcaagtgca agcagatagt      6660
accagcagcc ccaggctatc agagcccagt gaagagaagt accatgaaag ccacagctct      6720
aaccaccctg ttccagagtg acagacagtc cccaagacaa gccagcctga gccagagaga      6780
gaactgcaag agaaagtttc taatttaggt tctgttagat tcagacaagt gcaggtcatc      6840
ctctctccac agctactcac ctctccagcc taacaaagcc tgcagtccac actccaaccc      6900
tggtgtctca cctcctagcc tctcccaaca tcctgctctc tgaccatctt ctgcatctct      6960
catctcacca tctcccactg tctacagcct actcttgcaa ctaccatctc attttctgac      7020
atcctgtcta catcttctgc catactctgc catctaccat accacctctt accatctacc      7080
acaccatctt ttatctccat ccctctcaga agcctccaag ctgaatcctg ctttatgtgt      7140
tcatctcagc ccctgcatgg aaagctgacc ccagaggcag aactattccc agagagcttg      7200
gccaagaaaa acaaaactac cagcctggcc aggctcagga gtagtaagct gcagtgtctg      7260
ttgtgttcta gcttcaacag ctgcaggagt tccactctca aatgctccac atttctcaca      7320
tcctcctgat tctggtcact acccatcttc aaagaacaga atatctcaca tcagcatact      7380
gtgaaggact agtcatgggt gcagctgctc agagctgcaa agtcattctg gatggtggag      7440
agcttacaaa catttcatga tgctcccccc gctctgatgg ctggagccca atccctacac      7500
agactcctgc tgtatgtgtt ttcctttcac tctgagccac agccagaggg caggcattca      7560
gtctcctctt caggctgggg ctggggcact gagaactcac ccaacacctt gctctcactc      7620
cttctgcaaa acaagaaaga gctttgtgct gcagtagcca tgaagaatga aaggaaggct      7680
ttaactaaaa aatgtcagag attattttca accccttact gtggatcacc agcaaggagg      7740
aaacacaaca cagagacatt ttttcccctc aaattatcaa aagaatcact gcatttgtta      7800
aagagagcaa ctgaatcagg aagcagagtt ttgaacatat cagaagttag gaatctgcat      7860
cagagacaaa tgcagtcatg gttgtttgct gcataccagc cctaatcatt agaagcctca      7920
tggacttcaa acatcattcc ctctgacaag atgctctagc ctaactccat gagataaaat      7980
aaatctgcct ttcagagcca agaagagtc caccagcttc ttctcagtgt gaacaagagc      8040
tccagtcagg ttagtcagtc cagtgcagta gaggagacca gtctgcatcc tctaattttc      8100
aaaggcaaga agatttgttt accctggaca ccaggcacaa gtgaggtcac agagctctta      8160
gatatgcagt cctcatgagt gaggagacta aagcgcatgc catcaagact tcagtgtaga      8220
gaaaacctcc aaaaaagcct cctcactact tctggaatag ctcagaggcc gaggcggcct      8280
cggcctctgc ataaataaaa aaaattagtc agccatgggg cggagaatgg gcggaactgg      8340
gcggagttag gggcgggatg ggcggagtta ggggcgggac tatggttgct gactaattga      8400
```

-continued

```
gatgcatgct ttgcatactt ctgcctgctg gggagcctgg ggactttcca cacctggttg    8460
ctgactaatt gagatgcatg ctttgcatac ttctgcctgc tggggagcct ggggactttc    8520
cacaccctaa ctgacacaca ttccacagct gcattaatga atcggccaac gcgcggggag    8580
aggcggtttg cgtattgggc gctcttccgc ttcctcgctc actgactcgc tgcgctcggt    8640
cgttcggctg cggcgagcgg tatcagctca ctcaaaggcg gtaatacggt tatccacaga    8700
atcaggggat aacgcaggaa agaacatgtg agcaaaaggc cagcaaaagg ccaggaaccg    8760
taaaaaggcc gcgttgctgg cgtttttcca taggctccgc cccctgacg agcatcacaa     8820 aaatcgacgc tcaagtcaga ggtggcgaaa cccgacagga ctataaagat accaggcgtt    8880
tccccctgga agctccctcg tgcgctctcc tgttccgacc ctgccgctta ccggatacct    8940
gtccgccttt ctcccttcgg gaagcgtggc gctttctcat agctcacgct gtaggtatct    9000
cagttcggtg taggtcgttc gctccaagct gggctgtgtg cacgaacccc ccgttcagcc    9060
cgaccgctgc gccttatccg gtaactatcg tcttgagtcc aacccggtaa gacacgactt    9120
atcgccactg gcagcagcca ctggtaacag gattagcaga gcgaggtatg taggcggtgc    9180
tacagagttc ttgaagtggt ggcctaacta cggctacact agaagaacag tatttggtat    9240
ctgcgctctg ctgaagccag ttaccttcgg aaaaagagtt ggtagctctt gatccggcaa    9300
acaaaccacc gctggtagcg gtggtttttt tgtttgcaag cagcagatta cgcgcagaaa    9360
aaaaggatct caagaagatc ctttgatctt ttctacgggg tctgacgctc agtggaacga    9420
aaactcacgt taagggattt tggtcatgag attatcaaaa aggatcttca cctagatcct    9480
tttaaattaa aaatgaagtt ttaaatcaat ctaaagtata tatgagtaaa cttggtctga    9540
cagttaccaa tgcttaatca gtgaggcacc tatctcagcg atctgtctat ttcgttcatc    9600
catagttgcc tgactcctgc aaaccacgtt gtgtctcaaa atctctgatg ttacattgca    9660
caagataaaa atatatcatc atgaacaata aaactgtctg cttacataaa cagtaataca    9720
aggggtgtta tgagccatat tcaacgggaa acgtcttgct cgaggccgcg attaaattcc    9780
aacatggatg ctgatttata tgggtataaa tgggctcgcg ataatgtcgg gcaatcaggt    9840
gcgacaatct atcgattgta tgggaagccc gatgcgccag agttgtttct gaaacatggc    9900
aaaggtagcg ttgccaatga tgttacagat gagatggtca gactaaactg gctgacggaa    9960
tttatgcctc ttccgaccat caagcatttt atccgtactc ctgatgatgc atggttactc    10020
accactgcga tccccgggaa aacagcattc caggtattag aagaatatcc tgattcaggt    10080
gaaaatattg ttgatgcgct ggcagtgttc ctgcgccggt tgcattcgat tcctgtttgt    10140
aattgtcctt ttaacagcga tcgcgtattt cgtctcgctc aggcgcaatc acgaatgaat    10200
aacggtttgg ttgatgcgag tgattttgat gacgagcgta atggctggcc tgttgaacaa    10260
gtctggaaag aaatgcataa gcttttgcca ttctcaccgg attcagtcgt cactcatggt    10320
gatttctcac ttgataacct tattttttgac gaggggaaat taataggttg tattgatgtt    10380
ggacgagtcg gaatcgcaga ccgataccag gatcttgcca tcctatggaa ctgcctcggt    10440
gagttttctc cttcattaca gaaacggctt tttcaaaaat atggtattga taatcctgat    10500
atgaataaat tgcagtttca tttgatgctc gatgagtttt tctaagggcg gcctgccacc    10560
atacccacgc cgaaacaagc gctcatgagc ccgaagtggc gagcccgatc ttccccatcg    10620
gtgatgtcgg cgatataggc gccagcaacc gcacctgtgg cgccggtgat gagggcgcgc    10680
caagtcgacg tccggcagtc                                                10700
```

```
<210> SEQ ID NO 8
<211> LENGTH: 10700
<212> TYPE: DNA
<213> ORGANISM: Artificial Sequence
<220> FEATURE:
<223> OTHER INFORMATION: Synthetic polynucleotide

<400> SEQUENCE: 8
ttggccactc cctctctgcg cgctcgctcg ctcactgagg ccgggcgacc aaaggtcgcc       60
cgacgcccgg gctttgcccg ggcggcctca gtgagcgagc gagcgcgcag agagggagtg      120
gccaactatt agatctgatg gccgcgctag ctctgggtat ttaagcccga gtgagcacgc      180
agggtctcca tttgaagcg ggaggttacg cgttcgtcga ctactagtgg gtaccagagc       240
tccctaggtt ctagaaccgg tgacgtctcc catggtgaag cttggatctg aattcggtac      300
ctagttatta atagtaatca attacggggt cattagttca tagcccatat atggagttcc      360
gcgttacata acttacggta aatggcccgc ctggctgacc gcccaacgac ccccgcccat      420
tgacgtcaat aatgacgtat gttcccatag taacgccaat agggactttc cattgacgtc      480
aatgggtgga gtatttacgg taaactgccc acttggcagt acatcaagtg tatcatatgc      540
caagtacgcc ccctattgac gtcaatgacg gtaaatggcc cgcctggcat tatgcccagt      600
acatgacctt atgggacttt cctacttggc agtacatcta cgtattagtc atcgctatta      660
ccatggtcga ggtgagcccc acgttctgct tcactctccc catctccccc ccctccccac      720
ccccaatttt gtatttattt attttttaat tattttgtgc agcgatgggg gcgggggggg      780
ggggggggcg cgcgccaggc ggggcggggc ggggcgaggg gcggggcggg gcgaggcgga      840
gaggtgcggc ggcagccaat cagagcggcg cgctccgaaa gtttcctttt atggcgaggc      900
ggcggcggcg gcggccctat aaaaagcgaa gcgcgcggcg ggcgggagtc gctgcgacgc      960
tgccttcgcc ccgtgccccg ctccgccgcc gcctcgcgcc gcccgccccg gctctgactg     1020
accgcgttac tcccacaggt gagcgggcgg gacggccctt ctcctccggg ctgtaattag     1080
cgcttggttt aatgacggct tgtttctttt ctgtggctgc gtgaaagcct tgaggggctc     1140
cgggagctag agcctctgct aaccatgttc atgccttctt cttttttccta cagctcctgg     1200 gcaacgtgct ggttattgtg ctgtctcatc attttggcaa agaattcctc gaagatccga     1260
agggaaagtc ttccacgact gtgggatccg ttcgaagata tcaccggttg agccaccatg     1320
gaattcagca gccccagcag agaggaatgc cccaagcctc tgagccgggt gtcaatcatg     1380
gccggatctc tgacaggact gctgctgctt caggccgtgt cttgggcttc tggcgctaga     1440
ccttgcatcc ccaagagctt cggctacagc agcgtcgtgt gcgtgtgcaa tgccacctac     1500
tgcgacagct cgaccctcc tacctttcct gctctgggca ccttcagcag atacgagagc     1560
accagatccg gcagacggat ggaactgagc atgggaccca tccaggccaa tcacacaggc     1620
actggcctgc tgctgacact gcagcctgag cagaaattcc agaaagtgaa aggcttcggc     1680
ggagccatga cagatgccgc cgctctgaat atcctggctc tgtctccacc agctcagaac     1740
ctgctgctca agagctactt cagcgaggaa ggcatcggct acaacatcat cagagtgccc     1800
atggccagct gcgacttcag catcaggacc tacacctacg ccgacacacc cgacgatttc     1860
cagctgcaca acttcagcct gcctgaagag gacaccaagc tgaagatccc tctgatccac     1920
agagccctgc agctggcaca aagacccgtg tcactgctgg cctctccatg gacatctccc     1980
acctggctga aaacaaatgg cgccgtgaat ggcaagggca gcctgaaagg ccaacctggc     2040
gacatctacc accagacctg ggccagatac ttcgtgaagt tcctggacgc ctatgccgag     2100
```

-continued

```
cacaagctgc agttttgggc cgtgacagcc gagaacgaac cttctgctgg actgctgagc    2160
ggctacccct ttcagtgcct gggctttaca cccgagcacc agcgggactt tatcgcccgt    2220
gatctgggac ccacactggc caatagcacc caccataatg tgcggctgct gatgctggac    2280
gaccagagac tgcttctgcc ccactgggct aaagtggtgc tgacagatcc tgaggccgcc    2340
aaatacgtgc acggaatcgc cgtgcactgg tatctggact ttctggcccc tgccaaggcc    2400
acactgggag agacacacag actgttcccc aacaccatgc tgttcgccag cgaagcctgt    2460
gtgggcagca gttttgggga acagagcgtg cggctcggca gctgggatag aggcatgcag    2520
tacagccaca gcatcatcac caacctgctg taccacgtcg tcggctggac cgactggaat    2580
ctggccctga atcctgaagg cggccctaac tgggtccgaa acttcgtgga cagccccatc    2640
atcgtggaca tcaccaagga caccttctac aagcagccca tgttctacca cctgggacac    2700
ttcagcaagt tcatccccga gggctctcag cgcgttggac tggtggcttc ccagaagaac    2760
gatctggacg ccgtggctct gatgcaccct gatggatctg ctgtggtggt ggtcctgaac    2820
cgcagcagca aagatgtgcc cctgaccatc aaggatcccg ccgtgggatt cctggaaaca    2880
atcagccctg gctactccat ccacacctac ctgtggcgta gacagtgaca attgttaatt    2940
aagtttaaac cctcgaggcc gcaagcttat cgataatcaa cctctggatt acaaaatttg    3000
tgaaagattg actggtattc ttaactatgt tgctcctttt acgctatgtg gatacgctgc    3060
tttaatgcct ttgtatcatg ctattgcttc ccgtatggct ttcattttct cctccttgta    3120
taaatcctgg ttgctgtctc tttatgagga gttgtggccc gttgtcaggc aacgtggcgt    3180
ggtgtgcact gtgtttgctg acgcaacccc cactggttgg ggcattgcca ccacctgtca    3240
gctcctttcc gggactttcg ctttccccct ccctattgcc acggcggaac tcatcgccgc    3300
ctgccttgcc cgctgctgga caggggctcg gctgttgggc actgacaatt ccgtggtgtt    3360
gtcggggaaa tcatcgtcct ttccttggct gctcgcctgt gttgccacct ggattctgcg    3420
cgggacgtcc ttctgctacg tcccttcggc cctcaatcca gcggaccttc cttcccgcgg    3480
cctgctgccg gctctgcggc ctcttccgcg tcttcgcctt cgccctcaga cgagtcggat    3540
ctccctttgg gccgcctccc cgcatcgata ccgtcgacta gagctcgctg atcagcctcg    3600
actgtgcctt ctagttgcca gccatctgtt gtttgcccct cccccgtgcc ttccttgacc    3660
ctggaaggtg ccactcccac tgtcctttcc taataaaatg aggaaattgc atcgcattgt    3720
ctgagtaggt gtcattctat tctggggggt ggggtggggc aggacagcaa ggggggaggat    3780 tgggaagaca atagcaggca tgctggggag agatccacga taacaaacag cttttttggg    3840
gtgaacatat tgactgaatt ccctgcaggt tggccactcc ctctctgcgc gctcgctcgc    3900
tcactgaggc cgcccgggca aagcccgggc gtcgggcgac ctttggtcgc ccggcctcag    3960
tgagcgagcg agcgcgcaga gagggagtgg ccaactccat cactaggggt tcctgcggcc    4020
gctcgtacgg tctcgaggaa ttcctgcagg ataacttgcc aacctcattc taaaatgtat    4080
atagaagccc aaaagacaat aacaaaaata ttcttgtaga acaaaatggg aaagaatgtt    4140
ccactaaata tcaagattta gagcaaagca tgagatgtgt ggggatagac agtgaggctg    4200
ataaaataga gtagagctca gaaacagacc cattgatata tgtaagtgac ctatgaaaaa    4260
aatatggcat tttacaatgg gaaaatgatg gtctttttct tttttagaaa aacagggaaa    4320
tatatttata tgtaaaaaat aaaagggaac ccatatgtca taccatacac acaaaaaaat    4380
tccagtgaat tataagtcta aatggagaag gcaaaacttt aaatctttta gaaaataata    4440
tagaagcatg cagaccagcc tggccaacat gatgaaaccc tctctactaa taataaaatc    4500
```

-continued

```
agtagaacta ctcaggacta ctttgagtgg gaagtccttt tctatgaaga cttctttggc   4560
caaaattagg ctctaaatgc aaggagatag tgcatcatgc ctggctgcac ttactgataa   4620
atgatgttat caccatcttt aaccaaatgc acaggaacaa gttatggtac tgatgtgctg   4680
gattgagaag gagctctact tccttgacag gacacatttg tatcaactta aaaaagcaga   4740
tttttgccag cagaactatt cattcagagg taggaaactt agaatagatg atgtcactga   4800
ttagcatggc ttccccatct ccacagctgc ttcccaccca ggttgcccac agttgagttt   4860
gtccagtgct cagggctgcc cactctcagt aagaagcccc acaccagccc ctctccaaat   4920
atgttggctg ttccttccat taaagtgacc ccactttaga gcagcaagtg gatttctgtt   4980
tcttacagtt caggaaggag gagtcagctg tgagaacctg gagcctgaga tgcttctaag   5040
tcccactgct actggggtca gggaagccag actccagcat cagcagtcag gagcactaag   5100
cccttgccaa catcctgttt ctcagagaaa ctgcttccat tataatggtt gtcctttttt   5160
aagctatcaa gccaaacaac cagtgtctac cattattctc atcacctgaa gccaagggtt   5220
ctagcaaaag tcaagctgtc ttgtaatggt tgatgtgcct ccagcttctg tcttcagtca   5280
ctccactctt agcctgctct gaatcaactc tgaccacagt tccctggagc ccctgccacc   5340
tgctgcccct gccaccttct ccatctgcag tgctgtgcag ccttctgcac tcttgcagag   5400
ctaataggtg gagacttgaa ggaagaggag gaaagtttct cataatagcc ttgctgcaag   5460
ctcaaatggg aggtgggcac tgtgcccagg agccttggag caaaggctgt gcccaacctc   5520
tgactgcatc caggtttggt cttgacagag ataagaagcc ctggcttttg gagccaaaat   5580
ctaggtcaga cttaggcagg attctcaaag tttatcagca gaacatgagg cagaagaccc   5640
tttctgctcc agcttcttca ggctcaacct tcatcagaat agatagaaag agaggctgtg   5700
agggttctta aaacagaagc aaatctgact cagagaataa acaacctcct agtaaactac   5760
agcttagaca gagcatctgg tggtgagtgt gctcagtgtc ctactcaact gtctggtatc   5820
agccctcatg aggacttctc ttctttccct catagacctc catctctgtt ttccttagcc   5880
tgcagaaatc tggatggcta ttcacagaat gcctgtgctt tcagagttgc attttttctc   5940
tggtattctg gttcaagcat ttgaaggtag gaaaggttct ccaagtgcaa gaaagccagc   6000
cctgagcctc aactgcctgg ctagtgtggt cagtaggatg caaaggctgt tgaatgccac   6060
aaggccaaac tttaacctgt gtaccacaag cctagcagca gaggcagctc tgctcactgg   6120
aactctctgt cttctttctc ctgagccttt tcttttcctg agttttctag ctctcctcaa   6180
ccttacctct gccctaccca ggacaaaccc aagagccact gtttctgtga tgtcctctcc   6240
agccctaatt aggcatcatg acttcagcct gaccttccat gctcagaagc agtgctaatc   6300
cacttcagat gagctgctct atgcaacaca ggcagagcc acaaaccttt gcaccagagc   6360
cctccacata tcagtgtttg ttcatactca cttcaacagc aaatgtgact gctgagatta   6420
agattttaca caagatggtc tgtaatttca cagttagttt tatcccatta ggtatgaaag   6480
aattagcata attcccctta aacatgaatg aatcttagat tttttaataa atagttttgg   6540
aagtaaagac agagacatca ggagcacaag gaatagcctg agaggacaaa cagaacaaga   6600
aagagtctgg aaatacacag gatgttcttg gcctcctcaa agcaagtgca agcagatagt   6660
accagcagcc ccaggctatc agagcccagt gaagagaagt accatgaaag ccacagctct   6720
aaccaccctg ttccagagtg acagacagtc cccaagacaa gccagcctga gccagagaga   6780
gaactgcaag agaaagtttc taatttaggt tctgttagat tcagacaagt gcaggtcatc   6840
```

-continued

```
ctctctccac agctactcac ctctccagcc taacaaagcc tgcagtccac actccaaccc    6900
tggtgtctca cctcctagcc tctcccaaca tcctgctctc tgaccatctt ctgcatctct    6960
catctcacca tctcccactg tctacagcct actcttgcaa ctaccatctc attttctgac    7020
atcctgtcta catcttctgc catactctgc catctaccat accacctctt accatctacc    7080
acaccatctt ttatctccat ccctctcaga agcctccaag ctgaatcctg ctttatgtgt    7140
tcatctcagc ccctgcatgg aaagctgacc ccagaggcag aactattccc agagagcttg    7200
gccaagaaaa acaaaactac cagcctggcc aggctcagga gtagtaagct gcagtgtctg    7260
ttgtgttcta gcttcaacag ctgcaggagt tccactctca aatgctccac atttctcaca    7320
tcctcctgat tctggtcact acccatcttc aaagaacaga atatctcaca tcagcatact    7380
gtgaaggact agtcatgggt gcagctgctc agagctgcaa agtcattctg gatggtggag    7440
agcttacaaa catttcatga tgctcccccc gctctgatgg ctggagccca atccctacac    7500
agactcctgc tgtatgtgtt ttcctttcac tctgagccac agccagaggg caggcattca    7560
gtctcctctt caggctgggg ctgggcact gagaactcac ccaacacctt gctctcactc    7620
cttctgcaaa acaagaaaga gctttgtgct gcagtagcca tgaagaatga aaggaaggct    7680
ttaactaaaa aatgtcagag attattttca accccttact gtggatcacc agcaaggagg    7740
aaacacaaca cagagacatt ttttcccctc aaattatcaa aagaatcact gcatttgtta    7800
aagagagcaa ctgaatcagg aagcagagtt ttgaacatat cagaagttag gaatctgcat    7860
cagagacaaa tgcagtcatg gttgtttgct gcataccagc cctaatcatt agaagcctca    7920
tggacttcaa acatcattcc ctctgacaag atgctctagc ctaactccat gagataaaat    7980
aaatctgcct ttcagagcca aagaagagtc caccagcttc ttctcagtgt gaacaagagc    8040
tccagtcagg ttagtcagtc cagtgcagta gaggagacca gtctgcatcc tctaattttc    8100
aaaggcaaga agatttgttt accctggaca ccaggcacaa gtgaggtcac agagctctta    8160
gatatgcagt cctcatgagt gaggagacta aagcgcatgc catcaagact tcagtgtaga    8220
gaaaacctcc aaaaaagcct cctcactact tctggaatag ctcagaggcc gaggcggcct    8280
cggcctctgc ataaataaaa aaaattagtc agccatgggg cggagaatgg gcggaactgg    8340
gcggagttag gggcgggatg ggcggagtta ggggcgggac tatggttgct gactaattga    8400
gatgcatgct ttgcatactt ctgcctgctg gggagcctgg ggactttcca cacctggttg    8460
ctgactaatt gagatgcatg ctttgcatac ttctgcctgc tggggagcct ggggactttc    8520
cacaccctaa ctgacacaca ttccacagct gcattaatga atcggccaac gcgcggggag    8580
aggcggtttg cgtattgggc gctcttccgc ttcctcgctc actgactcgc tgcgctcggt    8640
cgttcggctg cggcgagcgg tatcagctca ctcaaaggcg gtaatacggt tatccacaga    8700
atcaggggat aacgcaggaa agaacatgtg agcaaaaggc cagcaaaagg ccaggaaccg    8760
taaaaaggcc gcgttgctgg cgttttttcca taggctccgc cccctgacg agcatcacaa    8820 aaatcgacgc tcaagtcaga ggtggcgaaa cccgacagga ctataaagat accaggcgtt    8880
tccccctgga agctccctcg tgcgctctcc tgttccgacc ctgccgctta ccggatacct    8940
gtccgccttt ctcccttcgg gaagcgtggc gctttctcat agctcacgct gtaggtatct    9000
cagttcggtg taggtcgttc gctccaagct gggctgtgtg cacgaacccc ccgttcagcc    9060
cgaccgctgc gccttatccg gtaactatcg tcttgagtcc aacccggtaa gacacgactt    9120
atcgccactg gcagcagcca ctggtaacag gattagcaga gcgaggtatg taggcggtgc    9180
tacagagttc ttgaagtggt ggcctaacta cggctacact agaagaacag tatttggtat    9240
```

-continued

```
ctgcgctctg ctgaagccag ttaccttcgg aaaaagagtt ggtagctctt gatccggcaa      9300
acaaaccacc gctggtagcg gtggtttttt tgtttgcaag cagcagatta cgcgcagaaa      9360
aaaaggatct caagaagatc ctttgatctt ttctacgggg tctgacgctc agtggaacga      9420
aaactcacgt taagggattt tggtcatgag attatcaaaa aggatcttca cctagatcct      9480
tttaaattaa aaatgaagtt ttaaatcaat ctaaagtata tatgagtaaa cttggtctga      9540
cagttaccaa tgcttaatca gtgaggcacc tatctcagcg atctgtctat ttcgttcatc      9600
catagttgcc tgactcctgc aaaccacgtt gtgtctcaaa atctctgatg ttacattgca      9660
caagataaaa atatatcatc atgaacaata aaactgtctg cttacataaa cagtaataca      9720
aggggtgtta tgagccatat tcaacgggaa acgtcttgct cgaggccgcg attaaattcc      9780
aacatggatg ctgatttata tgggtataaa tgggctcgcg ataatgtcgg gcaatcaggt      9840
gcgacaatct atcgattgta tgggaagccc gatgcgccag agttgtttct gaaacatggc      9900
aaaggtagcg ttgccaatga tgttacagat gagatggtca gactaaactg gctgacggaa      9960
tttatgcctc ttccgaccat caagcatttt atccgtactc ctgatgatgc atggttactc     10020
accactgcga tccccgggaa aacagcattc caggtattag aagaatatcc tgattcaggt     10080
gaaaatattg ttgatgcgct ggcagtgttc ctgcgccggt tgcattcgat tcctgtttgt     10140
aattgtcctt ttaacagcga tcgcgtattt cgtctcgctc aggcgcaatc acgaatgaat     10200
aacggtttgg ttgatgcgag tgattttgat gacgagcgta atggctggcc tgttgaacaa     10260
gtctggaaag aaatgcataa gcttttgcca ttctcaccgg attcagtcgt cactcatggt     10320
gatttctcac ttgataacct tattttttgac gaggggaaat taataggttg tattgatgtt     10380
ggacgagtcg gaatcgcaga ccgataccag gatcttgcca tcctatggaa ctgcctcggt     10440
gagttttctc cttcattaca gaaacggctt tttcaaaaat atggtattga taatcctgat     10500
atgaataaat tgcagtttca tttgatgctc gatgagtttt tctaagggcg gcctgccacc     10560
atacccacgc cgaaacaagc gctcatgagc ccgaagtggc gagcccgatc ttccccatcg     10620
gtgatgtcgg cgatataggc gccagcaacc gcacctgtgg cgccggtgat gagggcgcgc     10680
caagtcgacg tccggcagtc                                                 10700
```

<210> SEQ ID NO 9
<211> LENGTH: 10700
<212> TYPE: DNA
<213> ORGANISM: Artificial Sequence
<220> FEATURE:
<223> OTHER INFORMATION: Synthetic polynucleotide

<400> SEQUENCE: 9

```
ttggccactc cctctctgcg cgctcgctcg ctcactgagg ccgggcgacc aaaggtcgcc        60
cgacgcccgg gctttgcccg ggcggcctca gtgagcgagc gagcgcgcag agagggagtg       120
gccaactcca tcactagggg ttcctgctag ctctgggtat ttaagcccga gtgagcacgc       180
agggtctcca tttttgaagcg ggaggttacg cgttcgtcga ctactagtgg gtaccagagc      240
tccctaggtt ctagaaccgg tgacgtctcc catggtgaag cttggatctg aattcggtac       300
ctagttatta atagtaatca attacggggt cattagttca tagcccatat atggagttcc       360
gcgttacata acttacggta aatggcccgc ctggctgacc gcccaacgac ccccgcccat       420
tgacgtcaat aatgacgtat gttcccatag taacgccaat agggactttc cattgacgtc       480
aatgggtgga gtatttacgg taaactgccc acttggcagt acatcaagtg tatcatatgc       540
```

-continued

```
caagtacgcc ccctattgac gtcaatgacg gtaaatggcc cgcctggcat tatgcccagt      600
acatgacctt atgggacttt cctacttggc agtacatcta cgtattagtc atcgctatta      660
ccatggtcga ggtgagcccc acgttctgct tcactctccc catctccccc ccctccccac      720
ccccaatttt gtatttattt attttttaat tattttgtgc agcgatgggg gcggggggggg      780 gggggggggcg cgcgccaggc ggggcggggc ggggcgaggg gcggggcggg gcgaggcgga      840
gaggtgcggc ggcagccaat cagagcggcg cgctccgaaa gtttcctttt atggcgaggc      900
ggcggcggcg gcggccctat aaaaagcgaa gcgcgcggcg ggcgggagtc gctgcgacgc      960
tgccttcgcc ccgtgccccg ctccgccgcc gcctcgcgcc gcccgccccg gctctgactg     1020
accgcgttac tcccacaggt gagcgggcgg gacggcccct ctcctccggg ctgtaattag     1080
cgcttggttt aatgacggct tgtttctttt ctgtggctgc gtgaaagcct tgaggggctc     1140
cgggagctag agcctctgct aaccatgttc atgccttctt cttttttccta cagctcctgg     1200 gcaacgtgct ggttattgtg ctgtctcatc attttggcaa agaattcctc gaagatccga     1260
agggaaagtc ttccacgact gtgggatccg ttcgaagata tcaccggttg agccaccatg     1320
gaattcagca gccccagcag agaggaatgc cccaagcctc tgagccgggt gtcaatcatg     1380
gccggatctc tgacaggact gctgctgctt caggccgtgt cttgggcttc tggcgctaga     1440
ccttgcatcc ccaagagctt cggctacagc agcgtcgtgt gcgtgtgcaa tgccacctac     1500
tgcgacagct cgaccctcc taccttcct gctctgggca ccttcagcag atacgagagc     1560
accagatccg gcagacggat ggaactgagc atgggaccca tccaggccaa tcacacaggc     1620
actggcctgc tgctgacact gcagcctgag cagaaattcc agaaagtgaa aggcttcggc     1680
ggagccatga cagatgccgc cgctctgaat atcctggctc tgtctccacc agctcagaac     1740
ctgctgctca agagctactt cagcgaggaa ggcatcggct acaacatcat cagagtgccc     1800
atggccagct gcgacttcag catcaggacc tacacctacg ccgacacacc cgacgatttc     1860
cagctgcaca acttcagcct gcctgaagag gacaccaagc tgaagatccc tctgatccac     1920
agagccctgc agctggcaca aagacccgtg tcactgctgg cctctccatg gacatctccc     1980
acctggctga aaacaaatgg cgccgtgaat ggcaagggca gcctgaaagg ccaacctggc     2040
gacatctacc accagacctg ggccagatac ttcgtgaagt tcctggacgc ctatgccgag     2100
cacaagctgc agtttgggc cgtgacagcc gagaacgaac cttctgctgg actgctgagc     2160
ggctacccct ttcagtgcct gggctttaca cccgagcacc agcgggactt tatcgcccgt     2220
gatctgggac ccacactggc caatagcacc caccataatg tgcggctgct gatgctggac     2280
gaccagagac tgcttctgcc ccactgggct aaagtggtgc tgacagatcc tgaggccgcc     2340
aaatacgtgc acggaatcgc cgtgcactgg tatctggact ttctggcccc tgccaaggcc     2400
acactgggag agacacacag actgttcccc aacaccatgc tgttcgccag cgaagcctgt     2460
gtgggcagca gtttggga acagagcgtg cggctcggca ctgggatag aggcatgcag     2520 tacagccaca gcatcatcac caacctgctg taccacgtcg tcggctggac cgactggaat     2580 ctggcctga tcctgaagg cggccctaac tgggtccgaa acttcgtgga cagccccatc     2640
atcgtggaca tcaccaagga caccttctac aagcagccca tgttctacca cctgggacac     2700
ttcagcaagt tcatccccga gggctctcag cgcgttggac tggtggcttc ccagaagaac     2760
gatctggacg ccgtggctct gatgcaccct gatggatctg ctgtggtggt ggtcctgaac     2820
cgcagcagca aagatgtgcc cctgaccatc aaggatcccg ccgtgggatt cctgaaaaca     2880
atcagccctg gctactccat ccacacctac ctgtggcgta gacagtgaca attgttaatt     2940
```

-continued

```
aagtttaaac cctcgaggcc gcaagcttat cgataatcaa cctctggatt acaaaatttg   3000
tgaaagattg actggtattc ttaactatgt tgctcctttt acgctatgtg gatacgctgc   3060
tttaatgcct ttgtatcatg ctattgcttc ccgtatggct ttcattttct cctccttgta   3120
taaatcctgg ttgctgtctc tttatgagga gttgtggccc gttgtcaggc aacgtggcgt   3180
ggtgtgcact gtgtttgctg acgcaacccc cactggttgg ggcattgcca ccacctgtca   3240
gctcctttcc gggactttcg ctttcccct cctattgcc acggcggaac tcatcgccgc    3300
ctgccttgcc cgctgctgga caggggctcg gctgttgggc actgacaatt ccgtggtgtt   3360
gtcggggaaa tcatcgtcct ttccttggct gctcgcctgt gttgccacct ggattctgcg   3420
cgggacgtcc ttctgctacg tcccttcggc cctcaatcca gcggaccttc cttcccgcgg   3480
cctgctgccg gctctgcggc ctcttccgcg tcttcgcctt cgccctcaga cgagtcggat   3540
ctccctttgg gccgcctccc cgcatcgata ccgtcgacta gagctcgctg atcagcctcg   3600
actgtgcctt ctagttgcca gccatctgtt gtttgcccct cccccgtgcc ttccttgacc   3660
ctggaaggtg ccactcccac tgtcctttcc taataaaatg aggaaattgc atcgcattgt   3720
ctgagtaggt gtcattctat tctggggggt ggggtggggc aggacagcaa ggggggaggat  3780 tgggaagaca atagcaggca tgctggggag agatccacga taacaaacag cttttttggg   3840
gtgaacatat tgactgaatt ccctgcaggt tggccactcc ctctctgcgc gctcgctcgc   3900
tcactgaggc cgcccgggca agcccgggc gtcgggcgac ctttggtcgc ccggcctcag    3960
tgagcgagcg agcgcgcaga gagggagtgg ccaactccat cactagggt tcctgcggcc    4020 gctcgtacgg tctcgaggaa ttcctgcagg ataacttgcc aacctcattc taaaatgtat   4080
atagaagccc aaaagacaat aacaaaaata ttcttgtaga acaaaatggg aaagaatgtt   4140
ccactaaata tcaagattta gagcaaagca tgagatgtgt ggggatagac agtgaggctg   4200
ataaaataga gtagagctca gaaacagacc cattgatata tgtaagtgac ctatgaaaaa   4260
aatatggcat tttacaatgg gaaaatgatg gtctttttct tttttagaaa aacagggaaa   4320
tatatttata tgtaaaaaat aaaagggaac ccatatgtca taccatacac acaaaaaaat   4380
tccagtgaat tataagtcta aatggagaag gcaaaacttt aaatctttta gaaaataata   4440
tagaagcatg cagaccagcc tggccaacat gatgaaaccc tctctactaa taataaaatc   4500
agtagaacta ctcaggacta ctttgagtgg gaagtccttt tctatgaaga cttctttggc   4560
caaaattagg ctctaaatgc aaggagatag tgcatcatgc ctggctgcac ttactgataa   4620
atgatgttat caccatcttt aaccaaatgc acaggaacaa gttatggtac tgatgtgctg   4680
gattgagaag gagctctact tccttgacag gacacatttg tatcaactta aaaaagcaga   4740
tttttgccag cagaactatt cattcagagg taggaaactt agaatagatg atgtcactga   4800
ttagcatggc ttcccatct ccacagctgc ttcccaccca ggttgccac agttgagttt     4860 gtccagtgct cagggctgcc cactctcagt aagaagcccc acaccagccc ctctccaaat   4920
atgttggctg ttccttccat taaagtgacc ccactttaga gcagcaagtg gatttctgtt   4980
tcttacagtt caggaaggag gagtcagctg tgagaacctg gagcctgaga tgcttctaag   5040
tcccactgct actggggtca gggaagccag actccagcat cagcagtcag gagcactaag   5100
cccttgccaa catcctgttt ctcagagaaa ctgcttccat tataatggtt gtcctttttt   5160
aagctatcaa gccaaacaac cagtgtctac cattattctc atcacctgaa gccaagggtt   5220
ctagcaaaag tcaagctgtc ttgtaatggt tgatgtgcct ccagcttctg tcttcagtca   5280
```

-continued

```
ctccactctt agcctgctct gaatcaactc tgaccacagt tccctggagc ccctgccacc    5340
tgctgcccct gccaccttct ccatctgcag tgctgtgcag ccttctgcac tcttgcagag    5400
ctaataggtg gagacttgaa ggaagaggag gaaagtttct cataatagcc ttgctgcaag    5460
ctcaaatggg aggtgggcac tgtgcccagg agccttggag caaaggctgt gcccaacctc    5520
tgactgcatc caggtttggt cttgacagag ataagaagcc ctggcttttg gagccaaaat    5580
ctaggtcaga cttaggcagg attctcaaag tttatcagca gaacatgagg cagaagaccc    5640
tttctgctcc agcttcttca ggctcaacct tcatcagaat agatagaaag agaggctgtg    5700
agggttctta aaacagaagc aaatctgact cagagaataa acaacctcct agtaaactac    5760
agcttagaca gagcatctgg tggtgagtgt gctcagtgtc ctactcaact gtctggtatc    5820
agccctcatg aggacttctc ttcttttccct catagacctc catctctgtt ttccttagcc    5880
tgcagaaatc tggatggcta ttcacagaat gcctgtgctt tcagagttgc atttttttctc   5940 tggtattctg gttcaagcat ttgaaggtag gaaaggttct ccaagtgcaa gaaagccagc    6000
cctgagcctc aactgcctgg ctagtgtggt cagtaggatg caaaggctgt tgaatgccac    6060
aaggccaaac tttaacctgt gtaccacaag cctagcagca gaggcagctc tgctcactgg    6120
aactctctgt cttctttctc ctgagccttt tcttttcctg agttttctag ctctcctcaa    6180
ccttacctct gccctaccca ggacaaaccc aagagccact gtttctgtga tgtcctctcc    6240
agccctaatt aggcatcatg acttcagcct gaccttccat gctcagaagc agtgctaatc    6300
cacttcagat gagctgctct atgcaacaca ggcagagcct acaaaccttt gcaccagagc    6360
cctccacata tcagtgtttg ttcatactca cttcaacagc aaatgtgact gctgagatta    6420
agattttaca caagatggtc tgtaatttca cagttagttt tatcccatta ggtatgaaag    6480
aattagcata attcccctta aacatgaatg aatcttagat tttttaataa atagttttgg    6540
aagtaaagac agagacatca ggagcacaag gaatagcctg agaggacaaa cagaacaaga    6600
aagagtctgg aaatacacag gatgttcttg gcctcctcaa agcaagtgca agcagatagt    6660
accagcagcc ccaggctatc agagcccagt gaagagaagt accatgaaag ccacagctct    6720
aaccaccctg ttccagagtg acagacagtc cccaagacaa gccagcctga gccagagaga    6780
gaactgcaag agaaagtttc taatttaggt tctgttagat tcagacaagt gcaggtcatc    6840
ctctctccac agctactcac ctctccagcc taacaaagcc tgcagtccac actccaaccc    6900
tggtgtctca cctcctagcc tctcccaaca tcctgctctc tgaccatctt ctgcatctct    6960
catctcacca tctcccactg tctacagcct actcttgcaa ctaccatctc attttctgac    7020
atcctgtcta catcttctgc catactctgc catctaccat accacctctt accatctacc    7080
acaccatctt ttatctccat ccctctcaga agcctccaag ctgaatcctg ctttatgtgt    7140
tcatctcagc ccctgcatgg aaagctgacc ccagaggcag aactattccc agagagcttg    7200
gccaagaaaa acaaaactac cagcctggcc aggctcagga gtagtaagct gcagtgtctg    7260
ttgtgttcta gcttcaacag ctgcaggagt tccactctca aatgctccac atttctcaca    7320
tcctcctgat tctggtcact acccatcttc aaagaacaga atatctcaca tcagcatact    7380
gtgaaggact agtcatgggt gcagctgctc agagctgcaa agtcattctg gatggtggag    7440
agcttacaaa catttcatga tgctcccccc gctctgatgg ctggagccca tccctacac     7500 agactcctgc tgtatgtgtt ttcctttcac tctgagccac agccagaggg caggcattca    7560
gtctcctctt caggctgggg ctggggcact gagaactcac ccaacacctt gctctcactc    7620
cttctgcaaa acaagaaaga gctttgtgct gcagtagcca tgaagaatga aaggaaggct    7680
```

```
ttaactaaaa aatgtcagag attattttca accccttact gtggatcacc agcaaggagg   7740
aaacacaaca cagagacatt ttttcccctc aaattatcaa aagaatcact gcatttgtta   7800
aagagagcaa ctgaatcagg aagcagagtt ttgaacatat cagaagttag gaatctgcat   7860
cagagacaaa tgcagtcatg gttgtttgct gcataccagc cctaatcatt agaagcctca   7920
tggacttcaa acatcattcc ctctgacaag atgctctagc ctaactccat gagataaaat   7980
aaatctgcct ttcagagcca aagaagagtc caccagcttc ttctcagtgt gaacaagagc   8040
tccagtcagg ttagtcagtc cagtgcagta gaggagacca gtctgcatcc tctaattttc   8100
aaaggcaaga agatttgttt accctggaca ccaggcacaa gtgaggtcac agagctctta   8160
gatatgcagt cctcatgagt gaggagacta aagcgcatgc catcaagact tcagtgtaga   8220
gaaaacctcc aaaaaagcct cctcactact tctggaatag ctcagaggcc gaggcggcct   8280
cggcctctgc ataaataaaa aaaattagtc agccatgggg cggagaatgg gcggaactgg   8340
gcggagttag gggcgggatg ggcggagtta ggggcgggac tatggttgct gactaattga   8400
gatgcatgct ttgcatactt ctgcctgctg gggagcctgg ggactttcca cacctggttg   8460
ctgactaatt gagatgcatg ctttgcatac ttctgcctgc tggggagcct ggggactttc   8520
cacaccctaa ctgacacaca ttccacagct gcattaatga atcggccaac gcgcggggag   8580
aggcggtttg cgtattgggc gctcttccgc ttcctcgctc actgactcgc tgcgctcggt   8640
cgttcggctg cggcgagcgg tatcagctca ctcaaaggcg gtaatacggt tatccacaga   8700
atcaggggat aacgcaggaa agaacatgtg agcaaaaggc cagcaaaagg ccaggaaccg   8760
taaaaaggcc gcgttgctgg cgtttttcca taggctccgc ccccctgacg agcatcacaa   8820
aaatcgacgc tcaagtcaga ggtggcgaaa cccgacagga ctataaagat accaggcgtt   8880
tccccctgga agctccctcg tgcgctctcc tgttccgacc ctgccgctta ccggatacct   8940
gtccgccttt ctcccttcgg gaagcgtggc gctttctcat agctcacgct gtaggtatct   9000
cagttcggtg taggtcgttc gctccaagct gggctgtgtg cacgaacccc ccgttcagcc   9060
cgaccgctgc gccttatccg gtaactatcg tcttgagtcc aacccggtaa gacacgactt   9120
atcgccactg gcagcagcca ctggtaacag gattagcaga gcgaggtatg taggcggtgc   9180
tacagagttc ttgaagtggt ggcctaacta cggctacact agaagaacag tatttggtat   9240
ctgcgctctg ctgaagccag ttaccttcgg aaaaagagtt ggtagctctt gatccggcaa   9300
acaaaccacc gctggtagcg gtggtttttt tgtttgcaag cagcagatta cgcgcagaaa   9360
aaaaggatct caagaagatc ctttgatctt ttctacgggg tctgacgctc agtggaacga   9420
aaactcacgt taagggattt tggtcatgag attatcaaaa aggatcttca cctagatcct   9480
tttaaattaa aaatgaagtt ttaaatcaat ctaaagtata tatgagtaaa cttggtctga   9540
cagttaccaa tgcttaatca gtgaggcacc tatctcagcg atctgtctat ttcgttcatc   9600
catagttgcc tgactcctgc aaaccacgtt gtgtctcaaa atctctgatg ttacattgca   9660
caagataaaa atatatcatc atgaacaata aaactgtctg cttacataaa cagtaataca   9720
aggggtgtta tgagccatat tcaacgggaa acgtcttgct cgaggccgcg attaaattcc   9780
aacatggatg ctgatttata tgggtataaa tgggctcgcg ataatgtcgg gcaatcaggt   9840
gcgacaatct atcgattgta tgggaagccc gatgcgccag agttgtttct gaaacatggc   9900
aaaggtagcg ttgccaatga tgttacagat gagatggtca gactaaactg gctgacggaa   9960
tttatgcctc ttccgaccat caagcatttt atccgtactc ctgatgatgc atggttactc   10020
```

```
accactgcga tccccgggaa aacagcattc caggtattag aagaatatcc tgattcaggt   10080
gaaaatattg ttgatgcgct ggcagtgttc ctgcgccggt tgcattcgat tcctgtttgt   10140
aattgtcctt ttaacagcga tcgcgtattt cgtctcgctc aggcgcaatc acgaatgaat   10200
aacggtttgg ttgatgcgag tgattttgat gacgagcgta atggctggcc tgttgaacaa   10260
gtctggaaag aaatgcataa gcttttgcca ttctcaccgg attcagtcgt cactcatggt   10320
gatttctcac ttgataacct tatttttgac gagggggaaat taataggttg tattgatgtt   10380
ggacgagtcg gaatcgcaga ccgataccag gatcttgcca tcctatggaa ctgcctcggt   10440 gagtttctc cttcattaca gaaacggctt tttcaaaaat atggtattga taatcctgat   10500
atgaataaat tgcagtttca tttgatgctc gatgagtttt tctaagggcg gcctgccacc   10560
atacccacgc cgaaacaagc gctcatgagc ccgaagtggc gagcccgatc ttccccatcg   10620
gtgatgtcgg cgatataggc gccagcaacc gcacctgtgg cgccggtgat gagggcgcgc   10680
caagtcgacg tccggcagtc                                             10700
```

```
<210> SEQ ID NO 10
<211> LENGTH: 10700
<212> TYPE: DNA
<213> ORGANISM: Artificial Sequence
<220> FEATURE:
<223> OTHER INFORMATION: Synthetic polynucleotide

<400> SEQUENCE: 10
```

```
ttggccactc cctctctgcg cgctcgctcg ctcactgagg ccgcccgggc aaagcccggg     60
cgtcgggcga cctttggtcg cccggcctca gtgagcgagc gagcgcgcag agagggagtg    120
gccaactcca tcactagggg ttcctgctag ctctgggtat ttaagcccga gtgagcacgc    180
agggtctcca ttttgaagcg ggaggttacg cgttcgtcga ctactagtgg gtaccagagc    240
tccctaggtt ctagaaccgg tgacgtctcc catggtgaag cttggatctg aattcggtac    300
ctagttatta atagtaatca attacggggt cattagttca tagcccatat atggagttcc    360
gcgttacata acttacggta aatggcccgc ctggctgacc gcccaacgac ccccgcccat    420
tgacgtcaat aatgacgtat gttcccatag taacgccaat agggactttc cattgacgtc    480
aatgggtgga gtatttacgg taaactgccc acttggcagt acatcaagtg tatcatatgc    540
caagtacgcc ccctattgac gtcaatgacg gtaaatggcc cgcctggcat tatgcccagt    600
acatgacctt atgggacttt cctacttggc agtacatcta cgtattagtc atcgctatta    660
ccatggtcga ggtgagcccc acgttctgct tcactctccc catctccccc ccctccccac    720
ccccaatttt gtatttattt attttttaat tattttgtgc agcgatgggg gcggggggggg    780 ggggggggcg cgcgccaggc ggggcggggc ggggcgaggg gcgggcgggg gcgaggcgga    840
gaggtgcggc ggcagccaat cagagcggcg cgctccgaaa gtttcctttt atggcgaggc    900
ggcggcggcg gcggccctat aaaaagcgaa gcgcgcggcg ggcgggagtc gctgcgacgc    960
tgccttcgcc ccgtgccccg ctccgccgcc gcctcgcgcc gcccgccccg gctctgactg   1020
accgcgttac tcccacaggt gagcgggcgg gacggccctt ctcctccggg ctgtaattag   1080
cgcttggttt aatgacggct tgtttctttt ctgtggctgc gtgaaagcct tgagggggctc   1140 cgggagctag agcctctgct aaccatgttc atgccttctt ctttttccta cagctcctgg   1200
gcaacgtgct ggttattgtg ctgtctcatc attttggcaa agaattcctc gaagatccga   1260
agggaaagtc ttcacgact gtgggatccg ttcgaagata tcaccggttg agccaccatg   1320
gaattcagca gccccagcag agaggaatgc cccaagcctc tgagccgggt gtcaatcatg   1380
```

-continued

```
gccggatctc tgacaggact gctgctgctt caggccgtgt cttgggcttc tggcgctaga   1440
ccttgcatcc ccaagagctt cggctacagc agcgtcgtgt gcgtgtgcaa tgccacctac   1500
tgcgacagct tcgaccctcc tacctttcct gctctgggca ccttcagcag atacgagagc   1560
accagatccg gcagacggat ggaactgagc atgggaccca tccaggccaa tcacacaggc   1620
actggcctgc tgctgacact gcagcctgag cagaaattcc agaaagtgaa aggcttcggc   1680
ggagccatga cagatgccgc cgctctgaat atcctggctc tgtctccacc agctcagaac   1740
ctgctgctca agagctactt cagcgaggaa ggcatcggct acaacatcat cagagtgccc   1800
atggccagct gcgacttcag catcaggacc tacacctacg ccgacacacc cgacgatttc   1860
cagctgcaca acttcagcct gcctgaagag gacaccaagc tgaagatccc tctgatccac   1920
agagccctgc agctggcaca aagacccgtg tcactgctgg cctctccatg gacatctccc   1980
acctggctga aaacaaatgg cgccgtgaat ggcaagggca gcctgaaagg ccaacctggc   2040
gacatctacc accagacctg ggccagatac ttcgtgaagt tcctggacgc ctatgccgag   2100
cacaagctgc agttttgggc cgtgacagcc gagaacgaac cttctgctgg actgctgagc   2160
ggctacccct ttcagtgcct gggctttaca cccgagcacc agcgggactt tatcgcccgt   2220
gatctgggac ccacactggc caatagcacc caccataatg tgcggctgct gatgctggac   2280
gaccagagac tgcttctgcc ccactgggct aaagtggtgc tgacagatcc tgaggccgcc   2340
aaatacgtgc acggaatcgc cgtgcactgg tatctggact ttctggcccc tgccaaggcc   2400
acactgggag agacacacag actgttcccc aacaccatgc tgttcgccag cgaagcctgt   2460
gtgggcagca gttttgggga acagagcgtg cggctcggca gctgggatag aggcatgcag   2520
tacagccaca gcatcatcac caacctgctg taccacgtcg tcggctggac cgactggaat   2580
ctggccctga tcctgaagg cggccctaac tgggtccgaa acttcgtgga cagccccatc   2640
atcgtggaca tcaccaagga caccttctac aagcagccca tgttctacca cctgggacac   2700
ttcagcaagt tcatccccga gggctctcag cgcgttggac tggtggcttc ccagaagaac   2760
gatctggacg ccgtggctct gatgcaccct gatggatctg ctgtggtggt ggtcctgaac   2820
cgcagcagca aagatgtgcc cctgaccatc aaggatcccg ccgtgggatt cctggaaaca   2880
atcagccctg ctactccat ccacacctac ctgtggcgta gacagtgaca attgttaatt   2940
aagtttaaac cctcgaggcc gcaagcttat cgataatcaa cctctggatt acaaaatttg   3000
tgaaagattg actggtattc ttaactatgt tgctcctttt acgctatgtg gatacgctgc   3060
tttaatgcct ttgtatcatg ctattgcttc ccgtatggct ttcattttct cctccttgta   3120
taaatcctgg ttgctgtctc tttatgagga gttgtggccc gttgtcaggc aacgtggcgt   3180
ggtgtgcact gtgtttgctg acgcaacccc cactggttgg ggcattgcca ccacctgtca   3240
gctcctttcc gggactttcg ctttccccct cccattgcc acggcggaac tcatcgccgc   3300
ctgccttgcc cgctgctgga caggggctcg gctgttgggc actgacaatt ccgtggtgtt   3360
gtcggggaaa tcatcgtcct tccttggct gctcgcctgt gttgccacct ggattctgcg   3420
cgggacgtcc ttctgctacg tcccttcggc cctcaatcca gcggaccttc cttcccgcgg   3480
cctgctgccg gctctgcggc ctcttccgcg tcttcgcctt cgccctcaga cgagtcggat   3540 ctcccttgg gccgcctccc cgcatcgata ccgtcgacta gagctcgctg atcagcctcg   3600
actgtgcctt ctagttgcca gccatctgtt gtttgcccct ccccgtgcc ttccttgacc   3660 ctggaaggtg ccactcccac tgtcctttcc taataaaatg aggaaattgc atcgcattgt   3720
```

-continued

```
ctgagtaggt gtcattctat tctggggggt ggggtggggc aggacagcaa gggggaggat    3780
tgggaagaca atagcaggca tgctggggag agatccacga taacaaacag cttttttggg    3840
gtgaacatat tgactgaatt ccctgcagga ggaacccta gtgatggagt tggccactcc    3900
ctctctgcgc gctcgctcgc tcactgaggc cgcccgggca aagcccgggc gtcgggcgac    3960
ctttggtcgc ccggcctcag tgagcgagcg agcgcgcaga gagggagtgg ccaagcggcc    4020
gctcgtacgg tctcgaggaa ttcctgcagg ataacttgcc aacctcattc taaaatgtat    4080
atagaagccc aaaagacaat aacaaaaata ttcttgtaga acaaatgggg aaagaatgtt    4140
ccactaaata tcaagattta gagcaaagca tgagatgtgt ggggatagac agtgaggctg    4200
ataaaataga gtagagctca gaaacagacc cattgatata tgtaagtgac ctatgaaaaa    4260
aatatggcat tttacaatgg gaaaatgatg gtcttttct tttttagaaa aacagggaaa    4320
tatatttata tgtaaaaaat aaaagggaac ccatatgtca taccatacac acaaaaaaat    4380
tccagtgaat tataagtcta aatggagaag gcaaaacttt aaatctttta gaaaataata    4440
tagaagcatg cagaccagcc tggccaacat gatgaaaccc tctctactaa taataaaatc    4500
agtagaacta ctcaggacta ctttgagtgg gaagtccttt tctatgaaga cttctttggc    4560
caaaattagg ctctaaatgc aaggagatag tgcatcatgc ctggctgcac ttactgataa    4620
atgatgttat caccatcttt aaccaaatgc acaggaacaa gttatggtac tgatgtgctg    4680
gattgagaag gagctctact tccttgacag gacacatttg tatcaactta aaaaagcaga    4740
tttttgccag cagaactatt cattcagagg taggaaactt agaatagatg atgtcactga    4800
ttagcatggc ttccccatct ccacagctgc ttcccaccca ggttgcccac agttgagttt    4860
gtccagtgct cagggctgcc cactctcagt aagaagcccc acaccagccc ctctccaaat    4920
atgttggctg ttccttccat taaagtgacc ccactttaga gcagcaagtg gatttctgtt    4980
tcttacagtt caggaaggag gagtcagctg tgagaacctg gagcctgaga tgcttctaag    5040
tcccactgct actggggtca gggaagccag actccagcat cagcagtcag gagcactaag    5100
cccttgccaa catcctgttt ctcagagaaa ctgcttccat tataatggtt gtcctttttt    5160
aagctatcaa gccaaacaac cagtgtctac cattattctc atcacctgaa gccaagggtt    5220
ctagcaaaag tcaagctgtc ttgtaatggt tgatgtgcct ccagcttctg tcttcagtca    5280
ctccactctt agcctgctct gaatcaactc tgaccacagt tccctggagc ccctgccacc    5340
tgctgcccct gccaccttct ccatctgcag tgctgtgcag ccttctgcac tcttgcagag    5400
ctaataggtg gagacttgaa ggaagaggag gaaagtttct cataatagcc ttgctgcaag    5460
ctcaaatggg aggtgggcac tgtgcccagg agccttggag caaaggctgt gcccaacctc    5520
tgactgcatc caggtttggt cttgacagag ataagaagcc ctggcttttg gagccaaaat    5580
ctaggtcaga cttaggcagg attctcaaag tttatcagca gaacatgagg cagaagaccc    5640
tttctgctcc agcttcttca ggctcaacct tcatcagaat agatagaaag agaggctgtg    5700
agggttctta aaacagaagc aaatctgact cagagaataa acaacctcct agtaaactac    5760
agcttagaca gagcatctgg tggtgagtgt gctcagtgtc ctactcaact gtctggtatc    5820
agccctcatg aggacttctc ttctttccct catagacctc catctctgtt ttccttagcc    5880
tgcagaaatc tggatggcta ttcacagaat gcctgtgctt tcagagttgc attttttctc    5940
tggtattctg gttcaagcat ttgaaggtag gaaaggttct ccaagtgcaa gaaagccagc    6000
cctgagcctc aactgcctgg ctagtgtggt cagtaggatg caaaggctgt tgaatgccac    6060
aaggccaaac tttaacctgt gtaccacaag cctagcagca gaggcagctc tgctcactgg    6120
```

-continued

```
aactctctgt cttctttctc ctgagccttt tcttttcctg agttttctag ctctcctcaa   6180
ccttacctct gccctaccca ggacaaaccc aagagccact gtttctgtga tgtcctctcc   6240
agccctaatt aggcatcatg acttcagcct gaccttccat gctcagaagc agtgctaatc   6300
cacttcagat gagctgctct atgcaacaca ggcagagcct acaaaccttt gcaccagagc   6360
cctccacata tcagtgtttg ttcatactca cttcaacagc aaatgtgact gctgagatta   6420
agattttaca caagatggtc tgtaatttca cagttagttt tatcccatta ggtatgaaag   6480
aattagcata attcccctta aacatgaatg aatcttagat tttttaataa atagttttgg   6540
aagtaaagac agagacatca ggagcacaag gaatagcctg agaggacaaa cagaacaaga   6600
aagagtctgg aaatacacag gatgttcttg gcctcctcaa agcaagtgca agcagatagt   6660
accagcagcc ccaggctatc agagcccagt gaagagaagt accatgaaag ccacagctct   6720
aaccaccctg ttccagagtg acagacagtc cccaagacaa gccagcctga gccagagaga   6780
gaactgcaag agaaagtttc taatttaggt tctgttagat tcagacaagt gcaggtcatc   6840
ctctctccac agctactcac ctctccagcc taacaaagcc tgcagtccac actccaaccc   6900
tggtgtctca cctcctagcc tctcccaaca tcctgctctc tgaccatctt ctgcatctct   6960
catctcacca tctcccactg tctacagcct actcttgcaa ctaccatctc attttctgac   7020
atcctgtcta catcttctgc catactctgc catctaccat accacctctt accatctacc   7080
acaccatctt ttatctccat ccctctcaga agcctccaag ctgaatcctg ctttatgtgt   7140
tcatctcagc ccctgcatgg aaagctgacc ccagaggcag aactattccc agagagcttg   7200
gccaagaaaa acaaaactac cagcctggcc aggctcagga gtagtaagct gcagtgtctg   7260
ttgtgttcta gcttcaacag ctgcaggagt tccactctca aatgctccac atttctcaca   7320
tcctcctgat tctggtcact acccatcttc aaagaacaga atatctcaca tcagcatact   7380
gtgaaggact agtcatgggt gcagctgctc agagctgcaa agtcattctg gatggtggag   7440
agcttacaaa catttcatga tgctcccccc gctctgatgg ctggagccca atccctacac   7500
agactcctgc tgtatgtgtt ttcctttcac tctgagccac agccagaggg caggcattca   7560
gtctcctctt caggctgggg ctggggcact gagaactcac ccaacacctt gctctcactc   7620
cttctgcaaa acaagaaaga gctttgtgct gcagtagcca tgaagaatga aaggaaggct   7680
ttaactaaaa aatgtcagag attatttttca accccttact gtggatcacc agcaaggagg   7740
aaacacaaca cagagacatt ttttcccctc aaattatcaa aagaatcact gcatttgtta   7800
aagagagcaa ctgaatcagg aagcagagtt ttgaacatat cagaagttag gaatctgcat   7860
cagagacaaa tgcagtcatg gttgtttgct gcataccagc cctaatcatt agaagcctca   7920
tggacttcaa acatcattcc ctctgacaag atgctctagc ctaactccat gagataaaat   7980
aaatctgcct ttcagagcca aagaagagtc caccagcttc ttctcagtgt gaacaagagc   8040
tccagtcagg ttagtcagtc cagtgcagta gaggagacca gtctgcatcc tctaatttc   8100 aaaggcaaga agatttgttt accctggaca ccaggcacaa gtgaggtcac agagctctta   8160
gatatgcagt cctcatgagt gaggagacta aagcgcatgc catcaagact tcagtgtaga   8220
gaaaacctcc aaaaaagcct cctcactact tctggaatag ctcagaggcc gaggcggcct   8280
cggcctctgc ataaataaaa aaaattagtc agccatgggg cggagaatgg gcggaactgg   8340
gcggagttag gggcgggatg ggcggagtta ggggcgggac tatggttgct gactaattga   8400
gatgcatgct ttgcatactt ctgcctgctg gggagcctgg ggactttcca cacctggttg   8460
```

-continued

```
ctgactaatt gagatgcatg ctttgcatac ttctgcctgc tggggagcct ggggactttc    8520
cacaccctaa ctgacacaca ttccacagct gcattaatga atcggccaac gcgcggggag    8580
aggcggtttg cgtattgggc gctcttccgc ttcctcgctc actgactcgc tgcgctcggt    8640
cgttcggctg cggcgagcgg tatcagctca ctcaaaggcg gtaatacggt tatccacaga    8700
atcaggggat aacgcaggaa agaacatgtg agcaaaaggc cagcaaaagg ccaggaaccg    8760
taaaaaggcc gcgttgctgg cgttttccca taggctccgc cccctgacg agcatcacaa     8820 aaatcgacgc tcaagtcaga ggtggcgaaa cccgacagga ctataaagat accaggcgtt    8880
tccccctgga agctccctcg tgcgctctcc tgttccgacc ctgccgctta ccggatacct    8940
gtccgccttt ctcccttcgg gaagcgtggc gctttctcat agctcacgct gtaggtatct    9000
cagttcggtg taggtcgttc gctccaagct gggctgtgtg cacgaacccc ccgttcagcc    9060
cgaccgctgc gccttatccg gtaactatcg tcttgagtcc aacccggtaa gacacgactt    9120
atcgccactg gcagcagcca ctggtaacag gattagcaga gcgaggtatg taggcggtgc    9180
tacagagttc ttgaagtggt ggcctaacta cggctacact agaagaacag tatttggtat    9240
ctgcgctctg ctgaagccag ttaccttcgg aaaaagagtt ggtagctctt gatccggcaa    9300
acaaaccacc gctggtagcg gtggtttttt tgtttgcaag cagcagatta cgcgcagaaa    9360
aaaaggatct caagaagatc ctttgatctt ttctacgggg tctgacgctc agtggaacga    9420
aaactcacgt taagggattt tggtcatgag attatcaaaa aggatcttca cctagatcct    9480
tttaaattaa aaatgaagtt ttaaatcaat ctaaagtata tatgagtaaa cttggtctga    9540
cagttaccaa tgcttaatca gtgaggcacc tatctcagcg atctgtctat ttcgttcatc    9600
catagttgcc tgactcctgc aaaccacgtt gtgtctcaaa atctctgatg ttacattgca    9660
caagataaaa atatatcatc atgaacaata aaactgtctg cttacataaa cagtaataca    9720
aggggtgtta tgagccatat tcaacgggaa acgtcttgct cgaggccgcg attaaattcc    9780
aacatggatg ctgatttata tgggtataaa tgggctcgcg ataatgtcgg gcaatcaggt    9840
gcgacaatct atcgattgta tgggaagccc gatgcgccag agttgtttct gaaacatggc    9900
aaaggtagcg ttgccaatga tgttacagat gagatggtca gactaaactg gctgacggaa    9960
tttatgcctc ttccgaccat caagcatttt atccgtactc ctgatgatgc atggttactc    10020
accactgcga tccccgggaa aacagcattc caggtattag aagaatatcc tgattcaggt    10080
gaaaatattg ttgatgcgct ggcagtgttc ctgcgccggt tgcattcgat tcctgtttgt    10140
aattgtcctt ttaacagcga tcgcgtattt cgtctcgctc aggcgcaatc acgaatgaat    10200
aacggtttgg ttgatgcgag tgattttgat gacgagcgta atggctggcc tgttgaacaa    10260
gtctggaaag aaatgcataa gcttttgcca ttctcaccgg attcagtcgt cactcatggt    10320
gatttctcac ttgataacct tattttgac gaggggaaat aataggttg tattgatgtt       10380 ggacgagtcg gaatcgcaga ccgataccag gatcttgcca tcctatggaa ctgcctcggt    10440
gagttttctc cttcattaca gaaacggctt tttcaaaaat atggtattga taatcctgat    10500
atgaataaat tgcagtttca tttgatgctc gatgagtttt tctaagggcg gcctgccacc    10560
atacccacgc cgaaacaagc gctcatgagc ccgaagtggc gagcccgatc ttccccatcg    10620
gtgatgtcgg cgatataggc gccagcaacc gcacctgtgg cgccggtgat gagggcgcgc    10680
caagtcgacg tccggcagtc                                                10700
```

<210> SEQ ID NO 11
<211> LENGTH: 11188

<212> TYPE: DNA
<213> ORGANISM: Artificial Sequence
<220> FEATURE:
<223> OTHER INFORMATION: Synthetic polynucleotide

<400> SEQUENCE: 11

```
ttggccactc cctctctgcg cgctcgctcg ctcactgagg ccgggcgacc aaaggtcgcc        60
cgacgcccgg gctttgcccg ggcggcctca gtgagcgagc gagcgcgcag agagggagtg       120
gccaactatt agatctgatg gccgcgctag ctctgggtat ttaagcccga gtgagcacgc       180
agggtctcca tttttgaagcg ggaggttacg cgttcgtcga ctactagtgg gtaccagagc       240
gtggtgactg agatgttttc taggaaacac aaaagataca aaaaagaaca cgtggaagga       300
tagccaaaaa gggggggctgc ccccatttcc tgcaccccgc tgcgatggct ggcaccattt       360
ggaagacttc gagatacact gttgagcgca gtaagacaac agtgtatctc gaagtcttcc       420
agatggggcc agccggtcca ctctgtatcc aggccagttc tgcaaggcgt tcgaggacca       480 ccccctccc ctcgccacca gggtggtctc atacagaact tataagattc ccaaatccaa       540
agacatttca cgtttatggt gatttcccag aacacatagc gacatgcaaa tattgcaggg       600
cgccactccc ctgtccctca cagccatctt cctgccaggg cgcacgcgcg ctgggtgttc       660
ccgcctagtg acactgggcc cgcgattcct tggagcgggt tgatgacgtc agcgtttccc       720
atggtgaatc cctaggttct agaaccggtg acgtctccca tggtgaagct tggatctgaa       780
ttcggtacct agttattaat agtaatcaat tacggggtca ttagttcata gcccatatat       840
ggagttccgc gttacataac ttacggtaaa tggcccgcct ggctgaccgc ccaacgaccc       900
ccgcccattg acgtcaataa tgacgtatgt tcccatagta acgccaatag ggactttcca       960
ttgacgtcaa tgggtggagt atttacggta aactgcccac ttggcagtac atcaagtgta      1020
tcatatgcca agtacgcccc ctattgacgt caatgacggt aaatggcccg cctggcatta      1080
tgcccagtac atgaccttat gggactttcc tacttggcag tacatctacg tattagtcat      1140
cgctattacc atggtcgagg tgagccccac gttctgcttc actctcccca tctccccccc      1200
ctccccaccc ccaattttgt atttatttat tttttaatta ttttgtgcag cgatggggc      1260 gggggggggg gggggcgcg cgccaggcgg ggcggggcgg ggcgagggc ggggcggggc      1320 gaggcggaga ggtgcggcgg cagccaatca gagcggcgcg ctccgaaagt ttcctttat      1380 ggcgaggcgg cggcggcggc ggccctataa aaagcgaagc gcgcggcggg cgggagtcgc      1440
tgcgacgctg ccttcgcccc gtgccccgct ccgccgccgc ctcgcgccgc ccgccccggc      1500
tctgactgac cgcgttactc ccacaggtga gcgggcggga cggcccttct cctccgggct      1560
gtaattagcg cttggtttaa tgacggcttg tttcttttct gtggctgcgt gaaagccttg      1620
aggggctccg ggagctagag cctctgctaa ccatgttcat gccttcttct ttttcctaca      1680
gctcctgggc aacgtgctgg ttattgtgct gtctcatcat tttggcaaag aattcctcga      1740
agatccgaag ggaaagtctt ccacgactgt gggatccgtt cgaagatatc accggttgag      1800
ccaccatgga attcagcagc cccagcagag aggaatgccc caagcctctg agccgggtgt      1860
caatcatggc cggatctctg acaggactgc tgctgcttca ggccgtgtct gggcttctg      1920 gcgctagacc ttgcatcccc aagagcttcg gctacagcag cgtcgtgtgc gtgtgcaatg      1980
ccacctactg cgacagcttc gaccctccta cctttcctgc tctgggcacc ttcagcagat      2040
acgagagcac cagatccggc agacggatgg aactgagcat gggacccatc caggccaatc      2100
acacaggcac tggcctgctg ctgacactgc agcctgagca gaaattccag aaagtgaaag      2160
```

-continued

```
gcttcggcgg agccatgaca gatgccgccg ctctgaatat cctggctctg tctccaccag    2220
ctcagaacct gctgctcaag agctacttca gcgaggaagg catcggctac aacatcatca    2280
gagtgcccat ggccagctgc gacttcagca tcaggaccta cacctacgcc gacacacccg    2340
acgatttcca gctgcacaac ttcagcctgc ctgaagagga caccaagctg aagatccctc    2400
tgatccacag agccctgcag ctggcacaaa gacccgtgtc actgctggcc tctccatgga    2460
catctcccac ctggctgaaa acaaatggcg ccgtgaatgg caagggcagc ctgaaaggcc    2520
aacctggcga catctaccac cagacctggg ccagatactt cgtgaagttc ctggacgcct    2580
atgccgagca caagctgcag ttttgggccg tgacagccga gaacgaacct tctgctggac    2640
tgctgagcgg ctacccccttt cagtgcctgg gctttacacc cgagcaccag cgggacttta    2700
tcgcccgtga tctgggaccc acactggcca atagcaccca ccataatgtg cggctgctga    2760
tgctggacga ccagagactg cttctgcccc actgggctaa agtggtgctg acagatcctg    2820
aggccgccaa atacgtgcac ggaatcgccg tgcactggta tctggacttt ctggcccctg    2880
ccaaggccac actgggagag acacacagac tgttccccaa caccatgctg ttcgccagcg    2940
aagcctgtgt gggcagcaag ttttgggaac agagcgtgcg gctcggcagc tgggatagag    3000
gcatgcagta cagccacagc atcatcacca acctgctgta ccacgtcgtc ggctggaccg    3060
actggaatct ggccctgaat cctgaaggcg ccctaactg ggtccgaaac ttcgtggaca    3120
gccccatcat cgtggacatc accaaggaca ccttctacaa gcagcccatg ttctaccacc    3180
tgggacactt cagcaagttc atccccgagg gctctcagcg cgttggactg gtggcttccc    3240
agaagaacga tctggacgcc gtggctctga tgcaccctga tggatctgct gtggtggtgg    3300
tcctgaaccg cagcagcaaa gatgtgcccc tgaccatcaa ggatcccgcc gtgggattcc    3360
tggaaacaat cagccctggc tactccatcc acacctacct gtggcgtaga cagtgacaat    3420
tgttaattaa gtttaaaccc tcgaggccgc aagcttatcg ataatcaacc tctggattac    3480
aaaatttgtg aaagattgac tggtattctt aactatgttg ctcctttac gctatgtgga    3540 tacgctgctt taatgccttt gtatcatgct attgcttccc gtatggcttt cattttctcc    3600
tccttgtata aatcctggtt gctgtctctt tatgaggagt tgtggcccgt tgtcaggcaa    3660
cgtggcgtgg tgtgcactgt gtttgctgac gcaacccccca ctggttgggg cattgccacc    3720
acctgtcagc tcctttccgg gactttcgct ttccccctcc ctattgccac ggcggaactc    3780
atcgccgcct gccttgcccg ctgctggaca ggggctcggc tgttgggcac tgacaattcc    3840
gtggtgttgt cggggaaatc atcgtccttt ccttggctgc tcgcctgtgt tgccacctgg    3900
attctgcgcg ggacgtcctt ctgctacgtc ccttcggccc tcaatccagc ggaccttcct    3960
tcccgcggcc tgctgccggc tctgcggcct cttccgcgtc ttcgccttcg ccctcagacg    4020
agtcggatct cccttgggc cgcctccccg catcgatacc gtcgactaga gctcgctgat    4080
cagcctcgac tgtgccttct agttgccagc catctgttgt ttgcccctcc cccgtgcctt    4140
ccttgaccct ggaaggtgcc actcccactg tcctttccta ataaaatgag gaaattgcat    4200
cgcattgtct gagtaggtgt cattctattc tggggggtgg ggtggggcag gacagcaagg    4260
gggaggattg ggaagacaat agcaggcatg ctggggagag atccacgata acaaacagct    4320
tttttggggt gaacatattg actgaattcc ctgcaggttg gccactccct ctctgcgcgc    4380
tcgctcgctc actgaggccg cccgggcaaa gcccgggcgt cgggcgacct ttggtcgccc    4440
ggcctcagtg agcgagcgag cgcgcagaga gggagtggcc aactccatca ctaggggttc    4500
ctgcggccgc tcgtacggtc tcgaggaatt cctgcaggat aacttgccaa cctcattcta    4560
```

```
aaatgtatat agaagcccaa aagacaataa caaaaatatt cttgtagaac aaaatgggaa    4620
agaatgttcc actaaatatc aagatttaga gcaaagcatg agatgtgtgg ggatagacag    4680
tgaggctgat aaaatagagt agagctcaga aacagaccca ttgatatatg taagtgacct    4740
atgaaaaaaa tatggcattt tacaatggga aaatgatggt ctttttcttt tttagaaaaa    4800
cagggaaata tatttatatg taaaaaataa aagggaaccc atatgtcata ccatacacac    4860
aaaaaaattc cagtgaatta taagtctaaa tggagaaggc aaaactttaa atcttttaga    4920
aaataatata gaagcatgca gaccagcctg gccaacatga tgaaaccctc tctactaata    4980
ataaaatcag tagaactact caggactact ttgagtggga agtccttttc tatgaagact    5040
tctttggcca aaattaggct ctaaatgcaa ggagatagtg catcatgcct ggctgcactt    5100
actgataaat gatgttatca ccatctttaa ccaaatgcac aggaacaagt tatggtactg    5160
atgtgctgga ttgagaagga gctctacttc cttgacagga cacatttgta tcaacttaaa    5220
aaagcagatt tttgccagca gaactattca ttcagaggta ggaaacttag aatagatgat    5280
gtcactgatt agcatggctt ccccatctcc acagctgctt cccacccagg ttgcccacag    5340
ttgagtttgt ccagtgctca gggctgccca ctctcagtaa gaagcccac accagcccct     5400 ctccaaatat gttggctgtt ccttccatta aagtgacccc actttagagc agcaagtgga    5460
tttctgtttc ttacagttca ggaaggagga gtcagctgtg agaacctgga gcctgagatg    5520
cttctaagtc ccactgctac tggggtcagg gaagccagac tccagcatca gcagtcagga    5580
gcactaagcc cttgccaaca tcctgtttct cagagaaact gcttccatta taatggttgt    5640 cctttttta gctatcaagc caaacaacca gtgtctacca ttattctcat cacctgaagc     5700
caagggttct agcaaaagtc aagctgtctt gtaatggttg atgtgcctcc agcttctgtc    5760
ttcagtcact ccactcttag cctgctctga atcaactctg accacagttc cctggagccc    5820
ctgccacctg ctgcccctgc caccttctcc atctgcagtg ctgtgcagcc ttctgcactc    5880
ttgcagagct aataggtgga gacttgaagg aagaggagga aagtttctca taatagcctt    5940
gctgcaagct caaatgggag gtgggcactg tgcccaggag ccttggagca aaggctgtgc    6000
ccaacctctg actgcatcca ggtttggtct tgacagagat aagaagccct ggcttttgga    6060
gccaaaatct aggtcagact taggcaggat tctcaaagtt tatcagcaga acatgaggca    6120
gaagaccctt tctgctccag cttcttcagg ctcaaccttc atcagaatag atagaaagag    6180
aggctgtgag ggttcttaaa acagaagcaa atctgactca gagaataaac aacctcctag    6240
taaactacag cttagacaga gcatctggtg gtgagtgtgc tcagtgtcct actcaactgt    6300
ctggtatcag ccctcatgag gacttctctt ctttccctca tagacctcca tctctgtttt    6360
ccttagcctg cagaaatctg gatggctatt cacagaatgc ctgtgctttc agagttgcat    6420
tttttctctg gtattctggt tcaagcattt gaaggtagga aaggttctcc aagtgcaaga    6480
aagccagccc tgagcctcaa ctgcctggct agtgtggtca gtaggatgca aaggctgttg    6540
aatgccacaa ggccaaactt taacctgtgt accacaagcc tagcagcaga ggcagctctg    6600
ctcactggaa ctctctgtct tctttctcct gagcctttc tttcctgag ttttctagct      6660 ctcctcaacc ttacctctgc cctacccagg acaaacccaa gagccactgt ttctgtgatg    6720
tcctctccag ccctaattag gcatcatgac ttcagcctga ccttccatgc tcagaagcag    6780
tgctaatcca cttcagatga gctgctctat gcaacacagg cagagcctac aaacctttgc    6840
accagagccc tccacatatc agtgtttgtt catactcact tcaacagcaa atgtgactgc    6900
```

-continued

```
tgagattaag attttacaca agatggtctg taatttcaca gttagtttta tcccattagg    6960
tatgaaagaa ttagcataat tccccttaaa catgaatgaa tcttagattt tttaataaat    7020
agttttggaa gtaaagacag agacatcagg agcacaagga atagcctgag aggacaaaca    7080
gaacaagaaa gagtctggaa atacacagga tgttcttggc ctcctcaaag caagtgcaag    7140
cagatagtac cagcagcccc aggctatcag agcccagtga agagaagtac catgaaagcc    7200
acagctctaa ccaccctgtt ccagagtgac agacagtccc caagacaagc cagcctgagc    7260
cagagagaga actgcaagag aaagtttcta atttaggttc tgttagattc agacaagtgc    7320
aggtcatcct ctctccacag ctactcacct ctccagccta acaaagcctg cagtccacac    7380
tccaaccctg gtgtctcacc tcctagcctc tcccaacatc ctgctctctg accatcttct    7440
gcatctctca tctcaccatc tcccactgtc tacagcctac tcttgcaact accatctcat    7500
tttctgacat cctgtctaca tcttctgcca tactctgcca tctaccatac cacctcttac    7560
catctaccac accatctttt atctccatcc ctctcagaag cctccaagct gaatcctgct    7620
ttatgtgttc atctcagccc ctgcatggaa agctgacccc agaggcagaa ctattcccag    7680
agagcttggc caagaaaaac aaaactacca gcctggccag gctcaggagt agtaagctgc    7740
agtgtctgtt gtgttctagc ttcaacagct gcaggagttc cactctcaaa tgctccacat    7800
ttctcacatc ctcctgattc tggtcactac ccatcttcaa agaacagaat atctcacatc    7860
agcatactgt gaaggactag tcatgggtgc agctgctcag agctgcaaag tcattctgga    7920
tggtggagag cttacaaaca tttcatgatg ctcccccccgc tctgatggct ggagcccaat    7980
ccctacacag actcctgctg tatgtgtttt cctttcactc tgagccacag ccagagggca    8040
ggcattcagt ctcctcttca ggctggggct ggggcactga gaactcaccc aacaccttgc    8100
tctcactcct tctgcaaaac aagaaagagc tttgtgctgc agtagccatg aagaatgaaa    8160
ggaaggcttt aactaaaaaa tgtcagagat tattttcaac cccttactgt ggatcaccag    8220
caaggaggaa acacaacaca gagacatttt ttccccctcaa attatcaaaa gaatcactgc    8280
atttgttaaa gagagcaact gaatcaggaa gcagagtttt gaacatatca gaagttagga    8340
atctgcatca gagacaaatg cagtcatggt tgtttgctgc ataccagccc taatcattag    8400
aagcctcatg gacttcaaac atcattccct ctgacaagat gctctagcct aactccatga    8460
gataaaataa atctgccttt cagagccaaa gaagagtcca ccagcttctt ctcagtgtga    8520
acaagagctc cagtcaggtt agtcagtcca gtgcagtaga ggagaccagt ctgcatcctc    8580
taattttcaa aggcaagaag atttgtttac cctggacacc aggcacaagt gaggtcacag    8640
agctcttaga tatgcagtcc tcatgagtga ggagactaaa gcgcatgcca tcaagacttc    8700
agtgtagaga aaacctccaa aaaagcctcc tcactacttc tggaatagct cagaggccga    8760
ggcggcctcg gcctctgcat aaataaaaaa aattagtcag ccatggggcg gagaatgggc    8820
ggaactgggc ggagttaggg gcgggatggg cggagttagg ggcgggacta tggttgctga    8880
ctaattgaga tgcatgcttt gcatacttct gcctgctggg gagcctgggg actttccaca    8940
cctggttgct gactaattga gatgcatgct ttgcatactt ctgcctgctg gggagcctgg    9000
ggactttcca caccctaact gacacacatt ccacagctgc attaatgaat cggccaacgc    9060 gcgggggagag gcggtttgcg tattgggcgc tcttccgctt cctcgctcac tgactcgctg    9120
cgctcggtcg ttcggctgcg gcgagcggta tcagctcact caaaggcggt aatacggtta    9180
tccacagaat caggggataa cgcaggaaag aacatgtgag caaaaggcca gcaaaaggcc    9240
aggaaccgta aaaaggccgc gttgctggcg tttttccata ggctccgccc ccctgacgag    9300
```

-continued

```
catcacaaaa atcgacgctc aagtcagagg tggcgaaacc cgacaggact ataaagatac     9360
caggcgtttc cccctggaag ctccctcgtg cgctctcctg ttccgaccct gccgcttacc     9420
ggatacctgt ccgcctttct cccttcggga agcgtggcgc tttctcatag ctcacgctgt     9480
aggtatctca gttcggtgta ggtcgttcgc tccaagctgg gctgtgtgca cgaacccccc     9540
gttcagcccg accgctgcgc cttatccggt aactatcgtc ttgagtccaa cccggtaaga     9600
cacgacttat cgccactggc agcagccact ggtaacagga ttagcagagc gaggtatgta     9660
ggcggtgcta cagagttctt gaagtggtgg cctaactacg gctacactag aagaacagta     9720
tttggtatct gcgctctgct gaagccagtt accttcggaa aaagagttgg tagctcttga     9780
tccggcaaac aaaccaccgc tggtagcggt ggtttttttg tttgcaagca gcagattacg     9840
cgcagaaaaa aaggatctca agaagatcct ttgatctttt ctacggggtc tgacgctcag     9900
tggaacgaaa actcacgtta agggattttg gtcatgagat tatcaaaaag gatcttcacc     9960
tagatccttt taaattaaaa atgaagtttt aaatcaatct aaagtatata tgagtaaact    10020
tggtctgaca gttaccaatg cttaatcagt gaggcaccta tctcagcgat ctgtctattt    10080
cgttcatcca tagttgcctg actcctgcaa accacgttgt gtctcaaaat ctctgatgtt    10140
acattgcaca agataaaaat atatcatcat gaacaataaa actgtctgct tacataaaca    10200
gtaatacaag gggtgttatg agccatattc aacgggaaac gtcttgctcg aggccgcgat    10260
taaattccaa catggatgct gatttatatg ggtataaatg ggctcgcgat aatgtcgggc    10320
aatcaggtgc gacaatctat cgattgtatg ggaagcccga tgcgccagag ttgtttctga    10380
aacatggcaa aggtagcgtt gccaatgatg ttacagatga gatggtcaga ctaaactggc    10440
tgacggaatt tatgcctctt ccgaccatca agcattttat ccgtactcct gatgatgcat    10500
ggttactcac cactgcgatc cccgggaaaa cagcattcca ggtattagaa gaatatcctg    10560
attcaggtga aaatattgtt gatgcgctgg cagtgttcct gcgccggttg cattcgattc    10620
ctgtttgtaa ttgtcctttt aacagcgatc gcgtatttcg tctcgctcag gcgcaatcac    10680
gaatgaataa cggtttggtt gatgcgagtg attttgatga cgagcgtaat ggctggcctg    10740
ttgaacaagt ctggaaagaa atgcataagc ttttgccatt ctcaccggat tcagtcgtca    10800
ctcatggtga tttctcactt gataacctta ttttttgacga ggggaaatta ataggttgta    10860
ttgatgttgg acgagtcgga atcgcagacc gataccagga tcttgccatc ctatggaact    10920
gcctcggtga gttttctcct tcattacaga aacggctttt tcaaaaatat ggtattgata    10980
atcctgatat gaataaattg cagtttcatt tgatgctcga tgagtttttc taagggcggc    11040
ctgccaccat acccacgccg aaacaagcgc tcatgagccc gaagtggcga gcccgatctt    11100
ccccatcggt gatgtcggcg atataggcgc cagcaaccgc acctgtggcg ccggtgatga    11160
gggcgcgcca agtcgacgtc cggcagtc                                       11188
```

```
<210> SEQ ID NO 12
<211> LENGTH: 11187
<212> TYPE: DNA
<213> ORGANISM: Artificial Sequence
<220> FEATURE:
<223> OTHER INFORMATION: Synthetic polynucleotide

<400> SEQUENCE: 12
ctagaaccgg tgacgtctcc catggtgaag cttggatctg aattcggtac ctagttataa       60
tagtaatcaa ttacggggtc attagttcat agcccatata tggagttccg cgttacataa      120
```

-continued

```
cttacggtaa atggcccgcc tggctgaccg cccaacgacc cccgcccatt gacgtcaata        180
atgacgtatg ttcccatagt aacgccaata gggactttcc attgacgtca atgggtggag        240
tatttacggt aaactgccca cttggcagta catcaagtgt atcatatgcc aagtacgccc        300
cctattgacg tcaatgacgg taaatggccc gcctggcatt atgcccagta catgacctta        360
tgggactttc ctacttggca gtacatctac gtattagtca tcgctattac catggtcgag        420
gtgagcccca cgttctgctt cactctcccc atctcccccc cctccccacc cccaattttg        480
tatttattta ttttttaatt attttgtgca gcgatggggg cggggggggg ggggggcgc        540 gcgccaggcg gggcggggcg gggcgagggg cggggcgggg cgaggcggag aggtgcggcg        600
gcagccaatc agagcggcgc gctccgaaag tttccttttta tggcgaggcg gcggcggcgg        660
cggccctata aaaagcgaag cgcgcggcgg gcgggagtcg ctgcgacgct gccttcgccc        720
cgtgccccgc tccgccgccg cctcgcgccg cccgccccgg ctctgactga ccgcgttact        780
cccacaggtg agcgggcggg acggcccttc tcctccgggc tgtaattagc gcttggttta        840
atgacggctt gtttcttttc tgtggctgcg tgaaagcctt gaggggctcc gggagctaga        900
gcctctgcta accatgttca tgccttcttc ttttttcctac agctcctggg caacgtgctg        960
gttattgtgc tgtctcatca ttttggcaaa gaattcctcg aagatccgaa gggaaagtct       1020
tccacgactg tgggatccgt tcgaagatat caccggttga gccaccatgg aattcagcag       1080
ccccagcaga gaggaatgcc ccaagcctct gagccgggtg tcaatcatgg ccggatctct       1140
gacaggactg ctgctgcttc aggccgtgtc ttgggcttct ggcgctagac cttgcatccc       1200
caagagcttc ggctacagca gcgtcgtgtg cgtgtgcaat gccacctact gcgacagctt       1260
cgaccctcct acctttcctg ctctgggcac cttcagcaga tacgagagca ccagatccgg       1320
cagacggatg gaactgagca tgggacccat ccaggccaat cacacaggca ctggcctgct       1380
gctgacactg cagcctgagc agaaattcca gaaagtgaaa ggcttcggcg agccatgac       1440 agatgccgcc gctctgaata tcctggctct gtctccacca gctcagaacc tgctgctcaa       1500
gagctacttc agcgaggaag gcatcggcta caacatcatc agagtgccca tggccagctg       1560
cgacttcagc atcaggacct acacctacgc cgacacaccc gacgatttcc agctgcacaa       1620
cttcagcctg cctgaagagg acaccaagct gaagatccct ctgatccaca gagccctgca       1680
gctggcacaa agaccgtgt cactgctggc ctctccatgg acatctccca cctggctgaa        1740
aacaaatggc gccgtgaatg gcaagggcag cctgaaaggc caacctggcg acatctacca       1800
ccagacctgg gccagatact cgtgaagtt cctggacgcc tatgccgagc acaagctgca       1860
gttttgggcc gtgacagccg agaacgaacc ttctgctgga ctgctgagcg gctacccctt       1920
tcagtgcctg ggctttacac ccgagcacca gcgggacttt atcgcccgtg atctgggacc       1980
cacactggcc aatagcaccc accataatgt gcggctgctg atgctggacg accagagact       2040
gcttctgccc cactgggcta aagtggtgct gacagatcct gaggccgcca aatacgtgca       2100
cggaatcgcc gtgcactggt atctggactt tctggcccct gccaaggcca cactgggaga       2160
gacacacaga ctgttcccca acaccatgct gttcgccagc gaagcctgtg tgggcagcaa       2220
gttttgggaa cagagcgtgc ggctcggcag ctgggtagaa ggcatgcagt acagccacag       2280
catcatcacc aacctgctgt accacgtcgt cggctggacc gactggaatc tggccctgaa       2340
tcctgaaggc ggccctaact gggtccgaaa cttcgtggac agcccatca tcgtggacat        2400 caccaaggac accttctaca agcagcccat gttctaccac ctgggacact tcagcaagtt       2460
catccccgag ggctctcagc gcgttggact ggtggcttcc cagaagaacg atctggacgc       2520
```

-continued

```
cgtggctctg atgcaccctg atggatctgc tgtggtggtg gtcctgaacc gcagcagcaa      2580
agatgtgccc ctgaccatca aggatcccgc cgtgggattc ctggaaacaa tcagccctgg      2640
ctactccatc cacacctacc tgtggcgtag acagtgacaa ttgttaatta agtttaaacc      2700
ctcgaggccg caagcttatc gataatcaac ctctggatta caaaatttgt gaaagattga      2760
ctggtattct taactatgtt gctccttta cgctatgtgg atacgctgct ttaatgcctt       2820
tgtatcatgc tattgcttcc cgtatggctt tcattttctc ctccttgtat aaatcctggt      2880
tgctgtctct ttatgaggag ttgtggcccg ttgtcaggca acgtggcgtg gtgtgcactg      2940
tgtttgctga cgcaacccccc actggttggg gcattgccac cacctgtcag ctcctttccg     3000
ggactttcgc tttcccccctc cctattgcca cggcggaact catcgccgcc tgccttgccc      3060
gctgctggac aggggctcgg ctgttgggca ctgacaattc cgtggtgttg tcggggaaat      3120
catcgtcctt tccttggctg ctcgcctgtg ttgccacctg gattctgcgc gggacgtcct      3180
tctgctacgt cccttcggcc ctcaatccag cggaccttcc ttcccgcggc ctgctgccgg      3240
ctctgcggcc tcttccgcgt cttcgccttc gccctcagac gagtcggatc tccctttggg      3300
ccgcctcccc gcatcgatac cgtcgactag agctcgctga tcagcctcga ctgtgccttc      3360
tagttgccag ccatctgttg tttgcccctc ccccgtgcct tccttgaccc tggaaggtgc      3420
cactcccact gtcctttcct aataaaatga ggaaattgca tcgcattgtc tgagtaggtg      3480
tcattctatt ctggggggtg gggtggggca ggacagcaag ggggaggatt gggaagacaa      3540
tagcaggcat gctggggaga gatccacgat aacaaacagc tttttttgggg tgaacatatt     3600 gactgaattc cctgcaggtt ggccactccc tctctgcgcg ctcgctcgct cactgaggcc      3660
gcccgggcaa agcccgggcg tcgggcgacc tttggtcgcc cggcctcagt gagcgagcga      3720
gcgcgcagag agggagtggc caactccatc actaggggtt cctgcggccg ctcgtacggt      3780
ctcgaggaat tcctgcagga taacttgcca acctcattct aaaatgtata tagaagccca      3840
aaagacaata acaaaaatat tcttgtagaa caaaatggga aagaatgttc cactaaatat      3900
caagatttag agcaaagcat gagatgtgtg gggatagaca gtgaggctga taaaatagag      3960
tagagctcag aaacagaccc attgatatat gtaagtgacc tatgaaaaaa atatggcatt      4020
ttacaatggg aaaatgatgg tctttttctt ttttagaaaa acaggggaaat atatttatat     4080 gtaaaaaata aaagggaacc catatgtcat accatacaca caaaaaaatt ccagtgaatt      4140
ataagtctaa atggagaagg caaaacttta aatcttttag aaaataatat agaagcatgc      4200
agaccagcct ggccaacatg atgaaaccct ctctactaat aataaaatca gtagaactac      4260
tcaggactac tttgagtggg aagtcctttt ctatgaagac ttctttggcc aaaattaggc      4320
tctaaatgca aggagatagt gcatcatgcc tggctgcact tactgataaa tgatgttatc      4380
accatcttta accaaatgca caggaacaag ttatggtact gatgtgctgg attgagaagg      4440
agctctactt ccttgacagg acacatttgt atcaacttaa aaaagcagat ttttgccagc      4500
agaactattc attcagaggt aggaaactta gaatagatga tgtcactgat tagcatggct      4560
tccccatctc cacagctgct tcccacccag ggttgccaca gttgagtttg tccagtgctc      4620
agggctgccc actctcagta agaagcccca caccagcccc tctccaaata tgttggctgt      4680
tccttccatt aaagtgaccc cactttagag cagcaagtgg atttctgttt cttacagttc      4740
aggaaggagg agtcagctgt gagaacctgg agcctgagat gcttctaagt cccactgcta      4800
ctggggtcag ggaagccaga ctccagcatc agcagtcagg agcactaagc ccttgccaac      4860
```

-continued

```
atcctgtttc tcagagaaac tgcttccatt ataatggttg tcctttttta agctatcaag     4920
ccaaacaacc agtgtctacc attattctca tcacctgaag ccaagggttc tagcaaaagt     4980
caagctgtct tgtaatggtt gatgtgcctc cagcttctgt cttcagtcac tccactctta     5040
gcctgctctg aatcaactct gaccacagtt ccctggagcc cctgccacct gctgccctg      5100 ccaccttctc catctgcagt gctgtgcagc cttctgcact cttgcagagc taataggtgg     5160
agacttgaag gaagaggagg aaagtttctc ataatagcct tgctgcaagc tcaaatggga     5220
ggtgggcact gtgcccagga gccttggagc aaaggctgtg cccaacctct gactgcatcc     5280
aggtttggtc ttgacagaga taagaagccc tggctttttgg agccaaaatc taggtcagac    5340
ttaggcagga ttctcaaagt ttatcagcag aacatgaggc agaagaccct ttctgctcca     5400
gcttcttcag gctcaacctt catcagaata gatagaaaga gaggctgtga gggttcttaa     5460
aacagaagca aatctgactc agagaataaa caacctccta gtaaactaca gcttagacag     5520
agcatctggt ggtgagtgtg ctcagtgtcc tactcaactg tctggtatca gccctcatga     5580
ggacttctct tctttccctc atagacctcc atctctgttt tccttagcct gcagaaatct     5640
ggatggctat tcacagaatg cctgtgcttt cagagttgca tttttttctct ggtattctgg    5700 ttcaagcatt tgaaggtagg aaaggttctc caagtgcaag aaagccagcc ctgagcctca     5760
actgcctggc tagtgtggtc agtaggatgc aaaggctgtt gaatgccaca aggccaaact     5820
ttaacctgtg taccacaagc ctagcagcag aggcagctct gctcactgga actctctgtc     5880
ttctttctcc tgagcctttt ctttttcctga gttttctagc tctcctcaac cttacctctg     5940
ccctacccag gacaaaccca agagccactg tttctgtgat gtcctctcca gccctaatta     6000
ggcatcatga cttcagcctg accttccatg ctcagaagca gtgctaatcc acttcagatg     6060
agctgctcta tgcaacacag gcagagccta caaacctttg caccagagcc ctccacatat     6120
cagtgtttgt tcatactcac ttcaacagca aatgtgactg ctgagattaa gattttacac     6180
aagatggtct gtaatttcac agttagtttt atcccattag gtatgaaaga attagcataa     6240
ttccccttaa acatgaatga atcttagatt ttttaataaa tagtttttgga agtaaagaca    6300 gagacatcag gagcacaagg aatagcctga gaggacaaac agaacaagaa agagtctgga     6360
aatacacagg atgttcttgg cctcctcaaa gcaagtgcaa gcagatagta ccagcagccc     6420
caggctatca gagcccagtg aagagaagta ccatgaaagc cacagctcta accaccctgt     6480
tccagagtga cagacagtcc ccaagacaag ccagcctgag ccagagagag aactgcaaga     6540
gaaagtttct aatttaggtt ctgttagatt cagacaagtg caggtcatcc tctctccaca     6600
gctactcacc tctccagcct aacaaagcct gcagtccaca ctccaaccct ggtgtctcac     6660
ctcctagcct ctcccaacat cctgctctct gaccatcttc tgcatctctc atctcaccat     6720
ctcccactgt ctacagccta ctcttgcaac taccatctca ttttctgaca tcctgtctac     6780
atcttctgcc atactctgcc atctaccata ccacctctta ccatctacca caccatcttt     6840
tatctccatc cctctcagaa gcctccaagc tgaatcctgc tttatgtgtt catctcagcc     6900
cctgcatgga aagctgaccc cagaggcaga actattccca gagagcttgg ccaagaaaaa     6960
caaaactacc agcctggcca ggctcaggag tagtaagctg cagtgtctgt tgtgttctag     7020
cttcaacagc tgcaggagtt ccactctcaa atgctccaca tttctcacat cctcctgatt     7080
ctggtcacta cccatcttca aagaacagaa tatctcacat cagcatactg tgaaggacta     7140
gtcatgggtg cagctgctca gagctgcaaa gtcattctgg atggtggaga gcttacaaac     7200
atttcatgat gctccccccg ctctgatggc tggagcccaa tccctacaca gactcctgct     7260
```

```
gtatgtgttt tcctttcact ctgagccaca gccagagggc aggcattcag tctcctcttc    7320
aggctggggc tggggcactg agaactcacc caacaccttg ctctcactcc ttctgcaaaa    7380
caagaaagag ctttgtgctg cagtagccat gaagaatgaa aggaaggctt taactaaaaa    7440
atgtcagaga ttattttcaa ccccttactg tggatcacca gcaaggagga aacacaacac    7500
agagacattt tttcccctca aattatcaaa agaatcactg catttgttaa agagagcaac    7560
tgaatcagga agcagagttt tgaacatatc agaagttagg aatctgcatc agagacaaat    7620
gcagtcatgg ttgtttgctg cataccagcc ctaatcatta gaagcctcat ggacttcaaa    7680
catcattccc tctgacaaga tgctctagcc taactccatg agataaaata aatctgcctt    7740
tcagagccaa agaagagtcc accagcttct tctcagtgtg aacaagagct ccagtcaggt    7800
tagtcagtcc agtgcagtag aggagaccag tctgcatcct ctaattttca aaggcaagaa    7860
gatttgttta ccctggacac caggcacaag tgaggtcaca gagctcttag atatgcagtc    7920
ctcatgagtg aggagactaa agcgcatgcc atcaagactt cagtgtagag aaaacctcca    7980
aaaaagcctc ctcactactt ctggaatagc tcagaggccg aggcggcctc ggcctctgca    8040
taaataaaaa aaattagtca gccatggggc ggagaatggg cggaactggg cggagttagg    8100
ggcgggatgg gcggagttag gggcgggact atggttgctg actaattgag atgcatgctt    8160
tgcatacttc tgcctgctgg ggagcctggg gactttccac acctggttgc tgactaattg    8220
agatgcatgc tttgcatact tctgcctgct ggggagcctg gggactttcc acaccctaac    8280
tgacacacat tccacagctg cattaatgaa tcggccaacg cgcggggaga ggcggtttgc    8340
gtattgggcg ctcttccgct tcctcgctca ctgactcgct gcgctcggtc gttcggctgc    8400
ggcgagcggt atcagctcac tcaaaggcgg taatacggtt atccacagaa tcaggggata    8460
acgcaggaaa gaacatgtga gcaaaaggcc agcaaaaggc caggaaccgt aaaaaggccg    8520
cgttgctggc gtttttccat aggctccgcc cccctgacga gcatcacaaa aatcgacgct    8580
caagtcagag gtggcgaaac ccgacaggac tataaagata ccaggcgttt ccccctggaa    8640
gctccctcgt gcgctctcct gttccgaccc tgccgcttac cggatacctg tccgcctttc    8700
tcccttcggg aagcgtggcg ctttctcata gctcacgctg taggtatctc agttcggtgt    8760
aggtcgttcg ctccaagctg ggctgtgtgc acgaaccccc cgttcagccc gaccgctgcg    8820
ccttatccgg taactatcgt cttgagtcca acccggtaag acacgactta cgccactgg     8880 cagcagccac tggtaacagg attagcagag cgaggtatgt aggcggtgct acagagttct    8940
tgaagtggtg gcctaactac ggctacacta gaagaacagt atttggtatc tgcgctctgc    9000
tgaagccagt taccttcgga aaaagagttg gtagctcttg atccggcaaa caaaccaccg    9060
ctggtagcgg tggttttttt gtttgcaagc agcagattac gcgcagaaaa aaaggatctc    9120
aagaagatcc tttgatcttt tctacggggt ctgacgctca gtggaacgaa aactcacgtt    9180
aagggatttt ggtcatgaga ttatcaaaaa ggatcttcac ctagatcctt ttaaattaaa    9240
aatgaagttt taaatcaatc taaagtatat atgagtaaac ttggtctgac agttaccaat    9300
gcttaatcag tgaggcacct atctcagcga tctgtctatt tcgttcatcc atagttgcct    9360
gactcctgca aaccacgttg tgtctcaaaa tctctgatgt tacattgcac aagataaaaa    9420
tatatcatca tgaacaataa aactgtctgc ttacataaac agtaatacaa ggggtgttat    9480
gagccatatt caacgggaaa cgtcttgctc gaggccgcga ttaaattcca acatggatgc    9540
tgatttatat gggtataaat gggctcgcga taatgtcggg caatcaggtg cgacaatcta    9600
```

-continued

```
tcgattgtat gggaagcccg atgcgccaga gttgtttctg aaacatggca aaggtagcgt      9660
tgccaatgat gttacagatg agatggtcag actaaactgg ctgacggaat ttatgcctct      9720
tccgaccatc aagcatttta tccgtactcc tgatgatgca tggttactca ccactgcgat      9780
cccggggaaa acagcattcc aggtattaga agaatatcct gattcaggtg aaaatattgt      9840
tgatgcgctg gcagtgttcc tgcgccggtt gcattcgatt cctgtttgta attgtccttt      9900
taacagcgat cgcgtatttc gtctcgctca ggcgcaatca cgaatgaata acggtttggt      9960
tgatgcgagt gattttgatg acgagcgtaa tggctggcct gttgaacaag tctggaaaga     10020
aatgcataag cttttgccat tctcaccgga ttcagtcgtc actcatggtg atttctcact     10080
tgataacctt attttttgacg aggggaaatt aataggttgt attgatgttg gacgagtcgg     10140
aatcgcagac cgataccagg atcttgccat cctatggaac tgcctcggtg agttttctcc     10200
ttcattacag aaacggcttt ttcaaaaata tggtattgat aatcctgata tgaataaatt     10260
gcagtttcat ttgatgctcg atgagttttt ctaagggcgg cctgccacca tacccacgcc     10320
gaaacaagcg ctcatgagcc cgaagtggcg agccgatct tccccatcgg tgatgtcggc     10380
gatataggcg ccagcaaccg cacctgtggc gccggtgatg agggcgcgcc aagtcgacgt     10440
ccggcagtct tggccactcc ctctctgcgc gctcgctcgc tcactgaggc cgggcgacca     10500
aaggtcgccc gacgcccggg ctttgcccgg gcggcctcag tgagcgagcg agcgcgcaga     10560
gagggagtgg ccaactccat cactaggggt tcctgctagc tctgggtatt taagcccgag     10620
tgagcacgca gggtctccat tttgaagcgg gaggttacgc gttcgtcgac tactagtggg     10680
taccagagct ggtgactga gatgtttttct aggaaacaca aaagatacaa aaaagaacac     10740
gtggaaggat agccaaaaag gggggctgcc cccatttcct gcaccccgct gcgatggctg     10800
gcaccatttg gaagacttcg agatacactg ttgagcgcag taagacaaca gtgtatctcg     10860
aagtcttcca gatggggcca gccggtccac tctgtatcca ggccagttct gcaaggcgtt     10920
cgaggaccac cccctcccc tcgccaccag ggtggtctca tacagaactt ataagattcc     10980
caaatccaaa gacatttcac gtttatggtg atttcccaga acacatagcg acatgcaaat     11040
attgcagggc gccactcccc tgtccctcac agccatcttc ctgccagggc gcacgcgcgc     11100
tgggtgttcc cgcctagtga cactgggccc gcgattcctt ggagcgggtt gatgacgtca     11160
gcgtttccca tggtgaatcc ctaggtt                                         11187
```

```
<210> SEQ ID NO 13
<211> LENGTH: 10960
<212> TYPE: DNA
<213> ORGANISM: Artificial Sequence
<220> FEATURE:
<223> OTHER INFORMATION: Synthetic polynucleotide

<400> SEQUENCE: 13
ttggccactc cctctctgcg cgctcgctcg ctcactgagg ccgggcgacc aaaggtcgcc        60
cgacgcccgg gctttgcccg gcggcctca gtgagcgagc gagcgcgcag agagggagtg       120
gccaactcca tcactagggg ttcctgctag ctctgggtat ttaagcccga gtgagcacgc       180
agggtctcca ttttgaagcg ggaggttacg cgttcgtcga ctactagtgg gtaccagagc       240
tccctaggtt ctagaaccgg tgacgtctcc catggtgaag cttggatctg aattcggtac       300
cctagttatt aatagtaatc aattacgggg tcattagttc atagcccata tatggagttc       360
cgcgttacat aacttacggt aaatggcccg cctggctgac cgcccaacga cccccgccca       420
ttgacgtcaa taatgacgta tgttcccata gtaacgccaa tagggacttt ccattgacgt       480
```

```
caatgggtgg actatttacg gtaaactgcc cacttggcag tacatcaagt gtatcatatg      540
ccaagtacgc cccctattga cgtcaatgac ggtaaatggc ccgcctggca ttatgcccag      600
tacatgacct tatgggactt tcctacttgg cagtacatct acgtattagt catcgctatt      660
accatggtcg aggtgagccc cacgttctgc ttcactctcc ccatctcccc ccctccccca      720
cccccaattt tgtatttatt tattttttaa ttattttgtg cagcgatggg ggcggggggg      780 ggggggggc gcgcgccagg cggggcgggg cggggcgagg ggcggggcgg ggcgaggcgg      840
agaggtgcgg cggcagccaa tcagagcggc gcgctccgaa agtttccttt tatggcgagg      900
cggcggcggc ggcggcccta taaaaagcga agcgcgcggc gggcgggagt cgctgcgacg      960
ctgccttcgc cccgtgcccc gctccgccgc cgcctcgcgc cgcccgcccc ggctctgact     1020
gaccgcgtta ctcccacagg tgagcgggcg ggacggccct tctcctccgg gctgtaatta     1080
gcgcttggtt taatgacggc ttgtcctggt ggcgagggga gggggtggt cctcgaacgc      1140 cttgcagaac tggcctggat acagagtgga ccggctggcc ccatctggaa gacttcgaga     1200
tacactgttg tcttactgcg ctcaacagtg tatctcgaag tcttccaaat ggtgccagcc     1260
atcgcagcgg ggtgcaggaa atgggggcag cccccctttt tggctatcct tccacgtgtt     1320 ctttttgta tcttttgtgt ttcctagaaa acatctcagt caccacctt ctgtggctgc       1380 gtgaaagcct tgaggggctc cgggagctag agcctctgct aaccatgttc atgccttctt     1440 cttttttccta cagctcctgg gcaacgtgct ggttattgtg ctgtctcatc attttggcaa     1500
agaattcctc gaagatccga agggaaagtc ttccacgact gtgggatccg ttcgaagata     1560
tcaccggttg agccaccatg gaattcagca gccccagcag agaggaatgc cccaagcctc     1620
tgagccgggt gtcaatcatg gccggatctc tgacaggact gctgctgctt caggccgtgt     1680
cttgggcttc tggcgctaga ccttgcatcc ccaagagctt cggctacagc agcgtcgtgt     1740
gcgtgtgcaa tgccacctac tgcgacagct cgaccctcc tacctttcct gctctgggca      1800
ccttcagcag atacgagagc accagatccg gcagacggat ggaactgagc atgggaccca     1860
tccaggccaa tcacacaggc actggcctgc tgctgacact gcagcctgag cagaaattcc     1920
agaaagtgaa aggcttcggc ggagccatga cagatgccgc cgctctgaat atcctggctc     1980
tgtctccacc agctcagaac ctgctgctca gagctactt cagcgaggaa ggcatcggct      2040
acaacatcat cagagtgccc atggccagct gcgacttcag catcaggacc tacacctacg     2100
ccgacacacc cgacgatttc cagctgcaca acttcagcct gcctgaagag gacaccaagc     2160
tgaagatccc tctgatccac agagccctgc agctggcaca agaccccgtg tcactgctgg     2220
cctctccatg gacatctccc acctggctga aaacaaatgg cgccgtgaat ggcaagggca     2280
gcctgaaagg ccaacctggc gacatctacc accagacctg gccagatac ttcgtgaagt       2340 tcctggacgc ctatgccgag cacaagctgc agttttgggc cgtgacagcc gagaacgaac     2400
cttctgctgg actgctgagc ggctaccccct ttcagtgcct gggctttaca cccgagcacc    2460
agcgggactt tatcgcccgt gatctgggac ccacactggc caatagcacc caccataatg     2520
tgcggctgct gatgctggac gaccagagac tgcttctgcc ccactgggct aaagtggtgc     2580
tgacagatcc tgaggccgcc aaatacgtgc acggaatcgc cgtgcactgg tatctggact     2640
ttctggcccc tgccaaggcc acactgggag agacacacag actgttcccc aacaccatgc     2700
tgttcgccag cgaagcctgt gtgggcagca gttttgggga acagagcgtg cggctcggca     2760
gctgggatag aggcatgcag tacagccaca gcatcatcac caacctgctg taccacgtcg     2820
```

-continued

```
tcggctggac cgactggaat ctggccctga atcctgaagg cggccctaac tgggtccgaa    2880
acttcgtgga cagccccatc atcgtggaca tcaccaagga caccttctac aagcagccca    2940
tgttctacca cctgggacac ttcagcaagt tcatccccga gggctctcag cgcgttggac    3000
tggtggcttc ccagaagaac gatctggacg ccgtggctct gatgcaccct gatggatctg    3060
ctgtggtggt ggtcctgaac cgcagcagca aagatgtgcc cctgaccatc aaggatcccg    3120
ccgtgggatt cctggaaaca atcagccctg gctactccat ccacacctac ctgtggcgta    3180
gacagtgaca attgttaatt aagtttaaac cctcgaggcc gcaagcttat cgataatcaa    3240
cctctggatt acaaaatttg tgaaagattg actggtattc ttaactatgt tgctcctttt    3300
acgctatgtg gatacgctgc tttaatgcct ttgtatcatg ctattgcttc ccgtatggct    3360
ttcattttct cctccttgta taaatcctgg ttgctgtctc tttatgagga gttgtggccc    3420
gttgtcaggc aacgtggcgt ggtgtgcact gtgtttgctg acgcaacccc cactggttgg    3480
ggcattgcca ccacctgtca gctcctttcc gggactttcg ctttcccct ccctattgcc    3540 acggcggaac tcatcgccgc ctgccttgcc cgctgctgga caggggctcg gctgttgggc    3600
actgacaatt ccgtggtgtt gtcggggaaa tcatcgtcct ttccttggct gctcgcctgt    3660
gttgccacct ggattctgcg cgggacgtcc ttctgctacg tcccttcggc cctcaatcca    3720
gcggaccttc cttcccgcgg cctgctgccg gctctgcggc ctcttccgcg tcttcgcctt    3780
cgccctcaga cgagtcggat ctccctttgg gccgcctccc cgcatcgata ccgtcgacta    3840
gagctcgctg atcagcctcg actgtgcctt ctagttgcca gccatctgtt gtttgcccct    3900
cccccgtgcc ttccttgacc ctggaaggtg ccactcccac tgtcctttcc taataaaatg    3960
aggaaattgc atcgcattgt ctgagtaggt gtcattctat tctggggggt ggggtggggc    4020
aggacagcaa gggggaggat tgggaagaca atagcaggca tgctggggag agatccacga    4080
taacaaacag ctttttttgg gtgaacatat tgactgaatt ccctgcaggt tggccactcc    4140
ctctctgcgc gctcgctcgc tcactgaggc cgcccgggca aagcccgggc gtcgggcgac    4200
ctttggtcgc ccggcctcag tgagcgagcg agcgcgcaga gagggagtgg ccaactccat    4260
cactaggggt tcctgcggcc gctcgtacgg tctcgaggaa ttcctgcagg ataacttgcc    4320
aacctcattc taaaatgtat atagaagccc aaaagacaat aacaaaaata ttcttgtaga    4380
acaaaatggg aaagaatgtt ccactaaata tcaagattta gagcaaagca tgagatgtgt    4440
ggggatagac agtgaggctg ataaaataga gtagagctca gaaacagacc cattgatata    4500
tgtaagtgac ctatgaaaaa aatatggcat tttacaatgg gaaaatgatg gtcttttttct    4560 ttttttagaaa aacagggaaa tatatttata tgtaaaaaat aaaagggaac ccatatgtca    4620
taccatacac acaaaaaaat tccagtgaat tataagtcta aatggagaag gcaaaacttt    4680
aaatctttta gaaaataata tagaagcatg cagaccagcc tggccaacat gatgaaaccc    4740
tctctactaa taataaaatc agtagaacta ctcaggacta ctttgagtgg gaagtccttt    4800
tctatgaaga cttctttggc caaaattagg ctctaaatgc aaggagatag tgcatcatgc    4860
ctggctgcac ttactgataa atgatgttat caccatcttt aaccaaatgc acaggaacaa    4920
gttatggtac tgatgtgctg gattgagaag gagctctact tccttgacag gacacatttg    4980
tatcaactta aaaaagcaga tttttgccag cagaactatt cattcagagg taggaaactt    5040
agaatagatg atgtcactga ttagcatggc ttccccatct ccacagctgc ttcccaccca    5100
ggttgcccac agttgagttt gtccagtgct cagggctgcc cactctcagt aagaagcccc    5160
acaccagccc ctctccaaat atgttggctg ttccttccat taaagtgacc ccactttaga    5220
```

-continued

```
gcagcaagtg gatttctgtt tcttacagtt caggaaggag gagtcagctg tgagaacctg      5280
gagcctgaga tgcttctaag tcccactgct actggggtca gggaagccag actccagcat      5340
cagcagtcag gagcactaag cccttgccaa catcctgttt ctcagagaaa ctgcttccat      5400
tataatggtt gtcctttttt aagctatcaa gccaaacaac cagtgtctac cattattctc      5460
atcacctgaa gccaagggtt ctagcaaaag tcaagctgtc ttgtaatggt tgatgtgcct      5520
ccagcttctg tcttcagtca ctccactctt agcctgctct gaatcaactc tgaccacagt      5580
tccctggagc ccctgccacc tgctgcccct gccaccttct ccatctgcag tgctgtgcag      5640
ccttctgcac tcttgcagag ctaataggtg gagacttgaa ggaagaggag gaaagtttct      5700
cataatagcc ttgctgcaag ctcaaatggg aggtgggcac tgtgcccagg agccttggag      5760
caaaggctgt gcccaacctc tgactgcatc caggtttggt cttgacagag ataagaagcc      5820
ctggcttttg gagccaaaat ctaggtcaga cttaggcagg attctcaaag tttatcagca      5880
gaacatgagg cagaagaccc tttctgctcc agcttcttca ggctcaacct tcatcagaat      5940
agatagaaag agaggctgtg agggttctta aaacagaagc aaatctgact cagagaataa      6000
acaacctcct agtaaactac agcttagaca gagcatctgg tggtgagtgt gctcagtgtc      6060
ctactcaact gtctggtatc agccctcatg aggacttctc ttctttccct catagacctc      6120
catctctgtt ttccttagcc tgcagaaatc tggatggcta ttcacagaat gcctgtgctt      6180
tcagagttgc attttttctc tggtattctg gttcaagcat ttgaaggtag gaaaggttct      6240
ccaagtgcaa gaaagccagc cctgagcctc aactgcctgg ctagtgtggt cagtaggatg      6300
caaaggctgt tgaatgccac aaggccaaac tttaacctgt gtaccacaag cctagcagca      6360
gaggcagctc tgctcactgg aactctctgt cttctttctc ctgagccttt tcttttcctg      6420
agttttctag ctctcctcaa ccttacctct gccctaccca ggacaaaccc aagagccact      6480
gtttctgtga tgtcctctcc agccctaatt aggcatcatg acttcagcct gaccttccat      6540
gctcagaagc agtgctaatc cacttcagat gagctgctct atgcaacaca ggcagagcct      6600
acaaaccttt gcaccagagc cctccacata tcagtgtttg ttcatactca cttcaacagc      6660
aaatgtgact gctgagatta agattttaca caagatggtc tgtaatttca cagttagttt      6720
tatcccatta ggtatgaaag aattagcata attcccctta aacatgaatg aatcttagat      6780
tttttaataa atagttttgg aagtaaagac agagacatca ggagcacaag gaatagcctg      6840
agaggacaaa cagaacaaga aagagtctgg aaatacacag gatgttcttg gcctcctcaa      6900
agcaagtgca agcagatagt accagcagcc ccaggctatc agagcccagt gaagagaagt      6960
accatgaaag ccacagctct aaccaccctg ttccagagtg acagacagtc cccaagacaa      7020
gccagcctga gccagagaga gaactgcaag agaaagtttc taatttaggt tctgttagat      7080
tcagacaagt gcaggtcatc ctctctccac agctactcac ctctccagcc taacaaagcc      7140
tgcagtccac actccaaccc tggtgtctca cctcctagcc tctcccaaca tcctgctctc      7200
tgaccatctt ctgcatctct catctcacca tctcccactg tctacagcct actcttgcaa      7260
ctaccatctc attttctgac atcctgtcta catcttctgc catactctgc catctaccat      7320
accacctctt accatctacc acaccatctt ttatctccat ccctctcaga agcctccaag      7380
ctgaatcctg ctttatgtgt tcatctcagc ccctgcatgg aaagctgacc ccagaggcag      7440
aactattccc agagagcttg gccaagaaaa acaaaactac cagcctggcc aggctcagga      7500
gtagtaagct gcagtgtctg ttgtgttcta gcttcaacag ctgcaggagt tccactctca      7560
```

-continued

```
aatgctccac atttctcaca tcctcctgat tctggtcact acccatcttc aaagaacaga    7620
atatctcaca tcagcatact gtgaaggact agtcatgggt gcagctgctc agagctgcaa    7680
agtcattctg gatggtggag agcttacaaa catttcatga tgctcccccc gctctgatgg    7740
ctggagccca atccctacac agactcctgc tgtatgtgtt ttcctttcac tctgagccac    7800
agccagaggg caggcattca gtctcctctt caggctgggg ctggggcact gagaactcac    7860
ccaacacctt gctctcactc cttctgcaaa acaagaaaga gctttgtgct gcagtagcca    7920
tgaagaatga aaggaaggct ttaactaaaa aatgtcagag attattttca accccttact    7980
gtggatcacc agcaaggagg aaacacaaca cagagacatt ttttcccctc aaattatcaa    8040
aagaatcact gcatttgtta aagagagcaa ctgaatcagg aagcagagtt ttgaacatat    8100
cagaagttag gaatctgcat cagagacaaa tgcagtcatg gttgtttgct gcataccagc    8160
cctaatcatt agaagcctca tggacttcaa acatcattcc ctctgacaag atgctctagc    8220
ctaactccat gagataaaat aaatctgcct ttcagagcca aagaagagtc caccagcttc    8280
ttctcagtgt gaacaagagc tccagtcagg ttagtcagtc cagtgcagta gaggagacca    8340
gtctgcatcc tctaattttc aaaggcaaga agatttgttt accctggaca ccaggcacaa    8400
gtgaggtcac agagctctta gatatgcagt cctcatgagt gaggagacta aagcgcatgc    8460
catcaagact tcagtgtaga gaaaacctcc aaaaaagcct cctcactact tctggaatag    8520
ctcagaggcc gaggcggcct cggcctctgc ataaataaaa aaaattagtc agccatgggg    8580
cggagaatgg gcggaactgg gcggagttag gggcgggatg ggcggagtta ggggcgggac    8640
tatggttgct gactaattga gatgcatgct ttgcatactt ctgcctgctg gggagcctgg    8700
ggactttcca cacctggttg ctgactaatt gagatgcatg ctttgcatac ttctgcctgc    8760
tggggagcct ggggactttc cacaccctaa ctgacacaca ttccacagct gcattaatga    8820
atcggccaac gcgcggggag aggcggtttg cgtattgggc gctcttccgc ttcctcgctc    8880
actgactcgc tgcgctcggt cgttcggctg cggcgagcgg tatcagctca ctcaaaggcg    8940
gtaatacggt tatccacaga atcaggggat aacgcaggaa agaacatgtg agcaaaaggc    9000
cagcaaaagg ccaggaaccg taaaaaggcc gcgttgctgg cgtttttcca taggctccgc    9060
ccccctgacg agcatcacaa aaatcgacgc tcaagtcaga ggtggcgaaa cccgacagga    9120
ctataaagat accaggcgtt tccccctgga agctccctcg tgcgctctcc tgttccgacc    9180
ctgccgctta ccggatacct gtccgccttt ctcccttcgg gaagcgtggc gctttctcat    9240
agctcacgct gtaggtatct cagttcggtg taggtcgttc gctccaagct gggctgtgtg    9300
cacgaacccc ccgttcagcc cgaccgctgc gccttatccg gtaactatcg tcttgagtcc    9360
aacccggtaa gacacgactt atcgccactg gcagcagcca ctggtaacag gattagcaga    9420
gcgaggtatg taggcggtgc tacagagttc ttgaagtggt ggcctaacta cggctacact    9480
agaagaacag tatttggtat ctgcgctctg ctgaagccag ttaccttcgg aaaaagagtt    9540
ggtagctctt gatccggcaa acaaaccacc gctggtagcg gtggtttttt tgtttgcaag    9600
cagcagatta cgcgcagaaa aaaaggatct caagaagatc ctttgatctt ttctacgggg    9660
tctgacgctc agtggaacga aaactcacgt taagggattt tggtcatgag attatcaaaa    9720
aggatcttca cctagatcct tttaaattaa aaatgaagtt ttaaatcaat ctaaagtata    9780
tatgagtaaa cttggtctga cagttaccaa tgcttaatca gtgaggcacc tatctcagcg    9840
atctgtctat ttcgttcatc catagttgcc tgactcctgc aaaccacgtt gtgtctcaaa    9900
atctctgatg ttacattgca caagataaaa atatatcatc atgaacaata aaactgtctg    9960
```

-continued

```
cttacataaa cagtaataca aggggtgtta tgagccatat tcaacgggaa acgtcttgct   10020
cgaggccgcg attaaattcc aacatggatg ctgatttata tgggtataaa tgggctcgcg   10080
ataatgtcgg gcaatcaggt gcgacaatct atcgattgta tgggaagccc gatgcgccag   10140
agttgtttct gaaacatggc aaaggtagcg ttgccaatga tgttacagat gagatggtca   10200
gactaaactg gctgacggaa tttatgcctc ttccgaccat caagcatttt atccgtactc   10260
ctgatgatgc atggttactc accactgcga tccccgggaa aacagcattc caggtattag   10320
aagaatatcc tgattcaggt gaaaatattg ttgatgcgct ggcagtgttc ctgcgccggt   10380
tgcattcgat tcctgtttgt aattgtcctt ttaacagcga tcgcgtattt cgtctcgctc   10440
aggcgcaatc acgaatgaat aacggtttgg ttgatgcgag tgattttgat gacgagcgta   10500
atggctggcc tgttgaacaa gtctggaaag aaatgcataa gcttttgcca ttctcaccgg   10560
attcagtcgt cactcatggt gatttctcac ttgataacct tattttgac gaggggaaat   10620 taataggttg tattgatgtt ggacgagtcg gaatcgcaga ccgataccag gatcttgcca   10680
tcctatggaa ctgcctcggt gagttttctc cttcattaca gaaacggctt tttcaaaaat   10740
atggtattga taatcctgat atgaataaat tgcagtttca tttgatgctc gatgagtttt   10800
tctaagggcg gcctgccacc atacccacgc cgaaacaagc gctcatgagc ccgaagtggc   10860
gagcccgatc ttccccatcg gtgatgtcgg cgatataggc gccagcaacc gcacctgtgg   10920
cgccggtgat gagggcgcgc caagtcgacg tccggcagtc                          10960
```

<210> SEQ ID NO 14
<211> LENGTH: 536
<212> TYPE: PRT
<213> ORGANISM: Homo sapiens

<400> SEQUENCE: 14

```
Met Glu Phe Ser Ser Pro Ser Arg Glu Glu Cys Pro Lys Pro Leu Ser
1               5                   10                  15

Arg Val Ser Ile Met Ala Gly Ser Leu Thr Gly Leu Leu Leu Leu Gln
            20                  25                  30

Ala Val Ser Trp Ala Ser Gly Ala Arg Pro Cys Ile Pro Lys Ser Phe
        35                  40                  45

Gly Tyr Ser Ser Val Val Cys Val Cys Asn Ala Thr Tyr Cys Asp Ser
    50                  55                  60

Phe Asp Pro Pro Thr Phe Pro Ala Leu Gly Thr Phe Ser Arg Tyr Glu
65                  70                  75                  80

Ser Thr Arg Ser Gly Arg Arg Met Glu Leu Ser Met Gly Pro Ile Gln
                85                  90                  95

Ala Asn His Thr Gly Thr Gly Leu Leu Leu Thr Leu Gln Pro Glu Gln
            100                 105                 110

Lys Phe Gln Lys Val Lys Gly Phe Gly Gly Ala Met Thr Asp Ala Ala
        115                 120                 125

Ala Leu Asn Ile Leu Ala Leu Ser Pro Pro Ala Gln Asn Leu Leu Leu
    130                 135                 140

Lys Ser Tyr Phe Ser Glu Glu Gly Ile Gly Tyr Asn Ile Ile Arg Val
145                 150                 155                 160

Pro Met Ala Ser Cys Asp Phe Ser Ile Arg Thr Tyr Thr Tyr Ala Asp
                165                 170                 175

Thr Pro Asp Asp Phe Gln Leu His Asn Phe Ser Leu Pro Glu Glu Asp
            180                 185                 190
```

-continued

```
Thr Lys Leu Lys Ile Pro Leu Ile His Arg Ala Leu Gln Leu Ala Gln
        195                 200                 205

Arg Pro Val Ser Leu Leu Ala Ser Pro Trp Thr Ser Pro Thr Trp Leu
        210                 215                 220

Lys Thr Asn Gly Ala Val Asn Gly Lys Gly Ser Leu Lys Gly Gln Pro
225                 230                 235                 240

Gly Asp Ile Tyr His Gln Thr Trp Ala Arg Tyr Phe Val Lys Phe Leu
                245                 250                 255

Asp Ala Tyr Ala Glu His Lys Leu Gln Phe Trp Ala Val Thr Ala Glu
                260                 265                 270

Asn Glu Pro Ser Ala Gly Leu Leu Ser Gly Tyr Pro Phe Gln Cys Leu
        275                 280                 285

Gly Phe Thr Pro Glu His Gln Arg Asp Phe Ile Ala Arg Asp Leu Gly
        290                 295                 300

Pro Thr Leu Ala Asn Ser Thr His His Asn Val Arg Leu Leu Met Leu
305                 310                 315                 320

Asp Asp Gln Arg Leu Leu Leu Pro His Trp Ala Lys Val Val Leu Thr
                325                 330                 335

Asp Pro Glu Ala Ala Lys Tyr Val His Gly Ile Ala Val His Trp Tyr
                340                 345                 350

Leu Asp Phe Leu Ala Pro Ala Lys Ala Thr Leu Gly Glu Thr His Arg
        355                 360                 365

Leu Phe Pro Asn Thr Met Leu Phe Ala Ser Glu Ala Cys Val Gly Ser
        370                 375                 380

Lys Phe Trp Glu Gln Ser Val Arg Leu Gly Ser Trp Asp Arg Gly Met
385                 390                 395                 400

Gln Tyr Ser His Ser Ile Ile Thr Asn Leu Leu Tyr His Val Val Gly
                405                 410                 415

Trp Thr Asp Trp Asn Leu Ala Leu Asn Pro Glu Gly Gly Pro Asn Trp
                420                 425                 430

Val Arg Asn Phe Val Asp Ser Pro Ile Ile Val Asp Ile Thr Lys Asp
        435                 440                 445

Thr Phe Tyr Lys Gln Pro Met Phe Tyr His Leu Gly His Phe Ser Lys
        450                 455                 460

Phe Ile Pro Glu Gly Ser Gln Arg Val Gly Leu Val Ala Ser Gln Lys
465                 470                 475                 480

Asn Asp Leu Asp Ala Val Ala Leu Met His Pro Asp Gly Ser Ala Val
                485                 490                 495

Val Val Val Leu Asn Arg Ser Ser Lys Asp Val Pro Leu Thr Ile Lys
        500                 505                 510

Asp Pro Ala Val Gly Phe Leu Glu Thr Ile Ser Pro Gly Tyr Ser Ile
        515                 520                 525

His Thr Tyr Leu Trp Arg Arg Gln
        530                 535
```

```
<210> SEQ ID NO 15
<211> LENGTH: 1608
<212> TYPE: DNA
<213> ORGANISM: Homo sapiens

<400> SEQUENCE: 15
atggaattca gcagccccag cagagaggaa tgccccaagc ctctgagccg ggtgtcaatc      60
atggccggat ctctgacagg actgctgctg cttcaggccg tgtcttgggc ttctggcgct     120
agaccttgca tccccaagag cttcggctac agcagcgtcg tgtgcgtgtg caatgccacc     180
```

-continued

```
tactgcgaca gcttcgaccc tcctaccttt cctgctctgg gcaccttcag cagatacgag      240
agcaccagat ccggcagacg gatggaactg agcatgggac ccatccaggc caatcacaca      300
ggcactggcc tgctgctgac actgcagcct gagcagaaat tccagaaagt gaaaggcttc      360
ggcggagcca tgacagatgc cgccgctctg aatatcctgg ctctgtctcc accagctcag      420
aacctgctgc tcaagagcta cttcagcgag gaaggcatcg gctacaacat catcagagtg      480
cccatggcca gctgcgactt cagcatcagg acctacacct acgccgacac acccgacgat      540
ttccagctgc acaacttcag cctgcctgaa gaggacacca agctgaagat ccctctgatc      600
cacagagccc tgcagctggc acaaagaccc gtgtcactgc tggcctctcc atggacatct      660
cccacctggc tgaaaacaaa tggcgccgtg aatggcaagg gcagcctgaa aggccaacct      720
ggcgacatct accaccagac ctgggccaga tacttcgtga agttcctgga cgcctatgcc      780
gagcacaagc tgcagttttg ggccgtgaca gccgagaacg aaccttctgc tggactgctg      840
agcggctacc cctttcagtg cctgggcttt acacccgagc accagcggga ctttatcgcc      900
cgtgatctgg acccacact  ggccaatagc acccaccata atgtgcggct gctgatgctg      960
gacgaccaga gactgcttct gccccactgg gctaaagtgg tgctgacaga tcctgaggcc     1020
gccaaatacg tgcacggaat cgccgtgcac tggtatctgg actttctggc ccctgccaag     1080
gccacactgg gagagacaca cagactgttc cccaacacca tgctgttcgc cagcgaagcc     1140
tgtgtgggca gcaagttttg ggaacagagc gtgcggctcg gcagctggga tagaggcatg     1200
cagtacagcc acagcatcat caccaacctg ctgtaccacg tcgtcggctg gaccgactgg     1260
aatctggccc tgaatcctga aggcggccct aactgggtcc gaaacttcgt ggacagcccc     1320
atcatcgtgg acatcaccaa ggacaccttc tacaagcagc ccatgttcta ccacctggga     1380
cacttcagca gttcatccc  cgagggctct cagcgcgttg gactggtggc ttcccagaag     1440
aacgatctgg acgccgtggc tctgatgcac cctgatggat ctgctgtggt ggtggtcctg     1500
aaccgcagca gcaaagatgt gcccctgacc atcaaggatc ccgccgtggg attcctggaa     1560
acaatcagcc ctggctactc catccacacc tacctgtggc gtagacag               1608
```

```
<210> SEQ ID NO 16
<211> LENGTH: 524
<212> TYPE: PRT
<213> ORGANISM: Homo sapiens

<400> SEQUENCE: 16

Met Tyr Ala Leu Phe Leu Leu Ala Ser Leu Leu Gly Ala Ala Leu Ala
1               5                   10                  15

Gly Pro Val Leu Gly Leu Lys Glu Cys Thr Arg Gly Ser Ala Val Trp
            20                  25                  30

Cys Gln Asn Val Lys Thr Ala Ser Asp Cys Gly Ala Val Lys His Cys
        35                  40                  45

Leu Gln Thr Val Trp Asn Lys Pro Thr Val Lys Ser Leu Pro Cys Asp
    50                  55                  60

Ile Cys Lys Asp Val Val Thr Ala Ala Gly Asp Met Leu Lys Asp Asn
65                  70                  75                  80

Ala Thr Glu Glu Glu Ile Leu Val Tyr Leu Glu Lys Thr Cys Asp Trp
                85                  90                  95

Leu Pro Lys Pro Asn Met Ser Ala Ser Cys Lys Glu Ile Val Asp Ser
            100                 105                 110

Tyr Leu Pro Val Ile Leu Asp Ile Ile Lys Gly Glu Met Ser Arg Pro
```

-continued

```
            115                  120                  125
Gly Glu Val Cys Ser Ala Leu Asn Leu Cys Glu Ser Leu Gln Lys His
    130                  135                  140

Leu Ala Glu Leu Asn His Gln Lys Gln Leu Glu Ser Asn Lys Ile Pro
145                  150                  155                  160

Glu Leu Asp Met Thr Glu Val Val Ala Pro Phe Met Ala Asn Ile Pro
                165                  170                  175

Leu Leu Leu Tyr Pro Gln Asp Gly Pro Arg Ser Lys Pro Gln Pro Lys
            180                  185                  190

Asp Asn Gly Asp Val Cys Gln Asp Cys Ile Gln Met Val Thr Asp Ile
        195                  200                  205

Gln Thr Ala Val Arg Thr Asn Ser Thr Phe Val Gln Ala Leu Val Glu
    210                  215                  220

His Val Lys Glu Glu Cys Asp Arg Leu Gly Pro Gly Met Ala Asp Ile
225                  230                  235                  240

Cys Lys Asn Tyr Ile Ser Gln Tyr Ser Glu Ile Ala Ile Gln Met Met
                245                  250                  255

Met His Met Gln Pro Lys Glu Ile Cys Ala Leu Val Gly Phe Cys Asp
            260                  265                  270

Glu Val Lys Glu Met Pro Met Gln Thr Leu Val Pro Ala Lys Val Ala
        275                  280                  285

Ser Lys Asn Val Ile Pro Ala Leu Glu Leu Val Glu Pro Ile Lys Lys
    290                  295                  300

His Glu Val Pro Ala Lys Ser Asp Val Tyr Cys Glu Val Cys Glu Phe
305                  310                  315                  320

Leu Val Lys Glu Val Thr Lys Leu Ile Asp Asn Asn Lys Thr Glu Lys
                325                  330                  335

Glu Ile Leu Asp Ala Phe Asp Lys Met Cys Ser Lys Leu Pro Lys Ser
            340                  345                  350

Leu Ser Glu Glu Cys Gln Glu Val Val Asp Thr Tyr Gly Ser Ser Ile
        355                  360                  365

Leu Ser Ile Leu Leu Glu Glu Val Ser Pro Glu Leu Val Cys Ser Met
    370                  375                  380

Leu His Leu Cys Ser Gly Thr Arg Leu Pro Ala Leu Thr Val His Val
385                  390                  395                  400

Thr Gln Pro Lys Asp Gly Gly Phe Cys Glu Val Cys Lys Lys Leu Val
                405                  410                  415

Gly Tyr Leu Asp Arg Asn Leu Glu Lys Asn Ser Thr Lys Gln Glu Ile
            420                  425                  430

Leu Ala Ala Leu Glu Lys Gly Cys Ser Phe Leu Pro Asp Pro Tyr Gln
        435                  440                  445

Lys Gln Cys Asp Gln Phe Val Ala Glu Tyr Glu Pro Val Leu Ile Glu
    450                  455                  460

Ile Leu Val Glu Val Met Asp Pro Ser Phe Val Cys Leu Lys Ile Gly
465                  470                  475                  480

Ala Cys Pro Ser Ala His Lys Pro Leu Leu Gly Thr Glu Lys Cys Ile
                485                  490                  495

Trp Gly Pro Ser Tyr Trp Cys Gln Asn Thr Glu Thr Ala Ala Gln Cys
            500                  505                  510

Asn Ala Val Glu His Cys Lys Arg His Val Trp Asn
            515                  520
```

<210> SEQ ID NO 17

<211> LENGTH: 1572
<212> TYPE: DNA
<213> ORGANISM: Homo sapiens

<400> SEQUENCE: 17
atgtacgccc tgttcctgct ggccagcctg ctgggcgccg ccctggccgg ccccgtgctg      60
ggcctgaagg agtgcacccg cggcagcgcc gtgtggtgcc agaacgtgaa gaccgccagc     120
gactgcggcg ccgtgaagca ctgcctgcag accgtgtgga acaagcccac cgtgaagagc     180 ctgcccctgcg acatctgcaa ggacgtggtg accgccgccg gcgacatgct gaaggacaac     240
gccaccgagg aggagatcct ggtgtacctg gagaagacct gcgactggct gcccaagccc     300
aacatgagcg ccagctgcaa ggagatcgtg gacagctacc tgcccgtgat cctggacatc     360
atcaagggcg agatgagccg ccccggcgag gtgtgcagcg ccctgaacct gtgcgagagc     420
ctgcagaagc acctggccga gctgaaccac cagaagcagc tggagagcaa caagatcccc     480
gagctggaca tgaccgaggt ggtggccccc ttcatggcca acatccccct gctgctgtac     540
ccccaggacg gcccccgcag caagcccag cccaaggaca acggcgacgt gtgccaggac     600
tgcatccaga tggtgaccga catccagacc gccgtgcgca ccaacagcac cttcgtgcag     660
gccctggtgg agcacgtgaa ggaggagtgc gaccgcctgg gccccggcat ggccgacatc     720
tgcaagaact acatcagcca gtacagcgag atcgccatcc agatgatgat gcacatgcag     780
cccaaggaga tctgcgccct ggtgggcttc tgcgacgagg tgaaggagat gcccatgcag     840
accctggtgc cgccaaggt ggccagcaag aacgtgatcc ccgccctgga gctggtggag     900
cccatcaaga gcacgaggt gcccgccaag agcgacgtgt actgcgaggt gtgcgagttc     960
ctggtgaagg aggtgaccaa gctgatcgac aacaacaaga ccgagaagga gatcctggac    1020
gccttcgaca agatgtgcag caagctgccc aagagcctga cgaggagtg ccaggaggtg    1080 gtggacacct acggcagcag catcctgagc atcctgctgg aggaggtgag ccccgagctg    1140
gtgtgcagca tgctgcacct gtgcagcggc acccgcctgc ccgccctgac cgtgcacgtg    1200
acccagccca aggacggcgg cttctgcgag gtgtgcaaga agctggtggg ctacctggac    1260
cgcaacctgg agaagaacag caccaagcag gagatcctgg ccgccctgga gaagggctgc    1320
agcttcctgc ccgacccta ccagaagcag tgcgaccagt tcgtggccga gtacgagccc    1380
gtgctgatcg agatcctggt ggaggtgatg gacccccagct tcgtgtgcct gaagatcggc    1440
gcctgcccca gcgcccacaa gccctgctg ggcaccgaga agtgcatctg gggccccagc    1500
tactggtgcc agaacaccga gaccgccgcc cagtgcaacg ccgtggagca ctgcaagcgc    1560
cacgtgtgga ac                                                       1572

<210> SEQ ID NO 18
<211> LENGTH: 478
<212> TYPE: PRT
<213> ORGANISM: Homo sapiens

<400> SEQUENCE: 18

Met Gly Arg Cys Cys Phe Tyr Thr Ala Gly Thr Leu Ser Leu Leu Leu
1               5                   10                  15

Leu Val Thr Ser Val Thr Leu Leu Val Ala Arg Val Phe Gln Lys Ala
            20                  25                  30

Val Asp Gln Ser Ile Glu Lys Lys Ile Val Leu Arg Asn Gly Thr Glu
        35                  40                  45

Ala Phe Asp Ser Trp Glu Lys Pro Pro Leu Pro Val Tyr Thr Gln Phe
    50                  55                  60

-continued

Tyr Phe Phe Asn Val Thr Asn Pro Glu Glu Ile Leu Arg Gly Glu Thr
65                  70                  75                  80

Pro Arg Val Glu Glu Val Gly Pro Tyr Thr Tyr Arg Glu Leu Arg Asn
                85                  90                  95

Lys Ala Asn Ile Gln Phe Gly Asp Asn Gly Thr Thr Ile Ser Ala Val
                100                 105                 110

Ser Asn Lys Ala Tyr Val Phe Glu Arg Asp Gln Ser Val Gly Asp Pro
                115                 120                 125

Lys Ile Asp Leu Ile Arg Thr Leu Asn Ile Pro Val Leu Thr Val Ile
        130                 135                 140

Glu Trp Ser Gln Val His Phe Leu Arg Glu Ile Ile Glu Ala Met Leu
145                 150                 155                 160

Lys Ala Tyr Gln Gln Lys Leu Phe Val Thr His Thr Val Asp Glu Leu
                165                 170                 175

Leu Trp Gly Tyr Lys Asp Glu Ile Leu Ser Leu Ile His Val Phe Arg
                180                 185                 190

Pro Asp Ile Ser Pro Tyr Phe Gly Leu Phe Tyr Glu Lys Asn Gly Thr
                195                 200                 205

Asn Asp Gly Asp Tyr Val Phe Leu Thr Gly Glu Asp Ser Tyr Leu Asn
        210                 215                 220

Phe Thr Lys Ile Val Glu Trp Asn Gly Lys Thr Ser Leu Asp Trp Trp
225                 230                 235                 240

Ile Thr Asp Lys Cys Asn Met Ile Asn Gly Thr Asp Gly Asp Ser Phe
                245                 250                 255

His Pro Leu Ile Thr Lys Asp Glu Val Leu Tyr Val Phe Pro Ser Asp
                260                 265                 270

Phe Cys Arg Ser Val Tyr Ile Thr Phe Ser Asp Tyr Glu Ser Val Gln
                275                 280                 285

Gly Leu Pro Ala Phe Arg Tyr Lys Val Pro Ala Glu Ile Leu Ala Asn
        290                 295                 300

Thr Ser Asp Asn Ala Gly Phe Cys Ile Pro Glu Gly Asn Cys Leu Gly
305                 310                 315                 320

Ser Gly Val Leu Asn Val Ser Ile Cys Lys Asn Gly Ala Pro Ile Ile
                325                 330                 335

Met Ser Phe Pro His Phe Tyr Gln Ala Asp Glu Arg Phe Val Ser Ala
                340                 345                 350

Ile Glu Gly Met His Pro Asn Gln Glu Asp His Glu Thr Phe Val Asp
                355                 360                 365

Ile Asn Pro Leu Thr Gly Ile Ile Leu Lys Ala Ala Lys Arg Phe Gln
        370                 375                 380

Ile Asn Ile Tyr Val Lys Lys Leu Asp Asp Phe Val Glu Thr Gly Asp
385                 390                 395                 400

Ile Arg Thr Met Val Phe Pro Val Met Tyr Leu Asn Glu Ser Val His
                405                 410                 415

Ile Asp Lys Glu Thr Ala Ser Arg Leu Lys Ser Met Ile Asn Thr Thr
                420                 425                 430

Leu Ile Ile Thr Asn Ile Pro Tyr Ile Ile Met Ala Leu Gly Val Phe
        435                 440                 445

Phe Gly Leu Val Phe Thr Trp Leu Ala Cys Lys Gly Gln Gly Ser Met
        450                 455                 460

Asp Glu Gly Thr Ala Asp Glu Arg Ala Pro Leu Ile Arg Thr
465                 470                 475

-continued

<210> SEQ ID NO 19
<211> LENGTH: 1434
<212> TYPE: DNA
<213> ORGANISM: Homo sapiens

<400> SEQUENCE: 19

```
atgggccgct gctgcttcta caccgccggc accctgagcc tgctgctgct ggtgaccagc      60
gtgaccctgc tggtggcccg cgtgttccag aaggccgtgg accagagcat cgagaagaag     120
atcgtgctgc gcaacggcac cgaggccttc gacagctggg agaagccccc cctgcccgtg     180
tacacccagt tctacttctt caacgtgacc aaccccgagg atcctgcg cggcgagacc       240 ccccgcgtgg aggaggtggg ccctacacc taccgcgagc tgcgcaacaa ggccaacatc     300
cagttcggcg acaacggcac caccatcagc gccgtgagca caaggccta cgtgttcgag      360 cgcgaccaga gcgtgggcga ccccaagatc gacctgatcc gcaccctgaa catccccgtg    420
ctgaccgtga tcgagtggag ccaggtgcac ttcctgcgcg agatcatcga ggccatgctg    480
aaggcctacc agcagaagct gttcgtgacc cacaccgtgg acgagctgct gtggggctac    540
aaggacgaga tcctgagcct gatccacgtg ttccgccccg catcagccc ctacttcggc     600 ctgttctacg agaagaacgg caccaacgac ggcgactacg tgttcctgac cggcgaggac    660
agctacctga acttcaccaa gatcgtggag tggaacggca agaccagcct ggactggtgg    720
atcaccgaca agtgcaacat gatcaacggc accgacggcg acagcttcca ccccctgatc    780
accaaggacg aggtgctgta cgtgttcccc agcgacttct gccgcagcgt gtacatcacc    840
ttcagcgact acgagagcgt gcagggcctg cccgccttcc gctacaaggt gcccgccgag    900
atcctggcca acaccagcga caacgccggc ttctgcatcc ccgagggcaa ctgcctgggc    960
agcggcgtgc tgaacgtgag catctgcaag aacggcgccc ccatcatcat gagcttcccc   1020
cacttctacc aggccgacga gcgcttcgtg agcgccatcg agggcatgca ccccaaccag   1080
gaggaccacg agaccttcgt ggacatcaac ccctgaccg gcatcatcct gaaggccgcc    1140
aagcgcttcc agatcaacat ctacgtgaag aagctggacg acttcgtgga accggcgac    1200 atccgcacca tggtgttccc cgtgatgtac ctgaacgaga gcgtgcacat cgacaaggag   1260
accgccagcc gcctgaagag catgatcaac accaccctga tcatcaccaa catcccctac   1320
atcatcatgg ccctgggcgt gttcttcggc ctggtgttca cctggctggc ctgcaagggc   1380
cagggcagca tggacgaggg caccgccgac gagcgcgccc ccctgatccg cacc          1434
```

<210> SEQ ID NO 20
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 20

```
tggaagactt cgagatacac tgt                                              23
```

<210> SEQ ID NO 21
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 21

```
acagtgtatc tcgaagtctt cca                                              23
```

```
<210> SEQ ID NO 22
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 22
tttagaaata agtggtagtc a                                              21

<210> SEQ ID NO 23
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 23
tgactaccac ttatttctaa a                                              21

<210> SEQ ID NO 24
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 24
agggtatcaa gactacgaa                                                 19

<210> SEQ ID NO 25
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 25
ttcgtagtct tgataccct                                                 19

<210> SEQ ID NO 26
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 26
tattagatct gatggccgc                                                 19

<210> SEQ ID NO 27
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 27
ctccatcact aggggttcct                                                20

<210> SEQ ID NO 28
<211> LENGTH: 60
<212> TYPE: DNA
<213> ORGANISM: Artificial Sequence
<220> FEATURE:
```

-continued

```
<223> OTHER INFORMATION: Synthetic polynucleotide

<400> SEQUENCE: 28
agctctgggt atttaagccc gagtgagcac gcagggtctc cattttgaag cgggaggtta        60

<210> SEQ ID NO 29
<211> LENGTH: 145
<212> TYPE: DNA
<213> ORGANISM: Unknown
<220> FEATURE:
<223> OTHER INFORMATION: AAV2 ITR

<400> SEQUENCE: 29
aggaacccct agtgatggag ttggccactc cctctctgcg cgctcgctcg ctcactgagg        60
ccgggcgacc aaaggtcgcc cgacgcccgg gctttgcccg ggcggcctca gtgagcgagc       120
gagcgcgcag agagggagtg gccaa                                            145

<210> SEQ ID NO 30
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 30
tattagatct gatggccgcg                                                   20

<210> SEQ ID NO 31
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 31
tccatcacta ggggttcctg                                                   20
```

1

GENE THERAPIES FOR LYSOSOMAL DISORDERS

RELATED APPLICATIONS

This Application is a continuation of U.S. patent application Ser. No. 17/024,117, filed Sep. 17, 2020 and issued as U.S. Pat. No. 11,060,113, which is a continuation of Ser. No. 16/689,865, filed Nov. 20, 2019 and issued as U.S. Pat. No. 10,837,028, which is a continuation of International Patent Application No. PCT/US2018/054225, filed Oct. 3, 2018, which claims the benefit under 35 U.S.C. 119(e) of the filing date of U.S. Provisional Application Ser. No. 62/567,296, filed Oct. 3, 2017, entitled "GENE THERAPIES FOR LYSOSOMAL DISORDERS", the entire contents of each of which are incorporated herein by reference.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: PRVL 002_04US_SeqListST25.txt, date recorded: Jul. 7, 2021, file size ~211,090 bytes).

BACKGROUND

Gaucher disease is a rare inborn error of glycosphingo-lipid metabolism due to deficiency of lysosomal acid β-glu-cocerebrosidase (Gcase, "GBA"). Patients suffer from non-CNS symptoms and findings including hepatosplenomegaly, bone marrow insufficiency leading to pancytopenia, lung disorders and fibrosis, and bone defects. In addition, a significant number of patients suffer from neurological manifestations, including defective saccadic eye movements and gaze, seizures, cognitive deficits, developmental delay, and movement disorders including Parkinson's disease.

Several therapeutics exist that address the peripheral disease and the principal clinical manifestations in hema-topoietic bone marrow and viscera, including enzyme replacement therapies, chaperone-like small molecule drugs that bind to defective Gcase and improve stability, and substrate reduction therapy that block the production of substrates that accumulate in Gaucher disease, leading to symptoms and pathology. However, other aspects of Gaucher disease and appear refractory to treatment.

SUMMARY

In addition to Gaucher disease patients (who possess mutations in both chromosomal alleles of GBA1 gene), patients with mutations in only one allele of GBA1 are at highly increased risk of Parkinson's disease (PD). The severity of PD symptoms—which include gait difficulty, a tremor at rest, rigidity, and often depression, sleep difficulties, and cognitive decline—correlate with the degree of enzyme activity reduction. Thus, Gaucher disease patients have the most severe course, whereas patient with a single mild mutation in GBA1 typically have a more benign course. Mutation carriers are also at high risk of other PD-related disorders, including Lewy Body Dementia, characterized by executive dysfunction, psychosis, and a PD-like movement disorder, and multi-system atrophy, with characteristic motor and cognitive impairments. No therapies exist that alter the inexorable course of these disorders.

Deficits in enzymes such as Gcase (e.g., the gene product of GBA1 gene), as well as common variants in many genes implicated in lysosome function or trafficking of macromolecules to the lysosome (e.g., Lysosomal Membrane Protein 1 (LIMP), also referred to as SCARB2), have been associated with increased PD risk. The disclosure is based, in part, on expression constructs (e.g., vectors) encoding Gcase (or a portion thereof), prosaposin (or a portion thereof), LIMP2 (or a portion thereof), or a combination of Gcase (or a portion thereof) and one or more additional gene products from PD-associated genes (e.g., LIMP2, Prosaposin, and/or α-Synuclein (α-Syn)). In some embodiments, combinations of gene products described herein act together (e.g., synergistically) to reduce one or more signs and symptoms of PD when expressed in a subject.

Accordingly, in some aspects, the disclosure provides an isolated nucleic acid comprising an expression construct encoding a Gcase (e.g., the gene product of GBA1 gene). In some embodiments, the isolated nucleic acid comprises a Gcase-encoding sequence that has been codon optimized (e.g., codon optimized for expression in mammalian cells, for example human cells). In some embodiments, the nucleic acid sequence encoding the Gcase encodes a protein comprising an amino acid sequence as set forth in SEQ ID NO: 14 (e.g., as set forth in NCBI Reference Sequence NP_000148.2). In some embodiments, the isolated nucleic acid comprises the sequence set forth in SEQ ID NO: 15. In some embodiments the expression construct comprises adeno-associated virus (AAV) inverted terminal repeats (ITRs), for example AAV ITRs flanking the nucleic acid sequence encoding the Gcase.

In some aspects, the disclosure provides an isolated nucleic acid comprising an expression construct encoding Prosaposin (e.g., the gene product of PSAP gene). In some embodiments, the isolated nucleic acid comprises a prosaposin-encoding sequence that has been codon optimized (e.g., codon optimized for expression in mammalian cells, for example human cells). In some embodiments, the nucleic acid sequence encoding the prosaposin encodes a protein comprising an amino acid sequence as set forth in SEQ ID NO: 16 (e.g., as set forth in NCBI Reference Sequence NP_002769.1). In some embodiments, the isolated nucleic acid comprises the sequence set forth in SEQ ID NO: 17. In some embodiments the expression construct comprises adeno-associated virus (AAV) inverted terminal repeats (ITRs), for example AAV ITRs flanking the nucleic acid sequence encoding the prosaposin.

In some aspects, the disclosure provides an isolated nucleic acid comprising an expression construct encoding LIMP2/SCARB2 (e.g., the gene product of SCARB2 gene). In some embodiments, the isolated nucleic acid comprises a SCARB2-encoding sequence that has been codon optimized (e.g., codon optimized for expression in mammalian cells, for example human cells). In some embodiments, the nucleic acid sequence encoding the LIMP2/SCARB2 encodes a protein comprising an amino acid sequence as set forth in SEQ ID NO: 18 (e.g., as set forth in NCBI Reference Sequence NP_005497.1). In some embodiments, the isolated nucleic acid comprises the sequence set forth in SEQ ID NO: 29. In some embodiments the expression construct comprises adeno-associated virus (AAV) inverted terminal repeats (ITRs), for example AAV ITRs flanking the nucleic acid sequence encoding the SCARB2.

In some aspects, the disclosure provides an isolated nucleic acid comprising an expression construct encoding a first gene product and a second gene product, wherein each gene product independently is selected from the gene products, or portions thereof, set forth in Table 1.

In some embodiments, a first gene product or a second gene product is a Gcase protein, or a portion thereof. In some embodiments, a first gene product or a second gene product is LIMP2 or a portion thereof, or Prosaposin or a portion thereof. In some embodiments, the first gene product is a Gcase protein, and the second gene product is LIMP2 or a portion thereof, or Prosaposin or a portion thereof.

In some embodiments, an expression construct further encodes an interfering nucleic acid (e.g., shRNA, miRNA, dsRNA, etc.). In some embodiments, an interfering nucleic acid inhibits expression of α-Synuclein (α-Synuclein). In some embodiments, an interfering nucleic acid that targets α-Synuclein comprises a sequence set forth in any one of SEQ ID NOs: 20-25. In some embodiments, an interfering nucleic acid that targets α-Synuclein binds to (e.g., hybridizes with) a sequence set forth in any one of SEQ ID NO: 20-25.

In some embodiments, an expression construct further comprises one or more promoters. In some embodiments, a promoter is a chicken-beta actin (CBA) promoter, a CAG promoter, a CD68 promoter, or a JeT promoter. In some embodiments, a promoter is a RNA pol II promoter or an RNA pol III promoter (e.g., U6, etc.).

In some embodiments, an expression construct further comprises an internal ribosomal entry site (IRES). In some embodiments, an IRES is located between a first gene product and a second gene product.

In some embodiments, an expression construct further comprises a self-cleaving peptide coding sequence. In some embodiments, a self-cleaving peptide is a T2A peptide.

In some embodiments, an expression construct comprises two adeno-associated virus (AAV) inverted terminal repeat (ITR) sequences. In some embodiments, ITR sequences flank a first gene product and a second gene product (e.g., are arranged as follows from 5'-end to 3'-end: ITR-first gene product-second gene product-ITR). In some embodiments, one of the ITR sequences of an isolated nucleic acid lacks a functional terminal resolution site (trs). For example, in some embodiments, one of the ITRs is a ΔITR.

The disclosure relates, in some aspects, to rAAV vectors comprising an ITR having a modified "D" region (e.g., a D sequence that is modified relative to wild-type AAV2 ITR, SEQ ID NO: 29). In some embodiments, the ITR having the modified D region is the 5' ITR of the rAAV vector. In some embodiments, a modified "D" region comprises an "S" sequence, for example as set forth in SEQ ID NO: 26. In some embodiments, the ITR having the modified "D" region is the 3' ITR of the rAAV vector. In some embodiments, a modified "D" region comprises a 3'ITR in which the "D" region is positioned at the 3' end of the ITR (e.g., on the outside or terminal end of the ITR relative to the transgene insert of the vector). In some embodiments, a modified "D" region comprises a sequence as set forth in SEQ ID NO: 26 or 27.

In some embodiments, an isolated nucleic acid (e.g., an rAAV vector) comprises a TRY region. In some embodiments, a TRY region comprises the sequence set forth in SEQ ID NO: 28.

In some embodiments, an isolated nucleic acid described by the disclosure comprises or consists of the sequence set forth in any one of SEQ ID NOs: 1 to 13, 15, 17, and 19. In some embodiments, an isolated nucleic acid described by the disclosure encodes a peptide comprising or consisting of the sequence set forth in any one of SEQ ID NOs: 14, 16, and 18.

In some aspects, the disclosure provides a vector comprising an isolated nucleic acid as described by the disclosure. In some embodiments, a vector is a plasmid, or a viral vector. In some embodiments, a viral vector is a recombinant AAV (rAAV) vector. In some embodiments, an rAAV vector is single-stranded (e.g., single-stranded DNA).

In some aspects, the disclosure provides a host cell comprising an isolated nucleic acid as described by the disclosure or a vector as described by the disclosure.

In some aspects, the disclosure provides a recombinant adeno-associated virus (rAAV) comprising a capsid protein and an isolated nucleic acid or a vector as described by the disclosure.

In some embodiments, a capsid protein is capable of crossing the blood-brain barrier, for example an AAV9 capsid protein or an AAVrh.10 capsid protein. In some embodiments, an rAAV transduces neuronal cells and non-neuronal cells of the central nervous system (CNS).

In some aspects, the disclosure provides a method for treating a subject having or suspected of having Parkinson's disease, the method comprising administering to the subject a composition (e.g., a composition comprising an isolated nucleic acid or a vector or a rAAV) as described by the disclosure.

In some embodiments, administration comprises direct injection to the CNS of a subject. In some embodiments, direct injection is intracerebral injection, intraparenchymal injection, intrathecal injection, intra-cisterna magna injection, or any combination thereof. In some embodiments, direct injection to the CNS of a subject comprises convection enhanced delivery (CED).

In some embodiments, administration comprises peripheral injection. In some embodiments, peripheral injection is intravenous injection.

The coding sequences of Gcase and Prosaposin are separated by an internal ribosomal entry site (IRES).

Figure 1:
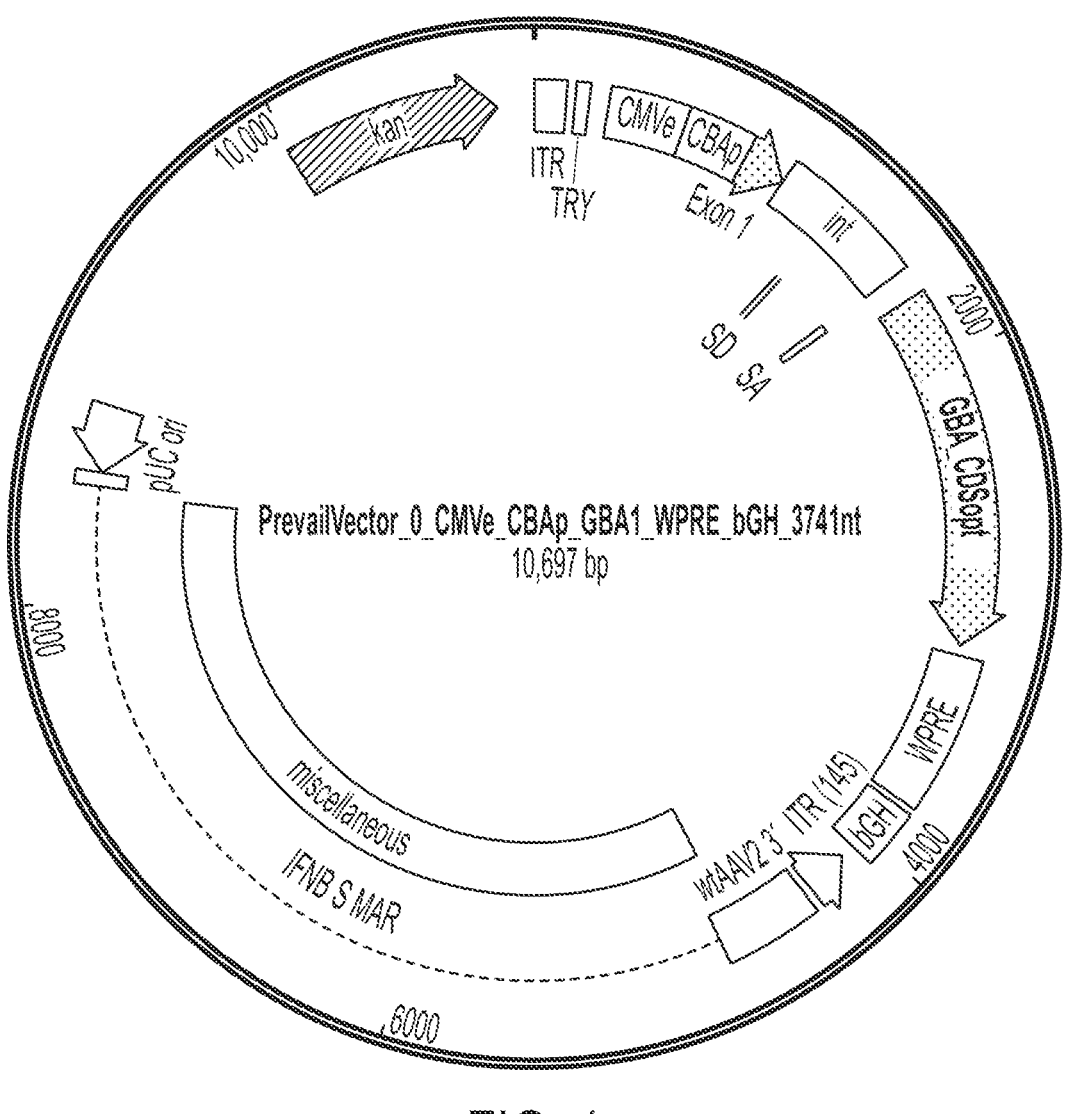
FIG. 1 is a schematic depicting one embodiment of a plasmid comprising an rAAV vector that includes an expression construct encoding Gcase (e.g., GBA1 or a portion thereof).
Figure 2:
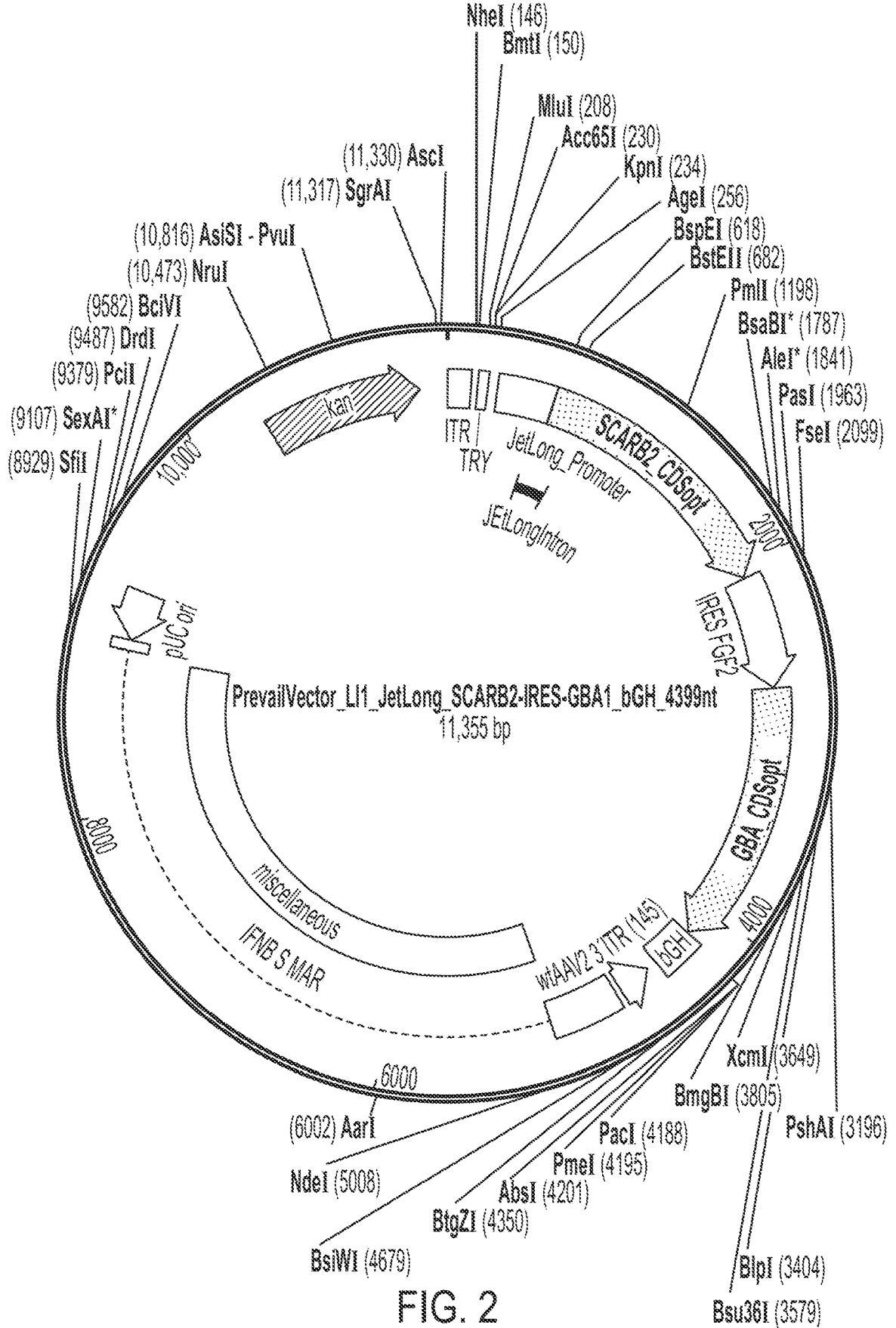
FIG. 2 is a schematic depicting one embodiment of a plasmid comprising an rAAV vector that includes an expression construct encoding Gcase (e.g., GBA1 or a portion thereof) and LIMP2 (SCARB2) or a portion thereof. The coding sequences of Gcase and LIMP2 are separated by an internal ribosomal entry site (IRES).
Figure 3:
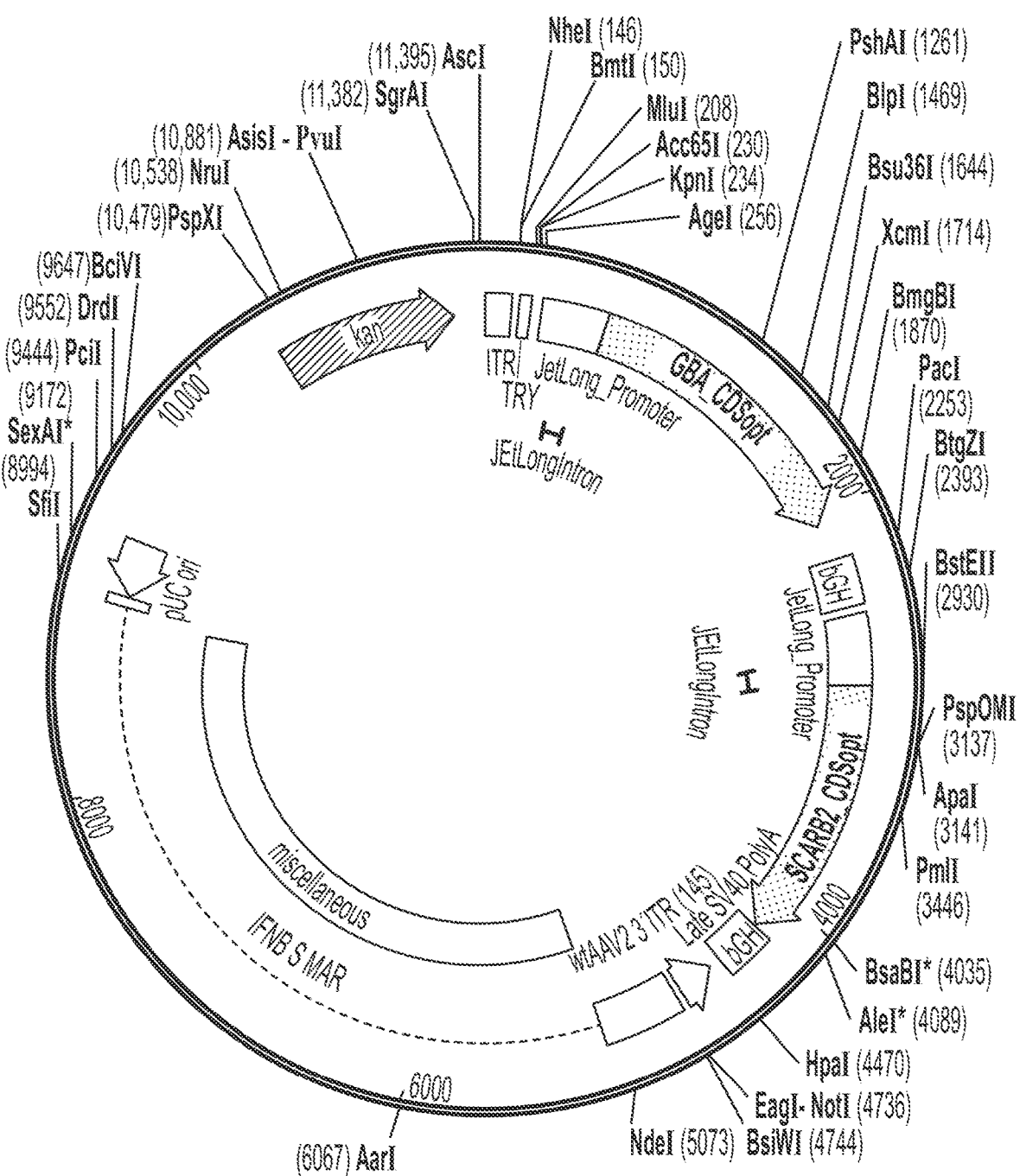
FIG. 3 is a schematic depicting one embodiment of a plasmid comprising an rAAV vector that includes an expression construct encoding Gcase (e.g., GBA1 or a portion thereof) and LIMP2 (SCARB2) or a portion thereof. Expression of the coding sequences of Gcase and LIMP2 are each driven by a separate promoter.
Figure 4:
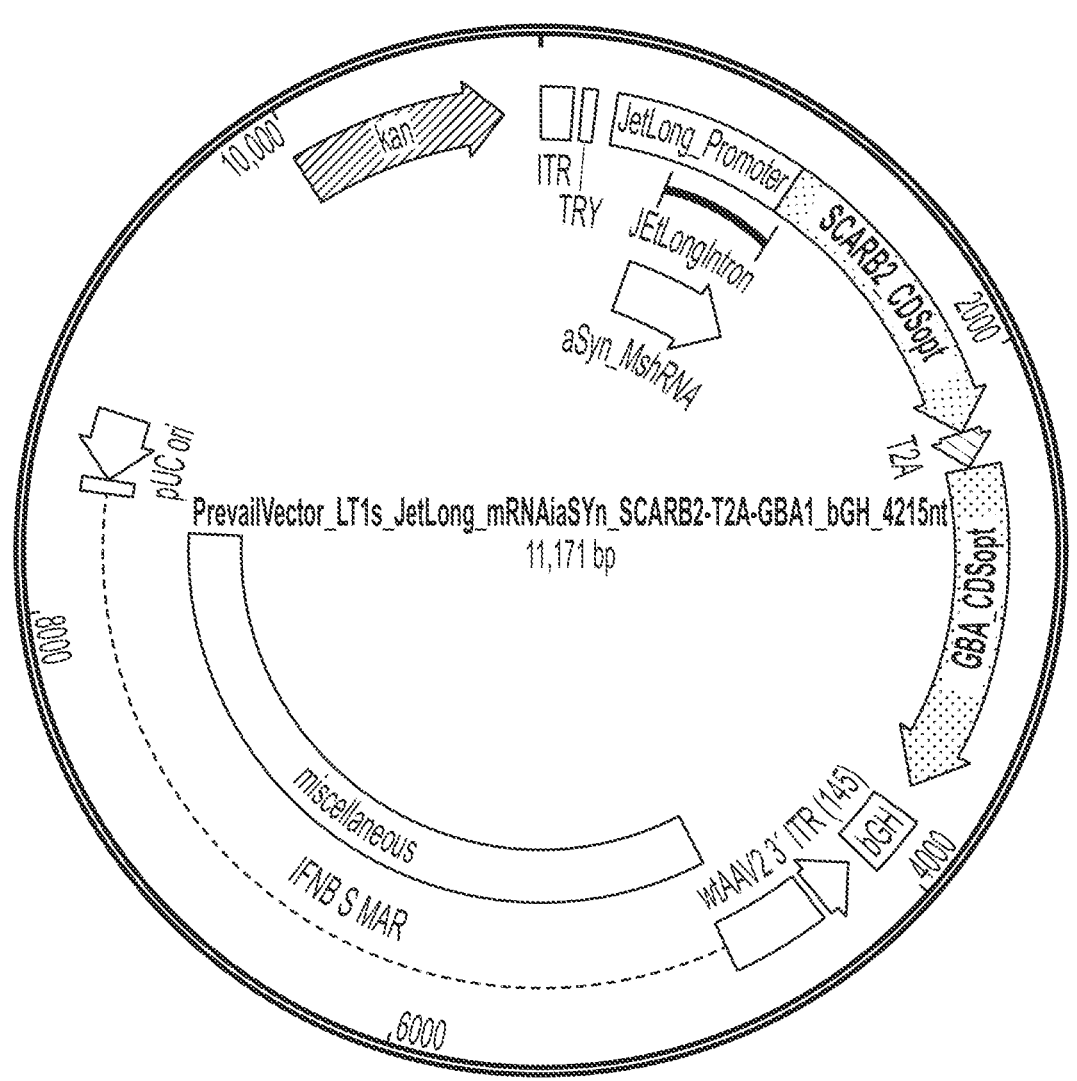
FIG. 4 is a schematic depicting one embodiment of a plasmid comprising an rAAV vector that includes an expression construct encoding Gcase (e.g., GBA1 or a portion thereof), LIMP2 (SCARB2) or a portion thereof, and an interfering RNA for α-Syn.
Figure 5:
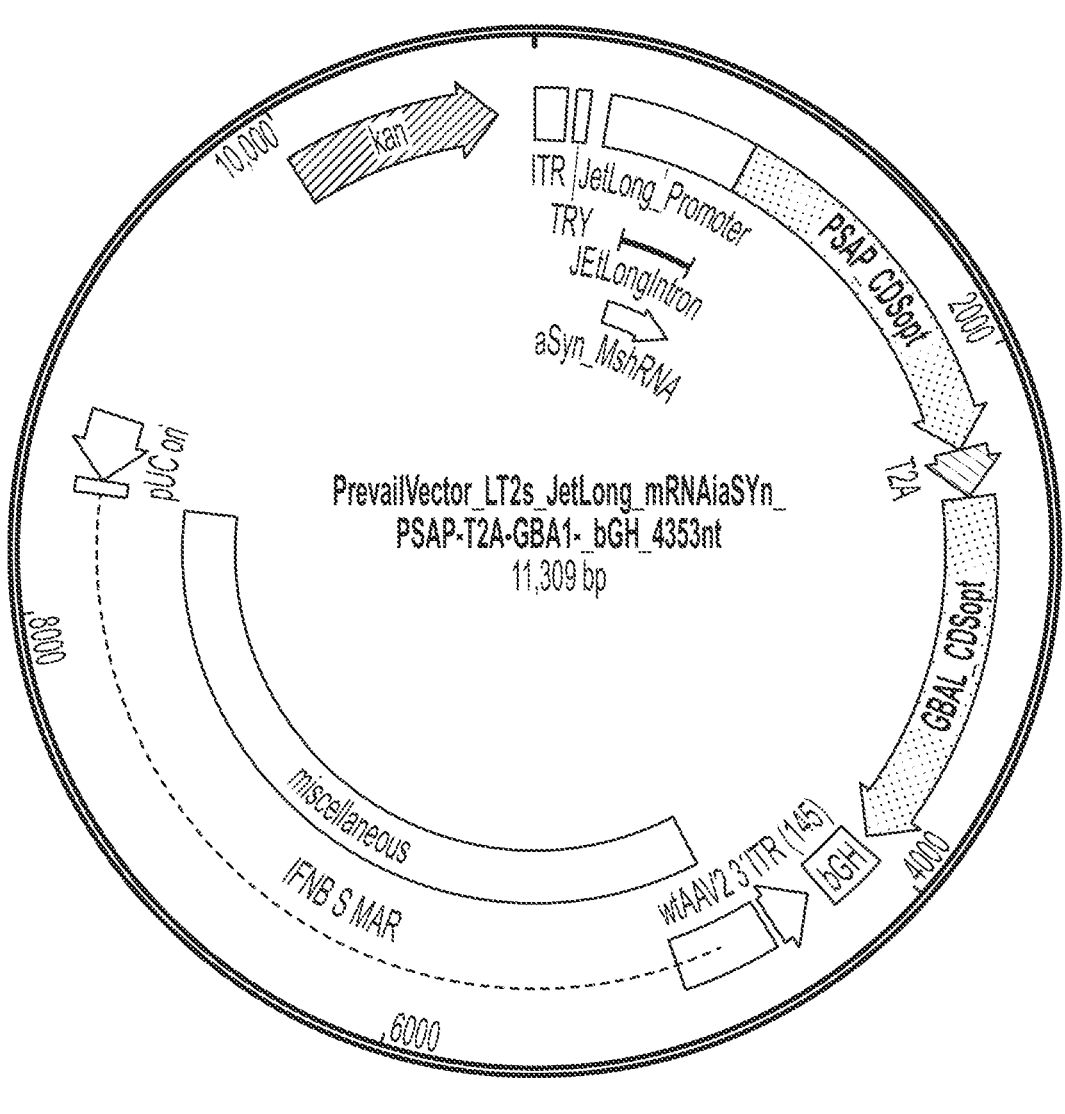
FIG. 5 is a schematic depicting one embodiment of a plasmid comprising an rAAV vector that includes an expression construct encoding Gcase (e.g., GBA1 or a portion thereof), Prosaposin (e.g., PSAP or a portion thereof), and an interfering RNA for α-Syn.
Figure 6:
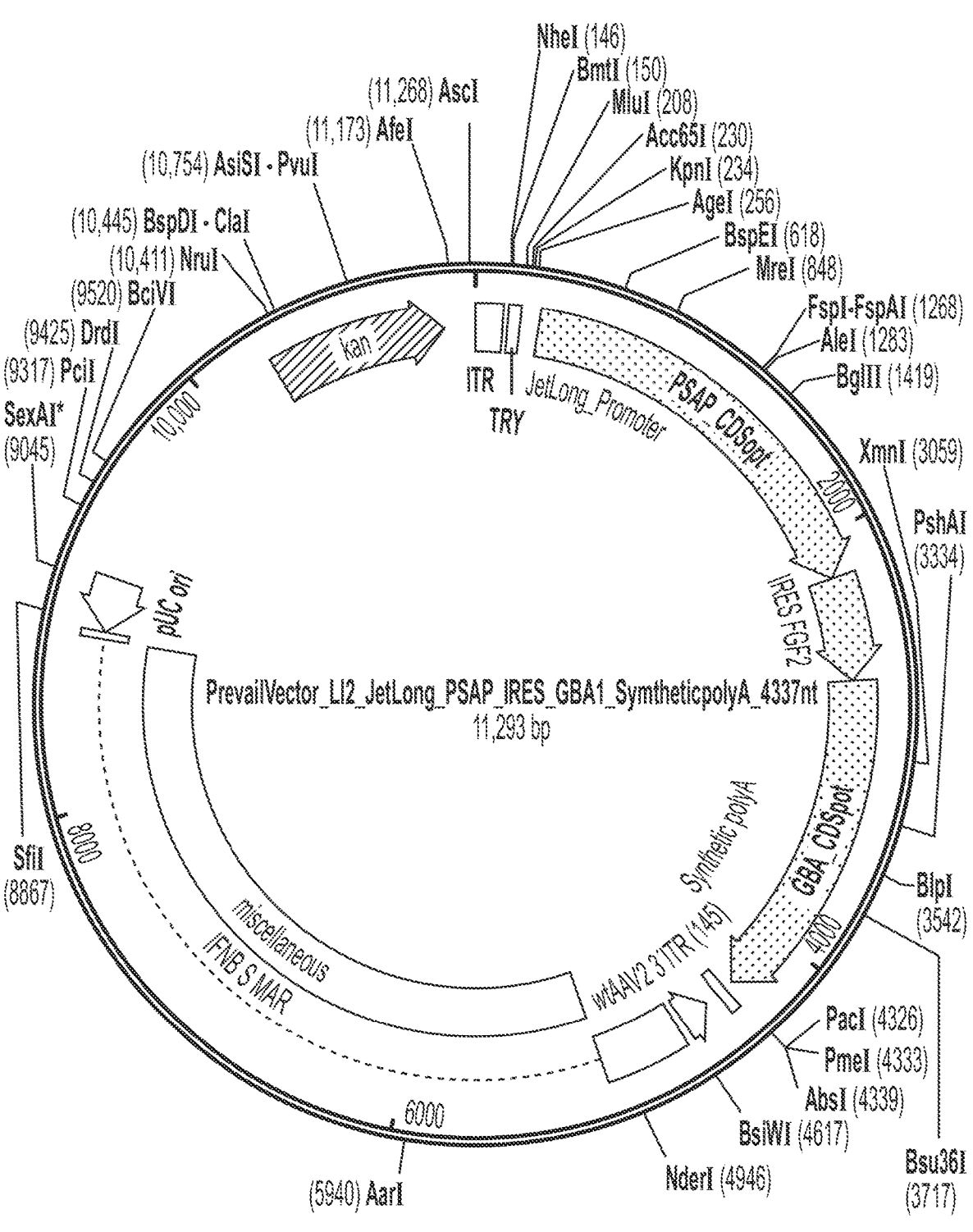
FIG. 6 is a schematic depicting one embodiment of a plasmid comprising an rAAV vector that includes an expression construct encoding Gcase (e.g., GBA1 or a portion thereof) and Prosaposin (e.g., PSAP or a portion thereof).
Figure 7:
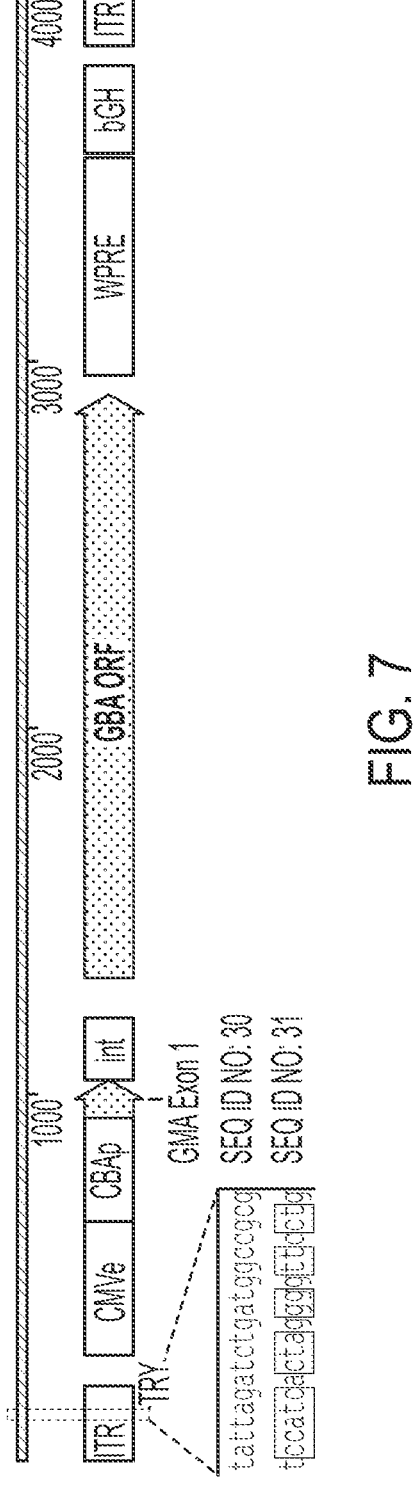

FIG. 7 is a schematic depicting one embodiment of an rAAV vector that includes an expression construct encoding a Gcase (e.g., GBA1 or a portion thereof). In this embodiment, the vector comprises a CBA promoter element (CBA), consisting of four parts: the CMV enhancer (CMVe), CBA promoter (CBAp), Exon 1, and intron (int) to constitutively express the codon optimized coding sequence of human GBA1. The 3' region also contains a WPRE regulatory element followed by a bGH polyA tail. Three transcriptional regulatory activation sites are included at the 5' end of the promoter region: TATA, RBS, and YY1. The flanking ITRs allow for the correct packaging of the intervening sequences. Two variants of the 5' ITR sequence (inset box) were evaluated; these have several nucleotide differences within the 20-nucleotide "D" region of wild-type AAV2 ITR. In some embodiments, an rAAV vector contains the "D" domain nucleotide sequence shown on the top line. In some embodiments, an rAAV vector comprises a mutant "D" domain (e.g., an "S" domain, with the nucleotide changes shown on the bottom line).

Figure 8:
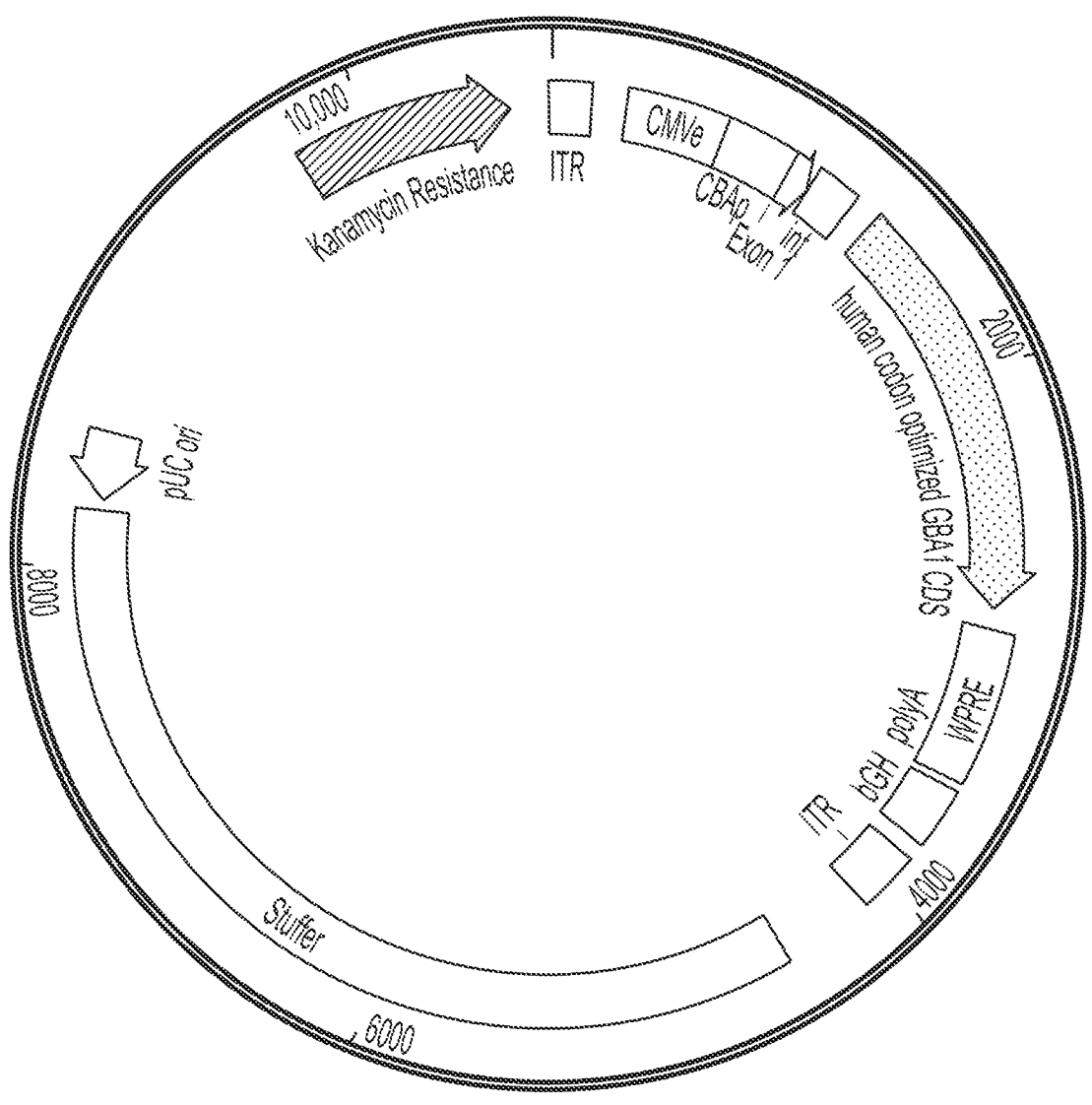

FIG. 8 is a schematic depicting one embodiment of a plasmid encoding the rAAV vector to described in FIG. 7.

Figure 9:
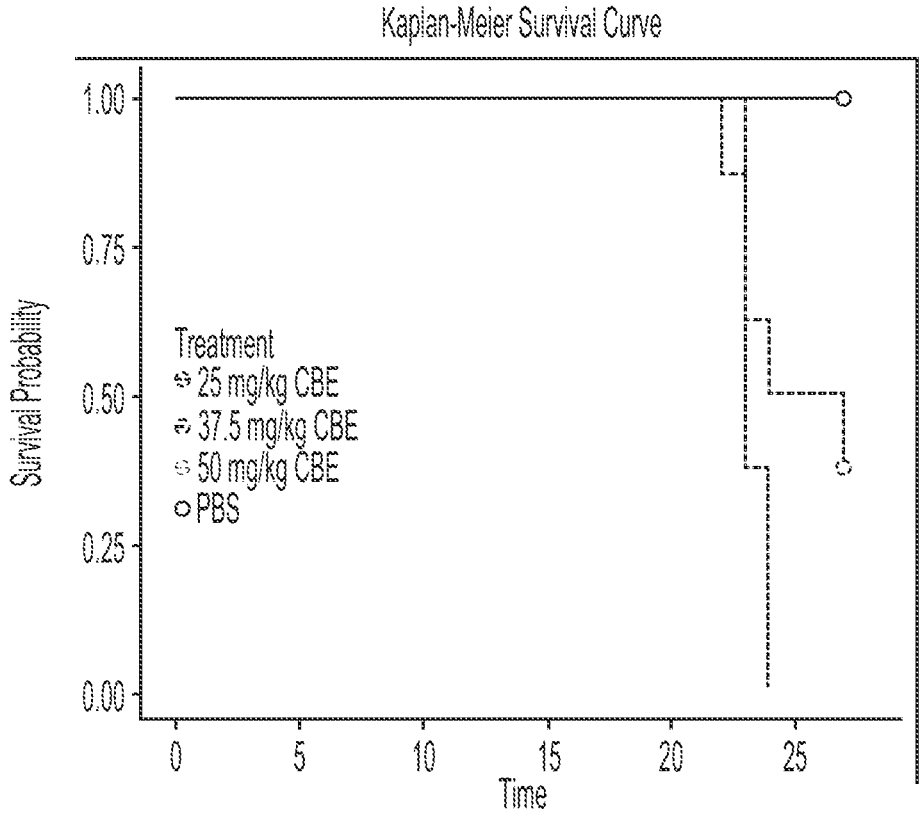
Figure 9:
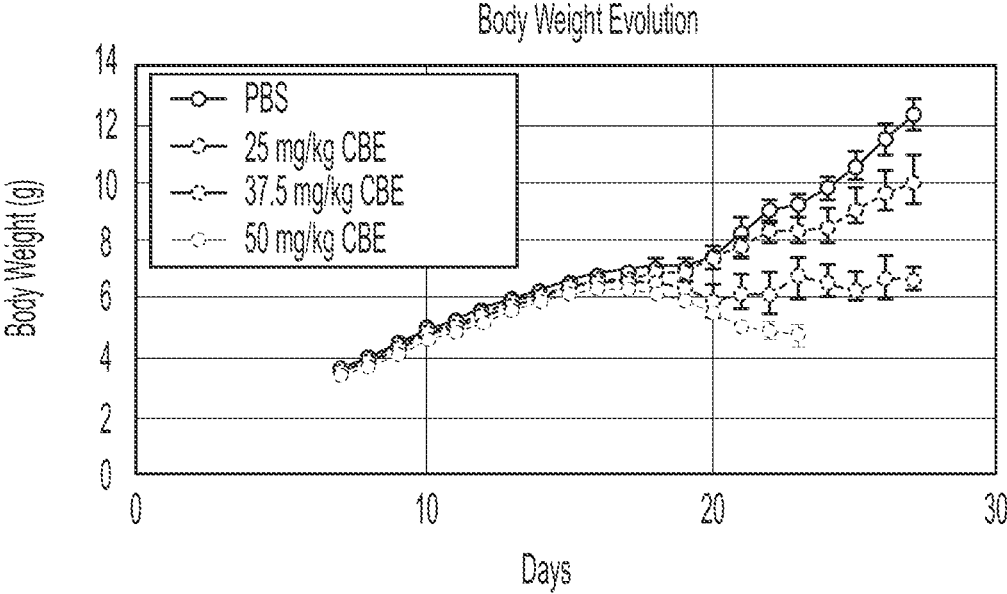
Figure 9:
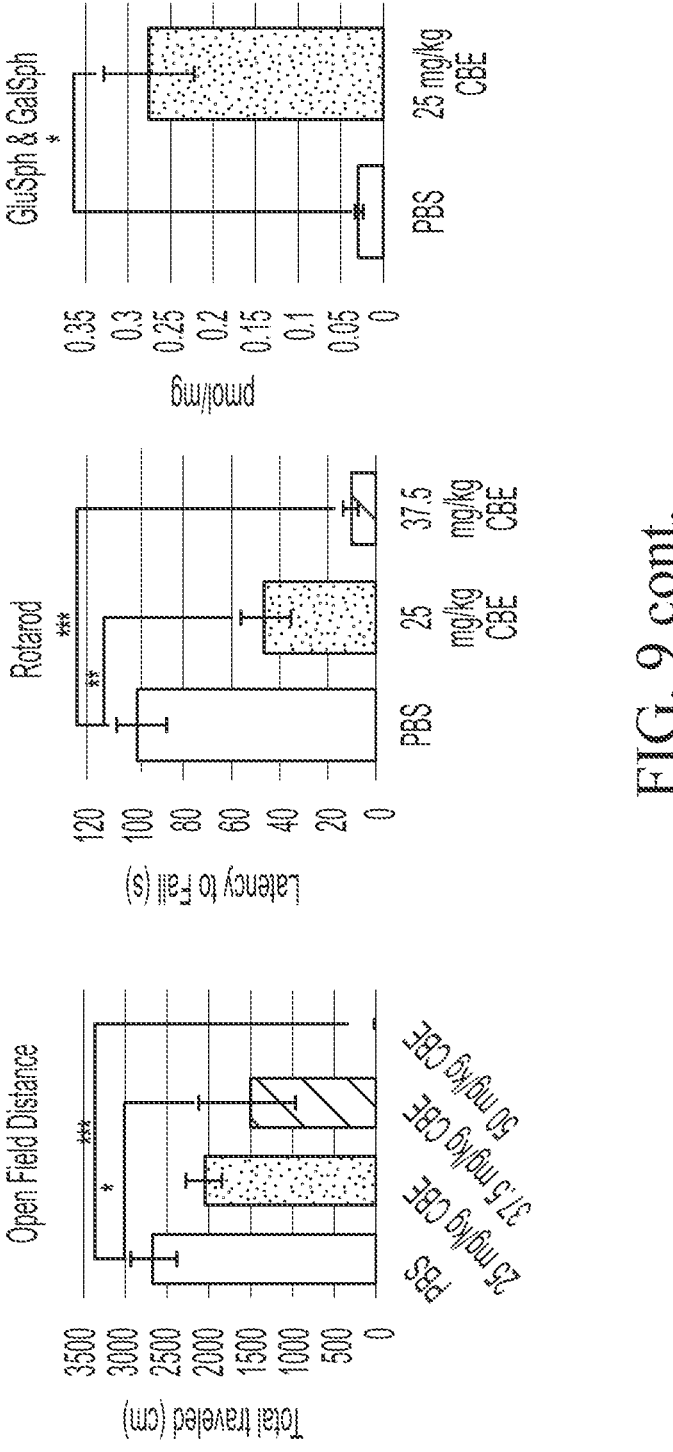

FIG. 9 shows representative data for delivery of an rAAV comprising a transgene encoding a Gcase (e.g., GBA1 or a portion thereof) in a CBE mouse model of Parkinson's disease. Daily IP delivery of PBS vehicle, 25 mg/kg CBE, 37.5 mg/kg CBE, or 50 mg/kg CBE (left to right) initiated at P8. Survival (top left) was checked two times a day and weight (top right) was checked daily. All groups started with n=8. Behavior was assessed by total distance traveled in Open Field (bottom left) at P23 and latency to fall on Rotarod (bottom middle) at P24. Levels of the GCase substrates were analyzed in the cortex of mice in the PBS and 25 mg/kg CBE treatment groups both with (Day 3) and without (Day 1) CBE withdrawal. Aggregate GluSph and GalSph levels (bottom right) are shown as pmol per mg wet weight of the tissue. Means are presented. Error bars are SEM. *p<0.05; p<0.01; *p<0.001, nominal p-values for treatment groups by linear regression.

Figure 10:
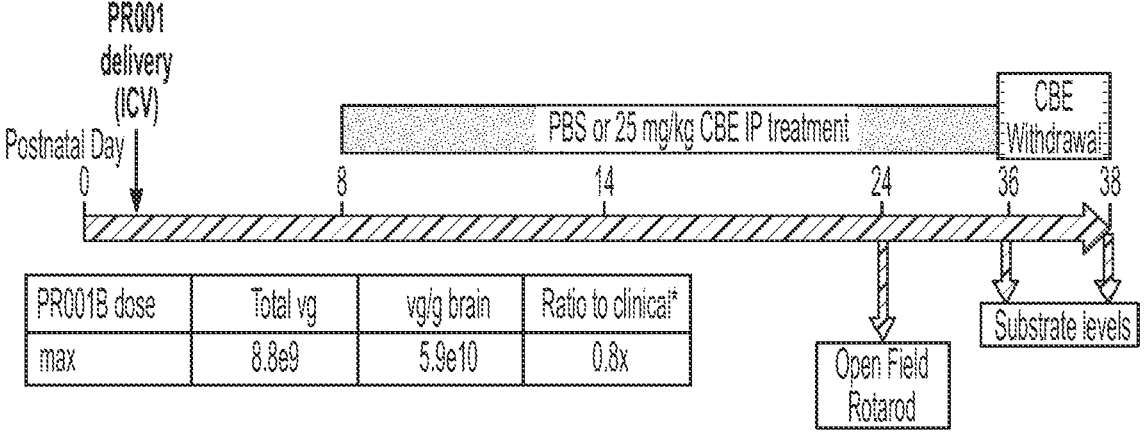

FIG. 10 is a schematic depicting one embodiment of a study design for maximal rAAV dose in a CBE mouse model. Briefly, rAAV was delivered by ICV injection at P3, and daily CBE treatment was initiated at P8. Behavior was assessed in the Open Field and Rotarod assays at P24-25 and substrate levels were measured at P36 and P38.

Figure 11:
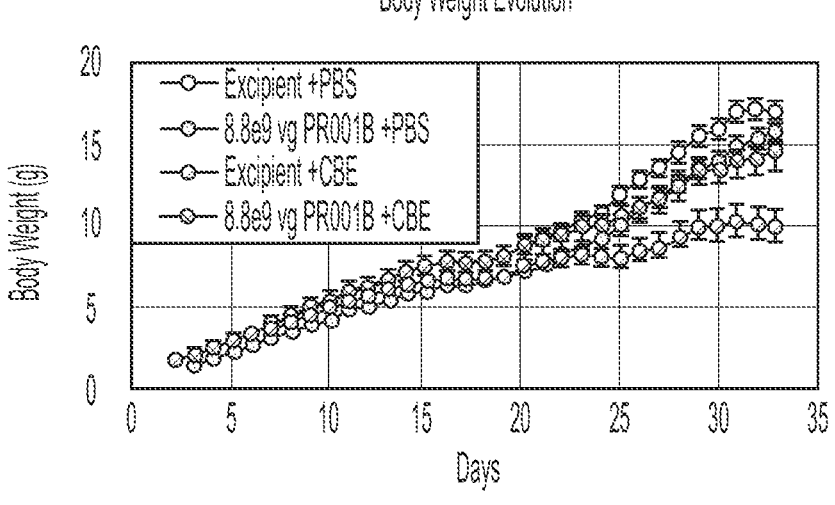
Figure 11:
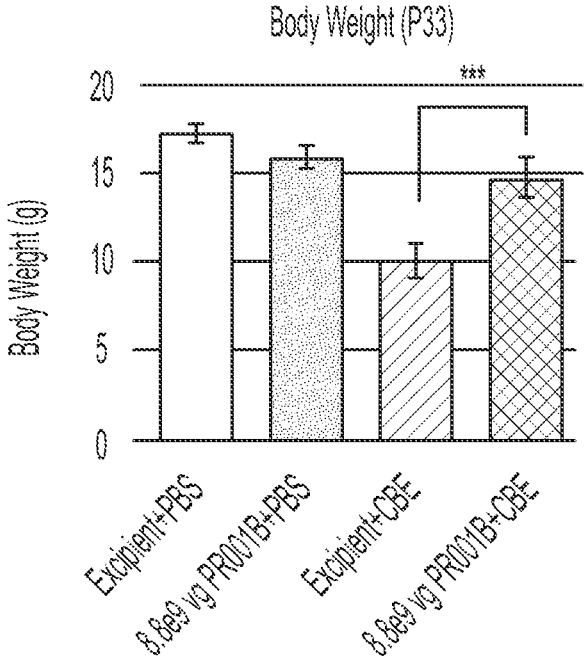
Figure 11:
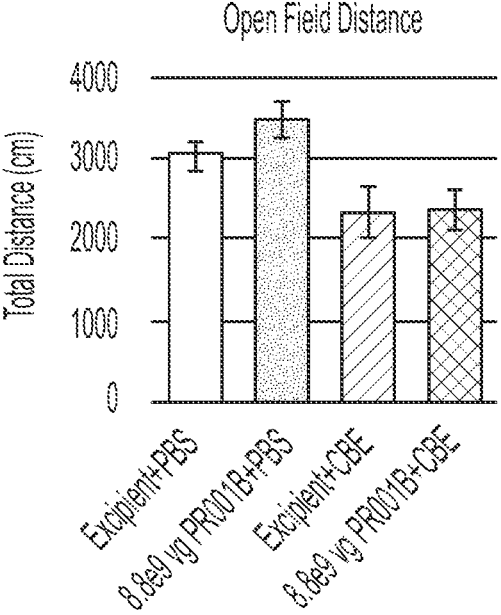

FIG. 11 shows representative data for in-life assessment of maximal rAAV dose in a CBE mouse model. At P3, mice were treated with either excipient or 8.8e9 vg rAAV via ICV delivery. Daily IP delivery of either PBS or 25 mg/kg CBE was initiated at P8. At the end of the study, half the mice were sacrificed one day after their last CBE dose at P36 (Day 1) while the remaining half went through 3 days of CBE withdrawal before sacrifice at P38 (Day 3). All treatment groups (excipient+PBS n=8, rAAV+PBS n=7, excipient+CBE n=8, and rAAV+CBE n=9) were weighed daily (top left), and the weight at P36 was analyzed (top right). Behavior was assessed by total distance traveled in Open Field at P23 (bottom left) and latency to fall on Rotarod at P24 (bottom right), evaluated for each animal as the median across 3 trials. Due to lethality, n=7 for the excipient+CBE group for the behavioral assays, while n=8 for all other groups. Means across animals are presented. Error bars are SEM. *p<0.05; ***p<0.001, nominal p-values for treatment groups by linear regression in the CBE-treated animals.

Figures 11, 12:
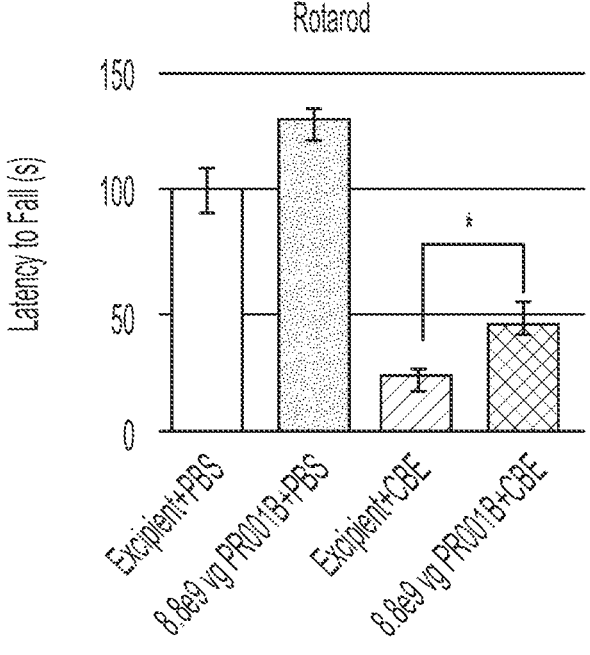
Figure 12:
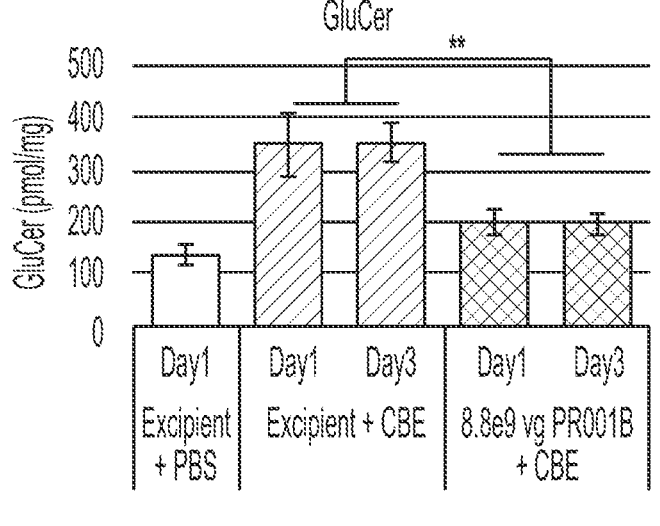
Figure 12:
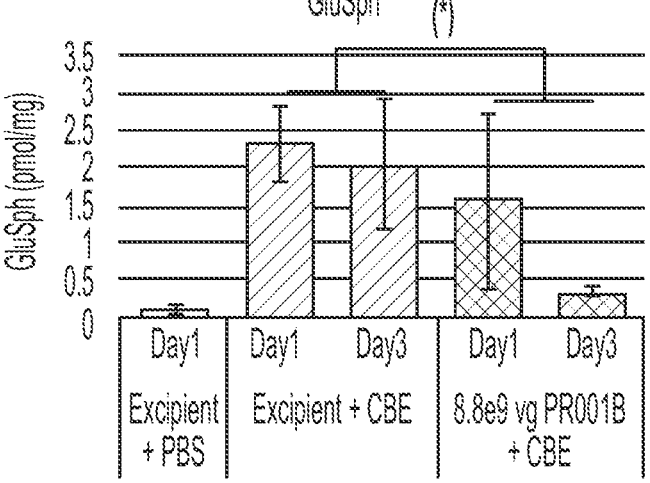
Figure 12:
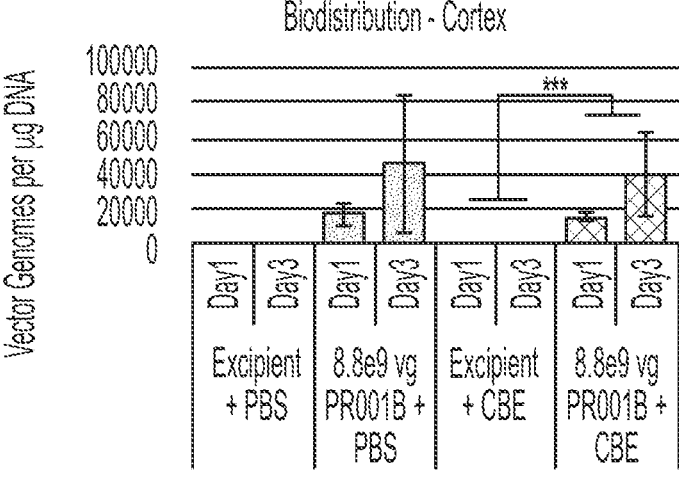

FIG. 12 shows representative data for biochemical assessment of maximal rAAV dose in a CBE mouse model. The cortex of all treatment groups (excipient+PBS n=8, rAAV+PBS n=7, excipient+CBE n=7, and rAAV+CBE n=9) was used to measure GCase activity (top left), GluSph levels (top right), GluCer levels (bottom left), and vector genomes (bottom right) in the groups before (Day 1) or after (Day 3) CBE withdrawal. Biodistribution is shown as vector genomes per 1 μg of genomic DNA. Means are presented. Error bars are SEM. (*)p<0.1; p<0.01; *p<0.001, nominal p-values for treatment groups by linear regression in the CBE-treated animals, with collection days and gender corrected for as covariates.

Figure 13:
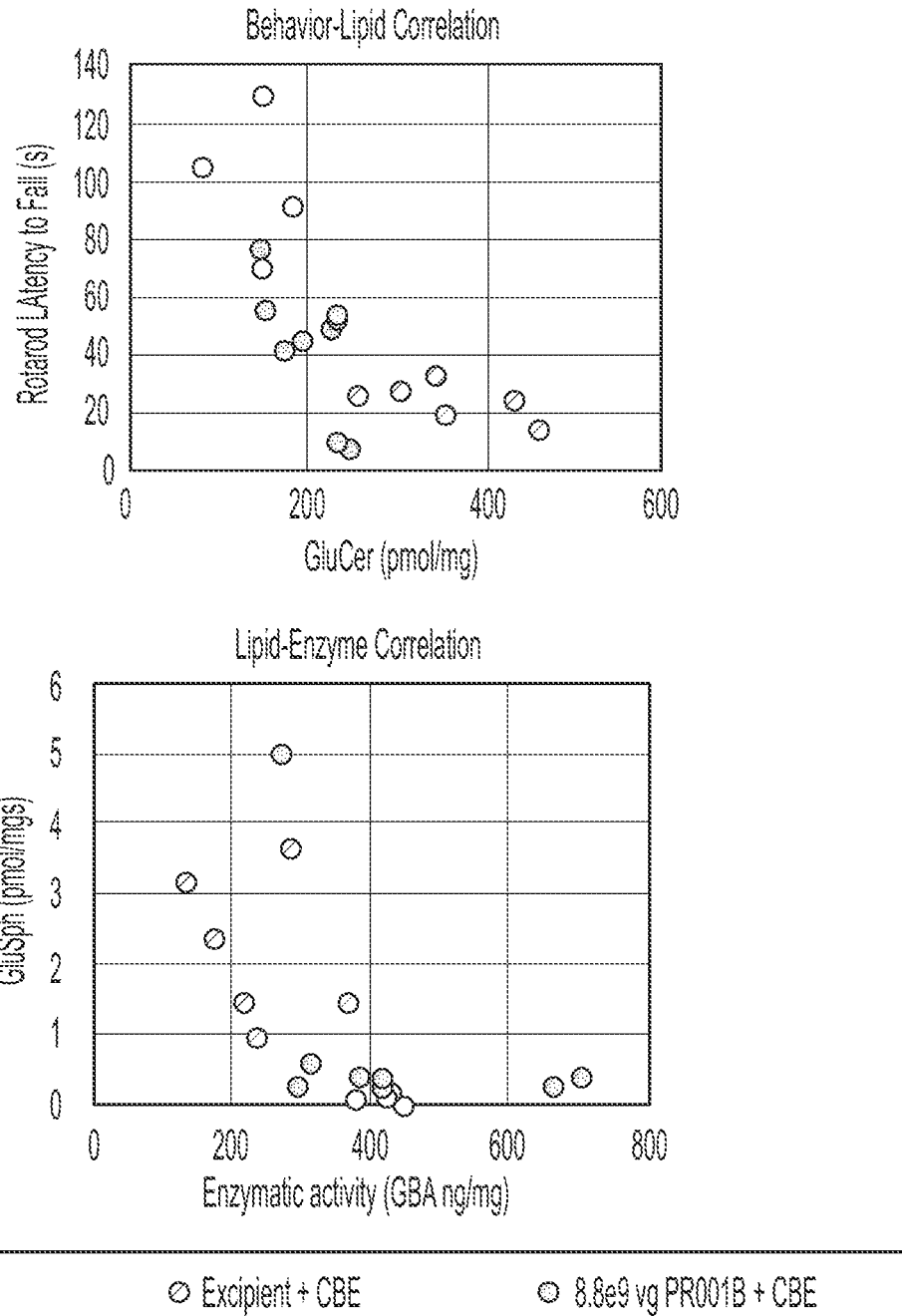

FIG. 13 shows representative data for behavioral and biochemical correlations in a CBE mouse model after administration of excipient+PBS, excipient+CBE, and rAAV+CBE treatment groups. Across treatment groups, performance on Rotarod was negatively correlated with GluCer accumulation (A, p=0.0012 by linear regression), and GluSph accumulation was negatively correlated with increased GCase activity (B, p=0.0086 by linear regression).

Figure 14:
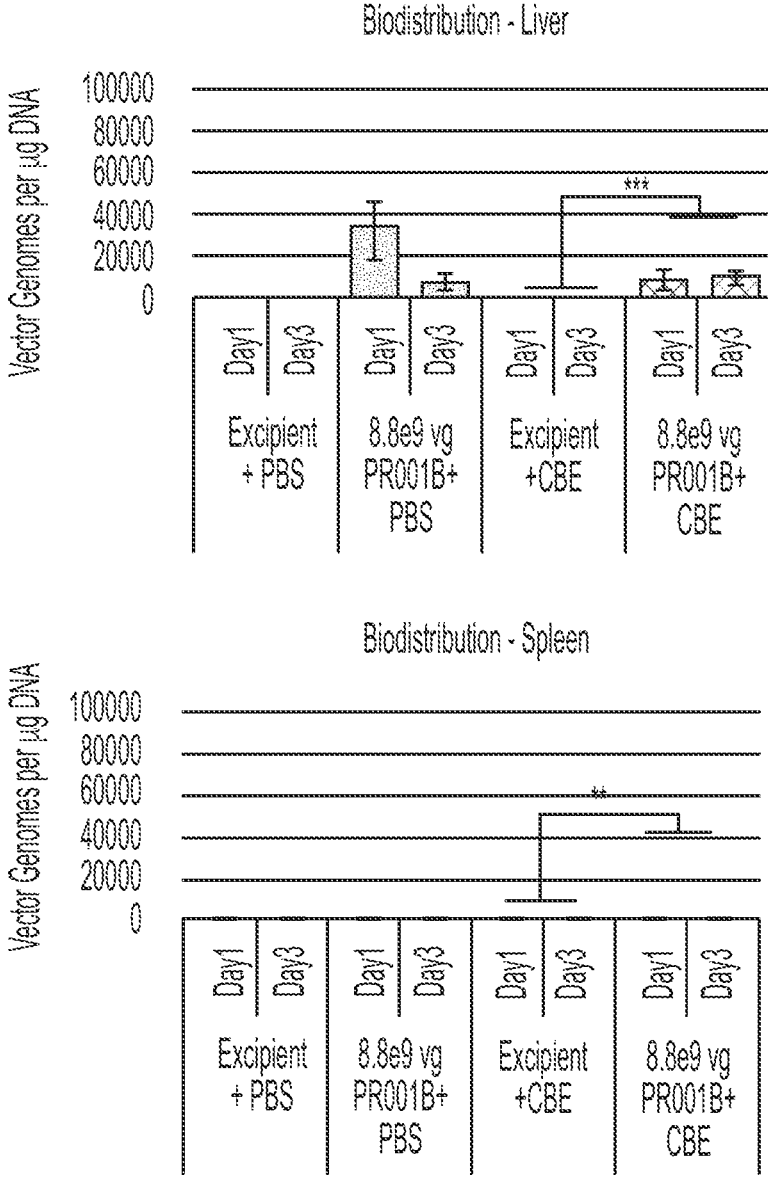
Figure 14:
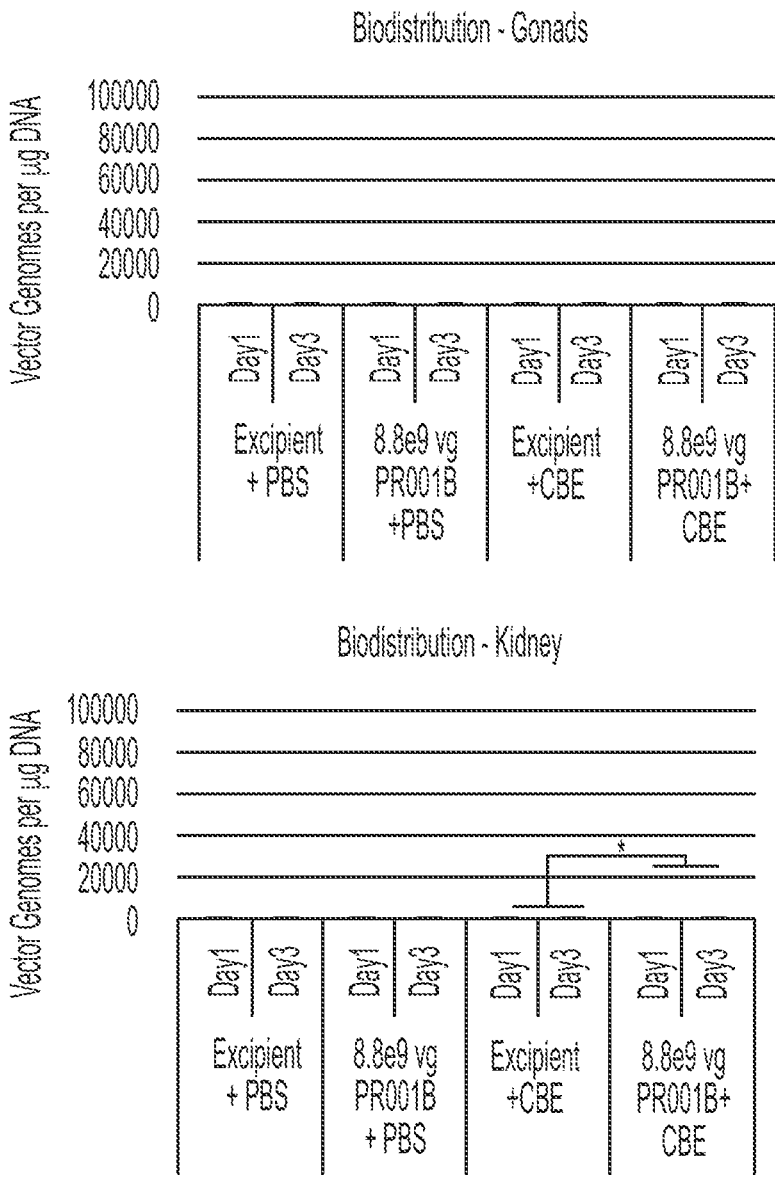

FIG. 14 shows representative data for biodistribution of GBA1 rAAV in a CBE mouse model. Presence of vector genomes was assessed in the liver, spleen, kidney, and gonads for all treatment groups (excipient+PBS n=8, rAAV+PBS n=7, excipient+CBE n=7, and rAAV+CBE n=9). Biodistribution is shown as vector genomes per 1 μg of genomic DNA. Vector genome presence was quantified by quantitative PCR using a vector reference standard curve; genomic DNA concentration was evaluated by A260 optical density measurement. Means are presented. Error bars are SEM. *p<0.05; p<0.01; *p<0.001, nominal p-values for treatment groups by linear regression in the CBE-treated animals, with collection days and gender corrected for as covariates.

Figure 15:
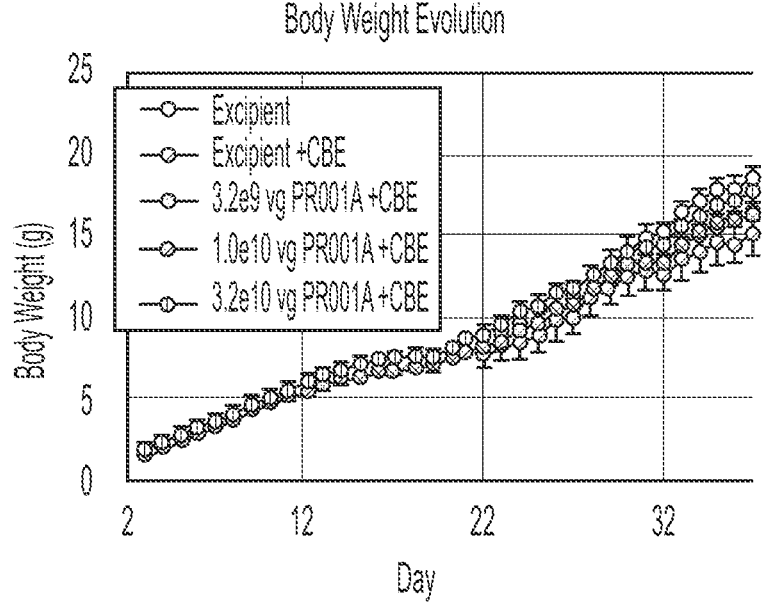
Figure 15:
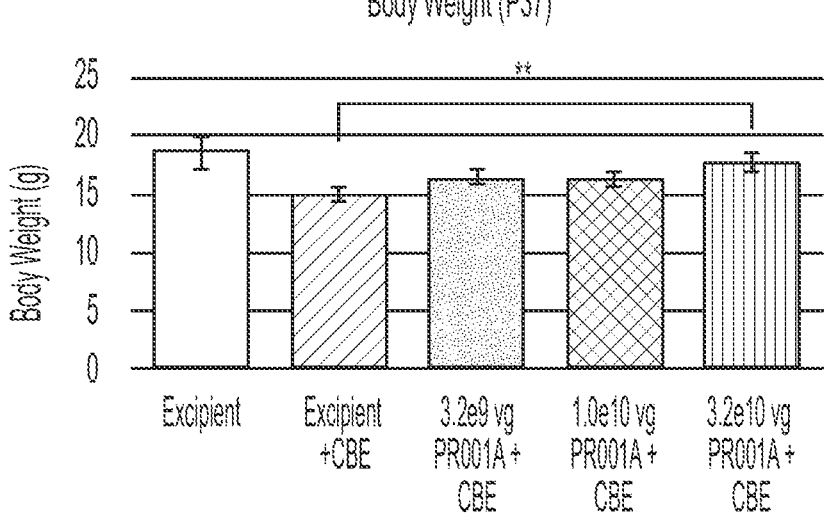
Figure 15:
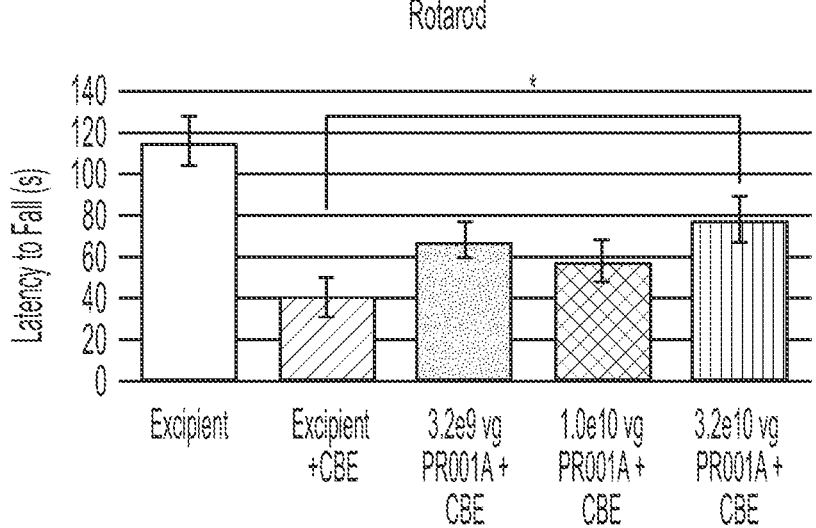
Figure 15:
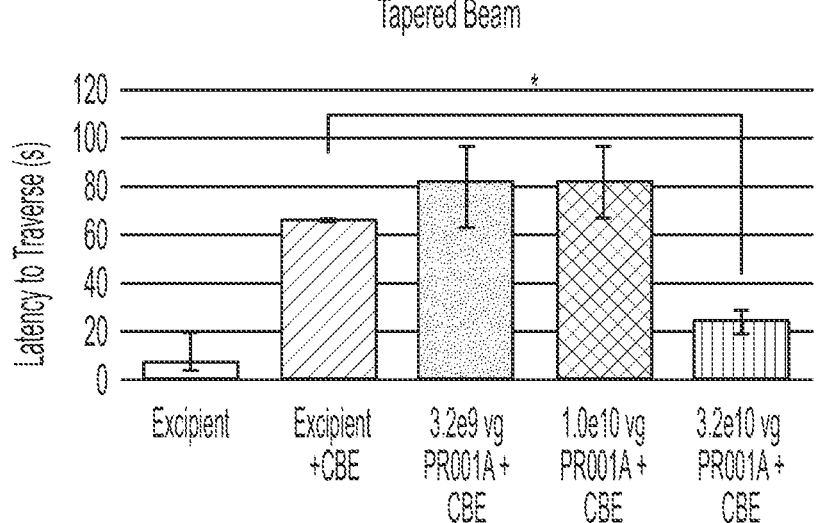

FIG. 15 shows representative data for in-life assessment of rAAV dose ranging in a CBE mouse model. Mice received excipient or one of three different doses of GBA1 rAAV by ICV delivery at P3: 3.2e9 vg, 1.0e10 vg, or 3.2e10 vg. At P8, daily IP treatment of 25 mg/kg CBE was initiated. Mice that received excipient and CBE or excipient and PBS served as controls. All treatment groups started with n=10 (5M/5F) per group. All mice were sacrificed one day after their final CBE dose (P38-P40). All treatment groups were weighed daily, and their weight was analyzed at P36. Motor performance was assessed by latency to fall on Rotarod at P24 and latency to traverse the Tapered Beam at P30. Due to early lethality, the number of mice participating in the behavioral assays was: excipient+PBS n=10, excipient+CBE n=9, and 3.2e9 vg rAAV+CBE n=6, 1.0e10 vg rAAV+CBE n=10, 3.2e10 vg rAAV+CBE n=7. Means are presented. Error bars are SEM; *p<0.05; **p<0.01 for nominal p-values by linear regression in the CBE-treated groups, with gender corrected for as a covariate.

Figure 16:
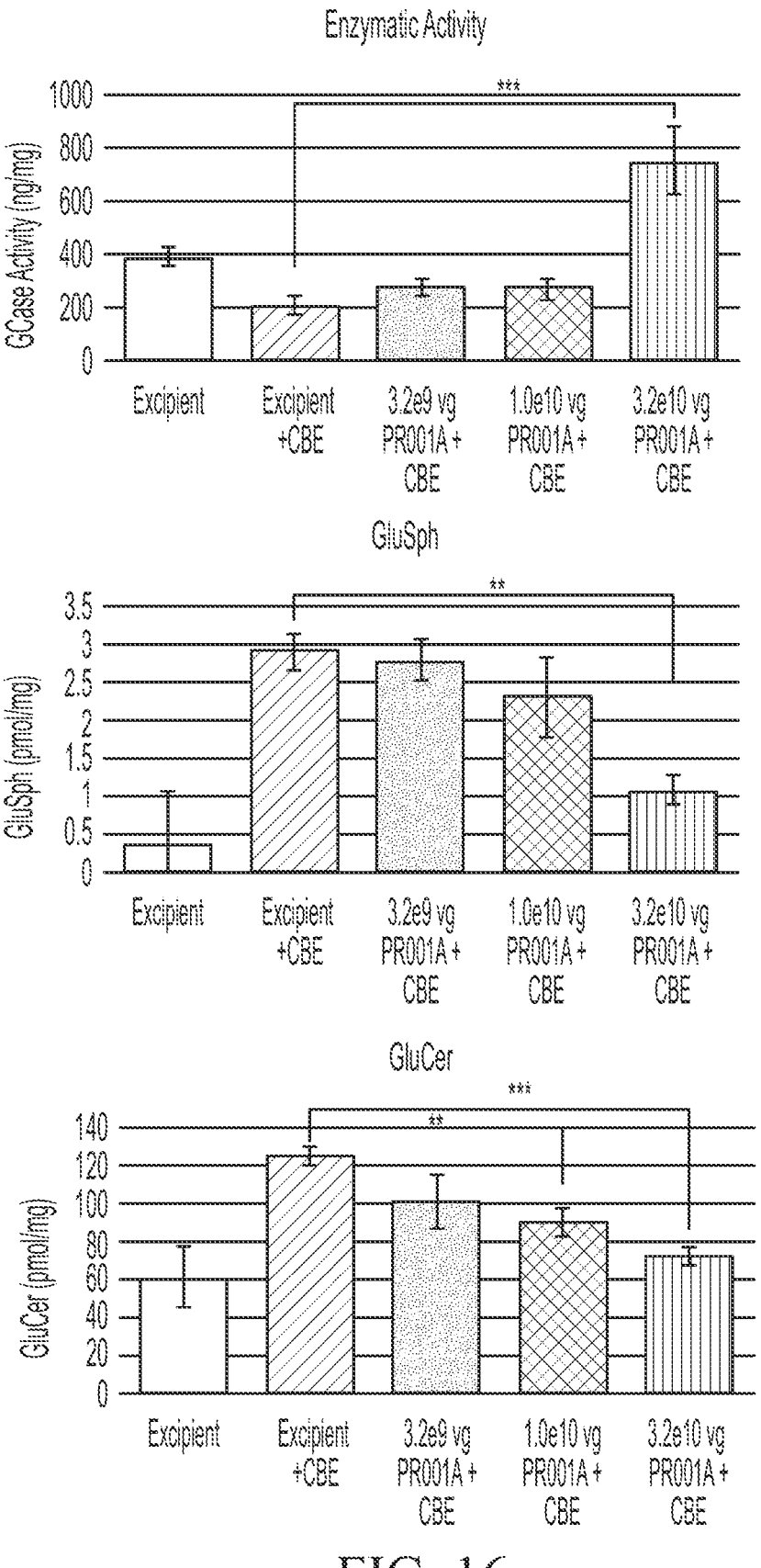
Figure 16:
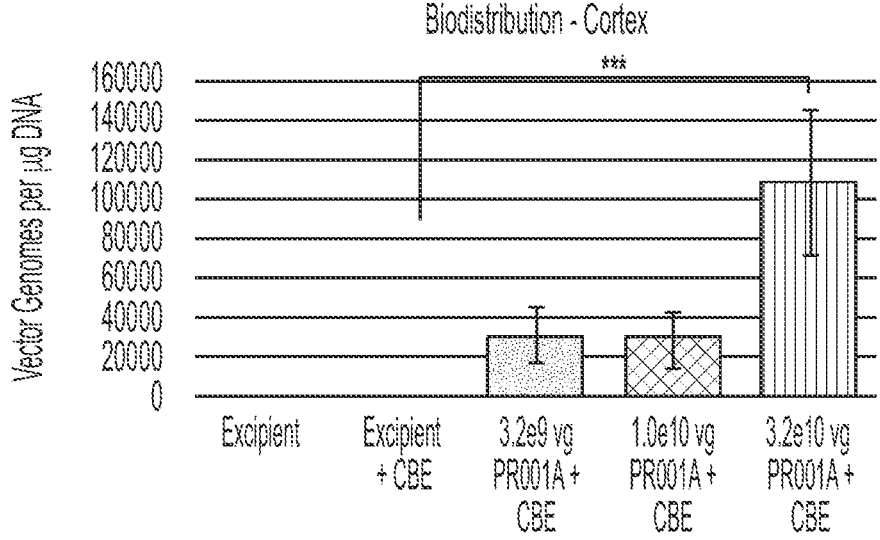
Figure 16:
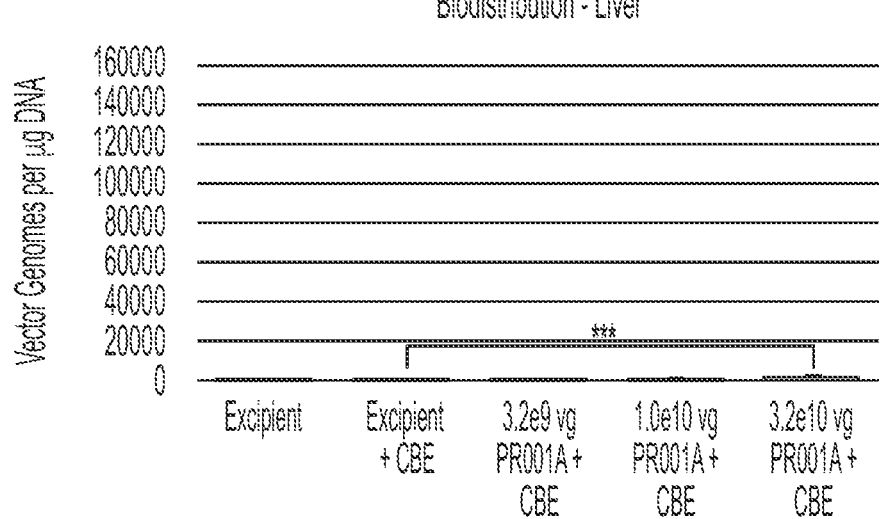

FIG. 16 shows representative data for biochemical assessment of rAAV dose ranging in a CBE mouse model. The cortex of all treatment groups (excipient+PBS n=10, excipient+CBE n=9, and 3.2e9 vg rAAV+CBE n=6, 1.0e10 vg rAAV+CBE n=10, 3.2e10 vg rAAV+CBE n=7) was used to measure GCase activity, GluSph levels, GluCer levels, and vector genomes. GCase activity is shown as ng of GCase per mg of total protein. GluSph and GluCer levels are shown as pmol per mg wet weight of the tissue. Biodistribution is shown as vector genomes per 1 μg of genomic DNA. Vector genome presence was quantified by quantitative PCR using a vector reference standard curve; genomic DNA concentration was evaluated by A260 optical density measurement. Vector genome presence was also measured in the liver (E). Means are presented. Error bars are SEM. p<0.01; *p<0.001 for nominal p-values by linear regression in the CBE-treated groups, with gender corrected for as a covariate.

Figure 17:
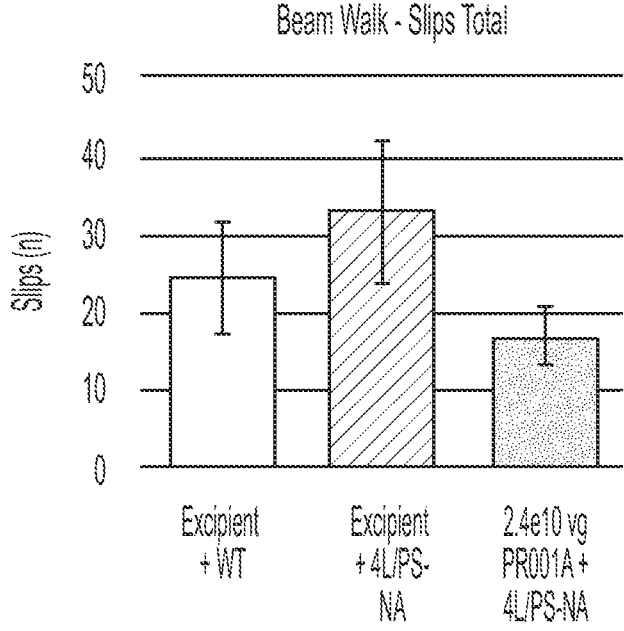
Figure 17:
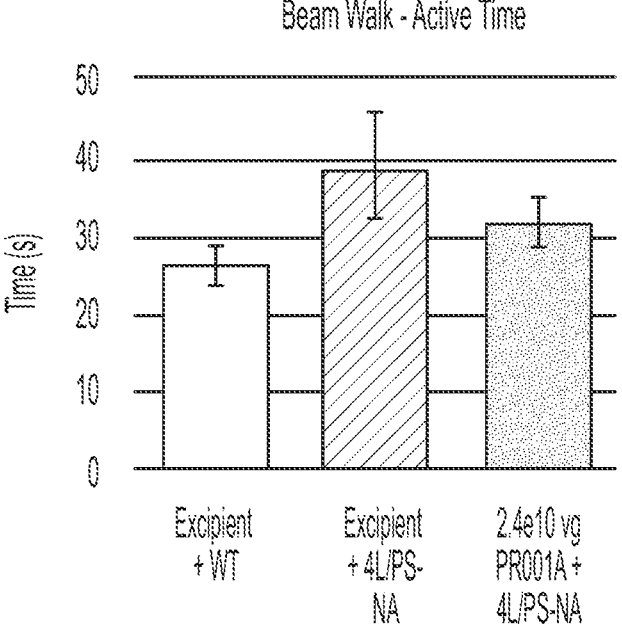
Figure 17:
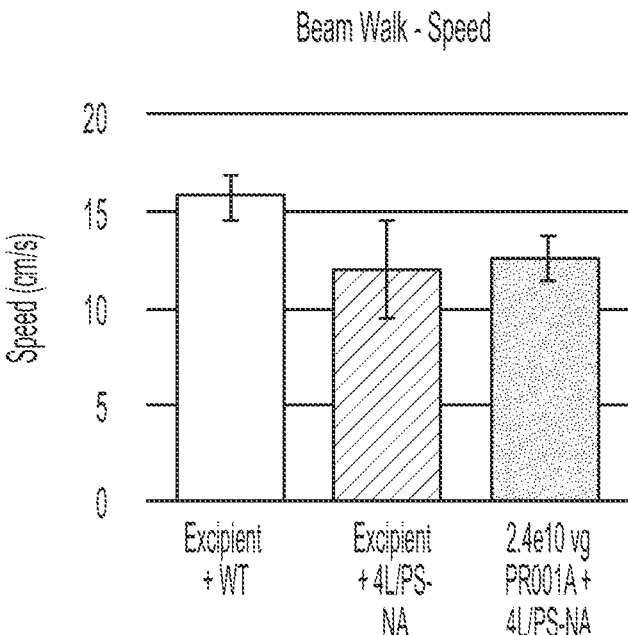
Figure 17:
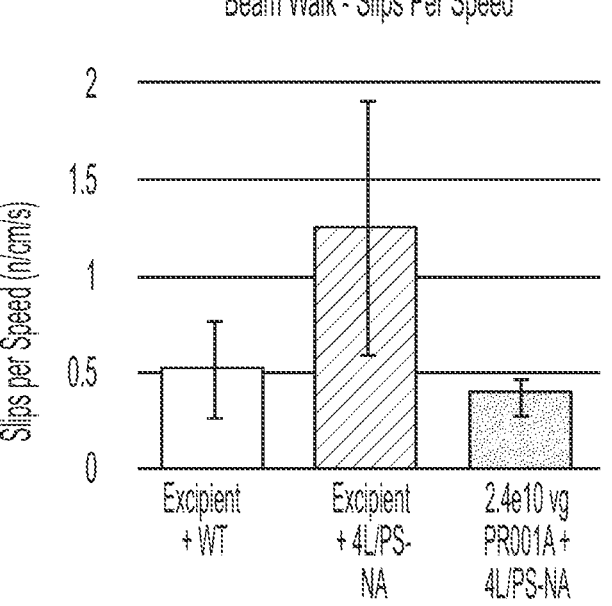

FIG. 17 shows representative data for tapered beam analysis in maximal dose GBA1 rAAV in a genetic mouse model. Motor performance of the treatment groups (WT+ excipient, n=5), 4 L/PS-NA+excipient (n=6), and 4 L/PS-NA+rAAV (n=5)) was assayed by Beam Walk 4 weeks post rAAV administration. The total slips and active time are shown as total over 5 trials on different beams. Speed and slips per speed are shown as the average over 5 trials on different beams. Means are presented. Error bars are SEM.

Figure 18:
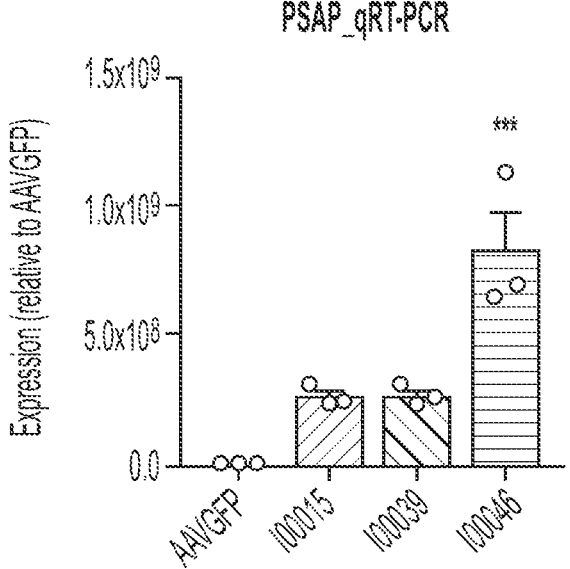
Figure 18:
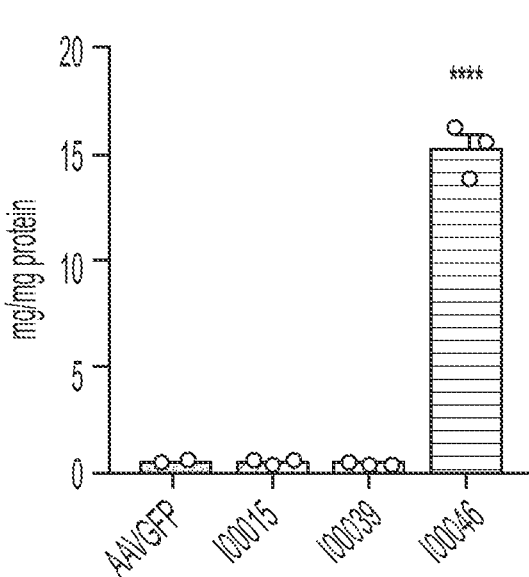
Figure 18:
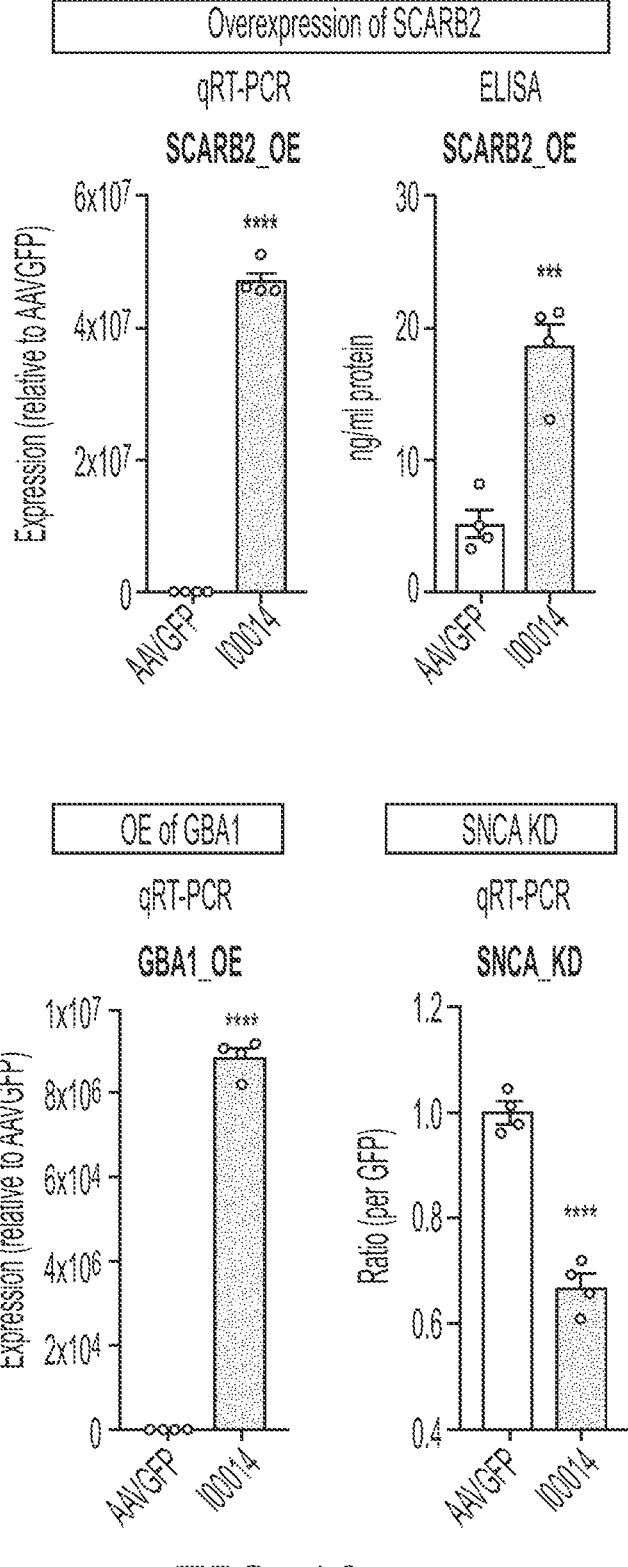

FIG. 18 shows representative data for in vitro expression of rAAV constructs encoding GBA1 in combination with Prosaposin (PSAP), SCARB2, and/or one or more inhibitory nucleic acids. Data indicate transfection of HEK293 cells with each construct resulted in overexpression of the transgenes of interest relative to GFP-transfected cells.

Figure 19:
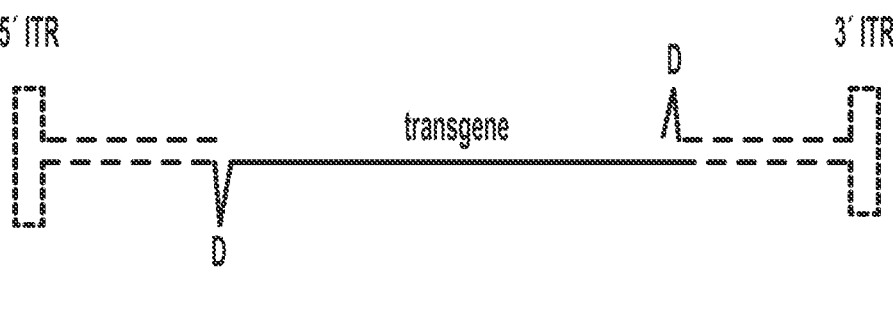
Figure 19:
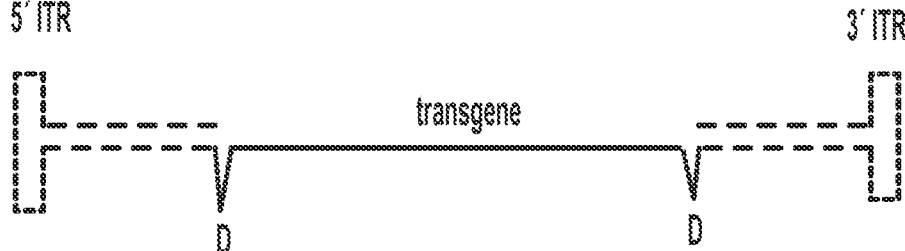

FIG. 19 is a schematic depicting an rAAV vectors comprising a "D" region located on the "outside" of the ITR (e.g., proximal to the terminus of the ITR relative to the transgene insert or expression construct) (top) and a wild-type rAAV vectors having ITRs on the "inside" of the vector (e.g., proximal to the transgene insert of the vector).

Figure 20:
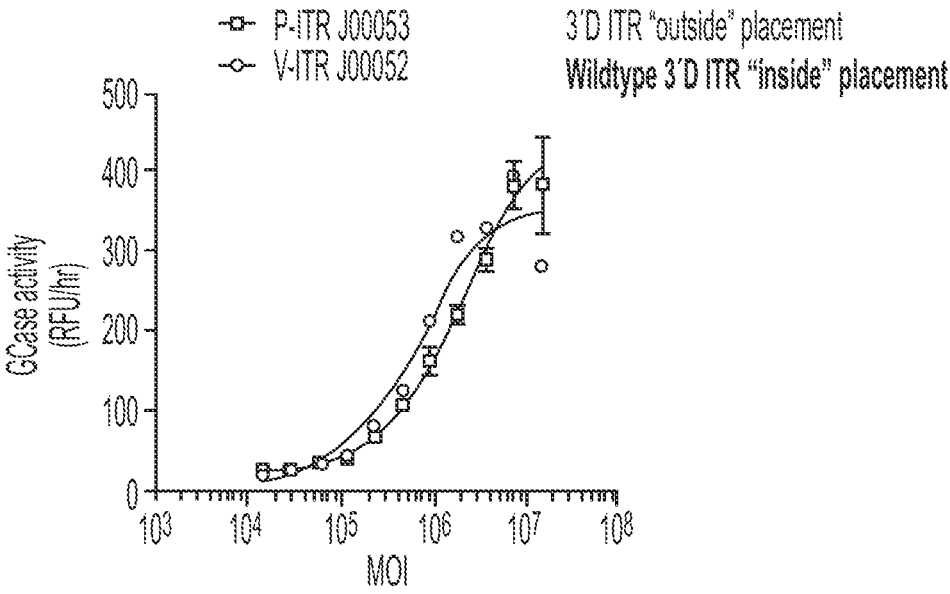

FIG. 20 shows data for transduction of HEK293 cells using rAAVs having ITRs with wild-type (circles) or alternative (e.g., "outside"; squares) placement of the "D" sequence. The rAAVs having ITRs placed on the "outside" were able to transduce cells as efficiently as rAAVs having wild-type ITRs.

DETAILED DESCRIPTION

The disclosure is based, in part, on compositions and methods for expression of combinations of PD-associated gene products in a subject. A gene product can be a protein, a fragment (e.g., portion) of a protein, an interfering nucleic acid that inhibits a PD-associated gene, etc. In some embodiments, a gene product is a protein or a protein fragment encoded by a PD-associated gene. In some embodiments, a gene product is an interfering nucleic acid (e.g., shRNA, siRNA, miRNA, amiRNA, etc.) that inhibits a PD-associated gene.

A PD-associated gene refers to a gene encoding a gene product that is genetically, biochemically or functionally associated with PD. For example, individuals having mutations in the GBA1 gene (which encodes the protein Gcase), have been observed to be have an increased risk of developing PD compared to individuals that do not have a mutation in GBA1. In another example, PD is associated with accumulation of protein aggregates comprising α-Synuclein (α-Syn) protein; accordingly, SCNA (which encodes α-Syn) is a PD-associated gene. In some embodiments, an expression cassette described herein encodes a wild-type or non-mutant form of a PD-associated gene (or coding sequence thereof). Examples of PD-associated genes are listed in Table 1.

TABLE 1

| Examples of PD-associated genes | | | |
| --- | --- | --- | --- |
| Name | Gene | Function | NCBI Accession No. |
| Lysosome membrane protein 2 | SCARB2/ LIMP2 | lysosomal receptor for glucosylceramidase (GBA targeting) | NP_005497.1 (Isoform 1), NP_ 001191184.1 (Isoform 2) |
| Prosaposin | PSAP | precursor for saposins A, B, C, and D, which localize to the lysosomal compartment and facilitate the catabolism of glycosphingolipids with short oligosaccharide groups | AAH01503.1, AAH07612.1, AAH04275.1, AAA60303.1 |
| beta-Glucocerebrosidase | GBA1 | cleaves the beta-glucosidic linkage of glucocerebroside | NP_ 001005742.1 (Isoform 1), NP_ 001165282.1 (Isoform 2), NP_ 001165283.1 (Isoform 3) |

Isolated Nucleic Acids and Vectors

An isolated nucleic acid may be DNA or RNA. The disclosure provides, in some aspects, an isolated nucleic acid comprising an expression construct encoding a Gcase (e.g., the gene product of GBA1 gene) or a portion thereof. Gcase, also referred to as β-glucocerebrosidase or GBA, refers to a lysosomal protein that cleaves the beta-glucosidic linkage of the chemical glucocerebroside, an intermediate in glycolipid metabolism. In humans, Gcase is encoded by the GBA1 gene, located on chromosome 1. In some embodiments, GBA1 encodes a peptide that is represented by NCBI Reference Sequence NP_000148.2 (SEQ ID NO: 14). In some embodiments, the isolated nucleic acid comprises a Gcase-encoding sequence that has been codon optimized (e.g., codon optimized for expression in mammalian cells, for example human cells), such as the sequence set forth in SEQ ID NO: 15.

In some aspects, the disclosure provides an isolated nucleic acid comprising an expression construct encoding Prosaposin (e.g., the gene product of PSAP gene). Prosaposin is a precursor glycoprotein for sphingolipid activator proteins (saponins) A, B, C, and D, which facilitate the catabolism of glycosphingolipids with short oligosaccharide groups. In humans, the PSAP gene is located on chromosome 10. In some embodiments, PSAP encodes a peptide that is represented by NCBI Reference Sequence NP_002769.1 (e.g., SEQ ID NO: 16). In some embodiments, the isolated nucleic acid comprises a prosaposin-encoding sequence that has been codon optimized (e.g., codon optimized for expression in mammalian cells, for example human cells), such as the sequence set forth in SEQ ID NO: 17.

Aspects of the disclosure relate to an isolated nucleic acid comprising an expression construct encoding LIMP2/ SCARB2 (e.g., the gene product of SCARB2 gene). SCARB2 refers to a membrane protein that regulates lysosomal and endosomal transport within a cell. In humans, SCARB2 gene is located on chromosome 4. In some embodiments, the SCARB2 gene encodes a peptide that is represented by NCBI Reference Sequence NP_005497.1 (SEQ ID NO: 18). In some embodiments, the isolated nucleic acid comprises the sequence set forth in SEQ ID NO: 19. In some embodiments the isolated nucleic acid comprises a SCARB2-encoding sequence that has been codon optimized.

In some aspects, the disclosure provides an isolated nucleic acid comprising an expression construct encoding a first gene product and a second gene product, wherein each gene product independently is selected from the gene products, or portions thereof, set forth in Table 1.

In some embodiments, a gene product is encoded by a coding portion (e.g., a cDNA) of a naturally occurring gene. In some embodiments, a first gene product is a protein (or a fragment thereof) encoded by the GBA1 gene. In some embodiments, a gene product is a protein (or a fragment thereof) encoded by the SCARB2/LIMP2 gene and/or the PSAP gene. However, the skilled artisan recognizes that the order of expression of a first gene product (e.g., Gcase) and a second gene product (e.g., LIMP2) can generally be reversed (e.g., LIMP2 is the first gene product and Gcase is the second gene product). In some embodiments, a gene product is a fragment (e.g., portion) of a gene listed in Table 1. A protein fragment may comprise about 50%, about 60%, about 70%, about 80% about 90% or about 99% of a protein encoded by the genes listed in Table 1. In some embodiments, a protein fragment comprises between 50% and 99.9% (e.g., any value between 50% and 99.9%) of a protein encoded by a gene listed in Table 1.

In some embodiments, an expression construct is monocistronic (e.g., the expression construct encodes a single fusion protein comprising a first gene product and a second gene product). In some embodiments, an expression construct is polycistronic (e.g., the expression construct encodes two distinct gene products, for example two different proteins or protein fragments).

A polycistronic expression vector may comprise a one or more (e.g., 1, 2, 3, 4, 5, or more) promoters. Any suitable promoter can be used, for example, a constitutive promoter, an inducible promoter, an endogenous promoter, a tissue-specific promoter (e.g., a CNS-specific promoter), etc. In some embodiments, a promoter is a chicken beta-actin promoter (CBA promoter), a CAG promoter (for example as described by Alexopoulou et al. (2008) *BMC Cell Biol.* 9:2; doi: 10.1186/1471-2121-9-2), a CD68 promoter, or a JeT promoter (for example as described by Tornoe et al. (2002) *Gene* 297(1-2):21-32). In some embodiments, a promoter is operably-linked to a nucleic acid sequence encoding a first gene product, a second gene product, or a first gene product and a second gene product. In some embodiments, an expression cassette comprises one or more additional regulatory sequences, including but not limited to transcription factor binding sequences, intron splice sites, poly(A) addition sites, enhancer sequences, repressor binding sites, or any combination of the foregoing.

In some embodiments, a nucleic acid sequence encoding a first gene product and a nucleic acid sequence encoding a second gene product are separated by a nucleic acid sequence encoding an internal ribosomal entry site (IRES). Examples of IRES sites are described, for example, by Mokrejs et al. (2006) *Nucleic Acids Res.* 34(Database issue): D125-30. In some embodiments, a nucleic acid sequence encoding a first gene product and a nucleic acid sequence encoding a second gene product are separated by a nucleic acid sequence encoding a self-cleaving peptide. Examples of self-cleaving peptides include but are not limited to T2A, P2A, E2A, F2A, BmCPV 2A, and BmIFV 2A, and those described by Liu et al. (2017) *Sci Rep.* 7: 2193. In some embodiments, the self-cleaving peptide is a T2A peptide.

Pathologically, disorders such as PD and Gaucher disease are associated with accumulation of protein aggregates composed largely of α-Synuclein (α-Syn) protein. Accordingly, in some embodiments, isolated nucleic acids described herein comprise an inhibitory nucleic acid that reduces or prevents expression of α-Syn protein. A sequence encoding an inhibitory nucleic acid may be placed in an untranslated region (e.g., intron, 5'UTR, 3'UTR, etc.) of the expression vector.

In some embodiments, an inhibitory nucleic acid is positioned in an intron of an to expression construct, for example in an intron upstream of the sequence encoding a first gene product. An inhibitory nucleic acid can be a double stranded RNA (dsRNA), siRNA, micro RNA (miRNA), artificial miRNA (amiRNA), or an RNA aptamer. Generally, an inhibitory nucleic acid binds to (e.g., hybridizes with) between about 6 and about 30 (e.g., any integer between 6 and 30, inclusive) contiguous nucleotides of a target RNA (e.g., mRNA). In some embodiments, the inhibitory nucleic acid molecule is an miRNA or an amiRNA, for example an miRNA that targets SNCA (the gene encoding α-Syn protein). In some embodiments, the miRNA does not comprise any mismatches with the region of SNCA mRNA to which it hybridizes (e.g., the miRNA is "perfected"). In some embodiments, the inhibitory nucleic acid is an shRNA (e.g., an shRNA targeting SNCA).

An isolated nucleic acid as described herein may exist on its own, or as part of a vector. Generally, a vector can be a plasmid, cosmid, phagemid, bacterial artificial chromosome (BAC), or a viral vector (e.g., adenoviral vector, adeno-associated virus (AAV) vector, retroviral vector, baculoviral vector, etc.). In some embodiments, the vector is a plasmid (e.g., a plasmid comprising an isolated nucleic acid as described herein). In some embodiments, the vector is a recombinant AAV (rAAV) vector. In some embodiments, an rAAV vector is single-stranded (e.g., single-stranded DNA). In some embodiments, a vector is a Baculovirus vector (e.g., an *Autographa californica* nuclear polyhedrosis (AcNPV) vector).

Typically an rAAV vector (e.g., rAAV genome) comprises a transgene (e.g., an expression construct comprising one or more of each of the following: promoter, intron, enhancer sequence, protein coding sequence, inhibitory RNA coding sequence, polyA tail sequence, etc.) flanked by two AAV inverted terminal repeat (ITR) sequences. In some embodiments the transgene of an rAAV vector comprises an isolated nucleic acid as described by the disclosure. In some embodiments, each of the two ITR sequences of an rAAV vector is a full-length ITR (e.g., approximately 145 bp in length, and containing functional Rep binding site (RBS) and terminal resolution site (trs)). In some embodiments, one of the ITRs of an rAAV vector is truncated (e.g., shortened or not full-length). In some embodiments, a truncated ITR lacks a functional terminal resolution site (trs) and is used for production of self-complementary AAV vectors (scAAV vectors). In some embodiments, a truncated ITR is a ΔITR, for example as described by McCarty et al. (2003) *Gene Ther.* 10(26):2112-8.

Aspects of the disclosure relate to isolated nucleic acids (e.g., rAAV vectors) comprising an ITR having one or more modifications (e.g., nucleic acid additions, deletions, substitutions, etc.) relative to a wild-type AAV ITR, for example relative to wild-type AAV2 ITR (e.g., SEQ ID NO: 29). The structure of wild-type AAV2 ITR is shown in FIG. 19. Generally, a wild-type ITR comprises a 125 nucleotide region that self-anneals to form a palindromic double-stranded T-shaped, hairpin structure consisting of two cross arms (formed by sequences referred to as B/B' and C/C', respectively), a longer stem region (formed by sequences A/A'), and a single-stranded terminal region referred to as the "D" region. (FIG. 19). Generally, the "D" region of an ITR is positioned between the stem region formed by the A/A' sequences and the insert containing the transgene of the rAAV vector (e.g., positioned on the "inside" of the ITR relative to the terminus of the ITR or proximal to the transgene insert or expression construct of the rAAV vector). In some embodiments, a "D" region comprises the sequence set forth in SEQ ID NO: 27. The "D" region has been observed to play an important role in encapsidation of rAAV vectors by capsid proteins, for example as disclosed by Ling et al. (2015) *J Mol Genet Med* 9(3).

The disclosure is based, in part, on the surprising discovery that rAAV vectors comprising a "D" region located on the "outside" of the ITR (e.g., proximal to the terminus of the ITR relative to the transgene insert or expression construct) are efficiently encapsidated by AAV capsid proteins than rAAV vectors having ITRs with unmodified (e.g., wild-type) ITRs. In some embodiments, rAAV vectors having a modified "D" sequence (e.g., a "D" sequence in the "outside" position) have reduced toxicity relative to rAAV vectors having wild-type ITR sequences.

In some embodiments, a modified "D" sequence comprises at least one nucleotide substitution relative to a wild-type "D" sequence (e.g., SEQ ID NO: 27). A modified "D" sequence may have at least 1, 2, 3, 4, 5, 6, 7, 8, 9, 10, or more than 10 nucleotide substitutions relative to a wild-type "D" sequence (e.g., SEQ ID NO: 27). In some embodiments, a modified "D" sequence comprises at least 10, 11, 12, 13, 14, 15, 16, 17, 18, or 19 nucleic acid substitutions relative to a wild-type "D" sequence (e.g., SEQ ID NO: 27). In some embodiments, a modified "D" sequence is between about 10% and about 99% (e.g., 10%, 15%, 20%, 25%, 30%, 40%, 45%, 50%, 55%, 60%, 65%, 70%, 75%, 80%, 85%, 90%, 95%, or 99%) identical to a wild-type "D" sequence (e.g., SEQ ID NO: 27). In some embodiments, a modified "D" sequence comprises the sequence set forth in SEQ ID NO: 26, also referred to as an "S" sequence as described in Wang et al. (1995) *J Mol Biol* 250(5):573-80.

An isolated nucleic acid or rAAV vector as described by the disclosure may further comprise a "TRY" sequence, for example as set forth in SEQ ID NO: 28 or as described in Francois, et al. The Cellular TATA Binding Protein Is Required for Rep-Dependent Replication of a Minimal Adeno-Associated Virus Type 2 p5 Element. J Virol. 2005. In some embodiments, a TRY sequence is positioned between an ITR (e.g., a 5' ITR) and an expression construct (e.g., a transgene-encoding insert) of an isolated nucleic acid or rAAV vector.

In some aspects, the disclosure relates to Baculovirus vectors comprising an isolated nucleic acid or rAAV vector as described by the disclosure. In some embodiments, the Baculovirus vector is an *Autographa californica* nuclear polyhedrosis (AcNPV) vector, for example as described by Urabe et al. (2002) *Hum Gene Ther* 13(16):1935-43 and Smith et al. (2009) *Mol Ther* 17(11):1888-1896.

In some aspects, the disclosure provides a host cell comprising an isolated nucleic acid or vector as described herein. A host cell can be a prokaryotic cell or a eukaryotic cell. For example, a host cell can be a mammalian cell, bacterial cell, yeast cell, insect cell, etc. In some embodiments, a host cell is a mammalian cell, for example a HEK293T cell. In some embodiments, a host cell is a bacterial cell, for example an *E. coli* cell.

rAAVs

In some aspects, the disclosure relates to recombinant AAVs (rAAVs) comprising a transgene that encodes a nucleic acid as described herein (e.g., an rAAV vector as described herein). The term "rAAVs" generally refers to viral particles comprising an rAAV vector encapsidated by one or more AAV capsid proteins. An rAAV described by the disclosure may comprise a capsid protein having a serotype selected from AAV1, AAV2, AAV3, AAV4, AAV5, AAV6, AAV7, AAV8, AAV9, and AAV10. In some embodiments, an rAAV comprises a capsid protein from a non-human host, for example a rhesus AAV capsid protein such as AAVrh.10, AAVrh.39, etc. In some embodiments, an rAAV described by the disclosure comprises a capsid protein that is a variant of a wild-type capsid protein, such as a capsid protein variant that includes at least 1, 2, 3, 4, 5, 6, 7, 8, 9, 10, or more than 10 (e.g., 15, 20 25, 50, 100, etc.) amino acid substitutions (e.g., mutations) relative to the wild-type AAV capsid protein from which it is derived.

In some embodiments, rAAVs described by the disclosure readily spread through the CNS, particularly when introduced into the CSF space or directly into the brain parenchyma. Accordingly, in some embodiments, rAAVs described by the disclosure comprise a capsid protein that is capable of crossing the blood-brain barrier (BBB). For example, in some embodiments, an rAAV comprises a capsid protein having an AAV9 or AAVrh.10 serotype. Production of rAAVs is described, for example, by Samulski et al. (1989) *J Virol.* 63(9):3822-8 and Wright (2009) *Hum Gene Ther.* 20(7): 698-706.

In some embodiments, an rAAV as described by the disclosure (e.g., comprising a recombinant rAAV genome encapsidated by AAV capsid proteins to form an rAAV capsid particle) is produced in a Baculovirus vector expression system (BEVS). Production of rAAVs using BEVS are described, for example by Urabe et al. (2002) *Hum Gene Ther* 13(16):1935-43, Smith et al. (2009) *Mol Ther* 17(11): 1888-1896, U.S. Pat. Nos. 8,945,918, 9,879,282, and International PCT Publication WO 2017/184879. However, an rAAV can be produced using any suitable method (e.g., using recombinant rep and cap genes).

Pharmaceutical Compositions

In some aspects, the disclosure provides pharmaceutical compositions comprising an isolated nucleic acid or rAAV as described herein and a pharmaceutically acceptable carrier. As used herein, the term "pharmaceutically acceptable" refers to a material, such as a carrier or diluent, which does not abrogate the biological activity or properties of the compound, and is relatively non-toxic, e.g., the material may be administered to an individual without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Additional ingredients that may be included in the pharmaceutical compositions used in the practice of the invention are known in the art and described, for example in Remington's Pharmaceutical Sciences (Genaro, Ed., Mack Publishing Co., 1985, Easton, PA), which is incorporated herein by reference.

Compositions (e.g., pharmaceutical compositions) provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition described herein is suitable for topical administration to the eye of a subject.

Methods

The disclosure is based, in part, on compositions for expression of combinations of PD-associated gene products in a subject that act together (e.g., synergistically) to treat Parkinson's disease. As used herein "treat" or "treating" refers to (a) preventing or delaying onset of Parkinson's disease; (b) reducing severity of Parkinson's disease; (c) reducing or preventing development of symptoms characteristic of Parkinson's disease; (d) and/or preventing worsening of symptoms characteristic of Parkinson's disease. Symptoms of Parkinson's disease include, for example, motor dysfunction (e.g., shaking, rigidity, slowness of movement, difficulty with walking), cognitive dysfunction (e.g., dementia, depression, anxiety), emotional and behavioral dysfunction.

Accordingly, in some aspects, the disclosure provides a method for treating a subject having or suspected of having Parkinson's disease, the method comprising administering to the subject a composition (e.g., a composition comprising an isolated nucleic acid or a vector or a rAAV) as described by the disclosure.

In some embodiments, a composition is administered directly to the CNS of the subject, for example by direct injection into the brain and/or spinal cord of the subject. Examples of CNS-direct administration modalities include but are not limited to intracerebral injection, intraventricular injection, intracisternal injection, intraparenchymal injection, intrathecal injection, and any combination of the foregoing. In some embodiments, direct injection into the CNS of a subject results in transgene expression (e.g., expression of the first gene product, second gene product, and if applicable, third gene product) in the midbrain, striatum and/or cerebral cortex of the subject. In some embodiments, direct injection into the CNS results in transgene expression (e.g., expression of the first gene product, second gene product, and if applicable, third gene product) in the spinal cord and/or CSF of the subject.

In some embodiments, direct injection to the CNS of a subject comprises convection enhanced delivery (CED). Convection enhanced delivery is a therapeutic strategy that involves surgical exposure of the brain and placement of a small-diameter catheter directly into a target area of the brain, followed by infusion of a therapeutic agent (e.g., a composition or rAAV as described herein) directly to the brain of the subject. CED is described, for example by Debinski et al. (2009) *Expert Rev Neurother.* 9(10):1519-27.

In some embodiments, a composition is administered peripherally to a subject, for example by peripheral injection. Examples of peripheral injection include subcutaneous injection, intravenous injection, intra-arterial injection, intraperitoneal injection, or any combination of the foregoing. In some embodiments, the peripheral injection is intra-arterial injection, for example injection into the carotid artery of a subject.

In some embodiments, a composition (e.g., a composition comprising an isolated nucleic acid or a vector or a rAAV) as described by the disclosure is administered both peripherally and directly to the CNS of a subject. For example, in some embodiments, a subject is administered a composition by intra-arterial injection (e.g., injection into the carotid artery) and by intraparenchymal injection (e.g., intraparenchymal injection by CED). In some embodiments, the direct injection to the CNS and the peripheral injection are simultaneous (e.g., happen at the same time). In some embodiments, the direct injection occurs prior (e.g., between 1 minute and 1 week, or more before) to the peripheral injection. In some embodiments, the direct injection occurs after (e.g., between 1 minute and 1 week, or more after) the peripheral injection.

The amount of composition (e.g., a composition comprising an isolated nucleic acid or a vector or a rAAV) as described by the disclosure administered to a subject will vary depending on the administration method. For example, in some embodiments, a rAAV as described herein is administered to a subject at a titer between about $10^9$ Genome copies (GC)/kg and about $10^{14}$ GC/kg (e.g., about $10^9$ GC/kg, about $10^{10}$ GC/kg, about $10^{11}$ GC/kg, about $10^{12}$ GC/kg, about $10^{12}$ GC/kg, or about $10^{14}$ GC/kg). In some embodiments, a subject is administered a high titer (e.g., $>10^{12}$ Genome Copies GC/kg of an rAAV) by injection to the CSF space, or by intraparenchymal injection.

A composition (e.g., a composition comprising an isolated nucleic acid or a vector or a rAAV) as described by the disclosure can be administered to a subject once or multiple times (e.g., 2, 3, 4, 5, 6, 7, 8, 9, 10, 20, or more) times. In some embodiments, a composition is administered to a subject continuously (e.g., chronically), for example via an infusion pump.

EXAMPLES

Example 1: rAAV Vectors

AAV vectors are generated using cells, such as HEK293 cells for triple-plasmid transfection. The ITR sequences flank an expression construct comprising a promoter/enhancer element for each transgene of interest, a 3' polyA signal, and posttranslational signals such as the WPRE element. Multiple gene products can be expressed simultaneously such as GBA1 and LIMP2 and/or Prosaposin, by fusion of the protein sequences; or using a 2A peptide linker, such as T2A or P2A, which leads 2 peptide fragments with added amino acids due to prevention of the creation of a peptide bond; or using an IRES element; or by expression with 2 separate expression cassettes. The presence of a short intronic sequence that is efficiently spliced, upstream of the expressed gene, can improve expression levels. shRNAs and other regulatory RNAs can potentially be included within these sequences. Examples of plasmids comprising rAAV vectors described by the disclosure are shown in FIGS. 1-6 and in Table 2 below.

TABLE 2

| Name | Promoter 1 | shRNA | CDS1 | PolyA1 | Bicistronic element | Promoter 2 | CDS2 | PolyA2 | Length between ITRs |
|---|---|---|---|---|---|---|---|---|---|
| CMVe_CBAp_ GBA1_WPRE_ bGH | CBA | | GBA1 | WPRE-bGH | | | | | 3741 |
| LT1s_JetLong_ mRNAiaSYn_ SCARB2-T2A-GBA1_bGH | JetLong | aSyn | SCARB2 | bGH | T2A | | GBA1 | | 4215 |
| LI1_JetLong_ SCARB2-IRES-GBA1_bGH | JetLong | | SCARB2 | bGH | IRES | | GBA1 | | 4399 |
| FP1_JetLong_ GBA1_bGH_ JetLong_ SCARB2_SV40L | JetLong | | GBA1 | bGH | | JetLong | SCARB2 | SV40L | 4464 |
| PrevailVector_ LT2s_JetLong_ mRNAiaSYn_ PSAP-T2A-GBA1_bGH_ 4353nt | JetLong | aSyn | PSAP | bGH | T2A | — | GBA1 | — | 4353 |
| PrevailVector_ LI2_JetLong_ PSAP_IRES_ GBA1_ SymtheticpolyA_ 4337nt | JetLong | — | PSAP | Synthetic pA | IRES | — | GBA1 | — | 4337 |

Example 2: Cell Based Assays of Viral Transduction into GBA-Deficient Cells

Cells deficient in GBA1 are obtained, for example as fibroblasts from GD patients, monocytes, or hES cells, or patient-derived induced pluripotent stem cells (iPSCs). These cells accumulate substrates such as glucosylceramide and glucosylsphingosine (GluCer and GluSph). Treatment of wild-type or mutant cultured cell lines with Gcase inhibitors, such as CBE, is also be used to obtain GBA deficient cells.

Using such cell models, lysosomal defects are quantified in terms of accumulation of protein aggregates, such as of α-Synuclein with an antibody for this protein or phospho-αSyn, followed by imaging using fluorescent microscopy. Imaging for lysosomal abnormalities by ICC for protein markers such as LAMP1, LAMP2, LIMP1, LIMP2, or using dyes such as Lysotracker, or by uptake through the endocytic compartment of fluorescent dextran or other markers is also performed. Imaging for autophagy marker accumulation due to defective fusion with the lysosome, such as for LC3, can also be performed. Western blotting and/or ELISA is used to quantify abnormal accumulation of these markers. Also, the accumulation of glycolipid substrates and products of GBA1 is measured using standard approaches.

Therapeutic endpoints (e.g., reduction of PD-associated pathology) are measured in the context of expression of transduction of the AAV vectors, to confirm and quantify activity and function. Gcase can is also quantified using protein ELISA measures, or by standard Gcase activity assays.

Example 3: In Vivo Assays Using Mutant Mice

This example describes in vivo assays of AAV vectors using mutant mice. In vivo studies of AAV vectors as above in mutant mice are performed using assays described, for example, by Liou et al. (2006) *J. Biol. Chem.* 281(7): 4242-4253, Sun et al. (2005) *J. Lipid Res.* 46:2102-2113, and Farfel-Becker et al. (2011) *Dis. Model Mech.* 4(6):746-752.

The intrathecal or intraventricular delivery of vehicle control and AAV vectors (e.g., at a dose of $2\times10^{11}$ vg/mouse) are performed using concentrated AAV stocks, for example at an injection volume between 5-10 μL. Intraparenchymal delivery by convection enhanced delivery is performed.

Treatment is initiated either before onset of symptoms, or subsequent to onset. Endpoints measured are the accumulation of substrate in the CNS and CSF, accumulation of Gcase enzyme by ELISA and of enzyme activity, motor and cognitive endpoints, lysosomal dysfunction, and accumulation of α-Synuclein monomers, protofibrils or fibrils.

Example 4: Chemical Models of Disease

This example describes in vivo assays of AAV vectors using a chemically-induced mouse model of Gaucher disease (e.g., the CBE mouse model). In vivo studies of these AAV vectors are performed in a chemically-induced mouse model of Gaucher disease, for example as described by Vardi et al. (2016) *J. Pathol.* 239(4):496-509.

Intrathecal or intraventricular delivery of vehicle control and AAV vectors (e.g., at a dose of $2\times10^{11}$ vg/mouse) are performed using concentrated AAV stocks, for example with injection volume between 5-10 μL. Intraparenchymal delivery by convection enhanced delivery is performed. Peripheral delivery is achieved by tail vein injection.

Treatment is initiated either before onset of symptoms, or subsequent to onset. Endpoints measured are the accumulation of substrate in the CNS and CSF, accumulation of Gcase enzyme by ELISA and of enzyme activity, motor and cognitive endpoints, lysosomal dysfunction, and accumulation of α-Synuclein monomers, protofibrils or fibrils.

Example 5: Clinical Trials in PD, LBD, Gaucher Disease Patients

In some embodiments, patients having certain forms of Gaucher disease (e.g., GD1) have an increased risk of developing Parkinson's disease (PD) or Lewy body dementia (LBD). This Example describes clinical trials to assess the safety and efficacy of rAAVs as described by the disclosure, in patients having Gaucher disease, PD and/or LBD.

Clinical trials of such vectors for treatment of Gaucher disease, PD and/or LBD are performed using a study design similar to that described in Grabowski et al. (1995) *Ann. Intern. Med.* 122(1):33-39.

Example 6: Treatment of Peripheral Disease

In some embodiments, patients having certain forms of Gaucher disease exhibit symptoms of peripheral neuropathy, for example as described in Biegstraaten et al. (2010) *Brain* 133(10):2909-2919.

This example describes in vivo assays of AAV vectors as described herein for treatment of peripheral neuropathy associated with Gaucher disease (e.g., Type 1 Gaucher disease). Briefly, Type 1 Gaucher disease patients identified as having signs or symptoms of peripheral neuropathy are administered a rAAV as described by the disclosure. In some embodiments, the peripheral neuropathic signs and symptoms of the subject are monitored, for example using methods described in Biegstraaten et al., after administration of the rAAV.

Levels of transduced gene products as described by the disclosure present in patients (e.g., in serum of a patient, in peripheral tissue (e.g., liver tissue, spleen tissue, etc.)) of a patient are assayed, for example by Western blot analysis, enzymatic functional assays, or imaging studies.

Example 7: Treatment of CNS Forms

This example describes in vivo assays of rAAVs as described herein for treatment of CNS forms of Gaucher disease. Briefly, Gaucher disease patients identified as having a CNS form of Gaucher disease (e.g., Type 2 or Type 3 Gaucher disease) are administered a rAAV as described by the disclosure. Levels of transduced gene products as described by the disclosure present in the CNS of patients (e.g., in serum of the CNS of a patient, in cerebrospinal fluid (CSF) of a patient, or in CNS tissue of a patient) are assayed, for example by Western blot analysis, enzymatic functional assays, or imaging studies.

Example 8: Gene Therapy of Parkinson's Disease in Subjects Having Mutations in GBA1

This example describes administration of a recombinant adeno-associated virus (rAAV) encoding GBA1 to a subject having Parkinson's disease characterized by a mutation in GBA1 gene.

The rAAV vector insert contains the CBA promoter element (CBA), consisting of four parts: the CMV enhancer (CMVe), CBA promoter (CBAp), Exon 1, and intron (int) to constitutively express the codon optimized coding sequence (CDS) of human GBA1 (maroon). The 3' region also contains a Woodchuck hepatitis virus Posttranscriptional Regulatory Element (WPRE) followed by a bovine Growth Hormone polyA signal (bGH polyA) tail. The flanking ITRs allow for the correct packaging of the intervening sequences. Two variants of the 5' ITR sequence (FIG. 7, inset box, bottom sequence) were evaluated; these variants have several nucleotide differences within the 20-nucleotide "D" region of the ITR, which is believed to impact the efficiency of packaging and expression. The rAAV product contains the "D" domain nucleotide sequence shown in FIG. 7 (inset box, top sequence). A variant vector, harboring a mutant "D" domain (termed an "S" domain herein, with the nucleotide changes shown by shading), performed similarly in preclinical studies. The backbone contains the gene to confer resistance to kanamycin as well as a stuffer sequence to prevent reverse packaging. A schematic depicting the rAAV vector is shown in FIG. 8. The rAAV vector is packaged into an rAAV using AAV9 serotype capsid proteins.

GBA1-rAAV is administered to a subject as a single dose via a fluoroscopy guided sub-occipital injection into the cisterna magna (intracisternal magna; ICM). One embodiment of a dosing regimen study is as follows:

A single dose of rAAV is administered to patients (N=12) at one of two dose levels (3e13 vg (low dose); 1e14 vg (high dose), etc.) which are determined based on the results of nonclinical pharmacology and toxicology studies.

Initial studies were conducted in a chemical mouse model involving daily delivery of conduritol-b-epoxide (CBE), an inhibitor of GCase to assess the efficacy and safety of the rAAV vector and a variant rAAV S-variant construct (as described further below). Additionally, initial studies were performed in a genetic mouse model, which carries a homozygous GBA1 mutation and is partially deficient in saponins (4 L/PS-NA). Additional dose-ranging studies in mice and nonhuman primates (NHPs) are conducted to further evaluate vector safety and efficacy.

Two slightly different versions of the 5' inverted terminal repeat (ITR) in the AAV backbone were tested to assess manufacturability and transgene expression (FIG. 7). The 20 bp "D" domain within the 145 bp 5' ITR is thought to be necessary for optimal viral vector production, but mutations within the "D" domain have also been reported to increase transgene expression in some cases. Thus, in addition to the viral vector, which harbors an intact "D" domain, a second vector form with a mutant D domain (termed an "S" domain herein) was also evaluated. Both rAAV and variant rAAV express the same transgene. While both vectors produced virus that was efficacious in vivo as detailed below, the rAAV which contains a wild-type "D" domain, was selected for further development.

To establish the CBE model of GCase deficiency, juvenile mice were dosed with CBE, a specific inhibitor of GCase. Mice were given CBE by IP injection daily, starting at postnatal day 8 (P8). Three different CBE doses (25 mg/kg, 37.5 mg/kg, 50 mg/kg) and PBS were tested to establish a model that exhibits a behavioral phenotype (FIG. 9). Higher doses of CBE led to lethality in a dose-dependent manner. All mice treated with 50 mg/kg CBE died by P23, and 5 of the 8 mice treated with 37.5 mg/kg CBE died by P27. There was no lethality in mice treated with 25 mg/kg CBE. Whereas CBE-injected mice showed no general motor deficits in the open field assay (traveling the same distance and at the same velocity as mice given PBS), CBE-treated mice exhibited a motor coordination and balance deficit as measured by the rotarod assay.

Mice surviving to the end of the study were sacrificed on the day after their last CBE dose (P27, "Day 1") or after three days of CBE withdrawal (P29, "Day 3"). Lipid analysis was performed on the cortex of mice given 25 mg/kg CBE to evaluate the accumulation of GCase substrates in both the Day 1 and Day 3 cohorts. GluSph and GalSph levels (measured in aggregate in this example) were significantly accumulated in the CBE-treated mice compared to PBS-treated controls, consistent with GCase insufficiency.

Based on the study described above, the 25 mg/kg CBE dose was selected since it produced behavioral deficits without impacting survival. To achieve widespread GBA1 distribution throughout the brain and transgene expression during CBE treatment, rAAV or excipient was delivered by intracerebroventricular (ICV) injection at postnatal day 3 (P3) followed by daily IP CBE or PBS treatment initiated at P8 (FIG. 10).

CBE-treated mice that received rAAV performed statistically significantly better on the rotarod than those that received excipient (FIG. 11). Mice in the variant vector treatment group did not differ from excipient treated mice in terms of other behavioral measures, such as the total distance traveled during testing (FIG. 11).

At the completion of the in-life study, half of the mice were sacrificed the day after the last CBE dose (P36, "Day 1") or after three days of CBE withdrawal (P38, "Day 3") for biochemical analysis (FIG. 12). Using a fluorometric enzyme assay performed in biological triplicate, GCase activity was assessed in the cortex. GCase activity was increased in mice that were treated with GBA1 rAAV, while CBE treatment reduced GCase activity. Additionally, mice that received both CBE and GBA1-rAAV had GCase activity levels that were similar to the PBS-treated group, indicating that delivery of rAAV is able to overcome the inhibition of GCase activity induced by CBE treatment. Lipid analysis was performed on the motor cortex of the mice to examine levels of the substrates GluCer and GluSph. Both lipids accumulated in the brains of mice given CBE, and rAAV treatment significantly reduced substrate accumulation.

Lipid levels were negatively correlated with both GCase activity and performance on the Rotarod across treatment groups. The increased GCase activity after rAAV administration was associated with substrate reduction and enhanced motor function (FIG. 13). As shown in FIG. 14, preliminary biodistribution was assessed by vector genome presence, as measured by qPCR (with >100 vector genomes per 1 μg genomic DNA defined as positive). Mice that received GBA1-rAAV, both with and without CBE, were positive for rAAV vector genomes in the cortex, indicating that ICV delivery results in rAAV delivery to the cortex. Additionally, vector genomes were detected in the liver, few in spleen, and none in the heart, kidney or gonads. For all measures, there was no statistically significant difference between the Day 1 and Day 3 groups.

A larger study in the CBE model further explored efficacious doses of GBA1-rAAV in the CBE model. Using the 25 mg/kg CBE dose model, excipient or GBA1-rAAV was delivered via ICV at P3, and daily IP PBS or CBE treatment initiated at P8. Given the similarity between the groups with and without CBE withdrawal observed in the previous studies, all mice were sacrificed one day after the final CBE dose (P38-40). The effect of three different rAAV doses was assessed, resulting in the following five groups, with 10 mice (5M/5F) per group:

Excipient ICV+PBS IP
Excipient ICV+25 mg/kg CBE IP
3.2e9 vg (2.13e10 vg/g brain) rAAV ICV+25 mg/kg CBE IP
1.0e10 vg (6.67e10 vg/g brain) rAAV ICV+25 mg/kg CBE IP
3.2e10 vg (2.13e11 vg/g brain) rAAV ICV+25 mg/kg CBE IP.
The highest dose of rAAV rescued the CBE treatment-related failure to gain weight at P37. Additionally, this dose resulted in a statistically significant increase in performance on the rotarod and tapered beam compared to the Excipient+CBE treated group (FIG. 15). Lethality was observed in several groups, including both excipient-treated and rAAV-treated groups (Excipient+PBS: 0; Excipient+25 mg/kg CBE: 1; 3.2e9 vg rAAV+25 mg/kg CBE: 4; 1.0e10 vg rAAV+25 mg/kg CBE: 0; 3.2e10 vg rAAV+25 mg/kg CBE: 3).

At the completion of the in-life study, mice were sacrificed for biochemical analysis (FIG. 16). GCase activity in the cortex was assessed in biological triplicates by a fluorometric assay. CBE-treated mice showed reduced GCase activity whereas mice that received a high rAAV dose showed a statistically significant increase in GCase activity compared to CBE treatment. CBE-treated mice also had accumulation of GluCer and GluSph, both of which were rescued by administering a high dose of rAAV.

In addition to the established chemical CBE model, GBA1-rAAV is also evaluated in the 4 L/PS-NA genetic model, which is homozygous for the V394 L GD mutation in Gba1 and is also partially deficient in saponins, which affect GCase localization and activity. These mice exhibit motor strength, coordination, and balance deficits, as evidenced by their performance in the beam walk, rotarod, and wire hang assays. Typically the lifespan of these mice is less than 22 weeks. In an initial study, 3 μl of maximal titer virus was delivered by ICV at P23, with a final dose of 2.4e10 vg (6.0e10 vg/g brain). With 6 mice per group, the treatment groups were:

WT+Excipient ICV
4 L/PS-NA+Excipient ICV
4 L/PS-NA+2.4e10 vg (6.0e10 vg/g brain) rAAV ICV
Motor performance by the beam walk test was assessed 4 weeks post-rAAV delivery. The group of mutant mice that received GBA1-rAAV showed a trend towards fewer total slips and fewer slips per speed when compared to mutant mice treated with excipient, restoring motor function to near WT levels (FIG. 17). Since the motor phenotypes become more severe as these mice age, their performance on this and other behavioral tests is assessed at later time points. At the completion of the in-life study, lipid levels, GCase activity, and biodistribution are assessed in these mice.

Additional lower doses of rAAV are currently being tested using the CBE model, corresponding to 0.03×, 0.1×, and 1× the proposed phase 1 high clinical dose. Each group includes 10 mice (5M/5F) per group:

Excipient ICV
Excipient ICV+25 mg/kg CBE IP
3.2e8 vg (2.13e9 vg/g brain) rAAV ICV+25 mg/kg CBE IP
1.0e9 vg (6.67e9 vg/g brain) rAAV ICV+25 mg/kg CBE IP
1.0e10 vg (6.67e10 vg/g brain) rAAV ICV+25 mg/kg CBE IP.
In addition to motor phenotypes, lipid levels and GCase activity are assessed in the cortex. Time course of treatments and analyses are also performed.

A larger dose ranging study was initiated to evaluate efficacy and safety data. 10 4 L/PS-NA mice (5M/5F per group) were injected with 10 μl of rAAV. Using an allometric brain weight calculation, the doses correlate to 0.15×, 1.5×, 4.4×, and 14.5× the proposed phase 1 high clinical dose. The injection groups consist of:

WT+Excipient ICV
4 L/PS-NA+Excipient ICV
4 L/PS-NA+4.3e9 vg (1.1e10 vg/g brain) rAAV ICV
4 L/PS-NA+4.3e10 vg (1.1e11 vg/g/brain) rAAV ICV
4 L/PS-NA+1.3e11 vg (3.2e11 vg/g brain) rAAV ICV
4 L/PS-NA+4.3e11 vg (1.1e12 vg/g brain) rAAV ICV.

A summary of nonclinical studies in the CBE model are shown in Table 3 below.

TABLE 3

Summary of Results in CBE Mouse Model

| Test Material | Study Number | Dose Cohort | Behavioral Changes | | | | | BD | |
|---|---|---|---|---|---|---|---|---|---|
| | | | Rotarod | Tapered Beam | Open Field | Lipids | Enzyme | Brain | Liver |
| GBA1-rAAV | PRV-2018-005 Dose-ranging rAAV in CBE Model | 3.2e9 vg (2.13e10 vg/g brain) | NS | NS | NS | NS | NS | + | − |
| | | 1.10e10 vg (6.67e10 vg/g brain) | T | NS | NS | T/S | NS | + | + |
| | | 2.3e10 vg (2.13e11 vg/g brain) | S | S | NS | S | S | + | + |
| variant GBA1-rAAV | PRV-2018-005 Dose-ranging rAAV in CBE Model | 8.8e9 vg (5.9e10 vg/g brain) | S | N/A | NS | S | S | + | + |

Note
that positive biodistribution is defined as >100 vg/1 µg genomic DNA.
Abbreviations: BD = biodistribution; NS = nonsignificant; T = trend; S = significant; N/A = not applicable; + = positive; − = negative.

Example 9: In Vitro Analysis of rAAV Vectors

A pilot study was performed to assess in vitro activity of rAAV vectors encoding Prosaposin (PSAP) and SCARB2, alone or in combination with GBA1 and/or one or more inhibitory RNAs. One construct encoding PSAP and progranulin (PGRN) was also tested. Vectors tested include those shown in Table 4. "Opt" refers to a nucleic acid sequence codon optimized for expression in mammalian cells (e.g., human cells). FIG. 18 shows representative data indicating that transfection of HEK293 cells with each of the constructs resulted in overexpression of the corresponding gene product compared to mock transfected cells.

TABLE 4

| ID | Promoter | Inhibitory RNA | Promoter | Transgene |
|---|---|---|---|---|
| I00015 | JL_intronic | SCNA | JetLong | Opt-PSAP_GBA1 |
| I00039 | — | — | JetLong | Opt-PSAP-GRN |
| I00046 | — | — | | Opt-PSAP |
| I00014 | JetLong | SCNA | JetLong | Opt-SCARB2_GBA1 |

Example 10: ITR "D" Sequence Placement and Cell Transduction

The effect of placement of ITR "D" sequence on cell transduction of rAAV vectors was investigated. HEK 293 cells were transduced with Gcase-encoding rAAVs having 1) wild-type ITRs (e.g., "D" sequences proximal to the transgene insert and distal to the terminus of the ITR) or 2) ITRs with the "D" sequence located on the "outside" of the vector (e.g., "D" sequence located proximal to the terminus of the ITR and distal to the transgene insert), as shown in FIG. 19. Surprisingly, data indicate that rAAVs having the "D" sequence located in the "outside" to position retain the ability to be packaged and transduce cells efficiently (FIG. 20).

Example 11: In Vitro Toxicity Studies

Fifty (50) mice were administered GBA1-encoding rAAVs via a 4 µl intracerebroventricular (ICV) injection on post-natal day 3. All mice received daily intraperitoneal (IP) injections of conduritol B-epoxide (CBE) or PBS, depending on treatment group, from post-natal day 8 to the end of the study. Animals were euthanized 24 hours after their last IP dose. After euthanasia, target tissues were harvested, drop fixed in chilled 4% paraformaldehyde and stored at 4° C., then sent for histopathological processing and evaluation. There were eight (8) early death animals over the course of the study, which were not sent to or analyzed.

Tissues from the forty-two (42) animals euthanized at 38-40 days were trimmed, processed, and embedded in paraffin blocks. They were then sectioned at −5 µm, stained with hematoxylin and eosin (H & E) and affixed to slides for evaluation.

There were no histopathologic findings or evidence of toxicity due to treatment with the rAAVs. In the mice treated with conduritol B-epoxide (CBE), there were findings in the central nervous system (CNS) that included glial scars and neuronal necrosis in the cerebral cortex, and neuronal necrosis in the brain stem and thoracic spinal cord. High dose rAAV treatment resulted in a notable reduction in the incidence of these CNS findings, while the low and mid dose virus had a dose dependent reduction in the incidence of glial scars in the cerebral cortex, with equivocal effects on the other CNS findings.

EQUIVALENTS

This application incorporates by reference the contents of the following documents in their entirety: International PCT Application No. PCT/US2018/054227, filed Oct. 3, 2018; International PCT Application No. PCT/US2018/054223, filed Oct. 3, 2018; Provisional Application Ser. Nos. 62/567,
311, filed Oct. 3, 2017, entitled "GENE THERAPIES FOR
LYSOSOMAL DISORDERS"; 62/567,319, filed Oct. 3,
2017, entitled "GENE THERAPIES FOR LYSOSOMAL
DISORDERS"; 62/567,301, filed Oct. 3, 2017, entitled
"GENE THERAPIES FOR LYSOSOMAL DISORDERS";
62/567,310, filed Oct. 3, 2017, entitled "GENE THERA-
PIES FOR LYSOSOMAL DISORDERS"; 62/567,303, filed
Oct. 3, 2017, entitled "GENE THERAPIES FOR LYSO-
SOMAL DISORDERS"; and 62/567,305, filed Oct. 3, 2017,
entitled "GENE THERAPIES FOR LYSOSOMAL DISOR-
DERS".

Having thus described several aspects of at least one
embodiment of this invention, it is to be appreciated that
various alterations, modifications, and improvements will
readily occur to those skilled in the art. Such alterations,
modifications, and improvements are intended to be part of
this disclosure, and are intended to be within the spirit and
scope of the invention. Accordingly, the foregoing descrip-
tion and drawings are by way of example only.

While several embodiments of the present invention have
been described and illustrated herein, those of ordinary skill
in the art will readily envision a variety of other means
and/or structures for performing the functions and/or obtain-
ing the results and/or one or more of the advantages
described herein, and each of such variations and/or modi-
fications is deemed to be within the scope of the present
invention. More generally, those skilled in the art will
readily appreciate that all parameters, dimensions, materials,
and configurations described herein are meant to be exem-
plary and that the actual parameters, dimensions, materials,
and/or configurations will depend upon the specific appli-
cation or applications for which the teachings of the present
invention is/are used. Those skilled in the art will recognize,
or be able to ascertain using no more than routine experi-
mentation, many equivalents to the specific embodiments of
the invention described herein. It is, therefore, to be under-
stood that the foregoing embodiments are presented by way
of example only and that, within the scope of the appended
claims and equivalents thereto, the invention may be prac-
ticed otherwise than as specifically described and claimed.
The present invention is directed to each individual feature,
system, article, material, and/or method described herein. In
addition, any combination of two or more such features,
systems, articles, materials, and/or methods, if such features,
systems, articles, materials, and/or methods are not mutually
inconsistent, is included within the scope of the present
invention.

The indefinite articles "a" and "an," as used herein in the
specification and in the claims, unless clearly indicated to
the contrary, should be understood to mean "at least one."

The phrase "and/or," as used herein in the specification
and in the claims, should be understood to mean "either or
both" of the elements so conjoined, i.e., elements that are
conjunctively present in some cases and disjunctively pres-
ent in other cases. Other elements may optionally be present
other than the elements specifically identified by the "and/
or" clause, whether related or unrelated to those elements
specifically identified unless clearly indicated to the con-
trary. Thus, as a non-limiting example, a reference to "A
and/or B," when used in conjunction with open-ended
language such as "comprising" can refer, in one embodi-
ment, to A without B (optionally including elements other
than B); in another embodiment, to B without A (optionally
including elements other than A); in yet another embodi-
ment, to both A and B (optionally including other elements);
etc.

As used herein in the specification and in the claims, "or"
should be understood to have the same meaning as "and/or"
as defined above. For example, when separating items in a
list, "or" or "and/or" shall be interpreted as being inclusive,
i.e., the inclusion of at least one, but also including more
than one, of a number or list of elements, and, optionally,
additional unlisted items. Only terms clearly indicated to the
contrary, such as "only one of" or "exactly one of," or, when
used in the claims, "consisting of," will refer to the inclusion
of exactly one element of a number or list of elements. In
general, the term "or" as used herein shall only be inter-
preted as indicating exclusive alternatives (i.e. "one or the
other but not both") when preceded by terms of exclusivity,
such as "either," "one of," "only one of," or "exactly one of"
"Consisting essentially of," when used in the claims, shall
have its ordinary meaning as used in the field of patent law.

As used herein in the specification and in the claims, the
phrase "at least one," in reference to a list of one or more
elements, should be understood to mean at least one element
selected from any one or more of the elements in the list of
elements, but not necessarily including at least one of each
and every element specifically listed within the list of
elements and not excluding any combinations of elements in
the list of elements. This definition also allows that elements
may optionally be present other than the elements specifi-
cally identified within the list of elements to which the
phrase "at least one" refers, whether related or unrelated to
those elements specifically identified. Thus, as a non-limit-
ing example, "at least one of A and B" (or, equivalently, "at
least one of A or B," or, equivalently "at least one of A and/or
B") can refer, in one embodiment, to at least one, optionally
including more than one, A, with no B present (and option-
ally including elements other than B); in another embodi-
ment, to at least one, optionally including more than one, B,
with no A present (and optionally including elements other
than A); in yet another embodiment, to at least one, option-
ally including more than one, A, and at least one, optionally
including more than one, B (and optionally including other
elements); etc.

In the claims, as well as in the specification above, all
transitional phrases such as "comprising," "including," "car-
rying," "having," "containing," "involving," "holding," and
the like are to be understood to be open-ended, i.e., to mean
including but not limited to. Only the transitional phrases
"consisting of" and "consisting essentially of" shall be
closed or semi-closed transitional phrases, respectively, as
set forth in the United States Patent Office Manual of Patent
Examining Procedures, Section 2111.03.

Use of ordinal terms such as "first," "second," "third,"
etc., in the claims to modify a claim element does not by
itself connote any priority, precedence, or order of one claim
element over another or the temporal order in which acts of
a method are performed, but are used merely as labels to
distinguish one claim element having a certain name from
another element having a same name (but for use of the
ordinal term) to distinguish the claim elements.

It should also be understood that, unless clearly indicated
to the contrary, in any methods claimed herein that include
more than one step or act, the order of the steps or acts of
the method is not necessarily limited to the order in which
the steps or acts of the method are recited.

SEQUENCES

In some embodiments, an expression cassette encoding
one or more gene products (e.g., a first, second and/or third
gene product) comprises or consists of (or encodes a peptide having) a sequence set forth in any one of SEQ ID NOs: 1, 2, 3, 4, 5, 6, 7, 8, 9, 10, 11, 12, 13, 14, 15, 16, 17, 18, 19, 20, 21, 22, 23, 24, or 25. In some embodiments, a gene product is encoded by a portion (e.g., fragment) of any one of SEQ ID NOs: 1, 2, 3, 4, 5, 6, 7, 8, 9, 10, 11, 12, 13, 14, 15, 16, 17, 18, 19, 20, 21, 22, 23, 24, or 25.

What is claimed is:

1. An isolated nucleic acid comprising: (i) an expression construct comprising a promoter operably linked to a transgene insert encoding a beta-glucocerebrosidase (Gcase) protein, wherein the transgene insert comprises the nucleotide sequence of SEQ ID NO: 15; and (ii) two adeno-associated virus (AAV) inverted terminal repeat (ITR) sequences flanking the expression construct, wherein the first ITR sequence is a 5' ITR, and the second ITR sequence is a 3' ITR.

2. The isolated nucleic acid of claim 1, wherein the promoter is a chicken beta actin (CBA) promoter.

3. The isolated nucleic acid of claim 1, further comprising a cytomegalovirus (CMV) enhancer (CMVe).

4. The isolated nucleic acid of claim 1, further comprising a Woodchuck Hepatitis Virus Posttranscriptional Regulatory Element (WPRE).

5. The isolated nucleic acid of claim 1, further comprising a Bovine Growth Hormone polyA signal tail.

6. The isolated nucleic acid of claim 1, wherein each of the two ITR sequences is a wild-type AAV2 ITR sequence.

7. The isolated nucleic acid of claim 1, wherein each of the two ITR sequences comprises a "D" region (SEQ ID NO: 27) that is proximal to the expression construct.

8. The isolated nucleic acid of claim 1, wherein at least one of the two ITR sequences comprises a "D" region (SEQ ID NO: 27) positioned on the outside of the ITR sequence relative to the expression construct.

9. The isolated nucleic acid of claim 1, wherein the 5' ITR sequence comprises a "D" region (SEQ ID NO: 27) that is proximal to the expression construct, and the 3' ITR sequence comprises a "D" region (SEQ ID NO: 27) positioned on the outside of the ITR sequence relative to the expression construct.

10. The isolated nucleic acid of claim 9, wherein the nucleic acid sequence of the 5' ITR is nucleotides 1-145 of SEQ ID NO: 1 and the nucleic acid sequence of the 3' ITR is nucleotides 3867-4011 of SEQ ID NO: 1.

11. The isolated nucleic acid of claim 9, further comprising a TRY region between the 5' ITR and the expression construct, wherein the TRY region has the sequence set forth in SEQ ID NO: 28.

12. An isolated nucleic acid comprising, in 5' to 3' order:
(a) a 5' AAV ITR;
(b) a CMVe;
(c) a CBA promoter;
(d) a transgene insert encoding a Gcase protein, wherein the transgene insert comprises the nucleotide sequence of SEQ ID NO: 15;
(e) a WPRE;
(f) a Bovine Growth Hormone polyA signal tail; and
(g) a 3' AAV ITR.

13. A plasmid comprising a nucleic acid comprising:
(i) an expression construct comprising a promoter operably linked to a transgene insert encoding a Gcase protein, wherein the transgene insert comprises the nucleotide sequence of SEQ ID NO: 15; and (ii) two AAV ITR sequences flanking the expression construct.

14. A Baculovirus vector comprising a nucleic acid comprising:

(i) an expression construct comprising a promoter operably linked to a transgene insert encoding a Gcase protein, wherein the transgene insert comprises the nucleotide sequence of SEQ ID NO: 15; and (ii) two AAV ITR sequences flanking the expression construct.

15. An isolated cell comprising:

(i) a first vector encoding one or more AAV rep proteins and/or one or more AAV cap proteins; and (ii) a second vector comprising a nucleic acid comprising:

(a) an expression construct comprising a promoter operably linked to a transgene insert encoding a Gcase protein, wherein the transgene insert comprises the nucleotide sequence of SEQ ID NO: 15; and (b) two AAV ITR sequences flanking the expression construct.

16. The cell of claim 15, wherein (i) the first vector is a plasmid and the second vector is a plasmid; or (ii) the first vector is a Baculovirus vector and the second vector is a Baculovirus vector.

17. The cell of claim 15, wherein the cell is a mammalian cell or an insect cell.

18. The cell of claim 17, wherein the mammalian cell is a HEK293 cell.

19. A method of producing a recombinant adeno-associated virus (rAAV), the method comprising:

(i) culturing the cell of claim 15 under conditions allowing for packaging the rAAV; and (ii) harvesting the cultured host cell or a culture medium for collection of the rAAV.

20. The method of claim 19, wherein the rAAV comprises an AAV9 capsid protein.

21. A rAAV vector comprising a nucleic acid comprising an expression construct comprising a promoter operably linked to a transgene insert encoding a Gcase protein, wherein the transgene insert is SEQ ID NO: 15.

22. A rAAV comprising:

(i) an AAV capsid protein; and the rAAV vector of claim 21.

23. The rAAV of claim 22, wherein the AAV capsid protein is AAV9 capsid protein.

* * * * *